US009879054B2

(12) United States Patent
Bannoehr et al.

(10) Patent No.: US 9,879,054 B2
(45) Date of Patent: Jan. 30, 2018

(54) STAPHYLOCOCCAL ANTIGENS

(75) Inventors: Jeanette Bannoehr, Edinburgh (GB); Ross J. Fitzgerald, Edinburgh (GB); Nouri L. Ben Zakour, Brisbane (AU)

(73) Assignee: THE UNIVERSITY COURT OF THE UNIVERSITY OF EDINBURGH, Edinburgh (GB)

( * ) Notice: Subject to any disclaimer, the term of this patent is extended or adjusted under 35 U.S.C. 154(b) by 0 days.

(21) Appl. No.: 13/446,958

(22) Filed: Apr. 13, 2012

(65) Prior Publication Data

US 2012/0282289 A1    Nov. 8, 2012

Related U.S. Application Data

(63) Continuation-in-part of application No. PCT/GB2010/001916, filed on Oct. 15, 2010.

(60) Provisional application No. 61/252,026, filed on Oct. 15, 2009.

(51) Int. Cl.
| | | |
|---|---|---|
| C07K 14/31 | (2006.01) | |
| C12N 15/63 | (2006.01) | |
| A61K 39/085 | (2006.01) | |
| C12N 1/00 | (2006.01) | |
| G01N 33/569 | (2006.01) | |
| A61K 39/00 | (2006.01) | |

(52) U.S. Cl.
CPC ............ *C07K 14/31* (2013.01); *A61K 39/085* (2013.01); *G01N 33/56938* (2013.01); *A61K 39/00* (2013.01); *A61K 2039/552* (2013.01)

(58) Field of Classification Search
None
See application file for complete search history.

(56) References Cited

U.S. PATENT DOCUMENTS

| 5,780,448 A | 7/1998 | Davis |
| 2009/0246218 A1 | 10/2009 | Foster et al. |

FOREIGN PATENT DOCUMENTS

| JP | 2007-55920 | 3/2007 |
| WO | WO 2001/031019 | 5/2001 |
| WO | WO 2002/076498 | 10/2002 |
| WO | WO 2009/095453 | 8/2009 |
| WO | WO 2011/045573 | 4/2011 |

OTHER PUBLICATIONS

Bowie et al (Science, 1990, 257:1306-1310).*
Burgess et al (J. of Cell Bio. 111:2129-2138, 1990).*
Lazar et al. (Molecular and Cellular Biology, 1988, 8:1247-1252).*
Bork (Genome Research, 2000,10:398-400).*
Ellis (Vaccines, W.B. Saunders Company, Chapter 29, 1988, pp. 568-574).*
Boslego et al (Vaccines and Immunotherapy, 1991, Chapter 17).*
Skolnick et al. (Trends in Biotechnology 18: 34-39, 2000).*
Colman (Res. Immunology, Jan. 1994, vol. 145, pp. 33-36).*
Curtis, C. F. et al., "Masked, Controlled Study to Investigate the Efficacy of a *Staphylococcus intermedius* Autogenous Bacterin for the Control of Canine Idiopathic Recurrent Superficial Pyoderma," European Society of Veterinary Dermatology, 2006, 17, 163-168.
Hill, P. B. et al., "Survey of the Prevalence, Diagnosis and Treatment of Dermatological Conditions in Small Animals in General Practice," The Veterinary Record, 2006, 158, 533-539.
Bannoehr et al; "Population Genetic Structure of the *Staphylococcus intermedius* Group . . . " Journal of Bacteriology, Dec. 2007, p. 8685-8692.
Galeotti et al; "Neisserial Antigenic Peptides"; Jan. 16, 2004; Abstract XP002632347.
Geoghegan et al; "*Staphylococcus pseudintermedius* Expresses Surface Proteins that Closely Resemble Those From *Staphylococcus aureus*"; Veterinary Microbiology 138 (2009) 345-352.
Guardabassi et al; "Pet Animals as Reservoirs of Antimicrobial-Resistant Bacteria"; Journal of Antimicrobial Chemotherapy; 2004; 54, 321-332.
Hobo et al; "*Streptococcus equi* subsp. *equi*"; Jul. 12, 2007; Abstract, XP002632348.
Hobo et al; "*Streptococcus equi* subsp. *equi*"; Jul. 12, 2007; Abstract, XP002632349.
Kuhn et al; "Evidence for Clonal Evolution Among Highly Polymorphic Genes in Methicillin-Resistant *Staphylococcus aureus*"; Abstract, XP002622924.
Moodley et al; "Tandem Repeat Sequence Analysis of *Staphylococcal* Protein A (spa) Gene in Methicillin-Resistant *Staphylococcs pseudintermedius*"; Veterinary Microbiology; 135; (2008); 320-326.
Shearer et al; "Aspects of the Humoral Immune Response to *Staphylococcus intermedius* in Dogs with Superficial Pyoderma, Deep Pyoderma and Anal Furunculosis"; Veterinary Immunology and Immunopathology; 58; (1997); 107-120.
International Search Report from the International Searching Authority (EP) for corresponding International Application No. PCT/GB2010/001916 dated Apr. 12, 2011.
Pizza, M. et al.: 'Identification of vaccine candidates against serogroup B meningococcus by whole-genome sequencing' Science vol. 287, 2000, pp. 1816-1820.
Otto, M.: 'Targeted immunotherapy for Staphylococcal infections : focus on anti-MSCRAMM antibodies' Biodrugs vol. 22, 2008, pp. 27-36.
Mazmanian, S.K. et al.: '*Staphylococcus aureus* sortase, an enzyme that anchors surface proteins to the cell wall' Science vol. 285, 1999, pp. 760-763.
Lindsay, J. A.; Moore, C. E.; Day, N. P.; Peacock, S. J.; Witney, A. A.; Stabler, R. A.; Husain, S. E.; Butcher, P. D.; Hinds, J.: 'Microarrays reveal that each of the ten dominant lineages of *Staphylococcus aureus* has a unique combination of surface-associated and regulatory genes' J Bacteriol vol. 188, 2006, pp. 669-676.

(Continued)

Primary Examiner — Robert A Zeman
(74) Attorney, Agent, or Firm — Hoxie & Associates LLC

(57) ABSTRACT

The present invention provides novel sequences encoding *Staphylococcus pseudintermedius* proteins/nucleic acids potentially useful in the treatment and/or prevention of canine disorders. In particular, the various protein and/or nucleic acid sequences described herein may find application as vaccines for use in treating and/or preventing a variety of canine diseases and/or conditions caused or contributed to by *Staphylococcus pseudintermedius*.

3 Claims, 7 Drawing Sheets

(56) References Cited

OTHER PUBLICATIONS

Figure 1:
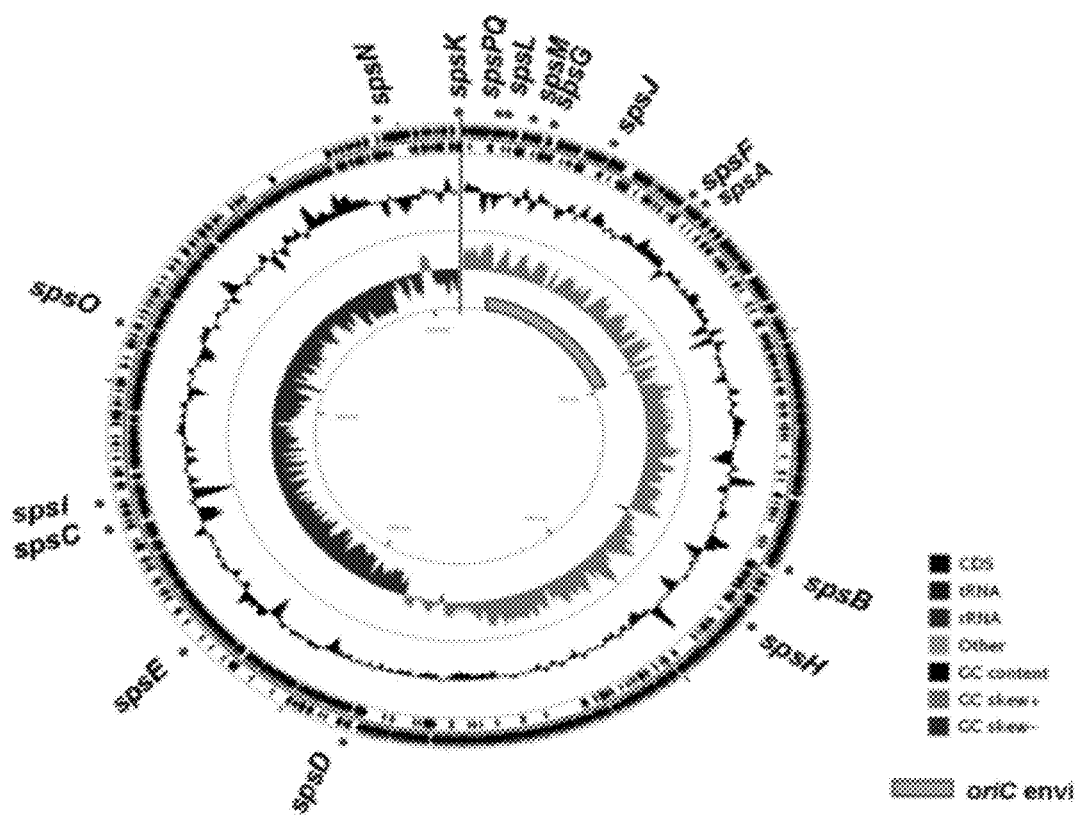

Corrigan, R. M.; Miajlovic, H.; Foster, T. J.: 'Surface proteins that promote adherence of *Staphylococcus aureus* to human desquamated nasal epithelial cells' BMC Microbiol vol. 9, 2009, p. 22.

Clarke, S. R.; Foster, S. J.: 'Surface adhesins of *Staphylococcus aureus*' Adv Microb Physiol vol. 51, 2006, pp. 187-224.

Ben Zakour; N. L., Guinane; C. M.; Fitzgerald, J. R.: 'Pathogenomics of the staphylococci: insights into niche adaptation and the emergence of new virulent strains' FEMS Microbiol Lett vol. 289, 2008, pp. 1-12.

Ganesh, V. K.; Rivera, J. J.; Smeds, E.; Ko, Y. P.; Bowden, M. G.; Wann, E. R.; Gurusiddappa, S.; Fitzgerald, J. R.; Hook, M.: 'A structural model of the *Staphylococcus aureus* ClfA-fibrinogen interaction opens new avenues for the design of anti-staphylococcal therapeutics' PLOS Pathog vol. 4, 2008.

Clarke, S. R.; Andre, G.; Walsh, E. J.; Dufrene, Y. F.; Foster, T. J.; Foster, S. J.: 'Iron-regulated surface determinant protein A mediates adhesion of *Staphylococcus aureus* to human comeocyte envelope proteins' Infect Immun vol. 77, 2009, pp. 2408-2416.

Bannoehr, J. et al.; 'Genomic and Surface Proteomic Analysis of the Canine Pathogen *Staphylococcus pseudintermedius* Reveals Proteins that Mediate Adherence to the Extracellular Matrix' Infect Immun vol. 79, 2011, pp. 3074-3086.

Forsythe et al., "Use of computerized image analysis to quantify Staphylococcal adhesion to canine corneocytes: does breed and body site have any relevance to the pathogenesis of pyoderma?", Vet Dermatol., 13(1):29-36; Feb. 2002; Abstract Only.

Foster et al., "Surface protein adhesins of *Staphylococcus aureus*", Trends in Microbiology, 6(12):484-488; Dec. 1998; Abstract Only.

Hall et al., "Characterization of a Protective Monoclonal Antibody Recognizing *Staphylococcus aureus* MSCRAMM Protein Clumping Factor A", Infection and Immunity, 71(12):6864-6870; Dec. 2003.

Josefsson et al., "Protection against Experimental *Staphylococcus aureus* Arthritis by Vaccination with Clumping Factor A, a Novel Virulence Determinant", The Journal of Infectious Diseases, 184:1572-1580; Dec. 2001.

Morozova et al., "Applications of next-generation sequencing technologies in functional genomics", Genomics, 92:255-264; Nov. 2008.

Nanra et al., "Heterogeneous in vivo expression of clumping factor A and capsular polysaccharide by *Staphylococcus aureus*: Implications for vaccine design", Vaccine, 27(25-26):3276-3280; May 2009; Abstract Only.

Patti, "A humanized monoclonal antibody targeting *Staphylococcus aureus*", Vaccine, 22(1): S39-S43 (Dec. 2004) Abstract Only.

Ronaghi, "Pyrosequencing Sheds Light on DNA Sequencing", Genome Research, 11:3-11; 2001.

Neuber et al., "Immunoglobulin G responses in 21 dogs with skin diseases to antigens from different isolates of *Staphylococcus intermedius*", Vet Rec, 2008, 162(3):75-79 (Abstract Only), Obtained via the Internet, Date Obtained: Apr. 6, 2017, 1 page URL: <https://www.ncbi.nlm.nih.gov/pubmed/18204030>.

Ponnuraj et al., "A "dock, lock, and latch" Structural Model for a Staphylococcal Adhesin Binding to Fibrinogen", Cell, 2003, 115:217-228.

Takeuchi et al., "Whole-Genome Sequencing of *Staphylococcus haemolyticus* Uncovers the Extreme Plasticity of Its Genome and the Evolution of Human-Colonizing Staphylococcal Species", Journal of Bacteriology, 2005, 187(21):7292-7308.

Stranger-Jones et al., "Vaccine assembly from surface proteins of *Staphylococcus aureus*", PNAS, 2006, 103(45):16942-16947.

\* cited by examiner

Figure 8 A & B

STAPHYLOCOCCAL ANTIGENS

CROSS-REFERENCE TO RELATED APPLICATIONS

This application is a continuation-in-part of PCT/GB2010/001916, filed Oct. 15, 2010, which claims the benefit under 35 U.S.C. § 119(e) to U.S. Provisional Application No. 61/252,026, filed Oct. 15, 2009, both of which are hereby incorporated by reference in their entirety.

FIELD OF THE INVENTION

The present invention provides novel staphylococcal cell wall associated proteins, genes encoding the same and vaccines for use in treating/preventing Staphylococcal infections.

BACKGROUND OF THE INVENTION

Skin diseases are a major cause of morbidity in dogs and an important animal welfare issue (Hill et al, 2006). In particular, superficial bacterial folliculitis (pyoderma) caused by *Staphylococcus pseudintermedius* (formerly known as *Staphylococcus intermedius*) is one of the most common diseases seen in small animal veterinary practice, worldwide (Hill et al, 2006). Superficial pyoderma is characterized by the formation of follicular pustules and is often associated with pruritus, alopecia, erythema and swelling. This may develop into deep pyoderma which typically includes pain, crusting, odor, and exudation of blood and pus. The disease often occurs as a secondary infection in dogs with atopic dermatitis (AD) resulting from a type I hypersensitivity reaction (IgE antibody-associated) to environmental allergens (Hill et al, 2006). Treatment of canine pyoderma is often difficult without resorting to aggressive, medium-term administration of systemic antibacterial agents to prevent relapse of infection, and such therapy predisposes to the development of bacterial resistance that may be transferred to bacteria infecting humans (Guardabassi et al, 2004). Worryingly, methicillin-resistant *S. pseudintermedius* has recently emerged as a major problem in veterinary clinics worldwide (Bannoehr et al, 2007). Although rare, several episodes of life-threatening infections of humans by *S. pseudintermedius* have been reported with the typical route of transmission being through dog bite wounds (Bannoehr et al, 2007). Previously, crude vaccine preparations based on *Staphylococcus aureus* phage lysate or *S. pseudintermedius* autogenous bacterin have shown promise as adjunctive therapies for treatment of pyoderma (Curtis et al, 2006), and a rationally-designed effective vaccine would be a highly desirable means to reducing or eliminating the suffering associated with the disease.

Accordingly, the present invention aims to obviate one or more of the problems associated with the prior art.

SUMMARY OF THE INVENTION

The present invention is based upon the identification of novel gene sequences encoding proteins potentially useful in the treatment and/or prevention of canine disorders. In particular, the proteins encoded by the genes described herein, may find application in the treatment and/or prevention of diseases caused or contributed to by the bacterial pathogen *Staphylococcus pseudintermedius*.

The inventors have identified a number of *Staphylococcus pseudintermedius* genes encoding proteins which may broadly be classed as members of the cell-wall anchored (CWA) family of proteins. In certain embodiments, these CWA proteins may be further grouped as surface proteins known as Microbial Surface Components Recognising adhesive Matrix Molecules (MSCRAMM). It should be understood that while a number microbial organisms may be known to express MSCRAMM type proteins, the term "MSCRAMM" describes the phenotypic function of a wide range of diverse surface-associated proteins of Gram-positive bacteria. As such, while MSCRAMM proteins may all possess cell-wall anchor motifs and signal sequences for cell wall transportation, the proteins belonging to this group may otherwise be structurally diverse. Furthermore, bacterial species within a particular genus, for example the genus *Staphylococcus*, may possess unique MSCRAMM profiles.

In view of the above, the present invention relates to a group of surface expressed proteins derived from *Staphylococcus pseudintermedius* that may be referred to either as CWA or MSCRAMM proteins.

As such, a first aspect of this invention provides an isolated and/or substantially purified *Staphylococcus pseudintermedius* CWA or MSCRAMM nucleic acid or protein sequence comprising a nucleic acid or amino acid sequence homologous or identical to any one of the nucleic acid or amino acid sequences provided as SEQ ID NOS: 1-38 below.

SEQ ID NO: 1
```
atggaaaacaaaaacttttttagtattcgtaaactatctattggtgtagg ttcttgcttaatcgcgagttctttacttgtaaacacgccaagttttgctg aagaaacagataatgcgaacattaatgacgcacaacaaaacgcctttat gaaattttacatttgccaaacttaactgaagagcaacaaaatggattcat ccaaagtcttaaagatgatccaagtgtgagcaacgacattttagtagaag ctaagaaattaaatgacactcaagctaaacctgattacagtgaagcacaa caaaatgcattttatgaaattttacatttgtcaaacttaactgaagagca acaaaatggattcatccaaagtcttaaagatgatccaagtgtgagcaacg acattttagtagaagctaagaagttaaatgacactcaagctaaacctgat tacagtgaagcacaacaaaatgcattttatgaaattttacatttgtcaaa cttaactgaagagcaacaaaatgggttcatccaaagccttaaagatgatc caagtgtaagtaaagaaattttagcagaagctaagaagttaaatgatagt caagcacctaaagttgataaagctaaaaaaactgacaaagctgaagcgaa agcagatgataaagctaaaggtgaagaagccaaaaaatctgaagacaaaa aagatagcaaagcagataaggcaaaatcgaaaaacgctacacatgttgtt aaacctggtgaaactttagataatattgctaaagatcatcatacaactgt tgataaaattgctaaagataacaaaataaaagataaaaatgtgattaaac taggtcaaaaacttgttgttgataaacaaaaagcaactcaaggaaaacaa gaagctgtagcgaaaaatgaagtgaaggctttacctaatactggtgaaaa tgatgatatcgcattattcagcacaacagttgcgggtggcgtaagtatcg ctttaggttcattattattaggaagaaacagaaaaactagctaa
```

The protein sequence translated from SEQ ID NO 1 is designated SEQ ID NO: 2 and is shown below:

SEQ ID NO: 2
MENKNFFSIRKLSIGVGSCLIASSLLVNTPSFAEETDNANINDAQQNAFY
EILHLPNLTEEQQNGFIQSLKDDPSVSNDILVEAKKLNDTQAKPDYSEAQ
QNAFYEILHLSNLTEEQQNGFIQSLKDDPSVSNDILVEAKKLNDTQAKPD
YSEAQQNAFYEILHLSNLTEEQQNGFIQSLKDDPSVSKEILAEAKKLNDS
QAPKVDKAKKTDKAEAKADDKAKGEEAKKSEDKKDSKADKAKSKNATHVV
KPGETLDNIAKDHHTTVDKIAKDNKIKDKNVIKLGQKLVVDKQKATQGKQ
EAVAKNEVKALPNTGENDDIALFSTTVAGGVSIALGSLLLGRNRKTS

SEQ ID NO: 3
atggaaaacaaaaacttttcagcattcgtaaattatcaattggggtggg
ttcatgtttaatcgcgagctctttacttgtgaatacaccaagtttcgcag
aagaaggagataataacgcagaagcgcaacaaaacgctttctctgaggta
gtaaaattacctaaccttagcgaagaacaacgtaatggtttcattcaaag
ccttaaagatgatccaagtacaagtcaagatgtgcttaatgaagctaaaa
aattaaatgatagtcaagagggatctcaacctgctcctgattacagtgat
gaacaacaaaatgcattttatgaaattttacaccttccaaacttaactga
agaacaacgcaatggctatattcaaagtcttaaagatgacccaagtgtaa
gcgctaatattcttgttgaagctaaaaatatgaatgttaaccaaacacct
acacaacctgcgccaagtttcgatgaagcgcaacaaaatgcattctatga
gattgtaaacttaccaaatcttactgaagagcaacgtaacggtttcatcc
aaagccttaaagacgatccaagtgtaagtaaagatatccttgttgaagct
aaaaagttaaatgacagccaagcaaaacctgattacagtgaagcgcaaca
aaatgcattttatgaaattttacaccttccaaacttaactgaagaacaac
gtaacggtttcatccaaagccttaaagacgatccgagtgtaagtagtgat
attcttgctgaagctaagaaattaaatgacagccaagcgcctaaagaaga
caacaacgtaaaagacaataattcaggtgaaaacaaagctgaagacaaag
gcaacaaagaaacaaagctgaagataaaggcagcaaagaagacaaagct
gaagataaaggcagcaaagaagacaaagctgaagataaaggcagcaaaga
agacaaagctgaagataaaggcagcaaagaagacaaagctgaagataaag
gcagcatagaagataaagctaaagacaaagacaacaaagaaggcaaagct
gcagacaaaggtatggacaaagcgaaagatgcaatgcatgtcgttcaacc
tggtgaaacagtagaaaaaattgctaaagctaataacacaactgtagaac
aaatcgctaaagataatcatttagaagataaaaacatgattttaccaggt
caaaaacttgttgttgacaaccaaaaagcaatgaaagacagccaagaagc
taaagcaaaccacgaaatgaaagctttacctgaaacaggtgaagaaaacg
atatggcattattcggtacatcacttacaggtggtcttagcttagcatta
ggtttatacatcttaggacgtggcagaaaaacaaactaa The protein sequence translated from SEQ ID NO 3 is designated SEQ ID NO: 4 and is shown below:

SEQ ID NO: 4
MENKNFFSIRKLSIGVGSCLIASSLLVNTPSFAEEGDNNAEAQQNAFSEV
VKLPNLSEEQRNGFIQSLKDDPSTSQDVLNEAKKLNDSQEGSQPAPDYSD
EQQNAFYEILHLPNLTEEQRNGYIQSLKDDPSVSANILVEAKNMNVNQTP
TQPAPSFDEAQQNAFYEIVNLPNLTEEQRNGFIQSLKDDPSVSKDILVEA
KKLNDSQAKPDYSEAQQNAFYEILHLPNLTEEQRNGFIQSLKDDPSVSSD
ILAEAKKLNDSQAPKEDNNVKDNNSGENKAEDKGNKENKAEDKGSKEDA
EDKGSKEDKAEDKGSKEDKAEDKGSKEDKAEDKGSIEDKAKDKDNKEGKA
ADKGMDKAKDAMHVVQPGETVEKIAKANNTTVEQIAKDNHLEDKNMILPG
QKLVVDNQKAMKDSQEAKANHEMKALPETGEENDMALFGTSLTGGLSLAL
GLYILGRGRKTN

SEQ ID NO: 5
gtgtacaaaaatgaagaagaaaagcattcaataagaaagttatctatagg
agccgcatctgtcattgttgggggactcatgtatggtgttttgggaaatg
atgaagctcaagcgaatgaagatgtcactgaaacaactgggagaaattca
gtgacaacgcaagcttctgagcaacatttgcaagtggaagcagtacctca
agaaggcaataatgtaaatgtatcctctgtaaaagtacctacgaatacgg
caacgcaagcacaagaagatgttgcaagtgtatccgatgttaaagcacat
gctgatgatgcattacaagtacaagaaagtagtcatactgatggtgtttc
ttcagaattcaagcaggagacagcttatgcgaatcctcaaacagctgaga
cagttaaacctaatagtgaagcagtgcatcagtctgaatacgaggataag
caaaaaccgtatcatctagccgcaaagaagatgagactatgcttcagca
gcaacaagttgaagccaaaaatgttgtgagtgcggaggaagtgtctaaag
aagaaaatactcaagtgatgcaatcccctcaagacgttgaacaacatgta
ggtggtaaagatatctctaatgaggttgtagtggataggagtgatatcaa
aggatttaacagcgaaactactattcgacctcatcagggacaaggtggta
ggttgaattatcaattaaagtttcctagcaatgtaaagccaggcgatcag
tttactataaaattatctgacaatatcaatacacatggtgtttctgttga
aagaaccgcaccgagaatcatggctaaaaatactgaaggtgcgacggatg
taattgctgaaggtctagtgttggaagatggtaaaaccatcgtatataca
tttaaagactatgtaaatggcaagcaaaatttgactgctgagttatcagt
gagctatttcgtaagtccggaaaaagtcttgactactgggacaaacat
tcacgacgatgatcggtaatcattcaacgcaatccaatattgacgtttat
tatgataatagtcattatgtagatggacgtatttcgcaagtgaacaaaaa
agaagctaaatttcaacaaatagcatacattaaccctaatggctatttaa
atggcaggggacaattgcagttaatggtgaagtggtcagtggtacgact
aaagacttaatgcaacctacagtgcgtgtatatcaatataaaggacaagg
tgttcctcctgaaagtattactatagacccgtaatatgtgggaagaaatca
gcataaacgatactatggtaagaaaatatgatggtgctatagcttgaat
ctggataccagcaagaatcaaaaatgccatctattatgaaggggcata
tgatgcgcaagctgacacactgttgtatagaacatatatacagtcattaa
acagttactatccgttcagttaccaaaaatgaacggtgtgaagttttac
gaaaacagtgcgagtggaagcggtgagttgaaaccgaaaccacctgaaca
accaaaaccagaacctgaaattcaagctgatgtagtagatattattgaag -continued

```
atagccatgtgattgatataggatggaatacagcagttggagaagaaagt
ggagcaaaccaaggccctcaagaagaaatcacggaaaatcacgacatcga
agtcattgaggaaaacaacttggtggaaatgacagaagatacagcagttg
gagaagaaagtggagcaaaccaaggccctcaagaagaaatcacggaaaat
cacgacatcgaagtcattgaagaaaacaacttagtggaaatgacagaaga
tacagcgttggaagaagaaagtggagcaaatcaaggtcctcaagaagaga
tcacagaaaaccacgatatcgaagtcattgaagaaaacaacttggtggaa
atgacagaagatacagcgttggaagaagaaagtggagcaaatcaaggtcc
tcaagaagagatcacagaaaaccacgacatcgaagtcattgaagaaaata
acttagtagaaatgacagaagatacagcgttggagaagaaagtggagca
aatcaaggtcctcaagaagagatcacagaaaaccacgatatcgaagtcat
tgaggaaaacaacttagtggaaatgacagaagatacagcagttggagaag
aaagtggagcaaaccaaggtcctcaagaagaaatcacggaaaatcacgac
atcgaagtcattgaagaaaacaacttggtggaaatgacagaagatacagc
gttggaagaagaaagtggagcaaatcaaggtcctcaagaagagatcacag
aaaaccacaacatcgaagtcattgaagaaaacaacttggtggaaatgaca
gaagatacagcagttggagaagaaagtggagcaaacccaggacctcaaga
agaagtaacagagaatcaacctcagcaagaagaaatcatggaaaaccaag
aagtcgaaaagaaaggcgatagtaacttggtagaaagtacaaaaactcca
aaggccgaagaatcagttagcgttcagccaactttagaagacaaaaacac
aaagaaccacgttaacacagtagtagtgaatacgaaggtatctgaagtta
aagaaaaggatccccaccataccaaaagcactaccagatacggggacaacc
tctcgaagtcattccatgatgattcctctccttcttgttgctgggtcagt
agtgttgttacgtcgaaagaaaaagcatagtaaggtgaattaa
```

The protein sequence translated from SEQ ID NO 5 is designated SEQ ID NO: 6 and is shown below:

SEQ ID NO: 6

```
VYKNEEEKHSIRKLSIGAASVIVGGLMYGVLGNDEAQANEDVTETTGRNS
VTTQASEQHLQVEAVPQEGNNVNVSSVKVPTNTATQAQEDVASVSDVKAH
ADDALQVQESSHTDGVSSEFKQETAYANPQTAETVKPNSEAVHQSEYEDK
QKPVSSSRKEDETMLQQQQVEAKNVVSAEEVSKEENTQVMQSPQDVEQHV
GGKDISNEVVVDRSDIKGFNSETTIRPHQGQGGRLNYQLKFPSNVKPGDQ
FTIKLSDNINTHGVSVERTAPRIMAKNTEGATDVIAEGLVLEDGKTIVYT
FKDYVNGKQNLTAELSVSYFVSPEKVLTTGTQTFTTMIGNHSTQSNIDVY
YDNSHYVDGRISQVNKKEAKFQQIAYINPNGYLNGRGTIAVNGEVVSGTT
KDLMQPTVRVYQYKGQGVPPESITIDPNMWEEISINDTMVRKYDGGYSLN
LDTSKNQKYAIYYEGAYDAQADTLLYRTYIQSLNSYYPFSYQKMNGVKFY
ENSASGSGELKPKPPEQPKPEPEIQADVVDIIEDSHVIDIGWNTAVGEES
GANQGPQEEITENHDIEVIEENNLVEMTEDTAVGEESGANQGPQEEITEN
HDIEVIEENNLVEMTEDTALEEESGANQGPQEEITENHDIEVIEENNLVE
MTEDTALEEESGANQGPQEEITENHDIEVIEENNLVEMTEDTAVGEESGA
NQGPQEEITENHDIEVIEENNLVEMTEDTAVGEESGANQGPQEEITENHD
IEVIEENNLVEMTEDTALEEESGANQGPQEEITENHNIEVIEENNLVEMT
EDTAVGEESGANPGPQEEVTENQPQQEEIMENQEVEKKGDSNLVESTKTP
KAEESVSVQPTLEDKNTKNHVNTVVVNTKVSEVKEKDPHHTKALPDTGTT
SRSHSMMIPLLLVAGSVVLLRRKKKHSKVN
```

SEQ ID NO: 7

```
atgaataaatcaagaactaaacattttaattttttatcaaaacgtcagaa
tcggtatgctattcgccacttttcagctggtactgtgtcagtgcttgtag
gagcagctttcttgctaggtgtccatacgagtgatgcatctgctgcagaa
caagatcaaacatctgaagcaaagcaaaacctctttgatgcttccgctat
ttttggcgctttaacagagacgaacgaaaaggtagcacaagtgacgccaa
cagaaaaaaatctttcatcagttgaagaaatgagagataaaggcgcaact
ggaaatggaccatcaataacatcactacaaactgtagaacaaaataatgc
agtacaacctacagcaacacctattaatgacacagaaaattcaaccgaag
cccctatgaaagaacaatcgaatgatgcacaaacgactgacgaaagtaac
aatgccactcagaaaaataatactgaaccccaagcaaacaatgaaatatc
agcgcgtaatgcaaaaacaacagcatatttaacaagtgaaaccctttacaa
cagcaacgtctacaactgatatgcctacacagaaacaagaatatccatct
ttagaaaatccaacaaatcaatcgcaaacgaacagagcacaaccaccaac
aatggaagcacccaaactggcagaaggattagacaatctattaaaaaaat
caactttcgaaagtatgtacgtgacaaaaagaaatcaatttgacaaagag
acggcttctaaaacaaaagcatggccgagtgatgttgttccagaaaatca
agtagagatacttgctgatgcaattcaaaatggctatatcaaatctgtaa
atgatgtgaccaataaagcacatacgttatctggacgtgcatggatgtta
gaccacggaacaccaacgacaatagctaatggtttaacacctgttccaga
gggcactaaagtttatttgcggtggatagatcaagatggtgccacttcgc
caatgtatacagcaaaaacgacaagtagattaagcgctgcggatggtaat
caagtgggtccaggtgcttatgctttcgatttacgcacaggttggataga
tgctaaaggaaaacaccacgtatatagagcagtaaagggtcaatattata
aaatatggatcaatgattttagaactaaagacggtaatatcgctacaatg
ttacgtgttgcaggaggatatgttccgggaacgtacgtggattctgtgac
atacaacaatatgggccaatttccattaattggtacaaatatgcaacgta
caggtatctttatgacaacgatacctcagaaaaatatttaatatcaaaa
cattacgtgaaagatacaaaaggtgctgcagcaaatccagccgtcacgat
aaattgaaaataactttgtgagcggcaaagtttggatagaaacaggtgctg
gagattatgtgaactcagcgacaggtccaaaccacaatgcgaaagatgtc
gttgcctctggatacaaagtggtcatgtcatcattaacagatcaaggtgc
taaagcctacgatgcgcaagtcaatcgcttgccgaagaaagatcgagcag
aagcagcacgtcaattattaataaaacatccagaatatatcgcagcaact
gtagaagggataacgaatgagtgggggagatatacattgcgtttccctaa
```

```
aggcacattcaacaaagaccatctttacggttacgtattggattttgatg
gtgaaattgtaaaaacttattcaggttttacttcaccagagttccggaga
ccgaattataatttgaccgttacaccgcaaacagctccctattatagacc
cgttcgacgtgcatgggtcaatgttaattttgcggttattgaagcaccac
aatctcaaatcgaaataaaagaatttgatgcaacctctaaccctgcgcat
cgtgggcaaacagcaactattgatatcataggtatgcctaaaacttcatt
acttacacgtgtacaatggaaagattcatcgggcagtattgttgaggata
gtggtcctgtttttacggaagaagaggctgaacatatagcggaatttgta
ataccgtctagcgcaaaatcaggcgaagtgtatactgtacaactcgtggt
aggtaatcatatcgtagcttcggactctcttattgtacatgtcaatgaag
aagcggcgacatatcatccgatatacccatcgacaacagtagaatcaggt
caaagagtaacgattccagcacctaagaatatggatggcaaacctttact
agatggcacaacttttgaaaaaggtcatcacgtaccaacttgggctttag
tgaatggtgatggctcgattacagtaaaacctggagaaaaagtagcagag
ggtgagtatgatattccagtgattgtgacatatccagatggtctaaaaaa
cacaatctttgcacctgtgaccgttgaagaaaaacaaccaatggcatcgc
aatatgagccaataacaactggagtatcgaaaccatttggaaacccagta
atgccaactgatgtaacagattcaattcaagtaccgaactatccattgga
agggcaacaaccgacagtaacagtggatgatgaaagtcaattaccagatg
gaacaacagaaggttacaaggatatagatgtaacagtgacatacccagac
ggaacaaaggatcgtgtcaaagttccagtcgtaacggaacaacaattaga
tagtgataaatatgatccggtcgcaacaggtatcttgaaaccgtttggta
ctccaacaacagaggaagacgttataaaattagtggagataccgaaatat
ccaacagacttaacacaaccaaaagtaacagtgacggttccaaatacttt
accggatgggcaaacgccaggtaaagtagacgttgatgtgacagtaacgt
atccagatggttccacagatcacatttcagttccagtttggacaaacaag
catctggataaagacaaatataacccaataacgactggggtatcgaaacc
atttggaatccagtaacgccaactgatgtaacagattcaattcaagtac
cgaactatccattggaagggcaacaactgacagtaacagtggatgatgaa
acacaattaccagatggaacaacagaaggtcacaaggatatagatgtaac
agtgacatacccagacggaacaaaggatcatatcaaagttccagtcgtaa
cggaaaaacaatcagataatgaaaaatatgagccaacaactaacggaatc
acgaaaaagtacggtatccctacgacagaggatgaagtgatagatatagt
tcgaattccatattttccagtagatggcgtgcaacctattgtaacggtaa
atgatcctagactattgccaaatggtcaaaaagaaggtcaaatcaatgtt
ccagtcacagtgacgtatccggatggcacaaaagatctcatgacagttcc
ggttattacaggtaagcaagcagaaaatgaaaaatacgatccaatcacat
taggagtaactaaagattatggtgatcctacaactgcaaacgatgtgaca
aagtcaatccaaataccaacatatccagcaggtggcgaacaaccaatcgc
aacagcggatgatgaaagtcaattaccggatggcacagtagaaggtaaag
tggatattccagtcacagtgacgtatccggatggtactcaggatcatatc
```

```
actgtcccagtatttaccaatcaacaacgagataatcaaaaagccagtaa
agctgtgacgaaaatacatggtatatcggtaacaggcactgatatgacag
atactaagaaaaatcataactatccagcaggtggtgaacaacctaaagtt
actgtgaaagatgacgatcaattatcagagggtaaagtcgattcaacagt
gggtgcggataatgtgacaactacagatgatttatcaagcgtaactgcgg
tatctcatggtcatcaaacaagtgtacaaacaacaaaagagaaccaatca
gtgcatgatgaagaggtgacgatcccaacagttgcacatgtgtctacaat
aatgacaggtgtggtaaagggtgagcaagaagcgacggatatcgtggcta
gaccacatgttgaaacaactcaactcccatcaatttcagctcaagcaaca
gttaaaaaactaccagaaacgggtgaaaacaatgaacaatcaggtgtttt
attaggtggatttattgcgttcatgggtagcttacttttattcggcagac
gtcgcaaaccaaagaaagattaa
```

The protein sequence translated from SEQ ID NO 7 is designated SEQ ID NO: 8 and is shown below:

```
                                          SEQ ID NO: 8
MNKSRTKHFN FLSKRQNRYA IRHFSAGTVS VLVGAAFLLG

VHTSDASAAE QDQTSEAKQN LFDASAIFGA LTETNEKVAQ

VTPTEKNLSS VEEMRDKGAT GNGPSITSLQ TVEQNNAVQP

TATPINDTEN STEAPMKEQS NDAQTTDESN NATQKNNTEP

QANNEISARN AKTTAYLTSE TFTTATSTTD MPTQKQEYPS

LENPTNQSQT NRAQPPTMEA PKLAEGLDNL LKKSTFESMY

VTKRNQFDKE TASKTKAWPS DVVPENQVEI LADAIQNGYI

KSVNDVTNKA HTLSGRAWML DHGTPTTIAN GLTPVPEGTK

VYLRWIDQDG ATSPMYTAKT TSRLSAADGN QVGPGAYAFD

LRTGWIDAKG KHHVYRAVKG QYYKIWINDF RTKDGNIATM

LRVAGGYVPG TYVDSVTYNN MGQFPLIGTN MQRTGIFMTT

IPSEKYLISK HYVKDTKGAA ANPAVTIIEN NFVSGKVWIE

TGAGDYVNSA TGPNHNAKDV VASGYKVVMS SLTDQGAKAY

DAQVNRLPKK DRAEAARQLL IKHPEYIAAT VEGITNEWGR

YTLRFPKGTF NKDHLYGYVL DFDGEIVKTY SGFTSPEFRR

PNYNLTVTPQ TAPYYRPVRR AWVNVNFAVI EAPQSQIEIK

EFDATSNPAH RGQTATIDII GMPKTSLLTR VQWKDSSGSI

VEDSGPVFTE EEAEHIAEFV IPSSAKSGEV YTVQLVVGNH

IVASDSLIVH VNEEAATYHP IYPSTTVESG QRVTIPAPKN

MDGKPLLDGT TFEKGHHVPT WALVNGDGSI TVKPGEKVAE

GEYDIPVIVT YPDGSKNTIF APVTVEEKQP MASQYEPITT

GVSKPFGNPV MPTDVTDSIQ VPNYPLEGQQ PTVTVDDESQ

LPDGTTEGYK DIDVTVTYPD GTKDRVKVPV VTEQQLDSDK

YDPVATGILK PFGTPTTEED VIKLVEIPKY PTDLTQPKVT

VTVPNTLPDG QTPGKVDVDV TVTYPDGSTD HISVPVWTNK
```

HLDKDKYNPI TTGVSKPFGI PVTPTDVTDS IQVPNYPLEG
QQLTVTVDDE TQLPDGTTEG HKDIDVTVTY PDGTKDHIKV
PVVTEKQSDN EKYEPTTNGI TKKYGIPTTE DEVIDIVRIP
YFPVDGVQPI VTVNDPRLLP NGQKEGQINV PVTVTYPDGT
KDLMTVPVIT GKQAENEKYD PITLGVTKDY GDPTTANDVT
KSIQIPTYPA GGEQPIATAD DESQLPDGTV EGKVDIPVTV
TYPDGTQDHI TVPVFTNQQR DNQKASKAVT KIHGISVTGT
DMTDTKKNHN YPAGGEQPKV TVKDDDQLSE GKVDSTVGAD
NVTTTDDLSS VTAVSHGHQT SVQTTKENQS VHDEEVTIPT
VAHVSTIMTG VVKGEQEATD IVARPHVETT QLPSISAQAT
VKKLPETGEN NEQSGVLLGG FIAFMGSLLL FGRRRKPKKD

SEQ ID NO: 9
atgtttaatcaacaaaaacaacactatggtatccggaaatatgcaatcgg
gacttcatcagtattattaggcatgacattatttatcacacatgacgcaa
ctgcatctgcagctgaaaacaatacaactgcaaagacagagacaaatcaa
gcagcaacaatttcttctcgcacttcgccaaccgacgtcgctcaacctaa
tgcagacacgaatgctacaacggcgactaaagagacaacaccacaatcag
attcaacagcattaccgcaagcagcagcgcaacctcaaacgggccaaaca
gcatcgaaagacacagtagatacaaataaaacgcaaacagcagattccac
aaccgctcctcctgtgacagacgcgccaaaagctaatgacgcacaacac
agccagaagctgcgactgtagccaaaaagaagatgctcagacaccatcg
actgcagaccctacaccacaagcgcaacaaccgcctcagtcaaaagcacc
tcaagaaacgcaacaacaatcaacagttgaagatacaacgccacaacaaa
acgcatcaactgaagcacaccctaaaaatgtagataccgcttcaacaaaa
caacaacaaacaacgccatcaaccgcaccgacaccttacacacaacaagc
agacgaagcaatgacagatgtcacaacaaccagtgtcgacagcaacgtac
agccgttagcccctgcagaagatcaacctaaaaatacgaacacagctgac
aaagcaaccgttgcgacaccaccacgtgacaatgctaagactgctgatcc
gaacaaaaagatgacacgtgcagcaacgacacaacaagatgatgccgtcg
atacattgaagtcaaaagaaatgacagcaacgatcgataaaagttttcca
gccgttaaatattacacgttgaaaaatggtaaaaaagtcgatgcacaact
gacgcgatgcacgtcaaatcatcgtcaatggtgaagtcattacaccaacag
tcaaatacaacaaaattgatgatcatacggctgaatatgacttaacagca
caaaatgattcacgttcgattgatgccaattttaaatttcgtttatcagt
tgaaggtaagaccgttgatttacaaatgacagattacacgaacaacaaca
cagatccacaaaacgtcattcgcaactttagctttgtaagtcaatcgctc
gtatctgtaaacaatcaacagaaaaatgccaaactgcaaacatcgaaact
gtctacaaatcaatgaaaagcggcgataaatcatatcatatcgatgaaa
atttcaaaaacgacttcaacgactttatgatgtacggtttcgtgtcaaat
gatgattacagtgcaggattgtggagtaacgcacaaattggcgtcggcat
tggtgaacaagacttcttacgtgtctacgcacagtctatacaaacagata tcggggtcgctgtcggtttaggctcaatgccatggtttatccaaaaagac
gctgcacatccagatgcgaaaaatcaaggactactcccacatgtcaaagt
tgcaattgcggaagatgaaaatcaagatggtgaaattaactggcaagacg
gtgcaattgcttatcgtagcattatgaacaatccatatggtgccgaagaa
gtacctgaccttgttgggtaccgtatcgcgatgaactttggttctcaagc
gcaaaacccattttttaaagacgttagatggtgtgaaaaaattctatctca
atacagatggtttagggcaatccatttattaaaaggttataacagtgaa
ggccacgactctggtcatttagattacgcgaatattggtcaacgtatagg
tggcgtgaaagactttaaaacgttacttcaaaaaggggcagattatggcg
cacgttccggtcttcatgtgaatgcatctgaaacatatccagagtctcaa
gcattcaatcctgccctcttacgtaaagatgcgaatggaaactatatgta
tggctggaactggctcgatcaaggctttaacatcgatgcagattacgatt
taatacacgggcgtaaagaacgcttcgaagcactcaaacaaattgtcggt
gatgacctcgactttatttatgtcgatgtatggggaatggacaatccgg
cgacaatacagcttggccatcacatcaattagccaaagaaatcaacgact
taggatggcgcgtcggtgtcgaatggggtcacggtatggaatatgactcc
acgttccaacattgggcagccgacttaacgtatggatcgtaccaaaataa
agggattaactcagaggtagcacgcttcttacgcaaccatcaaaaagatt
catgggtcggtaactatccaaaatactcaggtgcagctgacttcccattg
ctcggcggttatgacatgaaagattttgaaggttggcaaggtcgtaacga
ttactctgcttacattaaaaatatttttcaatgttgatgtaccaacaaagt
ttttacaacattataaagtgatgcgtattgtcgatggtgagcctgttaaa
atgactgccaatggtcaaacgattgactggacaccagaaatgcaagtcga
tttacaaaatgaagccggtgatcaagtcactgttaaacgtaaatctaacg
actatgaaaacgacactgacaactaccgctcacgtacaatcgaattgaat
ggtcgcacagtactcgatggcgattcatacctttttaccatggaattggga
tgcgaacggccaaccattaactggcgataacgaaaaattatatcactgga
ataaaaaaggcggttcaacgacttggacactgcctgaatcatgggataca
gaccaagtcgtgctatacgaattatctgaaacgggtcgtaagtcaccacg
tacagtggcagtgaaagaccatcaagtgacactcgataatattaaagcag
acacaccgtatgtcgtttataaagtcgcacaaccagacaacacagatgtg
aactggagcgaagacatgcacgtgaaagatgccggcttcaactcacaaca
actgacaccttggacaatcgaaggcaatcgagataaagtgagcatcgaaa
agtcgacaacatcaaatgaaatgctaaaaatcgatagtccaacaaaaaca
acgcaattaacgcaacaattgacaggtttagtgccaggacaacgttacgc
tgtctatgttggcatcgataaccgcagtgatgcagcggcgcatattgcag
tgacacataacggtaaaacgctcgcaagtaacgaaacaggtcaatcgatc
gcgaaaaactatgtgaaagcagatgcacatagtaacaatgctgcgacgtt
taaaaatggcggtagttacttccaaaacatgtacgtgtacttcgttgcgc
cagaagatggtaaagcagacttgacgattcaacgcgaccccaggtgaaggg
gccacttatttcgatgatattcgtgtgttagaaaataacgcgaatctcct -continued

```
tcaaaacggcacattcaaccaagacttcgaaaatgtaccacaagggttat
tcccgttcgtcgtgtcagaagttgaaggcgttgaagataatcgcgttcac
ttatctgaaaagcacgcaccgtatacacaacgcggatggaataataaacg
tgtcgatgatgtcattgatggcaaatggtcacttaaagtaaacggtcaaa
caggtaaagataaaatggtcatccaaacgattccgcaaaacttctacttc
gaaccaggaaaaacgtatgaagtgtcatttgattatgaagcaggttctga
tgatacgtatgcatttgcgacaggtagtggggacatttctaaaaatcgta
actttgaaaagacaccattgaaaaatacagtcgatggtggcaaagcgaaa
cgggtgacatttaaagtgacgggtgatgaaaatggtcaaacttggatcgg
tatttactcaacgaaaacacccaatgatccacgaggcgtgaaaaatggca
atcaaatcaacttcgaagggacgaaagatttcattctagacaacctttct
atccgtgaaattgacgcaccgaagcctgatgccacacaagaaagcggtga
tagcgcaccaatgaatgaaacagatgagcgtaacgtcaattcaaacggta
cattagccgatcatagtgagacaactgatgtcaatgtcagtgcaacggca
gatgatacagcagtcaaaggcgaaatgacgacaaacagaacagatgcacc
aactgttacactgcctgaagcaacgatagtagatgaaggcacgtcaaatc
ctgtcactacaacaccaacgaatacaacacaagctatgacaaataaggct
gatgagatgccacaaacgatgaacaatgttcctttaactagcatcgctac
cgatatgatgcagtctcatgcggtggattccatggcagcaacactagcag
ctacaaatcaagtggcggcacctgtgcgtcaaacagcaggacctatgcaa
catggtatggacagtgcttcaacgcaacacgcacccatacaagttgacaa
tgtcacagcaccaccattaccagatgaacagtttgccgaattacctaaaa
ctggggatacgactccaaatacacgtggaccttttaatggcgatgatagtt
ggcgcagtcttaacagcattcggattcagacgccaacgtaaagaaaaata
g
```

The protein sequence translated from SEQ ID NO 9 is designated SEQ ID NO: 10 and is shown below:

SEQ ID NO: 10
```
MFNQQKQHYGIRKYAIGTSSVLLGMTLFITHDATASAAENNTTAKTETNQ
AATISSRTSPTDVAQPNADTNATTATKETTPQSDSTALPQAAAQPQTGQT
ASKDTVDTNKTQTADSTTAPPVTDAPKANDDTTQPEAATVAKKEDAQTPS
TADPTPQAQQPPQSKAPQETQQQSTVEDTTPQQNASTEAHPKNVDTASTK
QQQTTPSTAPTPYTQQADEAMTDVTTTSVDSNVQPLAPAEDQPKNTNTAD
KATVATPPRDNAKTADPNKKMTRAATTQQDDAVDTLKSKEMTATIDKSFP
AVKYYTLKNGKKVDAQLTDARQIIVNGEVITPTVKYNKIDDHTAEYDLTA
QNDSRSIDANFKFRLSVEGKTVDLQMTDYTNNNTDPQNVIRNFSFVSQSL
VSVNNQQKNAKLQTSKLSTNTMKSGDKSYHIDENFKNDFNDFMMYGFVSN
DDYSAGLWSNAQIGVGIGEQDFLRVYAQSIQTDIGVAVGLGSMPWFIQKD
AAHPDAKNQGLLPHVKVAIAEDENQDGEINWQDGAIAYRSIMNNPYGAEE
VPDLVGYRIAMNFGSQAQNPFLKTLDGVKKFYLNTDGLGQSILLKGYNSE
GHDSGHLDYANIGQRIGGVKDFKTLLQKGADYGARFGLHVNASETYPESQ
AFNPALLRKDANGNYMYGWNWLDQGFNIDADYDLIHGRKERFEALKQIVG
DDLDFIYVDVWGNGQSGDNTAWPSHQLAKEINDLGWRVGVEWGHGMEYDS
TFQHWAADLTYGSYQNKGINSEVARFLRNHQKDSWVGNYPKYSGAADFPL
LGGYDMKDFEGWQGRNDYSAYIKNIFNVDVPTKFLQHYKVMRIVDGEPVK
MTANGQTIDWTPEMQVDLQNEAGDQVTVKRKSNDYENDTDNYRSRTIELN
GRTVLDGDSYLLPWNWDANGQPLTGDNEKLYHWNKKGGSTTWTLPESWDT
DQVVLYELSETGRKSPRTVAVKDHQVTLDNIKADTPYVVYKVAQPDNTDV
NWSEDMHVKDAGFNSQQLTPWTIEGNRDKVSIEKSTTSNEMLKIDSPTKT
TQLTQQLTGLVPGQRYAVYVGIDNRSDAAAHIAVTHNGKTLASNETGQSI
AKNYVKADAHSNNAATFKNGGSYFQNMYVYFVAPEDGKADLTIQRDPGEG
ATYFDDIRVLENNANLLQNGTFNQDFENVPQGLFPPFVVSEVEGVEDNRVH
LSEKHAPYTQRGWNNKRVDDVIDGKWSLKVNGQTGKDKMVIQTIPQNFYF
EPGKTYEVSFDYEAGSDDTYAFATGSGDISKNRNFEKTPLKNTVDGGKAK
RVTFKVTGDENGQTWIGIYSTKTPNDPRGVKNGNQINFEGTKDFILDNLS
IREIDAPKPDATQESGDSAPMNETDERNVNSNGTLADHSETTDVNVSATA
DDTAVKGEMTTNRTDAPTVTLPEATIVDEGTSNPVTTTPTNTTQAMTNKA
DEMPQTMNNVPLTSIATDMMQSHAVDSMAATLAATNQVAAPVRQTAGPMQ
HGMDSASTQHAPIQVDNVTAPPLPDEQFAELPKTGDTTPNTRGPLMAMIV
GAVLTAFGFRRQRKEK
```

SEQ ID NO: 11
```
atgacaagaaaatttagggaatttaagaaaagtttaagtgaagaaaagc
aagagtgaaactttacaagtcaggtaaaaactgggttaaagctggaatta
aagaatttcagttattaaaagcattaggcttatcttttttaagccatgac
attgtaaaggatgaaaatggagaagtaacgacacaatttggggaacagtt
gaagaaaaatgcattaagaacaactgcttttgcgggtggaatgttcacag
ttaatatgttgcatgaccaacaagcatttgcggcgtcggatgcacctata
acttctgaactggcaaccaaaagtcaaactattggcgatcaaacatcaat
tgttattgaaaagtctacatcgtcagatcaatcaacgaacccaataacag
aaagtgaaagtaaacacgattctgaaagtatctcattatctgagcatcaa
acatcagagtcaacaagtctttcaacgtcaacttccaaatcaatatcaac
ttcagtagaggaatcagaatcaacatcaaaagattctcatactaaaactc
aagatagtcaatcagatagtcatcagtcaacaagtcaagaggtaaatggc
tcttccaaccacgagcaatcaacaccacacactgcacaaagtcttacgag
cctatctattgagagccaaacgtcgacttcaaatacatcattgaaggaaa
ctaaagaaggggaattgtcaaaaaaccttcgaagttatctcaaaatcaa
aacatcaaacttcatgaagaacatacgatgcgttcagcagatttgagctc
aggttatacaggatttagagcggcttactatgtaccaagatcaagaacaa
caccaacgacaaaagtctacacagggcaaggaagcttcagaggtagaggt
agaattaaatataatattttctacaaagttgtcgttacaagtaatggcaa
agaaatgaagatccgctatacattgagtcaagatgatccaaacacgtcta
```

```
atgttgaaaaacctaggtgggcaggacagaaacgatttggtattcataat
acttgggatgaaggtcctggtcgcgggcaattaaagttagggtcggcatt
cggcaaaccaacagttatacaaggagaaactagaccgaattatggtagct
gggttggcacacctataacgaaatatgtttcaggcgatcgtacaaatggt
ttttactggcaagctgctgtacttgcaccgagacatggagagaagggaga
aggaatcacagcagaaattacagttcctattgttaacccttctggaagat
ttaattgggaattccatcctgtcggtcaacaggacggagttggtggcaaa
actgactactttgaaaatgtatggattcgagactatgacccatattacaa
atatattcaaactaaggaaggcagagcctcagtttcgcactctatttctc
aggtgaaagcaagtgaatcgagatcgacatcgctcatacaatcggagtct
attagaagatcacagtccatatctgagagtgaatctattgtagccgcaag
tcattcggcaagtgtagcaaaatcgcaatccatctcgagaagtcaatctg
tggcgaaatcacaatcgatctcaagaagtcagtcgatcgcacacagccga
tcagcaagtgtggcaaaatcgcaatccatctcaagaagtcagtcgatcgc
acacagccgatcagcaagtgtggcaaaatcacaatcgatttcaagaagtc
agtcgatcgcacacagccgatcagcaagtgtggcgaaatctcaatcgatt
tcaagaagtcagtcaattgcgcagagccaatcagcaagtgtggcaaaatc
acagtcgatttcaagaagtcagtcaattgcgcagagccaatcagcaagtg
tggcgaaatcgcaatcgatttcaagaagtcagtcgattgcacatagccga
tcagcaagtgtagcggaatcacagtcgatttcaagaagtcagtcgattgc
gaatagccaatctgtagcagcgagtgaatcagagagtctatcaatatcat
tgtctaaaaagcagtcaatatcgatgagtaattctgaaagtgcagcaaaa
tcacactcgctttcggtgaaaaggtctaactggattaaaaagtcaaaagc
ggcttcagtaagaaagtcacattcactttcggtaagaaaatctaattcgg
cgaaaaggtcacatgctatttcggtaagaaagtcaaagtcattatcagtt
aaaaagtcaatttcgcagagccaatcagcaagtgtggcgaaatcgcaatc
gatttcaagaagtcaatcagtagcagcgagtgagtcggcatcgctaagta
agtcgaagagcacatcgctcagtaactcagtgagtgcagagaaatcgacg
tcattaagtcgttcagcaagtgtagcaaaatcgcaatcgatttcaagaag
ccaatcagtagtagcgagcgaatcggcatcgttaagtaagtcgaagagca
catcgctcagtaactcagtgagtgcagagaaatcgacgtcattaagtcga
tcagcaagtgtagcaaaatcgcaatcgatttcaagaagccaatcggtggc
agcgagcgaatcggcatcgttaagtaagtcgaagagcacatcgctcagta
actcagtgagtgcagagaaatcgacgtcattaagtcgatcagcaagtgta
gcaaaatcgcaatcgatttcaagaagccaatcggtggcagcgagcgaatc
ggcatcgttaagtaagtcgaagagcacatcgctcagtaactcagtgagtg
cagagaaatcgacgtcattaagtcgatcagcaagtgtggcaaaatcgcaa
tcgatttcaagaagccaatcagtagtagcgagcgaatcggcatcgttaag
taagtcgaagagcacatcgctcagtaactcagtgagtgcagagaaatcga
cgtcattaagtcgatcagcaagtgtagcaaaatcgcaatcgatttcaaga
agccaatcggtggcagcgagcgaatcggcatcgttaagtaagtcgaagag
cacatcgctcagtaactcagtgagtgcagagaaatcgacgtcattaagtc
gatcagcaagtgtggcaaaatcgcaatcgatttcaagaagccagtcagta
gcagcaagtgagtcggcatcattaagtaagtcgaagagcacatctttaag
caactcagtgagtgtagagaaatcgacgtcattaagtcgatcagcaagtg
tggcgaaatcgcaatcgatttcaagaagtcaatcagtagcagcgagtgag
tcggcatcgctaagtaagtcgaagagcacatcgctcagtaactcagtgag
tgcagagaaatcgacgtcattaagtcgttcagcaagtgtagcaaaatcgc
aatcgatttcaagaagccagtcagtagcagcaagtgagtcggcatcattg
agtaaatcaacaagtacgtcaacaagtgactcagatagcgcgtcaacatc
aacatctgtatcagatagcgattcagcttcattgagtaagtcgactagta
catcaacaagcgattcagacagcgcgtcagcatcattgagcaagtcaaca
agtacatcaacgagcgactcagatagcgcatcgacatcaacatcagtatc
agatagcgactccgcatcgttgagtaaatcgacaagcacgtcaacaagtg
attcagacagcacgtctacttcattgagtaagtcgacaagtacatcgaca
agtgattcagatagtgcgtcaaaatcaacgtcagtatcagacagtacgtc
cgcatcattgagtaaatcgacaagcacgtcaacaagtgattcagatagtg
catcaaaatcaacgtcggtatcagatagcacgtcagcatcattaagaaag
tcggcaagtacgtcaacgagtgactcagacagcacgtctacttcattgag
taagtcgacaagtacatcgacaagtgattcagatagtgcatcaaaatcaa
catcagtatcagatagcgattcagcttcattgagtaagtcgactagtaca
tcaacaagcgattcagatagtgcgtcaaaatcaacgtcggtatcagatag
cgactccgcatcgttgagtaagtcgacaagtacgtcaacaagcgattcag
acagtgcatcaaaatcaacgtcggtatcagacagtacgtcaacatcatta
agtaagtcgacaagtacatcaacaagcgattcagatagtgcgtcaacatc
gacatcagtatcggacagtacgtctgcatcattgagtaagtcgacaagca
catcgacaagtgattcagatagcgcatcaacatcagtgtcagatagcgat
tcagcatcactaagcaagtcaacaagtacatcgacaagcgattcagacag
cgtatcaacatcaacatcagtatcagatagtgattccgcgtcattaagta
agtcgacaagtacgtcaacaagcgattcagatagtgcgtcaaaatcaaca
tcagtatcagatagcacgtcaacatcattgagtaaatcaacaagtacatc
gacaagtgactcagatagtgcgtcaacatcggtatcagacagtacgtccg
catcattgagtaaatcgacaagcacgtcaacaagtgattcagatagtgca
tcaaaatcaacatcagtatcagatagcgattcagcatcattaagcaagtc
gacaagtacatcgacaagtgattcagatagtgcgtcaacatcaacgtcag
tgtcagatagcgattcagcttcattaagcaaatcaacaagtacgtcaaca
agtgactcagatagcgcatcaacatcattaagcaagtcaacaagtacatc
gacaagcgattcagacagtacgtctacatcattaagtaagtcaacaagta
catcaacaagtgattcggatagtgcgtcaaaatcaacatcagtatcagat
agcgactcagcttcattaagcaagtcgacaagtacgtcaacaagtgactc
agacagtgcgtcaaaatcaacatctgtgtcagatagcgactccgcatcgt
```

-continued

```
tgagtaagtcgacaagtacgtcaacgagcgattcggatagtgcgtcaaaa
tcaacatcagtatcagatagtgaatccgcgtcattaagcaagtcgacaag
cacatcgacaagtgactcagatagtgcgtcaacatcgacatcggtatcag
acagcacatcagtttcattaagcaagtcgacaagcacgtcaacaagcgat
tcagacagtacgtctacttcattaagcaagtcgacaagcacgtcaacaag
tgactcagatagtgactcagcttcgttgagtaaatcgacaagcacgtcaa
cgagcgattcagatagcgtgtcaacatcaacatctgtgtcagatagcgat
tcagcttcattaagcaaatcgacaagtacatcaacaagcgattcagatag
tgcgtcaacatcaacgtcggtatcagatagcggctccgcatcgttgagta
agtcgacaagtacgtcaacgagcgattcagacagtgcatcaaaatcaacg
tcggtatcagatagtgattcagcatcactaagcaaatcgacaagcacgtc
aacaagtgactcagacagtgcgtcaacatcgacatcggtatcagatagca
catccgcgtcgttaagcaagtcgacaagtacgtcaacaagtgattcagac
agcgcatcgacatcaacatcagtatcagatagcgactccgcatcgttgag
taaatcgacaagcacgtcaacaagtgattcggacagtgcgtcaaaatcaa
catcagtgtcagatagcgattcagcttcattgagtaagtcgacaagcacg
tcaacaagcgaatcagacagcgcgtcaaaatcaacgtcagtgtcagatag
cgattccgcatcattaagtaaatcgacaagcacgtcaacaagtgactcag
atagtgcatcgacatcaacgtcagtatcagatagtgattccgcgtcatta
agcaagtcgacaagtacgtcaacaagtgactcagacagtgcgtcaaaatc
aacatcagtatcagatagcgattccgcatcattgagtaagtcgacaagca
cgtcaacaagcgaatcagacagtgcgtcaacatcgacattagtatcggat
agtacgtcggtttcattgagccaatcaacaagtgtggataaagatagtac
agcgaagggatcgacagaattagtaaatgttgcatcacttttcaatcagtg
cgagtcaatcaagtagtttatctgcttcaacatccacatcgattgaaaag
tctgagtctacatcaacaagtggctcaaattcaactaatgcgtcgttaag
tagctcatcttcacttagtacatcagcaagtacttctgtaagcgaagtga
catctgtcacacattctgaaaatgatttaagtgcatctaacgatagagat
acatccggatcagtaagtcaatttgcttctgaaaatacatcattaagtga
ttctgcatcaattagtggcgaagtttctagtagtacgtccgcgtcaactt
cgaaatcatcatcactttcagcaagcgcgttacatgataagcatgtatca
gaaagcacttctgcatcattaagtagtggagattcaagtcgtgcttcggc
atcagtgtcaacgtcattatcagaatcagatagtgcgttaatagactctg
aatcaattagcgtttccgagcacacatcaacattacaatcaggtagtcat
tcactatcacaacaacaatcagcagaattatcacaatcagagcaaacatc
acaatcacaacgcatttcaacaagtgcgtcagtatcggctatgaaatcag
aaagtgctgctaaggtatctgaatcgctatctacgtctcaatcaaaagta
gatagtcaatcacaatcggtatctgaatcagcgagcaactcacgagtgtc
aagagattcaaaatcaacaagcgcttcaatgcatcgatcattgtcagagt
cagtatctcaaagtatgtcacttattgatcagtcagaaagtgattcaaca
tctatatcgatttcgacgtcaatcagtgatgaagactctatgctgtattc
```

-continued

```
tatgagtgattccgcatcgatcagtactaaggcatcaagtagtatgtcta
cttcgacaagcgaagagcatgccaacagtcattctcagtctgaatcgaca
gcatcggttgaagtatctcaagaaatgagtgcatcggcttcaacaagcaa
atctgagtctcaatcagagtcagtatcagtaagtaacgaagaatcaaata
tctcatctatgcaagagtcttttgtagagagtgcaaaagcatcgcgtagt
gcatctatgagcgttgcaaaatctgaagcctctgaatcacagctattaag
tgagtctaatgcttcggtaagccaatcagcaagcacaagtagtaaagcat
cagcaagtacgtcagaatctatttcaacgtcactcagcgtatctgaagca
actcatggaaaaccgagaaatcattcagaaagtgcatcagcaagtcaatt
attagaagaaaatgagtcattaagcgattcagcatcaacaagtgttgaag
attcagaaagtgcatcagcatctctgtcggtgtatcaatcacaatcagca
agtgcattgaaatcaacacatgcatcagaaaaagcttcagtgaatacaag
tgcaaacgcatcgaagcgtgcatcagcatcgacatctatctctaactcga
aatctaaagtcattgcgagtgaatcgaagtcaacaagcatatcaacatat
gaatcgttgtcaatatcgactagtaaagaacaatcaacgcgtgtatcagt
gagtgagtcgacatcaacgtctaaagtgaagtcagaaagcgactcggcat
caacgtcgacatctgaatcaatctcaattagcgcaaatcgttcaggttac
acatcgtctaaacgttcggtacaaatgagtgaagcacaatcaacgagcga
ttcattatcagtaatgcaatctgaaggttcagtaagtgtatcgcaatctt
taagtatatcagataagacatcacagtccttatcggaatcaatatcgcat
tcagaaagtgactctgatagtaactcagtgtctattagtcaagagacatc
tgaacaacattcggtgtcagacagtgactcgatgtcaatttcggaaagcg
aatctattgcatatagtcaatcagcgagtgaatcagaatcaacaagtatc
gcaaaatctgatagtatttcgaactcattatctgtttcattaagtgaatc
agaaagtgaagcaagcacatcagcttcagtgagtacatctgaaagtacgt
ctgtaaagggttctctatcaacaagtatcttgaacagtcaatcagcatct
actcatcaatcaacagaagcttctcaaagtacatcaacttcaaaagttga
ggaagcatcattgagtgactctgcttctgtatcagattcacaatcacttt
caatgagtcatgagaaatcacaaagtgcatcgacttcaaaatctacgagt
ctgtcaaaaactatttctgagtcagagtctgtgagtgcatcaacatcaac
aagtgaagctgtaagtacagaagcaagcgaatttgtatcagcagtagact
cattgagtcaagtaacttctaacggaagcacaacgaaagaagatgcgagt
acatttgtatccacagtagattcattgaaagacaaagcatcaaataatgg
tacaccatcagagtttgcgtcagcagtgaaatcaacacacgcatcagtga
gtgtgtcagcatcagaaagtacgtcagcatcaacatcaacaagtgaagct
gtaagtacagaagcaagcgaatttgtatcagcagtgaattcgttgagtga
agcgacttctaacggaagcacaacgaaagaagatgcgagtacatttgtat
ccacagtagattcattgaaagacaaagcatcaaataatggtacaccatca
gagtttgcgtcagcagtgaaatcaacacacgcatcagtgagtgtgtcagc
atcagaaagtacatcagcatcaacatcaacaagtgaagctgtaagtacag
```

-continued

```
aagcaagcgaatttgtatcagcagtagactcattgagtcaagtaacttct
aacggaagcacaacgaaagaagatgcaagcacatttgtatccacagtaga
ttcattgaaagataaagcatcaaacaatggtacaccatcagaatttgaat
cagttgtgaaatcagtacacggatcaatgagtgcatcagcaagtgcgtca
acatcagcatctacatcagcatctacatctacaagtgaagctgcaagtgc
agaagcaagcgaattagaatcagtaaggaaatcattatccaatggagcat
caaacggtagcacagcaagagaaggtgcaagcacatttgtatcaacggta
gattcattgaaagataaagcatcaaacaatggtacagcatcagaatttga
atcagttgtgaagtcagtacacggatcaacaagtgcatcagcaagtgcgt
caacgtcagcatcaacatcagcaagtgaatcagcaagtacagaagcaagt
gaatttgtatcagcagtggcatcattaagcagttcagcatggaacggaag
cactacaggagaaggtgcaagcacatttgtatcaacagttgattcatcga
aagattcagcgtcagacaaagcttcaccatcagaatcagaatcagttgtg
aagtcagtacacggatcaacgagtacatcagcaagtgtgtcagcgtcggc
aagtacatcagcatcgacatcaacaagtgaagctgtaagcacagaagcaa
gtgagtttgtatcagcagtgaactcattaagcagtgaagcatcgaacggc
agcacaacaagagaaggtgcaagcacatttgtatcaacagtagattcatt
gaaagacaaagcatcaaacaatggtacagcatcagaatttgaatcagttg
tgaagtcagtacacggatcaatgagtacatcagcaagtgtgtcagcatca
gaaagtacgtcggcatcgacatcgacaagtgaagctgtaagtacagaagc
aagcgagtcagcatcgataagtgtatcaatgtcagtgagcgcatcaacaa
gtgcttcaatgagcgtatcagtgtcaaacagtgtgtcagtgagtgactct
atttcagtaagtgcatcaacaagtgaacctaactcggtaagcacttctat
gagtagttctctttcaacatcggcatcaacgccatcagaaattacttcaa
gttcgtcatcaagcgattcagcgacagttcaaaaagtagtttctaaagat
gaacagcacgctacaaataaagttgaaaaattacctgacacaggtcaatc
aacgacacaaactggtttattgggtggagtaggtgctttacttacaggcc
ttggtttactcaaaaaatcaagaaaacaaaaagatgaagaaacatcatca
catgaataa
```

The protein sequence translated from SEQ ID NO 11 is designated SEQ ID NO: 12 and is shown below:

```
                                         SEQ ID NO: 12
MTRKFREFKK SLSEEKARVK LYKSGKNWVK AGIKEFQLLK
ALGLSFLSHD IVKDENGEVT TQFGEQLKKN ALRTTAFAGG
MFTVNMLHDQ QAFAASDAPI TSELATKSQT IGDQTSIVIE
KSTSSDQSTN PITESESKHD SESISLSEHQ TSESTSLSTS
TSKSISTSVE ESESTSKDSH TKTQDSQSDS HQSTSQEVNG
SSNHEQSTPH TAQSLTSLSI ESQTSTSNTS LKETKEGELS
KNLSKLSQNQ NIKLHEEHTM RSADLSSGYT GFRAAYYVPR
SRTTPTTKVY TGQGSFRGRG RIKYNIFYKV VVTSNGKEMK
IRYTLSQDDP NTSNVEKPRW AGQKRFGIHN TWDEGPGRGQ
```

-continued

```
LKLGSAFGKP TVIQGETRPN YGSWVGTPIT KYVSGDRTNG
FYWQAAVLAP RHGEKGEGIT AEITVPIVNP SGRFNWEFHP
VGQQDGVGGK TDYFENVWIR DYDPYYKYIQ TKEGRASVSH
SISQVKASES RSTSLIQSES IRRSQSISES ESIVAASHSA
SVAKSQSISR SQSVAKSQSI SRSQSIAHSR SASVAKSQSI
SRSQSIAHSR SASVAKSQSI SRSQSIAHSR SASVAKSQSI
SRSQSIAQSQ SASVAKSQSI SRSQSIAQSQ SASVAKSQSI
SRSQSIAHSR SASVAESQSI SRSQSIANSQ SVAASESESL
SISLSKKQSI SMSNSESAAK SHSLSVKRSN WIKKSKAASV
RKSHSLSVRK SNSAKRSHAI SVRKSKSLSV KKSISQSQSA
SVAKSQSISR SQSVAASESA SLSKSKSTSL SNSVSAEKST
SLSRSASVAK SQSISRSQSV VASESASLSK SKSTSLSNSV
SAEKSTSLSR SASVAKSQSI SRSQSVAASE SASLSKSKST
SLSNSVSAEK STSLSRSASV AKSQSISRSQ SVAASESASL
SKSKSTSLSN SVSAEKSTSL SRSASVAKSQ SISRSQSVVA
SESASLSKSK STSLSNSVSA EKSTSLSRSA SVAKSQSISR
SQSVAASESA SLSKSKSTSL SNSVSAEKST SLSRSASVAK
SQSISRSQSV AASESASLSK SKSTSLSNSV SVEKSTSLSR
SASVAKSQSI SRSQSVAASE SASLSKSKST SLSNSVSAEK
STSLSRSASV AKSQSISRSQ SVAASESASL SKSTSTSTSD
SDSASTSTSV SDSDSASLSK STSTSTSDSD SASASLSKST
STSTSDSDSA STSTSVSDSD SASLSKSTST STSDSDSTST
SLSKSTSTST SDSDSASKST SVSDSTSASL SKSTSTSTSD
SDSASKSTSV SDSTSASLRK SASTSTSDSD STSTSLSKST
STSTSDSDSA SKSTSVSDSD SASLSKSTST STSDSDSASK
STSVSDSDSA SLSKSTSTST SDSDSASKST SVSDSTSTSL
SKSTSTSTSD SDSASTSTSV SDSTSASLSK STSTSTSDSD
SASTSVSDSD SASLSKSTST STSDSDSVST STSVSDSDSA
SLSKSTSTST SDSDSASKST SVSDSTSTSL SKSTSTSTSD
SDSASTSVSD STSASLSKST STSTSDSDSA SKSTSVSDSD
SASLSKSTST STSDSDSAST STSVSDSDSA SLSKSTSTST
SDSDSASTSL SKSTSTSTSD SDSTSTSLSK STSTSTSDSD
SASKSTSVSD SDSASLSKST STSTSDSDSA SKSTSVSDSD
SASLSKSTST STSDSDSASK STSVSDSESA SLSKSTSTST
SDSDSASTST SVSDSTSVSL SKSTSTSTSD SDSTSTSLSK
STSTSTSDSD SDSASLSKST STSDSDSV STSTSVSDSD
SASLSKSTST STSDSDSAST STSVSDSGSA SLSKSTSTST
SDSDSASKST SVSDSDSASL SKSTSTSTSD SDSASTSTSV
SDSTSASLSK STSTSTSDSD SASTSTSVSD SDSASLSKST
STSTSDSDSA SKSTSVSDSD SASLSKSTST STSESDSASK
```

-continued

STSVSDSDSA SLSKSTSTST SDSDSASTST SVSDSDSASL
SKSTSTSTSD SDSASKSTSV SDSDSASLSK STSTSTSESD
SASTSTLVSD STSVSLSQST SVDKDSTAKG STELVNVASL
SISASQSSSL SASTSTSIEK SESTSTSGSN STNASLSSSS
SLSTSASTSV SEVTSVTHSE NDLSASNDRD TSGSVSQFAS
ENTSLSDSAS ISGEVSSSTS ASTSKSSSLS ASALHDKHVS
ESTSASLSSG DSSRASASVS TSLSESDSAL IDSESISVSE
HTSTLQSGSH SLSQQQSAEL SQSEQTSQSQ RISTSASVSA
MKSESAAKVS ESLSTSQSKV DSQSQSVSES ASNSRVSRDS
KSTSASMHRS LSESVSQSMS LIDQSESDST SISISTSISD
EDSMLYSMSD SASISTKASS SMSTSTSEEH ANSHSQSEST
ASVEVSQEMS ASASTSKSES QSESVSVSNE ESNISSMQES
FVESAKASRS ASMSVAKSEA SESQLLSESN ASVSQSASTS
SKASASTSES ISTSLSVSEA THGKPRNHSE SASASQLLEE
NESLSDSAST SVEDSESASA SLSVYQSQSA SALKSTHASE
KASVNTSANA SKRASASTSI SNSKSKVIAS ESKSTSISTY
ESLSISTSKE QSTRVSVSES TSTSKVKSES DSASTSTSES
ISISANRSGY TSSKRSVQMS EAQSTSDSLS VMQSEGSVSV
SQSLSISDKT SQSLSESISH SESDSDSNSV SISQETSEQH
SVSDSDSMSI SESESIAYSQ SASESESTSI AKSDSISNSL
SVSLSESESE ASTSASVSTS ESTSVKGSLS TSILNSQSAS
THQSTEASQS TSTSKVEEAS LSDSASVSDS QSLSMSHEKS
QSASTSKSTS LSKTISESES VSASTSTSEA VSTEASEFVS
AVDSLSQVTS NGSTTKEDAS TFVSTVDSLK DKASNNGTPS
EFASAVKSTH ASVSVSASES TSASTSTSEA VSTEASEFVS
AVNSLSEATS NGSTTKEDAS TFVSTVDSLK DKASNNGTPS
EFASAVKSTH ASVSVSASES TSASTSTSEA VSTEASEFVS
AVDSLSQVTS NGSTTKEDAS TFVSTVDSLK DKASNNGTPS
EFESVVKSVH GSMSASASAS TSASTSASTS TSEAASAEAS
ELESVRKSLS NGASNGSTAR EGASTFVSTV DSLKDKASNN
GTASEFESVV KSVHGSTSAS ASASTSASTS ASESASTEAS
EFVSAVASLS SSAWNGSTTG EGASTFVSTV DSSKDSASDK
ASPSESESVV KSVHGSTSTS ASVSASASTS ASTSTSEAVS
TEASEFVSAV NSLSSEASNG STTREGASTF VSTVDSLKDK
ASNNGTASEF ESVVKSVHGS MSTSASVSAS ESTSASTSTS
EAVSTEASES ASISVSMSVS ASTSASMSVS VSNSVSVSDS
ISVSASTSEP NSVSTSMSSS LSTSASTPSE ITSSSSSSDS
ATVQKVVSKD EQHATNKVEK LPDTGQSTTQ TGLLGGVGAL
LTGLGLLKKS RKQKDEETSS HE

SEQ ID NO: 13 atgaaaaagtctagaaaaaagcgtatcgattttttacctaaccgtcaaaa
tcgatatgcgatacgtcgttttttcagtaggcactgcgtcaattctcgttg
gagcaacattaattttttggaattcattcaaatgatgcatcggcagcagta
gaagacgcaacatctcaagaagcaggaacaactaacgaaaattcaaatag
tacagaagaagcaacaacaaacgaaagtacaactgttgaagcaccaacaa
gtgaagaagcaacaacggaagagcaatcagtagaggcgccaacaagtgaa
gaagtaacaacggaagagcaatcagtagaggcaccaacaagtgaagaagt
aacaacggaagagcaatcagtagaagcgccaacaagtgaagaagtaacaa
cggaagagcaatcagtagaagcgccaacaagtgaagaagtaacaacggaa
gagcaatcagtagaggcaccaacaagtgaagaagtaacaacggaagagca
atcagtagaggcaccaactagtgaagaagtaactacggaagagcaatcag
tagaagcaccaacaagtgaagaagcaacaacggaagagcaatcagtagaa
gcaccaacaagtgaagaagcaactacaaaaactcctgtaaaagaagaaac
atcctcaacacaagaaaattcacccacgactacactagaagaacaatttt
caaatgaattcaatcagttaacatctacagaagataaaacaaactacaca
cgtgaatatttaactcaaaacacaaatctttcggcagaacaagtggaagc
aacagttgaacgcttgaatttaagtcaagaaaatgtaacagcccaagata
tctatttcgcattacttaaagatttagctgatcaacaagatgccttatta
ccacgtgtaacacttttggccgctagagattctgagctcacaaacgaagc
gtctatcgctttaactgaaaatagtccaatgttccgcgcagcattagcga
atagtccttctggcaatgatgtggtgtcagaagaagataatattattgtg
gctgatgcactcgcaaatggatacatcaattcacaaacagatgcaacaaa
tgcggcaaatacattgtctggtcgtgcatgggttgtggatacagggacac
cagcgacaatgtcaaacggcttaacagctgttccagaaggcacaaaagtc
tacatgcaatggattgatacagatggcgcggtttcaccagtgtatcaagc
aagcacaacaaataaattgagttcaagtggtggtagccaagtaggtccag
gtgcatatgcatttgatttacgtgaagcatggatagactcaaatggcaaa
gcgcacagatatgaagcgtcaagtggccaatattatcgtttatggattga
tgactacaaaacagtagatgggaatacggcaaccatgttacgccaagcag
gtggtttcttccctggttcatatgttaattcggtgacaggtaacaatatt
ggtcaattcccacttatcggaacgaacatgcaacgtacaggtatctttat
gggtgtgataccaacgaacgattacatgactacagatacaagcaattgga
ttcaagataatgaaggacctatttcaaacccagcagtaacgagcacaagt
gaatttgtcagtggtaaagtatggtctgagacaggttcaggtgactatgc
gaactctgcgacaggtccaaactttaactcaggtgatattgcacgtgaag
gttatcaagttgtcatgtcttcattaacaagtgctggtgcccaagcgtat
aaagcacaagtcgaatcgttgccaacagaccaacaagcggcagcagcaca
ccaattattcaaagaccacccagaatttatttctgcgacagtgacgggta
aaactgatgcaaacggtgcgtatacattacgtttcccttcaggctcattg
agtaaagattatctttatggttatgtgatggataataagggcaacttggt -continued

```
taagggctattcatcattcacgtcacctttattccgttcgcctaacagta
acttatctttcgcgccacaaacagcgccatatcatagaccagccaaaaat
gcttgggtgaatgtgaactttgcgcttgtagaaacaattgaaacaagtat
agacatcacgaactttgatgtgacagccaacccagcgcaacgtggtgata
cggctatcattgatgtgacttctacagcattgtcaccattacctacgcat
gttgagtggagagattcaaaagggaatgtcgttcaaaaaagtggagatgt
cactacggtagaagaagctgaaacggcaggcacatttactattcctgatg
atgcgaaaacaggtgaaatctatacagtttatattgtttcaggaggcaat
gaagttgcagcagactcactgattgtccaagtgcaagaaaatgcggcaac
ctatgaacctgtatatccaacaacaacagttgaacaagaccaaactgtaa
caattcctacacctacaaatgaagatggtttagcattaccagacggaaca
aagttcgaaggtggcaacaatgtacctgaatgggcaactgtgaatgaaga
tggttctatttcaatttcaccaaatcaagatgtggaaaaaggtaactata
atgtgcctgttgtcgtcacatatccagatggttcaaaagaaacagtattt
gcaccagttttagttcaagaagctgttccaactgcagaacaatacgatcc
aacaattgaaacaattaataaggaatatggtactactgcaacagaagatg
aaattaaaggcgcaatcacaattccggattacccaacagatggagatcaa
ccaacaatcacgattgacgacccaactcaaattccaaatggaacagaaga
aggcacagtgaatgtaggtgtcactgtcacttatccagatggttcaacag
acaaattaacagtaccagtcgttacaggtaagcaagcggataacgataag
tacacaccagaaacaacaccaattacgaaagacttcggtacaggtgtaac
agaagacgaagtgaaaggtgcagtcactgttccggattacccaacagatg
gagaccaaccaacaattacgattgacgacccaagtcagttgcctgatggt
tcaaaagaaggaacaacggatgtcgacgtaacagtggaatatccagacgg
cacaacagatcacatcacagttccagtgactgttggaaagcaagcggata
atgataagtacacaccagaaacaacaccaattacgaaagacttcggtaca
ggtgtaacagaagacgaagtgaaaggtgcagtcactgttccggattaccc
aacagacggtgaccaaccaacaattacaattgatgatccaaatcaattac
cggacggttcacaagaaggtacgactgatgtaaatgtaacagtggaatat
ccagatggcacaacagatcacatcacagttccagtgactgttggaaagca
agcggataatgataagtacacaccagaaacaacaccaattacgaaagact
tcggtacaggtgtaacagaagacgaagtgaaaggtgcagtcactgttccg
gattacccaacagatggagatcaaccaacggttacaattgatgatccaaa
tcaattaccggacggttcacaagaaggtacgactgatgtaaatgtaacag
tggaatatccagacggcacaacagatcacatcacagttccagtgactgtt
ggaaagcaagcggataatgataagtacacaccagaaacaacaccaattac
gaaagacttcggtacaggtgtaacagaagacgaagtgaaaggtgcagtca
ctgttccggattacccaacagacggtgaccaaccaacggttacaattgat
gatccaaatcaattaccggacggttcacaagaaggtacgactgatgtaaa
tgtaacagtggaatatccagatggcacaacagatcacatcacagttccag
tgactgttggaaagcaagcggataacgataagtacacaccagaaacaaca
ccaattacgaaagacttcggtacaggtgtaacagaagacgaagtgaaagg
tgcagtcactgttccggattacccaacagatggagatcaaccaacggtta
caattgacgatccgagtcagttaccagatggctcacaagaaggcacaaca
gatgtgaatgtaacagtggaatatccagatggcacaacagaccacatcac
agttccagtgactgttggtaagcaagcagataacgataagtacacgccag
aaacaacaccaattacgaaagacttcggtacaggtgtaacagaagacgaa
gtgaaaggtgcagtcactgttccggattacccaacagatggagaccaacc
aacaattacaattgacgatccgagtcagttaccagacggttcacaagaag
gtacgactgatgtaaatgtaacagtggaatatccagatggcacaacagat
cacatcacagttccagtgactgttggtaagcaagcagataacgataagta
cacaccagaaacaacaccaattacgaaagacttcggtacaggtgtaacag
aagacgaagtgaaaggtgcagtcactgttccggattacccaacagatgga
gaccaaccaacaattacaattgacgatccgagtcagttaccagacggttc
acaagaaggtacgactgatgtaaatgtaacagtggaatatccagatggca
acagatcacatcacagttccagtgactgttggaaagcaagcagataac
gataagtacacaccagaaacaacaccaattacgaaagacttcggtacagg
tgtaacagaaggcgaagtgaaagattcaatcacaattcccggttacccaa
cagatggagaccaaccaacaattacaattgacgacccaagtcagttacca
gatggttcacaagaaggtacgactgatgtcgatgtaacagtggaatatcc
agacggcacaacagatcacattacagttccagtgactgttggaaagcaag
cagataacgataagtacacaccagaaacagaaggtgtcaacaaagatcat
ggtacgtcagtaacagaagatgaagtgaaaggtgcagtcactgttccggg
atacccaacagatggagatcaaccaacggttacaattgatgatccaagtc
aattgccggacggttcacaagaaggtacgactgatgtaaatgtaacagtg
gaatatccagacggcacaacagaccacattacagtcccagtaactgttgg
taaacaacctactaaagataacggggctacagataatgatggcgacatga
atcaaggcacagatgaaggaaatagtgctactgatcatggcgacaatgta
aaacaagattcaaacggaaactatacgccggttgaacaacgtgacaatca
tgcgacttcacctgcaacagatatggatccaatgccaagcaatagccaaa
caacttttgatggcataaatgcaaaaggttcaacttcagagaaagcaaac
cataaacaacagtctgagcaattaccagacacaggtgaaagcaatacaca
aaatggtgcacttttaggcggattatttgcagcacttggaggcttattct
taatcggcagacgtcgtaaagaaaaagaaggcaaataa
```

The protein sequence translated from SEQ ID NO 13 is designated SEQ ID NO: 14 and is shown below:

SEQ ID NO: 14
MKKSRKKRID FLPNRQNRYA IRRFSVGTAS ILVGATLIFG
IHSNDASAAV EDATSQEAGT TNENSNSTEE ATTNESTTVE
APTSEEATTE EQSVEAPTSE EVTTEEQSVE APTSEEVTTE
EQSVEAPTSE EVTTEEQSVE APTSEEVTTE EQSVEAPTSE

-continued

```
EVTTEEQSVE APTSEEVTTE EQSVEAPTSE EATTEEQSVE
APTSEEATTK TPVKEETSST QENSPTTTLE EQFSNEFNQL
TSTEDKTNYT REYLTQNTNL SAEQVEATVE RLNLSQENVT
AQDIYFALLK DLADQQDALL PRVTLLAARD SELTNEASIA
LTENSPMFRA ALANSPSGND VVSEEDNIIV ADALANGYIN
SQTDATNAAN TLSGRAWVVD TGTPATMSNG LTAVPEGTKV
YMQWIDTDGA VSPVYQASTT NKLSSSGGSQ VGPGAYAFDL
REAWIDSNGK AHRYEASSGQ YYRLWIDDYK TVDGNTATML
RQAGGFFPGS YVNSVTGNNI GQFPLIGTNM QRTGIFMGVI
PTNDYMTTDT SNWIQDNEGP ISNPAVTSTS EFVSGKVWSE
TGSGDYANSA TGPNFNSGDI AREGYQVVMS SLTSAGAQAY
KAQVESLPTD QQAAAAHQLF KDHPEFISAT VTGKTDANGA
YTLRFPSGSL SKDYLYGYVM DNKGNLVKGY SSFTSPLFRS
PNSNLSFAPQ TAPYHRPAKN AWVNVNFALV ETIETSIDIT
NFDVTANPAQ RGDTAIIDVT STALSPLPTH VEWRDSKGNV
VQKSGDVTTV EEAETAGTFT IPDDAKTGEI YTVYIVSGGN
EVAADSLIVQ VQENAATYEP VYPTTTVEQD QTVTIPTPTN
EDGLALPDGT KFEGGNNVPE WATVNEDGSI SISPNQDVEK
GNYNVPVVVT YPDGSKETVF APVLVQEAVP TAEQYDPTIE
TINKEYGTTA TEDEIKGAIT IPDYPTDGDQ PTITIDDPTQ
IPNGTEEGTV NVGVTVTYPD GSTDKLTVPV VTGKQADNDK
YTPETTPITK DFGTGVTEDE VKGAVTVPDY PTDGDQPTIT
IDDPSQLPDG SKEGTTDVDV TVEYPDGTTD HITVPVTVGK
QADNDKYTPE TTPITKDFGT GVTEDEVKGA VTVPDYPTDG
DQPTITIDDP NQLPDGSQEG TTDVNVTVEY PDGTTDHITV
PVTVGKQADN DKYTPETTPI TKDFGTGVTE DEVKGAVTVP
DYPTDGDQPT VTIDDPNQLP DGSQEGTTDV NVTVEYPDGT
TDHITVPVTV GKQADNDKYT PETTPITKDF GTGVTEDEVK
GAVTVPDYPT DGDQPTVTID DPNQLPDGSQ EGTTDVNVTV
EYPDGTTDHI TVPVTVGKQA DNDKYTPETT PITKDFGTGV
TEDEVKGAVT VPDYPTDGDQ PTVTIDDPSQ LPDGSQEGTT
DVNVTVEYPD GTTDHITVPV TVGKQADNDK YTPETTPITK
DFGTGVTEDE VKGAVTVPDY PTDGDQPTIT IDDPSQLPDG
SQEGTTDVNV TVEYPDGTTD HITVPVTVGK QADNDKYTPE
TTPITKDFGT GVTEDEVKGA VTVPDYPTDG DQPTITIDDP
SQLPDGSQEG TTDVNVTVEY PDGTTDHITV PVTVGKQADN
DKYTPETTPI TKDFGTGVTE GEVKDSITIP GYPTDGDQPT
ITIDDPSQLP DGSQEGTTDV DVTVEYPDGT TDHITVPVTV
GKQADNDKYT PETEGVNKDH GTSVTEDEVK GAVTVPGYPT
DGDQPTVTID DPSQLPDGSQ EGTTDVNVTV EYPDGTTDHI
TVPVTVGKQP TKDNGATDND GDMNQGTDEG NSATDHGDNV
KQDSNGNYTP VEQRDNHATS PATDMDPMPS NSQTTFDGIN
AKGSTSEKAN HKQQSEQLPD TGESNTQNGA LLGGLFAALG
GLFLIGRRRK EKEGK
```

SEQ ID NO: 15

```
atgacagaacgaaaatccccttcatctcaaaacatgcgtcatcgtttagt
caaagctggtactgtcctttttattggttggtagtggactgcaaatgcctt
caacattgtcacacgaaatgacagcgatagctcagacagatgcgactgat
gatttgaaaacattacgtgaaaatgcagataaaaaagtgaaagcgttaca
atatttaaatacggattataaaaatgaatttcttgcgttaattcgtgaat
atgatacgtcgtcaaaaaatattgaagtggttgttgacgaagcagaagca
gccaatcgtctagctcatgacgctcaatcggacgatgaaatacaacctga
attagatgccattgatgaaaaaattagcgcgttaaaggcaaaggttgatg
aaggtcaacgagaatcaactgaagcgcgtcaagatgtaacgtcaacagag
acaaagagtgctgaatcagaaggaagagagccatccactgaaggcgagag
caaagtaaaggagtcatcttcagcacaaacgattgtagcacctcatcatg
gtcaacaagatgtgagcgcactgaaagaccatattaagaacgatgtcgat
acacttaaacaagactatgcaacgcaagacaagcaagtgacaccactcca
gggcattgacagtgcaatcacacgcattgaccatttcgtttcagaaagcg
tggatcacaagtctgacaattattttgaagaaaaacgtcaacatttacaa
aactttgaacaagacattaaaaaacgtacggacatttctgggactgagaa
ggcgactttgcttgatgatgcgaaaacggtagccaaccaactgaacgcgc
aaaatgatacgattttaactgaacttcaacagcatgacgataaacgtgca
gcagttgaatcgatattaggtgagattttttaatgcacaagaagcggctga
acgtgcgaaacagatagatgttaaaggtaaaacagatcaacaattggcaa
acgaaattcatcaacaagcggacggacttatcaaaacgtcgagtgatgat
ttattgttaggaatgttggaaaataattcaaatacacaaggtctagtgga
aagcattttacgaacacgtttgacaaacaagaagcgcacaaaattgccg
gcgaaatcatgcaaggcaagccttcaaatacagcgatactcgaccgcttg
aaagaccatttttaaagcgaatggtaaggcgagtggagatgatattttaaa
tgcgttaattaataatacggatgcagatgctgaagtgattgaatcaattc
taggggccgtcttaatgcagaaaatgcaaaattgattgccgatcgtgta
cagcaagataaaaagaagacacatcaaaacttaaaggcgattgaagacga
acttagtgcgcaagcgaatcgattgttaacgttacggaagcaattgcaac
aaatccgtcataatacgcaaacagatatgaatgacttgtttgcaccactg
cgtcgtattgcaaatattctcggtggtggtttaaatcgtgacgacattca
ctcttcaggtcgtacgaatgacaaattgcagcaactgttaaatcgtgatc
attcgttgttaggtcgtggtggtgatttattcaaacatgattttgcgcca
aagccgaatatcgatccatatcaagcgattaatagtcaaacggcatcaga
aggttttttagatggtttatttgatcaaaatggcgatttcaatttaccga
atacaggtgaaatagtgaagcggacttggctaccgttgggtattttagtc
```

-continued
gttgcaatcggtgtactgatcttaacggtgagatttcataaaaaaacacg caaacaataa

The protein sequence translated from SEQ ID NO 15 is designated SEQ ID NO: 16 and is shown below:

```
                                         SEQ ID NO: 16
MTERKSPSSQ NMRHRLVKAG TVLLLVGSGL QMPSTLSHEM

TAIAQTDATD DLKTLRENAD KKVKALQYLN TDYKNEFLAL

IREYDTSSKN IEVVVDEAEA ANRLAHDAQS DDEIQPELDA

IDEKISALKA KVDEGQREST EARQDVTSTE TKSAESEGRE

PSTEGESKVK ESSSAQTIVA PHHGQQDVSA LKDHIKNDVD

TLKQDYATQD KQVTPLQGID SAITRIDHFV SESVDHKSDN

YFEEKRQHLQ NFEQDIKKRT DISGTEKATL LDDAKTVANQ

LNAQNDTILT ELQQHDDKRA AVESILGEIF NAQEAAERAK

QIDVKGKTDQ QLANEIHQQA DGLIKTSSDD LLLGMLENNS

NTQGLVESIL RTRFDKQEAH KIAGEIMQGK PSNTAILDRL

KDHFKANGKA SGDDILNALI NNTDADAEVI ESILGGRLNA

ENAKLIADRV QQDKKKTHQN LKAIEDELSA QANRLLTLRK

QLQQIRHNTQ TDMNDLFAPL RRIANILGGG LNRDDIHSSG

RTNDKLQQLL NRDHSLLGRG GDLFKHDFAP KPNIDPYQAI

NSQTASEGFL DGLFDQNGDF NLPNTGEIVK RTWLPLGILV

VAIGVLILTV RFHKKTRKQ
```

```
                                         SEQ ID NO: 17
atgttaaaaaaattaattgttacaggtttgattgctacagcggcgacaca agtttatgcg catgacacgcaagcggcgaaaagggtgctacagatgct ccgaatgtgatggttaaggatgaggcgaaaaaagaagtgacaccgataat ccataaaccgacttgcatttacccgcatctagaaggcgaagatgatgctg cgtatttaaaacgtatggcaacgaatccaccagaaggcgcagtgccgtac ggtgtattgaataaagatggatcgattacagaaccgaatacaaatccaca ttttgatgttttaaaaattgaagatccaaatgcgatgaaagatttggttg atacaccggcagatgatcaagatacggtaccgagtgatttacaaattgaa ccaccagcattaataggaccagctactaaacatacggatggtacgggaga cgcaaaatctaatgatgaccacaaagtaacaaaatcttcgggagcgtcag cccaagatatgaagaaaaagacgtgacaacacaaactgcacaaccaaaa gcagataaaaagatggcgactgcaaaagtagcaccagcgaaacaacaaga taaagcagccaaaatgttaccagcagcaggggaaccacaagtgaatgcaa tcagtcaaacagcacttgcactttcaatgatcgcattaggtgtcatcgcg ttctttacacgacgacgcaaaacaaattaa
```

The protein sequence translated from SEQ ID NO 17 is designated SEQ ID NO: 18 and is shown below:

```
                                         SEQ ID NO: 18
MLKKLIVTGL IATAATQVYA HDTQAAEKGA TDAPNVMVKD

EAKKEVTPII HKPTCIYPHL EGEDDAAYLK RMATNPPEGA

VPYGVLNKDG SITEPNTNPH FDVLKIEDPN AMKDLVDTPA

DDQDTVPSDL QIEPPALIGP ATKHTDGTGD AKSNDDHKVT

KSSGASAQDM KKKDVTTQTA QPKADKKMAT AKVAPAKQQD

KAAKMLPAAG EPQVNAISQT ALALSMIALG VIAFFTRRRK

TN
```

```
                                         SEQ ID NO: 19
atggtagaatataaaaaagaacatagcgtaaagcgactattaaaattagg aatcggttcaacgagtattttatgtgttgtatcacctcttttattaacac atgacgttgttcaagcagcagatatcaataacaggatgccagctttgaat acattgaagaccacttcttcatatgatcaaagggcacacatggatgaatt acgaaacgccattacttcagatagtgacactactcaaacaccatcattca atgagataactgtgtcttcaactaatgaaacggatgcagcgtcaacggaa aatgtgaacccgagtgatgaggtcccggcaaaggatgaaagtgaatcaac gacaccgagtacagaacaagacacatctatagaagaaacgggtactgaag aagtgccatctcatgaagacaatcatcacaacaccccaagtcaagaagag caaccgtctccgcctgatcaaccaggaacaaacaaagatgaagagagtgg agaaaaaccgaataaagaaaatcatcggaagccgaatcaaccgaacaaag accaaccttcaaaagatgagaataaaaaacctgacaaaggaaacaaacca gcaccaccgtctaaaatgccaaatcgcccggatcaaaaggaagatggttc aaacaacacccaccacctgccactgataacggtggaaacagtaatgacg gtacaacaacgggtcccaatggtggaggtggcagtgaagcaagtccacca ccgaatgagcaaccgtcaaatggcaatgcaagcgatacccatcaaaacgg ttcagtttcaagcaccaatcattcgaatcagtatggtacatcggcttatg atgaatacgcaggtttattgaataataattataaatataatccattgttt aaagaagaggttgcgcgtttaagtcaatttggaagtcaagatcaacatga tattgcaagtttgagtcgtaaagaacaatttttctcaaaatgcatttttag atgacttgcaacaaagtacagattattttagatatcaatattttaacccg cttttccacagagcaatactatcatcgtttagataaacaagtattagcact cgttacgggggaatttggttcgatgccagatttcaagaaagtggtgata agtcattggttaataagcatcagcaagataaagtgaagaaaattgaacag caaggagaaatattaatacgcatcatatgaaaaatacgaaagaagatac aggaaaatcattaagttacaagccgatgatatattggcattgtcatgg tcggttttgtcggcctgatcagtatgatttatggaaacgactgcatcat ttttggaaataa
```

The protein sequence translated from SEQ ID NO 19 is designated SEQ ID NO: 20 and is shown below:

```
                                         SEQ ID NO: 20
MVEYKKEHSV KRLLKLGIGS TSILCVVSPL LLTHDVVQAA

DINNRMPALN TLKTTSSYDQ RAHMDELRNA ITSDSDTTQT

PSFNEITVSS TNETDAASTE NVNPSDEVPA KDESESTTPS
```

```
TEQDTSIEET GTEEVPSHED NHHNTPSQEE QPSPPDQPGT

NKDEESGEKP NKENHRKPNQ PNKDQPSKDE NKKPDKGNKP

APPSKMPNRP DQKEDGSNNT PPPATDNGGN SNDGTTTGPN

GGGGSEASPP PNEQPSNGNA SDTHQNGSVS STNHSNQYGT

SAYDEYAGLL NNNYKYNPLF KEEVARLSQF GSQDQHDIAS

LSRKEQFSQN AFLDDLQQST DYFRYQYFNP LSTEQYYHRL

DKQVLALVTG EFGSMPDFKK SGDKSLVNKH QQDKVKKIEQ

QGENINTHHM KNTKEDTGKS LSYKPMIYIG IVMVGFVGLI

SMILWKRLHH FWK

SEQ ID NO: 21
gtgattacaaataaaaatatatatagtattcgaaagcataaacttggcgt ggcatcattcttattggggacattatttgttgtagggcatgcaaataatg ctgaagcttcagaagtgagcgcaacaacacaagaacataatgtcgagact gagcaaacaaaaactgagggcgaactaacaactgaggtagcacaacaagc agtcagcgaatcagcacctatagctgaaaacatgcagaaaacaacatcag tggcaagtgaaaatgcgaaagaggttacagcttctgatagcacacaagaa gtcacaaaaactgaagcaaaagatacagcaacaatgaaagattcagaaat tgcacaacctgtatcagaagtgaataaacctgttactcaaacagctgcac ccgtagcagaaccatcaacagcaaacaaacaaacttcaccacgacaagta caagaacttactgcaccaatggacacaaaagtaattaatgtagaaaacgg aacagatgtgacaagtaaagtgaaagttgaaaaatcgtcaattacagggc atcagaataaagataaaacatatcatcaatcgaacactgtaaatccacat aaagctgaacgtgtgacattaaattatgattggtcatttgaaaatggaat taaagctggtgattattttgacttccaattaagcgataatgtcgatacaa atggaatatcaacaataaaaaaagtcccacacattatggatagtcaaaat agcgaacaaattattgcttacggggaaattaatgaaaacaaccgtgtccg ttaccgatttatggactatgtaaatcaaaaagaaaatttaaaaggtaaat tgtcattaaacttatttattaaaccagataaagttcaagatgaaggaaaa atcactgtcacttcacaattgggcaaggaaatgacaagtcaggaatttga cattaaatatattgatggtgtaaaaagcccttcaggtatcacattaaacg gtcgtcttgatgaattatcaaaagcagatcaatcatttacgcattattct atatttaaacctaagcataatacttaactaatgtaactttaagaggcac agtttcaaataacgcacagcaaatgaaaaaaatggtcaagttaatgtttt acgaatatattggtcaaggagaattgccacaaagtgcttatgccaatgta aatgatacgaagcagttcaatgacattactaagagtatgaaatcaatcaa aaataacagtaatggctatgaaattactttgacatgaacaaagacaatc atccttatatcatagtatatcaaggtcactttaacaataatgcaaaagac tttgatttctcaacaaatgcgacaggttatcaaaatttaaatcaatcgga atatagttattattggccttacaattattcattcaatttaacatgggata atggtgttgctttctactctaataatgcaagtggggaagggaacgacaaa cctgtaccgccgacttatggatatagtccgacagtaaatacaattcaaga
```

```
tactcatgcggattatcctgtaatgactttccaacaacctggaactctag aggagacgaagacagtatgccaatcactacacttaccgaatctggtgag gatcgtggtgaaaatacttctccaattatcgagacaacagaagattcaca gcctgttgagtttgaagaagagacaaatcatggcattcaagacgtgacac ttcatgcagatgctgttgattttgaggaagaaacaaaccatggtgaacaa gacacggtacaccactctgatgtcgttgaatacgacgaagatacgacaac tggcatgttaacaggtgccatttctgaccatacaacagaagaaggcacga tggagtacacaactgatggcttattgattgagtttgatgatgaaatgaat cctaatgtgagcggtcagtacgatgacatcacaacggatacgatagagga atcatctcatattgacacattcactgaacttgaatctgaatttggtcaac atgacggtatagtgacatttgaagaagatactatcgttgagaagccgaaa acagaaagggtaaccgagtaccacttgtaattgatttatcaacaccaaa acataaccatcagttcaatattcaacctaccgatccaaatattgatacct ctgctacgtatcgaattggcaattttgtatggcgcgatgaagatcacaat ggcgtacaaaatgatggtgaacatggtcttgaaggtgttcttgtcacact taaaacagctgatggtgtcgtttttaaatacaacgacaagtgatgccaatg gacactaccagttcactaatgttcaaaaaggaaaatatattgttgaattc actacacctgaaggttatgaagcaacaagcaaacatactacagcgaatac tgaaaaagactctgatgggttaatcgcaaatatcgatgttactcaagatg atatgtcaatcgatgctggtttcttcccgttagaaaactggaatcctcag ccagagccgaaaaaccctgatgatagagagaaaccggcacctgagcaacc tgatgtacctcagccagaaccgaaaaaccctgatgatagagagaaaccgg cacctgagcaacctgatgtacctcagccagaaccgaaaaatcctgatgat agagagaaaccggcacctgagcaacctgatgtacctcaaccagagccgaa aaatcctgatgataaagagaaaccggcacctgagcaacctgatgtacctc aaccagagccgaaaaatcctgatgataaagagaaaccggcacctgagcaa cctgatgcacctcaaccaaagccgatgctcccaggtgaaaaggtgaaacc caaaccaactcatcccggtgaagctatgcaaacaacacctcaggacaaat caacatctcaaacagatgaagcacttcctaaaacaggtgaatcatcatca caatcatctgctttaatcttcggtggtttactcagtctattaggacttgg tttattacgtcgatcatctaaacaaaaccgttcttcaatgaaataa
```

The protein sequence translated from SEQ ID NO 21 is designated SEQ ID NO: 22 and is shown below:

```
                                        SEQ ID NO: 22
VITNKNIYSI RKHKLGVASF LLGTLFVVGH ANNAEASEVS

ATTQEHNVET EQTKTEGELT TEVAQQAVSE SAPIAENMQK

TTSVASENAK EVTASDSTQE VTKTEAKDTA TMKDSEIAQP

VSEVNKPVTQ TAAPVAEPST ANKQTSPRQV QELTAPMDTK

VINVENGTDV TSKVKVEKSS ITGHQNKDKT YHQSNTVNPH

KAERVTLNYD WSFENGIKAG DYFDFQLSDN VDTNGISTIK

KVPHIMDSQN SEQIIAYGEI NENNRVRYRF MDYVNQKENL
```

-continued

```
KGKLSLNLFI KPDKVQDEGK ITVTSQLGKE MTSQEFDIKY

IDGVKSPSGI TLNGRLDELS KADQSFTHYS IFKPKHNNLT

NVTLRGTVSN NAQQNEKNGQ VNVYEYIGQG ELPQSAYANV

NDTKQFNDIT KSMKSIKNNS NGYEITFDMN KDNHPYIIVY

QGHFNNNAKD FDFSTNATGY QNLNQSEYSY YWPYNYSFNL

TWDNGVAFYS NNASGEGNDK PVPPTYGYSP TVNTIQDTHA

DYPVMTFQQP GTLEETEDSM PITTLTESGE DRGENTSPII

ETTEDSQPVE FEEETNHGIQ DVTLHADAVD FEEETNHGEQ

DTVHHSDVVE YDEDTTTGML TGAISDHTTE EGTMEYTTDG

LLIEFDDEMN PNVSGQYDDI TTDTIEESSH IDTFTELESE

FGQHDGIVTF EEDTIVEKPK TEKGNRVPLV IDLSTPKHNH

QFNIQPTDPN IDTSATYRIG NFVWRDEDHN GVQNDGEHGL

EGVLVTLKTA DGVVLNTTTS DANGHYQFTN VQKGKYIVEF

TTPEGYEATS KHTTANTEKD SDGLIANIDV TQDDMSIDAG

FFPLENWNPQ PEPKNPDDRE KPAPEQPDVP QPEPKNPDDR

EKPAPEQPDV PQPEPKNPDD REKPAPEQPD VPQPEPKNPD

DKEKPAPEQP DVPQPEPKNP DDKEKPAPEQ PDAPQPKPML

PGEKVKPKPT HPGEAMQTTP QDKSTSQTDE ALPKTGESSS

QSSALIFGGL LSLLGLGLLR RSSKQNRSSM K
```

SEQ ID NO: 23
```
atggcatttgatggtatgtttacaagaaaaatggtagaagatttacaatt
tctcgtttctgggcgtattcataaaatcaatcaaccggaaaacgatacaa
tcatcatggttataagacagcaacgccaaaatcatcaattgttgttgtcg
attcaccccgaattttgcacggattcacctcactacaaaaaaatatgataa
tccatttgaaccgccgatgtttgcgcgcgtctttcgtaaacatttagaag
gtggacgtatccttgccattcgccaaatcggaaatgaccgtcgcatcgaa
atggacgtggaaagtaaagatgaaattggtgacacgattcatcgtacagt
gattttagaaattatgggcaaacatagtaatctcattctcgttaatgaag
aacgtaaaattttagaaggttttaaacaccttacaccaaatacgaatcaa
tttagaaccgtgatgccaggttttcaatatgaagtgccgccaacacaaca
taaacagaacccttatgcatatactggtgcgcaagtgctccaacatattg
atttcaatgcgggcaaaattgatcgccaactgcttcaaacgtttgaaggt
ttttcaccgttaatcacaaaagaaatcacatcaagacgccattttatgac
cacacaaactttacctgaagcttttgacgaagtgatggccgaaacgaaag
cgacaccccaaccggtatttcataaaaataacgaaacaggtaaagaagac
ttttattttatgaagttacatcagttttacgatgattgcgtcacatatga
ttcactccatgaactgctcgaccgttttttatgatgcacgcggtaacgtg
aacgcgtcaaacaacgtgcaaacgatttagtcaaactcgtccaacaatta
cttcaaaaatatcaaaataaattaagtaagctcgtcgatgaacaagcggg
gactgaagaaaagaaatcaacaattgtacggcgagttaatcacagcga
atatttatcaactcaaacctggagatcgccagttagaaacagtaaattat
tatacaggagaaaacgtgactattccgttaaatccacaaaagtcacctgc
tgaaaatgcgcaatactattacaagcaatacaaccgaatgaaaacacgtg
agcgcgaattgacccatcaaattactttaacggaagaaaatatcgcttat
tttgaaaatatcgagcaacagttgtcacacattcaagttcatgaaattga
cgatattcgtgaagaactagcagaacaaggctttatcaaacaaaagaaac
agcagaaaagaaaaagcaacaaaaaatccagttacaatcctacgtttcg
actgatggcgatacgattttagtcggtaaaaataataagcaaaatgatta
tttaacgaataaacgtgcgcaaaaatcgcatttatggttccatacaaaag
atatcccaggaagccatgtcgtgattttaaatgatgcgccaagtgacaaa
acgattgaagaagcggcgatgattgcagcgtactttcaaaggcggggca
atcgggacaaattccagtggattatacaacaattcgcaatgtgcataagc
cgagtggcagtaaacctggatttgtaacgtacgataaccagaagacgctt
tacgcaacgccggattatgacatgattcgtcgattgaaagctgaagaagc
gtaa
```

The protein sequence translated from SEQ ID NO 23 is designated SEQ ID NO: 24 and is shown below:

SEQ ID NO: 24
```
MAFDGMFTRK MVEDLQFLVS GRIHKINQPE NDTIIMVIRQ

QRQNHQLLLS IHPNFARIHL TTKKYDNPFE PPMFARVFRK

HLEGGRILAI RQIGNDRRIE MDVESKDEIG DTIHRTVILE

IMGKHSNLIL VNEERKILEG FKHLTPNTNQ FRTVMPGFQY

EVPPTQHKQN PYAYTGAQVL QHIDFNAGKI DRQLLQTFEG

FSPLITKEIT SRRHFMTTQT LPEAFDEVMA ETKATPQPVF

HKNNETGKED FYFMKLHQFY DDCVTYDSLH ELLDRFYDAR

GERERVKQRA NDLVKLVQQL LQKYQNKLSK LVDEQAGTEE

KENQQLYGEL ITANIYQLKP GDRQLETVNY YTGENVTIPL

NPQKSPAENA QYYYKQYNRM KTRERELTHQ ITLTEENIAY

FENIEQQLSH IQVHEIDDIR EELAEQGFIK QKKQQKKKQ

QKIQLQSYVS TDGDTILVGK NNKQNDYLTN KRAQKSHLWF

HTKDIPGSHV VILNDAPSDK TIEEAAMIAA YFSKAGQSGQ

IPVDYTTIRN VHKPSGSKPG FVTYDNQKTL YATPDYDMIR

RLKAEEA
```

SEQ ID NO: 25
```
atggtcaaaaatttggttataaaacacctacaatcgttgcacttacttt
ggctggaactgcattttctgcacaccaagccaatgccgctgaacaagttg
cacctgaaaaaacacctcacgaatgtacttgatgatcaatacgcattaaaa
caagctgatgatgcgaaacaaacgacacaaggaacaacacttgcaggttc
aaaagaatacaaggatccttcacaaattgatacgactcaagtcgatacag
cagcacaaactgaaacgcccgtagaaggagggcaacaagacgcacaacaa
cctactacaactgatgaagcgacatcaacagatcatactgtatcaaaagg
tacaaacgaaagtgcatcacctgcaacagcttctatagatgaaggaacat
```

-continued

```
taaacgcacaagtcaattcagatgaaacggctactaaccgtacacaagac
gtcactgaaaatgtgacaaaatatccttatcattcaagtgaaatcgatac
acatgaagacgcaactgtgtcaccagatacatatcatgcactggacacgc
atgcgcaacaaccttcagcaatggatgtaagcgattcaacatcagcacaa
actgaagcgacgcaagtaaatacgtcaacaaatgtaaatgacaaagaggc
cgtttcgacaacagaagatgcacctactacacaacttcaagcagctgtac
aatctgaagccaacaaagaagcgaaggcaactactgaaacagctcaaaat
aaaacacctcaagttgaaaagaaagcaacagcaactcaaaatacagcaca
gttagcaacggggcatcaggatattactgacaaagtctcaaaacgcgtag
cagtgacaaatgaaacgaaagcggatgccacaacagcgaaaacacaagca
cctacttcagtgacacatcaagctgatacacaagcaaaaacgataacaga
caagaaggcaacaacttacagtgcacaaaccgcaactgaccaagacataa
atgcgaatccggacggtccaacacctccacgcgttggcggtaaagggggt
cccccctgcttcactttcactccaatcgactggtcaaacagcattccgttc
agctgtcgctagtaaaccgagtgcatatcaacctaaagtgaaatcgtcta
ttaatgactatattcgtaagcaaaactacaaagtgcctgtatatgaagaa
gattattcaagttacttccctaaatacggttatcgtaatggtgtcggtaa
acctgagggcatcatcgtgcatgatacagcaaatgacaactctacaattg
atggcgaaatcagttacatgaaaagaaattatcaaaatgctttcgtacat
ggctttattaatggtcaacgtattgttgaaacgcaacctacagattattt
agcatggggtgcaggtgcgattgcgaatgaacgctttattcatatcgaac
tcgttcatgttcacagtaaagaagatttcgcacgtcaaatgaacaatatg
gcagattatgcggcgacgaacttacaatattatggccttctccagatag
tgcggaatatgatggtcgtgggacagtttggacacatgatgctgtttcta
gattttaggtggtacagaccataccgatccgcacggctatttaaaacaa
catggttattcctttgatgcgttgtatgatttaatcaatgaaaaatatca
agtgaaaatgggttatgcctcacctgctaactcgtcttcaaaaccatcaa
caaatactggcttaacagttaaaaacacaacaggtttcggccgtattaac
acaacaaatagcggtttatatacgaccgtttatgatcaaaaggtaaagc
gacgaatcaaacgaatcaacgttaaaagttacaaaagaagcgacgttaa
atggcaacaaattctatttaatgagtgatgcaaaatctaatcaaacactc
ggttgggtcaaatcaaacgacgcaacatatcaagctgcccaagctgagaa
aaaagtaacgaaaacgtatactgtcaaaccaggaacaacagtatatcaag
tgccttgggggtgcctcatctcaaacagtaggcaaagctccaggtacgtca
aaccaatcattcaaatcaacgaaagaacaaactgttgcgaaaacgaaatg
gctttatgggacagttggcaaagtgacaggctggattaatgcaagtagtg
ttgtagcaaatgatcaaaaaccatcgacgaataccgcactaaaagtaaca
actgacactggtctcggtcgcattaaagacaaaaatagtggtttatacgc
aacggtatatgataaaactggtaaaagcacttcagccactaaccaaacat
taaaagtaacgaaaaaagcaagtgtcaatggccaatcattctatttagta
tcagattatgctaaaggtacaaatgttggttgggtgaaacagtcagatgt
cgaatatcaaacaagtaaagccccttctaaagtgaatcaaaattatacga
ttaaatcgggtgcgaaattgtatcaagtgccttggggtacaagtaaacaa
gttgccggtacagtgacaggtgctgcgacacaaacatttaaggcaacaca
atctcaaactgtaggtaaagcaacatacttgtatgggacagttggcaaat
tatctggttggattaattcaacagcattagcagctcaaaaaacaacaacg
aatgttactaaaacaatttctcaaatcggtcaactgaacacgaaaaatag
cggtgtcaaagcttctatttatgacaaaacagcaaaagatgcatccaaat
gggcaggtcaaacttataaaattactaaaacagcttctgccaataacgaa
gactatgtattactgcaaaatagtacaggaggcacgccactcggttggtt
caatgttaaagacgtcacaacacgcaacttaggtgctgaaacagctgtta
aagggcggtacactgttaatagtaaaacatctggactctacgctatgcct
tggggtacaacgaagcaacgtgtcgatacattaaaaaatgccacaagtcg
tttatttacagcttcaaaatcagttaaagtcggtaatgatacattcttat
tcggtacagtgaatcaaaaattgggctgattaatcaaaagacttaaca
gctgtagcagcaaaagttgcaaacatgaaaactgcatcgaatagcgcagt
caaaggtgccgcaatcacaactttgaaaaagtagaagattatgtgatta
cgaataaaaatggttattattacactaaagttggagattcaaaaacagct
ggtgctttaaaaggttttatcaacaattttaaagtcgaaaaacatc
tttactgaacggcattacttggtactatggcgcattccaaaacgggacga
aaggatggattaaagcagctgacatacgttcatcattcattcaacatact
gcggtcagtagcacattgaaagcagcactcgataaacaaatggcgctgac
ttacccgcctcaagttcaacgtgtagccggtaaatgggtcaatgcgaatc
gtgcagaaactgaaaaagcaatgaataccgcagcaattgaaaaagatccg
actctcatttaccaattttaaaacttgataaataccaaggtcttggcgt
agaagaacttaataaattgttaagaggcaaaggcattttagaaggtcaag
gtgccgcatttaaagaagccgcacaaaaacacaatattaatgaggtttac
ttaatgtctcacgcatttttagaaacaggtaacgggacttctcaattagc
caatggcggtcacgtagataaaaataataaagtcgtaacaaacggtaaac
cgaagtattacaacatgttcggtatcggggcaattgatacagacgcttta
cgcaatggctttaaaactgctgaaaaatatggttggaatacggtcagcaa
agcgattatcgtggcgcaaaattcatccgtgatcagtacatcggttcag
gacaaaacacattgtatcgtatgcgttggaatccagaacaccctgccaca
catcagtatgcgactgatattaattgggcaaatgtaaacgcacaacgcat
gaaatatttctatgatcaaattggtgaaacaggtaaatatttcgacgtcg
atgtatataagaagtag
```

The protein sequence translated from SEQ ID NO 25 is designated SEQ ID NO: 26 and is shown below:

SEQ ID NO: 26

MVKKFGYKTP TIVALTLAGT AFSAHQANAA EQVAPEKTPT

NVLDDQYALK QADDAKQTTQ GTTLAGSKEY KDPSQIDTTQ

VDTAAQTETP VEGGQQDAQQ PTTTDEATST DHTVSKGTNE
SASPATASID EGTLNAQVNS DETATNRTQD VTENVTKYPY
HSSEIDTHED ATVSPDTYHA LDTHAQQPSA MDVSDSTSAQ
TEATQVNTST NVNDKEAVST TEDAPTTQLQ AAVQSEANKE
AKATTETAQN KTPQVEKKAT ATQNTAQLAT GHQDITDKVS
KRVAVTNETK ADATTAKTQA PTSVTHQADT QAKTITDKKA
TTYSAQTATD QDINANPDGP TPPRVGGKGG PPASLSLQST
GQTAFRSAVA SKPSAYQPKV KSSINDYIRK QNYKVPVYEE
DYSSYFPKYG YRNGVGKPEG IIVHDTANDN STIDGEISYM
KRNYQNAFVH GFINGQRIVE TQPTDYLAWG AGAIANERFI
HIELVHVHSK EDFARQMNNM ADYAATNLQY YGLSPDSAEY
DGRGTVWTHD AVSRFLGGTD HTDPHGYLKQ HGYSFDALYD
LINEKYQVKM GYASPANSSS KPSTNTGLTV KNTTGFGRIN
TTNSGLYTTV YDQKGKATNQ TNQTLKVTKE ATLNGNKFYL
MSDAKSNQTL GWVKSNDATY QAAQAEKKVT KTYTVKPGTT
VYQVPWGASS QTVGKAPGTS NQSFKSTKEQ TVAKTKWLYG
TVGKVTGWIN ASSVVANDQK PSTNTALKVT TDTGLGRIKD
KNSGLYATVY DKTGKSTSAT NQTLKVTKKA SVNGQSFYLV
SDYAKGTNVG WVKQSDVEYQ TSKAPSKVNQ NYTIKSGAKL
YQVPWGTSKQ VAGTVTGAAT QTFKATQSQT VGKATYLYGT
VGKLSGWINS TALAAQKTTT NVTKTISQIG QLNTKNSGVK
ASIYDKTAKD ASKWAGQTYK ITKTASANNE DYVLLQNSTG
GTPLGWFNVK DVTTRNLGAE TAVKGRYTVN SKTSGLYAMP
WGTTKQRVDT LKNATSRLFT ASKSVKVGND TFLFGTVNQK
LGWINQKDLT AVAAKVANMK TASNSAVKGA AITTLKKVED
YVITNKNGYY YTKVGDSKTA GALKGFYQQI FKVEKTSLLN
GITWYYGAFQ NGTKGWIKAA DIRSSFIQHT AVSSTLKAAL
DKQMALTYPP QVQRVAGKWV NANRAETEKA MNTAAIEKDP
TLIYQFLKLD KYQGLGVEEL NKLLRGKGIL EGQGAAFKEA
AQKHNINEVY LMSHAFLETG NGTSQLANGG HVDKNNKVVT
NGKPKYYNMF GIGAIDTDAL RNGFKTAEKY GWNTVSKAII
GGAKFIRDQY IGSGQNTLYR MRWNPEHPAT HQYATDINWA
NVNAQRMKYF YDQIGETGKY FDVDVYKK

SEQ ID NO: 27
gtgtcgacagaaaaacaagatgatacacaagcaaaagcgaatgcactttc
tacagatgattcaacacctacaacagaacaatcaaaaagtgataccgaac
caacgcaaaatcaagaagtgaatgaaaaagaagcaacacaagttgagcaa
actccagataatgcatcatcagaatttaaagacagtgcagcacaagatga
aacaacatcgaaagacgctgacattgctcaaacaaaagaagcaaaaaatg
aagcattgcaaagtgactcatcagcaaacctatcaaatcaagaagcagaa
aaagaaaacacaactaacagtgaatctcaagtaaatgaacaacctaaagc
agatacaacttctgattcacaagtttcaaatacacctcaacaagatccta
catcgacagtaccttcaccagaaacatcagaagacaatcgaccttcaaca
gaattaaaaaatagtgaaacaactgcttctcaaacaactttaaacgaaca
acctactgaatcaacatccaatcaaactgaaacgacaaaagcaccaacaa
atacaacagtcgcaaacaaaaaagcacctgcacaattaaaagacattaaa
ggtacaactcaacttcgcgcagtcagtgcaagtcaacctactgctgttgc
agctggtgggacaaacgtaaatgacaaagtaacagcatcaaatatgaaaa
taactgaatcttatatcgagccaaacaactcaggaaacttttatttaaaa
agtaactttaacgtaaacgggactgttaaagaaggtgactactttactgt
aaaaaatgcctgacactgtcaatacttttggtgacacgcgccattcacctg
actttagagaaaaaattacaaatcaaaaaggtgaagttgtggctttaggt
gaatatgatgttgccaaccatactatgacatacacgttcactaatgtcgt
taataaatttagaaaatgtgtccggttcgtttaacttgactcaatttatgg
atcgtaaagtggcaacagattctcaaacatatccattaaaaatacgacatt
gcaggcgaatctttagatacacaaattaaagtgaattacggtcaatatta
cagtgaaggtgattctaacttaaaatcaatgatcacttcagaagatccta
aaactggggaatatgatcaatacatttatgtcaacccattacaaaaaacg
gcaaacggtacagttgtaagagttcaagggttccaagttgatccaactaa
gagtaatgggcaagtgaaaccagatacaacgcagatcaagattttaaaag
ttgctgatggtcaaccacttaatagtagtttcggtgtgaatgacagtgaa
tatgaagatgtcacaaaacaatttaatattgtttatcgtgataataatttt
ggcagatatttactttggaaacttaaatgggcaacgctatatcgttaaag
tgacgagcaaagaaaatttggattctaaagaggatttaaacttgcgtgct
attatggccactcaaaaccgatatggtcaatataactatattacttggga
taacgatattgtgaaaagctcttctggtggtacagccgacggaaatgaag
catcatatcaattaggcgacaaagtttggaatgatgtgaataaaaatggt
atccaagatcaaggtgaaactggtattgctgatgtaaaggttacttttaaa
agatcttgatggcaacattttggatacaacttatacaaacacgaatggta
aatatatctttgataaatttaaaaaaatggtaattatcaagtgggttttgaa
acaccggaaggctatgctgcaagtccatccaaccaaggtaatgacgccct
tgactctgatggtcctacaaatgtacaagctgtcattagtgatgggaaca
acttaactatcgaccaaggttttttaccaaactgaaacaccaacacacaac
gtcggcgacaaagtttgggaagacttaaataaagatggcatccaagacca
aaatgaaccaggtatcgctaacgttaaggtcacttttaaaagacgcggatg
gtaacgttgtggatacacgtacgactgatgataaagggaattacttattc
gaaaaagttaaagaaggcgaatatacaattgaatttgaaacgcctgaagg
ttatacaccgacacaaacaggccaaggcagagtcagcactgactctaatg
ggacatcttcccttattttagtcgaaggtaacgatgacttaacaatcgat
agcggttttctacaaagaacctgttacacacaaagttggcgacaaagtttg
ggatgacttaaataaagacggtatccaagatgacaatgaaccaggcatct

```
ctgacgttaaagtcactttaaaagatgcggatggtaacgtcgtagataca
cgtacaactgatgctaacggtaactatttatttgaaaacgtgaaagaagg
cgactatacgattgaatttgaaacgcctgaaggttacacaccgactgtta
caggtcaaggtacagctgataatgactctaacggtacatctacaaaagtt
acagttaaagatggcgatgacttaacaattgacagtggtttcactcaagt
tacacctgagccaccgacacataatgttggcgacaaagtttgggatgact
taaataaagacggtatccaagatgacaatgaaccaggcatctctgacgtt
aaagtcactttaaaagatgcggatggtaacgtcgtagatacacgtacaac
tgatgctaacggtaactatttatttgaaaacgtgaaagaaggcgactata
cgattgaatttgaaacgcctgaaggttacacaccgactgttacaggtcaa
ggtacagctgataatgactctaacggtacatctacaaaagttacagttaa
agatggcgatgacttaacaattgacagtggtttcactcaagttacacctg
agccaccgactgaacctgaaaaccctagtccagagcaaccttctgaaccg
ggtcaacctgaaaatcctagtccagagcaaccttctgaaccaggtcaacc
tgaaaatcctagtccagagcaaccttctgaaccaggtcaacctgaaaatc
ctagtccagaacaaccttctgaaccgggtcaacctgaaaatcctagtcca
gaacagccttctgagccaggacaacctaaaaatcctagtccagaacagcc
aaataatccaagtgtgccaggtgttcaaaatcctgaaaaaccaagcttaa
ctccagtcacacaaccggttcattcaaacggcaataaagcaaaaccatct
caacaacaaaaagctttacctgaaacaggtgaaactgaatcacatcaagg
tacattattcggtggtattttagctgcttaggcgcattactctttgcac
gtaaaaaacgccacgataaaaaacaatcacactaa
```

The protein sequence translated from SEQ ID NO 27 is designated SEQ ID NO: 28 and is shown below:

```
                                      SEQ ID NO: 28
VSTEKQDDTQ AKANALSTDD STPTTEQSKS DTEPTQNQEV
NEKEATQVEQ TPDNASSEFK DSAAQDETTS KDADIAQTKE
AKNEALQSDS SANLSNQEAE KENTTNSESQ VNEQPKADTT
SDSQVSNTPQ QDPTSTVPSP ETSEDNRPST ELKNSETTAS
QTTLNEQPTE STSNQTETTK APTNTTVANK KAPAQLKDIK
GTTQLRAVSA SQPTAVAAGG TNVNDKVTAS NMKITESYIE
PNNSGNFYLK SNFNVNGTVK EGDYFTVKMP DTVNTFGDTR
HSPDFREKIT NQKGEVVALG EYDVANHTMT YTFTNVVNNL
ENVSGSFNLT QFMDRKVATD SQTYPLKYDI AGESLDTQIK
VNYGQYYSEG DSNLKSMITS EDPKTGEYDQ YIYVNPLQKT
ANGTVVRVQG FQVDPTKSNG QVKPDTTQIK ILKVADGQPL
NSSFGVNDSE YEDVTKQFNI VYRDNNLADI YFGNLNGQRY
IVKVTSKENL DSKEDLNLRA IMATQNRYGQ YNYITWDNDI
VKSSSGGTAD GNEASYQLGD KVWNDVNKNG IQDQGETGIA
DVKVTLKDLD GNILDTTYTN TNGKYIFDNL KNGNYQVGFE
TPEGYAASPS NQGNDALDSD GPTNVQAVIS DGNNLTIDQG
FYQTETPTHN VGDKVWEDLN KDGIQDQNEP GIANVKVTLK
DADGNVVDTR TTDDKGNYLF EKVKEGEYTI EFETPEGYTP
TQTGQGRVST DSNGTSSLIL VEGNDDLTID SGFYKEPVTH
KVGDKVWDDL NKDGIQDDNE PGISDVKVTL KDADGNVVDT
RTTDANGNYL FENVKEGDYT IEFETPEGYT PTVTGQGTAD
NDSNGTSTKV TVKDGDDLTI DSGFTQVTPE PPTHNVGDKV
WDDLNKDGIQ DDNEPGISDV KVTLKDADGN VVDTRTTDAN
GNYLFENVKE GDYTIEFETP EGYTPTVTGQ GTADNDSNGT
STKVTVKDGD DLTIDSGFTQ VTPEPPTEPE NPSPEQPSEP
GQPENPSPEQ PSEPGQPENP SPEQPSEPGQ PENPSPEQPS
EPGQPENPSP EQPSEPGQPK NPSPEQPNNP SVPGVQNPEK
PSLTPVTQPV HSNGNKAKPS QQQKALPETG ETESHQGTLF
GGILAALGAL LFARKKRHDK KQSH
                                      SEQ ID NO: 29
atgaagaaaacaatttcagtacttggtctagggctattagcaacatttttt
tgtaagtaacgaatcatatgccgcagaaacgattcaaaacaatacgtcat
caagtgaaacgaatcaaaattcagatcagacgccgttagatcattatatt
cgaaaagcagatggcacactggttgaaccgaacgtgtacccacataaaga
ttatgtagagaatgaaggacctttaccagagtttaaatttcaagttgact
ctaagaaagattcatctgatccaaatcaagcaccgttagatcattatatt
cgaaaagcggatgcacgttggttgaaccgaatgtatatccacacaaaga
ttatgtcgaaaatgaagggcctttaccagagtttaaatttatgtatgctg
acaaacaaaatcatcatgaccaacagagtaaaaacaacaaggataagcag
cgtgcaaattacagtgacaaaaagcataatgatcagccgggtcatccaaa
agcagtcacgccagctgtacaacatgataaagcagtcacttcaaacgcta
ctgtaaaagcattgccaaacacaggtgaatctgataaaacaacacaatta
ccaatcgtattatcattgttatctgtggggattttagttttattaaaatt
gagaaaataa
```

The protein sequence translated from SEQ ID NO 29 is designated SEQ ID NO: 30 and is shown below:

```
                                      SEQ ID NO: 30
MKKTISVLGL GLLATFFVSN ESYAAETIQN NTSSSETNQN
SDQTPLDHYI RKADGTLVEP NVYPHKDYVE NEGPLPEFKF
QVDSKKDSSD PNQAPLDHYI RKADGTLVEP NVYPHKDYVE
NEGPLPEFKF MYADKQNHHD QQSKNNKDKQ RANYSDKKHN
DQPGHPKAVT PAVQHDKAVT SNATVKALPN TGESDKTTQL
PIVLSLLSVG ILVLLKLRK
                                      SEQ ID NO: 31
atgaaagtaaatatgattttttacctaatagacttaataaattttctat
acgaaaatttactgttggtagtgtatcagtgctaataggagccactttat
tattcgggtttgtagaaggagaagcatcagcatcagtaaaagaaggtcaa
```

-continued caaagtatataaattctagtgagaaagaaagcgccgatcctacagtagttga
tttaattagtaagaagaaacaaatttagatggactagatgtatcaagag
aagaaacgaccaaagtaccaataaatgaaaacaaaagaggtgaggaacaa
agtatttctgataaagctataacagaaaaagctgatacaccagtaagcaa
tttatcaagtaaggaagttgaggagcaaggtgtttctgataaagctataa
cagaaaaagctgatacaccagtaaccaatttatcaagtaaggaagctaag
gagcaaggtgcttctgatagagttataacagaaaaagctgatacaccagt
aagcaatttatcaagtaaggaagctaaggagcaaggtgcttctgatagag
ttataacagaaaaagctgatacaccagtaagcaatttatcaagtaaggaa
gttgaggagcaaggtgtttctgataaagctatagagaaaatagctgatgc
atcagctactgatttgtcaagtaaggaagaagtagaacaagatatatcta
cacaaggtaaagtaaaatcaaaggaagcagtacaagtagaaagtagtcag
ttacaaaatttaaatagtgaaataaatgctgaacctaatgaaattaaggc
aatagatagaagttcaatattacctttaaatttaaatgatgaagaaaata
acaaaaaagttaataaagggactcgggttccagaagctacattaagaaat
gcctctaataaccaactcaatacacgaatgagatcagtgagtttatttag
agttgctagactaacagaaatcaatagaaatgttaatgataaagtaaagg
tttcggatatcgacatcgcaatagccccaccgcatactaaccctaaaact
ggaaaagaagaattttgggcgacatcttcttcagttttaaagttaaaggc
aagctatgaattggataatagcatttctaaagggatcaatttactattc
aatttggtcaaaatattcgtccaggtggattaaatttaccaagaccttat
aatttttatatgataaggataaaaaattagttgcaactggccgttacaa
taaagaatcaaatacaatcacatatacatttacggattatgtagataaac
atcaaaacattaaaggtagttttgagatgaatgcattttctagaaaggaa
aatgctactactgacaaaacagcatatccaatggatgttactattgcgaa
tcaaaaatatagtgaaaatattattgtagactatggtaataaaaagaatg
ctgctatttatttcaagtacagaatatattgatttagatggtagtagaaaa
atgacaacatatattaatcaaaatggtagtaaaaattccatctatcgtgc
tgatatgcaaattgatttgaacggttataaatttgatccatccaaaaaca
atttttaaaatttatgaagtggaaaatagcagtgactttgtggatagcttt
tcaccagatgtgagcaagttaagggatgttacgagtcaatttaatattca
atatacaaataataatacaatggcaaaagtggattttggtactaacctttt
ggaggggtaaaaaatatattattcagcaagtggcgaatatagacgacagt
aaattagtgaaaaatgcttcaatcaattatacattgaataaaatggattt
taataataaaagaacggtagaaacacataacaatacttattctacagtga
aagataaatcaacagcactaggtgacgtacaggaaagtcaatctattagt
gagagccaatcagttagtgaaagcgagtcactaagtgagagccaatcaat
cagtgaaagcgaatcattaagtgagagccaatcaatcagtgaaagcgaat
cattaagtgaaagtcaatcaatctcagagagcgaatcactaagtgaaagt
cagtcaatttcagaaagcgaatcattaagtgaaagccaatcaatctcaga
gagtgaatcattaagtgaaagtcagtcaatttcagagagtgaatcactaa -continued gtgaaagtcagtcaatttcagaaagcgaatcattaagcgagagtcagtca
atttcagaaagcgaatcattaagcgagagtcagtcaatttcagaaagcga
atcattaagtgaaagccaatcaatcagtgaaagcgaatcactaagcgaga
gccaatcaatctcagagagtgaatcattaagcgagagtcaatcaatctca
gagagcgaatcattaagtgagagtcaatcaatcagtgaaagcgagtcact
aagtgagagtcaatcaatttcagagagcgaatcattaagtgaaagccaat
caatctcagagagtgaatcactaagtgagagccaatcaatctcagagagt
gaatcattaagtgagagccaatcaatctcagagagcgagtcactaagcga
gagccaatcaatttcagagagtgaatcactaagtgaaagtcaatcaattt
cagagagcgaatcactaagtgagagccaatcaatctcagagagcgaatca
ctaagtgaaagtcaatcaatttcagagagtgaatcactaagcgagagcca
atcaatctcagagagtgaatcattaagtgaaagtcagtcaatttcagaga
gtgaatcactaagtgaaagtcagtcaatttcagaaagcgaatcattaagt
gaaagccaatcaatcagtgaaagcgaatcactaagcgagagtcaatcaat
ctcagagagcgaatcattaagtgaaagtcaatcaatttcagaaagcgagt
cattaagcgagagtcagtcaatctcagagagcgaatcactaagcgagagt
caatcaatctcagagtgaatcattaagtgagagccaatcagttagtga
aagcgaatcactaagtgaaagtcagtcaatttcagaaagcgaatcattaa
gtgagagtcaatcaatttcagaaagcgaatcattaagtgaaagccaatca
atcagtgaaagcgaatcactaagcgagagccaatcaatcagtgaaagcga
atcattaagtgagagtcaatcaatctcagaaagcgaatcattaagtgaga
gtcaatcaatcagtgaaagcgaatcactaagcgagagccaatcaatctca
gagagcgaatcactaagcgagagccaatcaatctcagagagcgagtcact
aagcgagagccaatcaatcagtgaaagcgaatcattaagtgagagtcaat
caatcagtgaaagcgagtcactaagtgagagccaatcaatctcagagagt
gaatcattgagtgagagccaatcaatctcagagagcgagtcactaagtga
gagtcaatcaatttcagagagcgaatcattaagtgaaagccaatcaatct
cagagagtgaatcattgagtgagagccaatcagttagtgaaagcgagtca
ctaagtgagagtcaatcaatcagtgaaagcgagtcactaagtgagagtca
atcaatttcagagagcgaatcattaagcgagagtcagtcaatctcagaga
gtgaatcactaagtgagagccaatcaatctcagagagtgaatcattaagt
gagagccaatcaatctcagagagtgaatcactaagtgagagtcaatcaat
cagtgaaagcgaatcactaagcgagagccaatcaatttcagagagtgaat
cattaagtgagagccaatcagttagtgaaagcgaatcactaagcgagagc
caatcaatctcagagagcgaatcattgagtgagagccaatcaatctcaga
gagtgaatcattgagtgagagtcaatcaatcagtgaaagcgaatcactaa
gcgaaagtcaatcaatttcagagagtgaatcattgagtgagagccaatca
atttcagagagtgaatcactaagtgaaagtcagtcaatttcagaaagcga
atcactaagcgagagccaatcaatctcagagagcgaatcactaagtgaaa
gtcagtcaatttcagaaagcgaatcattaagtgaaagccaatcaatctca -continued

```
gagagtgaatcattaagtgaaagtcagtcaatttcagagagtgaatcact
aagtgaaagtcagtcaatttcagaaagcgaatcattaagcgagagtcagt
caatttcagaaagcgaatcattaagtgaaagccaatcaatcagtgaaagc
gaatcactaagcgagagccaatcaatctcagagagcgaatcactaagcga
gagccaatcaatctcagagagcgaatcactaagtgaaagtcaatcaattt
cagagagtgaatcattgagtgagagtcaatcaatttcagagagtgaatca
ctaagtgaaagtcaatcaatttcagagagtgaatcactaagcgagagcca
atcaatctcagagagtgaatcattaagtgaaagtcagtcaatttcagaga
gggaatcactaagtgaaagtcagtcaatttcagaaagcgaatcattaagt
gaaagccaatcaatcagtgaaagcgaatcactaagtgaaagtcaatcaat
ctcagagagtgaatcactaagtgagagccaatcaatctcagagagtgaat
cattgagtgagagccaatcaatctcagagagcgaatcactaagtgaaagt
caatcaatttcagaaagcgagtcattaagcgagagtcagtcaatctcaga
gagtgaatcactaagtgagagccaatcaatctcagagagtgaatcactaa
gtgagagtcaatcaatcagtgaaagcgaatcactaagcgagagccaatca
atttcagagagtgaatcattaagtgagagccaatcagttagtgaaagcga
atcactaagcgagagccaatcaatctcagagagcgagtcactaagcgaga
gtcaatcaatctcagagagtgaatcactaagtgaaagtcagtcaatttca
gaaagcgagtcactaagcgagagtcaatcaatctcagagagtgaatcatt
gagtgagagccaatcaatctcagagagcgaatcattgagtgagagccaat
caatctcagagagtgaatcattgagtgagagccaatcaatttcagagagc
gaatcactaagcgagagccaatcaatcagtgaaagcgaatcattaagtga
gagtcagtcaattagcgaaagcgaatcactaagtgagagtcaatcaatct
cagagagtgaatcactaagtgaaagtcagtcaatcagcgaaagcgaatct
aaatctttacctaataccggtactggagaaaagatttctaattatccagg
tattttaggaggattattaagcatattaggtataagtttgcttaaaagaa
aagacagagagaaaaaattaggacaaaaatctaataagtag
```

The protein sequence translated from SEQ ID NO 31 is designated SEQ ID NO: 32 and is shown below:

```
                                        SEQ ID NO: 32
MKSKYDFLPN RLNKFSIRKF TVGSVSVLIG ATLLFGFVEG

EASASVKEGQ QSINSSEKES ADPTVVDLIS KKETNLDGLD

VSREETTKVP INENKRGEEQ SISDKAITEK ADTPVSNLSS

KEVEEQGVSD KAITEKADTP VTNLSSKEAK EQGASDRVIT

EKADTPVSNL SSKEAKEQGA SDRVITEKAD TPVSNLSSKE

VEEQGVSDKA IEKIADASAT DLSSKEEVEQ DISTQGKVKS

KEAVQVESSQ LQNLNSEINA EPNEIKAIDR SSILPLNLND

EENNKKVNKG TRVPEATLRN ASNNQLNTRM RSVSLFRVAR

LTEINRNVND KVKVSDIDIA IAPPHTNPKT GKEEFWATSS

SVLKLKASYE LDNSISKGDQ FTIQFGQNIR PGGLNLPRPY

NFLYDKDKKL VATGRYNKES NTITYTFTDY VDKHQNIKGS

FEMNAFSRKE NATTDKTAYP MDVTIANQKY SENIIVDYGN

KKNAAIISST EYIDLDGSRK MTTYINQNGS KNSIYRADMQ

IDLNGYKFDP SKNNFKIYEV ENSSDFVDSF SPDVSKLRDV

TSQFNIQYTN NNTMAKVDFG TNLWRGKKYI IQQVANIDDS

KLVKNASINY TLNKMDFNNK RTVETHNNTY STVKDKSTAL

GDVQESQSIS ESQSVSESES LSESQSISES ESLSESQSIS

ESESLSESQS ISESESLSES QSISESESLS ESQSISESES

LSESQSISES ESLSESQSIS ESESLSESQS ISESESLSES

QSISESESLS ESQSISESES LSESQSISES ESLSESQSIS

ESESLSESQS ISESESLSES QSISESESLS ESQSISESES

LSESQSISES ESLSESQSIS ESESLSESQS ISESESLSES

QSISESESLS ESQSISESES LSESQSISES ESLSESQSIS

ESESLSESQS ISESESLSES QSISESESLS ESQSISESES

LSESQSISES ESLSESQSIS ESESLSESQS ISESESLSES

QSISESESLS ESQSVSESES LSESQSISES ESLSESQSIS

ESESLSESQS ISESESLSES QSISESESLS ESQSISESES

LSESQSISES ESLSESQSIS ESESLSESQS ISESESLSES

QSISESESLS ESQSISESES LSESQSISES ESLSESQSIS

ESESLSESQS ISESESLSES QSISESESLS ESQSVSESES

LSESQSISES ESLSESQSIS ESESLSESQS ISESESLSES

QSISESESLS ESQSISESES LSESQSISES ESLSESQSIS

ESESLSESQS VSESESLSES QSISESESLS ESQSISESES

LSESQSISES ESLSESQSIS ESESLSESQS ISESESLSES

QSISESESLS ESQSISESES LSESQSISES ESLSESQSIS

ESESLSESQS ISESESLSES QSISESESLS ESQSISESES

LSESQSISES ESLSESQSIS ESESLSESQS ISESESLSES

QSISESESLS ESQSISESES LSESQSISES ESLSESQSIS

ESESLSESQS ISERESLSES QSISESESLS ESQSISESES

LSESQSISES ESLSESQSIS ESESLSESQS ISESESLSES

QSISESESLS ESQSISESES LSESQSISES ESLSESQSIS

ESESLSESQS ISESESLSES QSVSESESLS ESQSISESES

LSESQSISES ESLSESQSIS ESESLSESQS ISESESLSES

QSISESESLS ESQSISESES LSESQSISES ESLSESQSIS

ESESLSESQS ISESESLSES QSISESESLS ESQSISESES

KSLPNTGTGE KISNYPGILG GLLSILGISL LKRKDREKKL

GQKSNK
                                        SEQ ID NO: 33
atgttaagaacaaattataaactaagaaagcttaaagtaggtttagtatc gacaggtgtggcgttgacttttgtgatggcaagtgggaatgcagaggcgt cggagaacgagcagactgaagtaaaaggggaggcgcaagttgcttctgtg aatgaaaaagagagtgaagcagaattacctgtagcgcaacaagaagcatc
``` tattcaactagacaaagtacaaccaggcgatgcacagctttcaggctata
cacagccaaacaaagcgatttctgtaaagatcgacaataaagatattgtg
tctgtagatgatggctatgaagaggtattatcggatgatacaggtaaatt
tgtatatgatttgaaagggcgtcaaattgtttacaatcaaaaagttgatg
ttgaagcgatgacgccatttaattttgaagattttgatgaatcagcactt
gagagcgaagaggcattggaggcgttaggtcaattggaagacgaagaaac
agcgacagcttctgtgacgacgcctagatatgaaggtgcgtatacagttc
ctgaagaacgcttgacacccattcaaggccaacagcaagtattcatcgaa
cctattttagaaggggcaagtaaaatcaaaggacatacatctgtacaagg
taaagtcgcgttagcaatcaatcaagaacatgtgcacctaggtgatacgt
tagaagaacaagcagcactcactgatcaagagtggcaaggtcgttatgac
gggatttggcgccatattgatgatcaaggttttttcgagtttgacttgaa
ccgtctttacaataaatcttacccattgaagtctggcgatttagtgactt
tatcttttaaatctaatgacgaagtaggccattattcaatgtgaacgtt
gagcctttcgaacgtgtggcacaagctaaaacaaagtatgagcagaatga
cagtccagtagtcaacaaattggatgatactaaaagtgacttggaggttc
aacctatctatggagaccttacacaagcagcagtacatggcgagtcgaaa
gtgttgataccggggacgtcaaaagttgaaggacgtacgaattatgcaca
tgcatggatagatggcatctaatttaggggaatatcgtagtttcccta
aattacaagctgatgcgacaggtgcgtttatatttgatttaaaagcggca
gacatacaattgttaaacggagaacgtttgacattcagagccgttgaccc
acatacaaaacaacagttagctgaaactacatcagaagtacgcccagtag
atatgcaagatgaagagtcagaggttgtgcagacttcaagcactgagaaa
tcagcacttgcggatgaaattcttcgttctatgacaattgacaaatcatt
taatcctgaagttaccgagataccgggtcatgtatatcctaagaaaacag
aggataaaggtgctgaaaatacagaacaagcctcagagaattctgagaag
ccatctcagactacagaatctcaaaatgatgccgtacaagatgtagagaa
atcctctgttaatgaggaggttacgccaccttcaacagaatctgctcaag
ttgaaaaggggcaaaatacagaaggggctttgcttccaaaaaatgtagaa
caacatgtagagagtataccataccaaaaacgtaaagcgttgataggact
gacaaaacatcaaggatcagggcacatgccgccattttctttaagcttta
ataataaagaagatgacgtatccacaaaggttaacgaagcaaacgagcat
gaacgtaagcagggtacagtttatccagagcaaatagaacaattacctca
aacaggtttaactgaaaaatcgccattctgggcattgttatttgttgtat
caggcacaggtttattattattcaaacgttctagacgacaacgccaatct
taa The protein sequence translated from SEQ ID NO 33 is designated SEQ ID NO: 34 and is shown below:

SEQ ID NO: 34
MLRTNYKLRKLKVGLVSTGVALTFVMASGNAEASENEQTEVKGEAQVASV
NEKESEAELPVAQQEASIQLDKVQPGDAQLSGYTQPNKAISVKIDNKDIV

SVDDGYEEVLSDDTGKFVYDLKGRQIVYNQKVDVEAMTPFNFEDFDESAL
ESEEALEALGQLEDEETATASVTTPRYEGAYTVPEERLTPIQGQQQVFIE
PILEGASKIKGHTSVQGKVALAINQEHVHLGDTLEEQAALTDQEWQGRYD
GIWRHIDDQGFFEFDLNRLYNKSYPLKSGDLVTLSFKSNDEVGPLFNVNV
EPFERVAQAKTKYEQNDSPVVNKLDDTKSDLEVQPIYGDLTQAAVHGESK
VLIPGTSKVEGRTNYAHAWIEMASNLGEYRSFPKLQADATGAFIFDLKAA
DIQLLNGERLTFRAVDPHTKQQLAETTSEVRPVDMQDEESEVVQTSSTEK
SALADEILRSMTIDKSFNPEVTEIPGHVYPKKTEDKGAENTEQASENSEK
PSQTTESQNDAVQDVEKSSVNEEVTPPSTESAQVEKGQNTEGALLPKNVE
QHVESIPYQKRKALIGLTKHQGSGHMPPFSLSFNNKEDDVSTKVNEANEH
ERKQGTVYPEQIEQLPQTGLTEKSPFWALLFVVSGTGLLLFKRSRRQRQS

SEQ ID NO: 35
atgaaaactaaatacacagcaaaattattaattggggcagcaacaatatc
tttagcaacatttatttcacaagggaacgcacatgcgagcgaacaaacta
caggactcgcaccggcacaacctgtcaactttgattcaatcaatgtaacg
ccagaccaaaaaacattctatcaagtcttacatatggaaggcatttcaga
agaccaacgtgaacaatatttgaaacaattgcacgaagacccaagtagcg
cacaaaatgtttttcagaatcaattaaagatgccatccacccggaacgt
cgtgttgcgcaacaaaatgcgttttacagcgtattacacaacgatgactt
atccgaagagcaacgtgatgcatacattggtagaattaaagaagatccag
atcaaagccaagaagtatttgttgagtctttaaatgtggcacctaaagca
gaatcacatgaagatcgcctcattgaattacaaaacaaaatttaatgga
agcgaatgaagcacttaaagcgttacaacaagaagacgcattcagaata
gacgtgcggctcaacgtgctgtcaacaaattgacgccggatagcgcgaac
gcattccaaaaagaattagatcaaatcaatgccccacgcgacgctaaaat
taaagctgacgctgaagcaaaaaaacaagcacctgaagtaagcgcaccac
aaattgaagatgcacctactactgaagttgcaccatctccaaaacaagat
atgccaaagtagataaaaaagaagaagataaagtagaaagtgatactga
ggtcaaagaagtacctaaagctgatacagagaaaaaccctcaatctaaag
acacttctaaaactgaacaagctaaagaaacacctaaagtagagcaatca
cctaaaacagaaaggctgaagaagcacctaaagcagaaacacctcaaaa
tggaaataaagcacaaactgaagaagctaaaccagaagtaaaagacaatg
tgaaaaacactccatctgcacctgtgttacctgaaacaggaaaagcaaca
acttcaacacttgaaagctactggaattctttcaaagacagtgtgaataa
aggttatacttacattaaacaaagcttagaaagtggttatcaatatttaa
aaggtcaatacgactatatcactaaaaaatacaatgatgcgaaatactat
acaaaaatgtattcaaatcataagtctacaattgatcagtctgtattagc
tatattaggtaaaactggatctagcgcatatatcaagccattaaatatcg
aagaaaattcaaacgtattttacaaagcttatgcaaaaacaagaaacttt
gctacagaaaagcattaacacaggaaaagtattatacacattatatcaaaa -continued
ccctactgtagttaaatctgctttcactgcaattgaaacagcaaatacag taaaaaatgcaataagcaatctttctctctcttcaaataa The protein sequence translated from SEQ ID NO 35 is designated SEQ ID NO: 36 and is shown below:

SEQ ID NO: 36
MKTKYTAKLLIGAATISLATFISQGNAHASEQTTGLAPAQPVNFDSINVT

PDQKTFYQVLHMEGISEDQREQYLKQLHEDPSSAQNVFSESIKDAIHPER

RVAQQNAFYSVLHNDDLSEEQRDAYIGRIKEDPDQSQEVFVESLNVAPKA

ESHEDRLIELQNKNLMEANEALKALQQEDSIQNRRAAQRAVNKLTPDSAN

AFQKELDQINAPRDAKIKADAEAKKQAPEVSAPQIEDAPTTEVAPSPKQD

MPKVDKKEEDKVESDTEVKEVPKADTEKNPQSKDTSKTEQAKETPKVEQS

PKTEKAEEAPKAETPQNGNKAQTEEAKPEVKDNVKNTPSAPVLPETGKAT

TSTLESYWNSFKDSVNKGYTYIKQSLESGYQYLKGQYDYITKKYNDAKYY

TKMYSNHKSTIDQSVLAILGKTGSSAYIKPLNIEENSNVFYKAYAKTRNF

ATESINTGKVLYTLYQNPTVVKSAFTAIETANTVKNAISNLFSLFK

An active domain from the protein of SEQ ID NO: 6 is designated SEQ ID NO: 37

SEQ ID NO: 37
NEDVTETTGRNSVTTQASEQHLQVEAVPQEGNNVNVSSVKVPTNTATQAQ

EDVASVSDVKAHADDALQVQESSHTDGVSSEFKQETAYANPQTAETVKPN

SEAVHQSEYEDKQKPVSSSRKEDETMLQQQQVEAKNVVSAEEVSKEENTQ

VMQSPQDVEQHVGGKDISNEVVVDRSDIKGFNSETTIRPHQGQGGRLNYQ

LKFPSNVKPGDQFTIKLSDNINTHGVSVERTAPRIMAKNTEGATDVIAEG

LVLEDGKTIVYTFKDYVNGKQNLTAELSVSYFVSPEKVLTTGTQTFTTMI

GNHSTQSNIDVYYDNSHYVDGRISQVNKKEAKFQQIAYINPNGYLNGRGT

IAVNGEVVSGTTKDLMQPTVRVYQYKGQGVPPESITIDPNMWEEISINDT

MVRKYDGGYSLNLDTSKNQKYAIYYEGAYDAQADTLLYRTYIDSLNSYYP

FSYQKMNGVKFYENSASGSGELKPKPPEQPKPEPEIQADVVDIIEDSHVI

DIGW

An spsl gene fragment corresponding to A domain is designated SEQ ID NO: 38, which encodes the protein of SEQ ID NO: 37

SEQ ID NO: 38
AATGAAGATGTCACTGAAACAACTGGGAGAAATTCAGTGACAACGCAAGC

TTCTGAGCAACATTTGCAAGTGGAAGCAGTACCTCAAGAAGGCAATAATG

TAAATGTATCCTCTGTAAAAGTACCTACGAATACGGCAACGCAAGCACAA

GAAGATGTTGCAAGTGTATCCGATGTTAAAGCACATGCTGATGATGCATT

ACAAGTACAAGAAAGTAGTCATACTGATGGTGTTTCTTCAGAATTCAAGC

AGGAGACAGCTTATGCGAATCCTCAAACAGCTGAGACAGTTAAACCTAAT

AGTGAAGCAGTGCATCAGTCTGAATACGAGGATAAGCAAAAACCCGTATC

ATCTAGCCGCAAAGAAGATGAGACTATGCTTCAGCAGCAACAAGTTGAAG

CCAAAAATGTTGTGAGTGCGGAGGAAGTGTCTAAAGAAGAAAATACTCAA

GTGATGCAATCCCCTCAAGACGTTGAACAACATGTAGGTGGTAAAGATAT

CTCTAATGAGGTTGTAGTGGATAGGAGTGATATCAAAGGATTTAACAGCG

AAACTACTATTCGACCTCATCAGGGACAAGGTGGTAGGTTGAATTATCAA

TTAAAGTTTCCTAGCAATGTAAAGCCAGGCGATCAGTTTACTATAAAATT

ATCTGACAATATCAATACACATGGTGTTTCTGTTGAAAGAACCGCACCGA

GAATCATGGCTAAAAATACTGAAGGTGCGACGGATGTAATTGCTGAAGGT

CTAGTGTTGGAAGATGGTAAAACCATCGTATATACATTTAAAGACTATGT

AAATGGCAAGCAAAATTTGACTGCTGAGTTATCAGTGAGCTATTTCGTAA

GTCCGGAAAAAGTCTTGACTACTGGGACACAAACATTCACGACGATGATC

GGTAATCATTCAACGCAATCCAATATTGACGTTTATTATGATAATAGTCA

TTATGTAGATGGACGTATTTCGCAAGTGAACAAAAAAGAAGCTAAATTTC

AACAAATAGCATACATTAACCCTAATGGCTATTTAAATGGCAGGGGGACA

ATTGCAGTTAATGGTGAAGTGGTCAGTGGTACGACTAAAGACTTAATGCA

ACCTACAGTGCGTGTATATCAATATAAAGGACAAGGTGTTCCTCCTGAAA

GTATTACTATAGACCCTAATATGTGGGAAGAAATCAGCATAAACGATACT

ATGGTAAGAAAATATGATGGTGGCTATAGCTTGAATCTGGATACCAGCAA

GAATCAAAAATATGCCATCTATTATGAAGGGGCATATGATGCGCAAGCTG

ACACACTGTTGTATAGAACATATATACAGTCATTAAACAGTTACTATCCG

TTCAGTTACCAAAAAATGAACGGTGTGAAGTTTTACGAAAACAGTGCGAG

TGGAAGCGGTGAGTTGAAACCGAAACCACCTGAACAACCAAAACCAGAAC

CTGAAATTCAAGCTGATGTAGTAGATATTATTGAAGATAGCCATGTGATT

GATATAGGATGG

Since each of the abovementioned proteins/nucleic acid sequences is derived from *Staphylococcus pseudintermedius*, the inventors have designated these (and the corresponding protein sequences) *Staphylococcus pseudintermedius* surface genes/nucleic acids/proteins (Sps). For simplicity, the bulk of this specification will use the term "Sps" or "Sps genes" or "Sps nucleic acids" which are intended to encompass all of the nucleic acid sequences described above (i.e. SEQ ID NOS: 1, 3, 5, 7, 9, 11, 13, 15, 17, 19, 21, 23, 25, 27, 29, 31, 33 and 35.

Furthermore, in addition to encompassing the entire or complete gene/nucleic sequences listed above, it is to be understood that the designation "Sps" also encompasses fragments, portions, mutants, derivatives and/or homologoues/orthologues of any of these genes.

In addition, the term "Sps" or "Sps proteins" encompasses the proteinaceous products of the Sps genes/nucleic acids or fragments, portions, analogues, variants or derivatives thereof (for example short peptide fragments). In particular, the term "Sps proteins" encompasses the sequences given as SEQ ID NOS: 2, 4, 6, 8, 10, 12, 14, 16, 18, 20, 22, 24, 26, 28, 30, 32, 34, 36 and 37 above.

Typically, the gene/nucleic acid fragments, portions, mutants, variants, derivatives and/or homologues/orthologues of the invention are functional or active—that is, they retain the function and/or activity of the wild type or native Sps genes/nucleic acids. Advantageously, fragments, portions, mutants, variants, derivatives and/or homologues/orthologues of any of the Sps genes/nucleic acids provided by this invention, encode proteins (or peptides, peptide fragments) retaining the ability to bind to or associate with extracellular matrix proteins such as, for example, fibrinogen, fibronectin and/or collagen. In other embodiments, the proteins and/or peptides encoded by the nucleic acid sequences described herein are immunogenic or antigenic. Furthermore, fragments, portions, variants or derivatives of any of the proteins encoded by the nucleic acid sequences described herein may also retain the immunogenicity and/or antigenicity of a corresponding wild type Sps protein (for example the proteins listed above). Where the invention relates to immunogenic compositions and/or vaccines, the use of proteins and/or peptides which are immunogenic (or antigenic) is important.

The term "mutants" may encompass naturally occurring mutants or those artificially created by the introduction of one or more nucleic acid additions, deletions, substitutions or inversions.

Homologous or identical genes, nucleic acid or protein sequences may exhibit as little as approximately 20 or 30% sequence homology or identity to certain reference sequences, however, in other cases, homologous or identical genes/nucleic acids and/or proteins may exhibit at least 40, 50, 60, 65, 70, 75, 80, 85, 90, 91, 92, 93, 94, 95, 96, 97, 98, 99% homology or identity to the various sequences given above as SEQ ID NOS: 1-36 or 37-38. It should be understood that mutant, variant, derivative and/or orthologuous sequences may exhibit similar levels of homology/identity to each other and/or to the Sps genes/nucleic acids shown as SEQ ID NOS 1, 3, 5, 7, 9, 11, 13, 15, 17, 19, 21, 23, 25, 27, 29, 31, 33, 35 and/or 38 above.

One of skill in this field will readily understand that genes/nucleic acids homologous/identical to the Sps genes detailed herein may be found in other bacterial species. As such, homologous genes from other species may be included within the scope of this invention. Using the various nucleic acid and amino acid sequences described herein, one of skill in the art could readily identify related sequences in other microbial (particularly bacterial) species. For example, nucleic acid obtained from a particular bacterial species may be probed using the probes derived from the sequences of this invention, to identify homologous or closely related sequences.

It should be understood that Sps nucleic acid sequences of this invention may be single-stranded or double-stranded and a single-stranded nucleic acid molecule may include a polynucleotide fragment having a nucleotide sequence that is complementary to a nucleotide sequence that encodes a Sps protein or fragment thereof. As used herein, the term "complementary" refers to the ability of two single stranded polynucleotide fragments to base pair with each other.

A single-stranded nucleic acid molecule of the invention may further include a polynucleotide fragment having a nucleotide sequence that is substantially complementary to a nucleotide sequence that encodes a Sps protein or fragment thereof according to the invention, or to the complement of the nucleotide sequence that encodes said Sps protein or fragment thereof. Substantially complementary polynucleotide fragments can include at least one base pair mismatch, such that at least one nucleotide present on a first polynucleotide fragment will not base pair to at least one nucleotide present on a second polynucleotide fragment, however the two polynucleotide fragments will still have the capacity to hybridize. The present invention therefore encompasses polynucleotide fragments which are substantially complementary. Two polynucleotide fragments are substantially complementary if they hybridize under hybridization conditions exemplified by 2×SSC(SSC: 150 mM NaCl, 15 mM trisodium citrate, pH 7.6) at 55° C. Substantially complementary polynucleotide fragments for purposes of the present invention may preferably share at least about 60, 65, 70, 75, 80 or 85% nucleotide identity, preferably at least about 90%, 95% or 99% nucleotide identity. Locations and levels of nucleotide sequence identity between two nucleotide sequences can be readily determined using, for example, CLUSTALW multiple sequence alignment software.

In addition, it should be understood that the present invention also relates to the products of the genes/nucleic acids encompassed by this invention and in particular to proteins or peptides homologous/identical to those having sequences provided by SEQ ID NOS: 2, 4, 6, 8, 10, 12, 14, 16, 18, 20, 22, 24, 26, 28, 30, 32, 34, 36 and 37. Furthermore, fragments, portions, analogues, variants, derivatives of any of these or homologous and/or identical or modified proteins are also within the scope of this invention. Typically, fragments, portions, derivatives, variants and/or homologous or modified proteins or peptides of the invention are functional or active—that is they retain the function of a wild type Sps protein. In certain embodiments fragments, portions, derivatives or variants of, and/or modified sequences or sequences with homology or identity to, the amino acid sequences provided by this invention, retain the ability to bind to or associate with extracellular matrix proteins such as, for example, fibrinogen, fibronectin and/or collagen.

Additionally or alternatively, fragments, portions, mutants, variants, derivatives and/or homologues/orthologues of the Sps genes provided by this invention, may encode proteins (or peptide fragments) that are antigenically similar or identical to the proteins encoded by the genes described herein. Similarly, fragments, portions, derivatives and/or variants of and/or modified sequences or sequences with homology or identity to, the amino acid sequences provided by this invention are also antigenically similar or identical to the proteins encoded by the genes described herein. It should be understood that the term "antigenically similar or identical" may encompass proteins or peptides eliciting an immune response similar or identical to the immune response elicited by any of the Sps proteins described herein. In certain embodiments fragments, portions, derivatives and/or variants of and/or modified sequences or sequences with homology or identity to, the amino acid sequences described herein, elicit immune responses which protect against *Staphylococcus pseudinrermedius* infection and/or prevent, reduce or neutralise *Staphylococcus pseudintermedius* cell/tissue adhesion and/or colonisation. One of skill will readily understand that the antigenicity of a polypeptide can be evaluated in vitro by, for example, performing a Western blot on the purified polypeptide (for example, an affinity purified polypeptide) using polyclonal antisera from an animal, such as a rabbit that was vaccinated with at least an antigenic portion of an Sps protein of the present invention.

One of skill in this field will readily understand that for the various nucleic acid sequences and polypeptides described herein, natural variations due to, for example, polymorphisms, may exist between Sps genes and proteins isolated from different microbial species and even different strains of the same species. Gene or protein variants may manifest as proteins and/or genes that exhibit one or more amino acid/nucleic acid substitutions, additions, deletions and/or inversions relative to a reference sequence (for example any of the sequences described above). As such, it is to be understood that all such natural variants, especially those that are functional or display the desired activity, are to be included within the scope of this invention.

In another embodiment, the invention relates to derivatives of any of the Sps sequences described herein. The term "derivatives" may encompass Sps genes or peptide sequences which, relative to those described herein, comprise one or more amino acid substitutions, deletions, additions and/or inversions.

Additionally, or alternatively, analogues of the various peptides described herein may be produced by introducing one or more conservative amino acid substitutions into the primary sequence. One of skill in this field will understand that the term "conservative substitution" is intended to embrace the act of replacing one or more amino acids of a protein or peptide with an alternate amino acid with similar properties and which does not substantially alter the physcio-chemical properties and/or structure or function of the native (or wild type) protein. Analogues of this type are also encompassed with the scope of this invention. In one embodiment, substitute amino acids may be selected from other members of the class to which the amino acid belongs. For example, nonpolar (hydrophobic) amino acids include alanine, leucine, isoleucine, valine, praline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Examples of preferred conservative substitutions include Lys for Arg and vice versa to maintain a positive charge; Glu for Asp and vice versa to maintain a negative charge; Ser for Thr so that a free —OH is maintained; and Gln for Asn to maintain a free $NH_2$.

As is well known in the art, the degeneracy of the genetic code permits substitution of one or more bases in a codon without changing the primary amino acid sequence. Consequently, although the sequences described in this application are known to encode the Sps proteins described herein, the degeneracy of the code may be exploited to yield variant nucleic acid sequences which encode the same primary amino acid sequences.

The present invention may further provide modified Sps proteins. For example, a "modified" Sps protein may be chemically and/or enzymatically derivatised at one or more constituent amino acids, including side chain modifications, backbone modifications, and N- and C-terminal modifications including acetylation, hydroxylation, methylation, amidation, phosphorylation and the attachment of carbohydrate or lipid moieties, cofactors, and the like.

One of skill in this field will appreciate that the amino acid and/or nucleic acid sequences described herein may be used to generate recombinant Sps genes/proteins and as such, the present invention further contemplates methods of generating and/or expressing recombinant Sps genes and/or proteins, and products for use in such methods. Accordingly, in addition to providing substantially purified or isolated recombinant Sps sequences, a second aspect of this invention provides DNA constructs comprising a replicable expression vector and nucleic acid encoding one or more of the Sps protein(s) described herein.

Expression vectors for the production of the molecules of the invention include plasmids, phagemids, viruses, bacteriophages, integratable DNA fragments, and other vehicles, which enable the integration of DNA fragments into the genome of the host. Expression vectors are typically self-replicating DNA or RNA constructs containing the desired gene or its fragments, and operably linked genetic control elements that are recognised in a suitable host cell to effect expression of the desired genes.

Generally, the genetic control elements can include a prokaryotic promoter system or a eukaryotic promoter expression control system. Such systems typically include a transcriptional promoter, an optional operator to control the onset of transcription, transcription enhancers to elevate the level of RNA expression, a sequence that encodes a suitable ribosome binding site, RNA splice junctions, sequences that terminate transcription and translation and so forth. Expression vectors usually contain an origin of replication that allows the vector to replicate independently of the host cell.

A vector may additionally include appropriate restriction sites, antibiotic resistance or other markers for selection of vector containing cells.

Plasmids are the most commonly used form of vector but other forms of vectors which serve an equivalent function and which are, or become, known in the art are suitable for use herein. See, e.g., Pouwels et al. Cloning Vectors: a Laboratory Manual (1985 and supplements), Elsevier, N.Y.; and Rodriquez, et al. (ads.) Vectors: a Survey of Molecular Cloning Vectors and their Uses, Buttersworth, Boston, Mass. (1988).

In general, such vectors may contain specific genes, which are capable of providing phenotypic selection in transformed cells. The use of prokaryotic and eukaryotic viral expression vectors to express the nucleic acid sequences coding for the recombinant proteins of the present invention are also contemplated.

The vector is introduced into a host cell by methods known to those of skill in the art. Introduction of the vector into the host cell can be accomplished by any method that introduces the construct into the cell, including, for example, electroporation, heat shock, chemical compounds such, for example, calcium phosphate, stronitium phosphate, microinjection techniques and/or gene guns. See, e.g., Current Protocols in Molecular Biology, Ausuble, F. M., ea., John Wiley & Sons, N.Y. (1989).

Another aspect relates to a host cell transformed with any one of the nucleic acid constructs of the present invention. Suitable host cells include prokaryote cells, lower eukaryotic and higher eukaryotic cells. Prokaryotes include Gram negative and Gram positive organisms, e.g., *E. coli* and *B. subtilis*. Lower eukaryotes include yeast, *S. cerevisiae* and *Pichia*, and species of the genus *Diclyostelium*.

"Host cell" as used herein refers to cell which can be recombinantly transformed with vectors constructed using recombinant DNA techniques.

A drug resistance or other selectable marker is intended in part to facilitate the selection of the transformants. Additionally, the presence of a selectable marker, such as a drug resistance marker may be of use in keeping contaminating microorganisms from multiplying in the culture medium. Such a pure culture of the transformed host cells would be obtained by culturing the cells under conditions which require the induced phenotype for survival.

PCR techniques may be exploited to selectively obtain Sps gene sequences from samples of Staphylococcal DNA. These amplified sequences may be introduced into any of the vectors described above. In one embodiment, the vector may further comprise a nucleotide sequence of a tag or label to assist in protein purification procedures.

Techniques used to purify recombinant proteins generated in this way are known and, where the recombinant protein is tagged or labelled, these may include the use of, for example, affinity chromatography techniques.

In view of the above, a fourth aspect of this invention provides a process for the production of recombinant Sps protein(s) or peptide(s) of the invention, said process comprising the steps of (a) transforming a host cell with the nucleotide sequence of the invention or transfecting a host cell with a nucleic acid construct of the invention; (b) culturing the cells obtained in (a) under conditions in which expression of the protein takes place; and (c) isolating the expressed recombinant protein or peptide from the cell culture or/and the culture supernatant.

The polypeptide may be partially purified from the host and where the polypeptide is secreted from the host cell, the cells may be separated from the media by centrifugation, the cells being pelleted. Alternatively, the polypeptide may be partially purified from this supernatant, for example using affinity chromatography.

A fifth aspect of this invention provides monoclonal or polyclonal antibodies, whether derived from rodents, mammals, avians, ungulates, or other organisms, that bind to the Sps proteins described herein. Production and isolation of monoclonal and polyclonal antibodies to a selected polypeptide sequence is routine in the art see for example "Basic methods in Antibody production and characterisation" Howard & Bethell, 2000, Taylor & Francis Ltd. Such antibodies may be used in diagnostic procedures, as well as for passive immunisation.

*Staphylococcus pseudintermedius* is known to cause cutaneous inflammatory diseases in a variety of animals. One such cutaneous inflammatory disease is canine pyoderma which is a major cause or morbidity in dogs. Pydoderma associated with *Staphylococcus pseudintermedius* infection is common among dogs and is often associated with puritis, alopecia, erythema and swelling. At present, the treatment of this infection is difficult, requiring the use of aggressive, systemically administered antibiotics. The present inventors have discovered that Sps genes (and their protein products) play a role in *Staphylococcus pseudintermedius* colonisation and pathogenesis. As such, the Sps genes and proteins described herein may find application in the treatment and/or prevention of cutaneous disorders such as canine pyoderma.

Accordingly, a sixth aspect of this invention provides an Sps protein or gene as substantially defined above, for use in raising an immune response in an organism. The proteins and genes described herein may find particular application as a vaccine, but could also be used to obtain an immune serum potentially useful in passive vaccination techniques.

Advantageously, the invention may provide a vaccine for use in preventing or controlling disease in canine species caused or contributed to by *Staphylococcus* pseudintermedius. In other embodiments, the vaccines provided by this invention may be used to protect against the development of infections caused or contributed to by *Staphylococcus pseudintermedius*. In other embodiments, the vaccines may be used to protect against instances of canine pyoderma.

In one embodiment, the vaccine may be a polypeptide and/or polynucleotide vaccine.

A polynucleotide vaccine may comprise a polynucleotide fragment, preferably a DNA fragment, having a nucleotide sequence encoding an antigenic polypeptide comprising at least an antigenic portion any one or more of the Sps proteins described herein. Vaccines of this type may otherwise be referred to as "DNA vaccines"—such vaccines may be introduced to host cells (such as mammalian, for example, canine cells) where they express antigens which elicit immune responses.

A polypeptide or protein vaccine may comprises one or more of the Sps proteins (or antigenic fragments or portions) described herein. One of skill will appreciate that the one or more Sps protein(s) may be naturally occurring and isolated from *Staphylococcus* pseudintermedius, or recombinant.

A protein vaccine may be administered by any suitable route. Advantageously, a protein vaccine may be administered orally (by ingestion), topically or by direct injection— preferably intraperitoneal or intramuscular injection. A protein subunit vaccine formulated for oral administration can contain the polypeptide encapsulated in for example, a biodegradable polymer as described hereinafter.

In view of the above, the invention further provides a method of immunising a dog against *Staphylococcus pseudintermedius*, said method comprising administering to the dog a DNA or protein vaccine of the invention.

Conveniently, the protein vaccines described herein may further include or comprise one or more adjuvant(s). Further, one or more booster vaccinations are preferably administered at time periods subsequent to the initial administration to create a higher level of immune response in the animal.

In yet another aspect, the vaccine of the invention may comprise a fusion protein comprising a carrier polypeptide and one or more Sps protein(s) of the invention. The Sps protein(s) for use in this aspect of the invention can itself be antigenic or non-antigenic; in embodiments wherein the protein is non-antigenic, the carrier polypeptide is antigenic, stimulating the immune system to react to the fusion protein thereby generating an immune response in an organism— such as, for example a canine immune response to *Staphylococcus pseudintermedius*. A non-antigenic protein thus functions as a hapten. An example of an antigenic carrier polypeptide is keyhole limpet hemocyanim (KLH). Conventional fusion constructs between carriers such as glutathione sulfotransferase (GST) and said Sps protein(s) of the invention are also included as protein vaccines according to the invention, as are fusions of the Sps protein(s) and an affinity tag such as a polyhistidine sequence. A fusion construct may be preferred for use as a protein vaccine when the antigenic Sps analog, fragment, or modification thereof is small.

In a seventh aspect, the present invention provides a method for immunising dogs against *Staphylococcus pseudintermedius*, said method comprising administering to the dog a vaccine of the invention.

A polynucleotide vaccine may further comprises a promoter, such as the CMV promoter, operably linked to the coding sequence for the Sps polypeptide or antigenic fragment thereof (e.g., U.S. Pat. No. 5,780,44, Davis). The polynucleotide may be cloned within a vector such as a plasmid. There are numerous plasmids known to those of ordinary skill in the art useful for the production of polynucleotide vaccines.

Other possible additions to the polynucleotide vaccine constructs include nucleotide sequences encoding cytokines, such as granulocyte macrophage colony stimulating factor (GM-CSF), interleukin-12 (IL-12) and co-stimulatory molecules such B7-1, B7-2, CD40. The cytokines can be used in various combinations to fine-tune the response of the animal's immune system, including both antibody and cytotoxic T lymphocyte responses, to bring out the specific level of response needed to affect the animal's reproductive system. A polynucleotide vaccine of the invention can also encode a fusion product containing the antigenic polypeptide and a molecule, such as CTLA-4, that directs the fusion product to antigen-presenting cells inside the host.

Plasmid DNA can also be delivered using attenuated bacteria as delivery system, a method that is suitable for DNA vaccines that are administered orally. Bacteria are transformed with an independently replicating plasmid, which becomes released into the host cell cytoplasm following the death of the attenuated bacterium in the host cell. An alternative approach to delivering the polynucleotide to an animal involves the use of a viral or bacterial vector. Examples of suitable viral vectors include adenovirus, polio virus, pox viruses such as vaccinia, canary pox, and fowl pox, herpes viruses, including catfish herpes virus, adenovirus-associated vector, retroviruses and bacteriophage. Exemplary bacterial vectors include attenuated forms of *Salmonella, Shigella, Edwardsiella ictaluri,* and *Yersinia ruckeri.* Preferably, the polynucleotide is a vector, such as a plasmid, that is capable of autologous expression of the nucleotide sequence encoding said Sps protein or fragment thereof.

In one embodiment, the vaccine may be a DNA vaccine comprising a DNA fragment having a nucleotide sequence that encodes a polypeptide having an amino acid sequence homologous or identic to a sequence selected from the group consisting of SEQ ID NOS: 2, 4, 6, 8, 10, 12, 14, 16, 18, 20, 22, 24, 26, 28, 30, 32, 34, 36 or 37 or an antigenic analog, fragment, or modified version thereof.

Polynucleotide-based immunisation induces an immune response to an antigen expressed in vivo from a heterologous polynucleotide fragment introduced into a cell. DNA vaccine may be particularly useful as the heterologous nucleic acid expression may continue for a length of time sufficient to induce a relatively strong and sustained immune response without the need for subsequent "booster" vaccinations, as may be required when using protein based vaccines. A polynucleotide vaccine comprising a polynucleotide fragment having a nucleotide sequence encoding said Sps can be administered to dog (or rather to a particular tissue or cells thereof) using biolistic bombardment, ingestion or direct injection, as described for example, in U.S. Pat. No. 5,780,448 (Davis), preferably intraperitoneal or intramuscular injection. A preferred method of administration is biolistic bombardment, as with a "gene gun". A polynucleotide vaccine formulated for oral administration preferably contains DNA encapsulated in a biodegradable polymer. Examples of a suitable biodegradable polymer include chitosan and homo- or co-polyers of polylactic acid and polyglycolic acid. Accordingly, the present invention further provides a method for immunising dogs against *Staphylococcus pseudintermedius* by administering to the dog a polynucleotide vaccine of the invention, preferably a DNA vaccine.

Other methods of administering nucleic acid vaccines of the type described herein may include, for example, use of the technology described in WO02/076498.

The amount of protein/polynucleotide vaccine to be administered to an animal depends on the type and size of animal, the condition being treated, and the nature of the protein/polynucleotide, and can be readily determined by one of skill in the art. In some applications, one or more booster administrations of the protein/polynucleotide vaccine at time periods subsequent to the initial administration are useful to create a higher level of immune response in the animal.

In one embodiment of the vaccine of the invention and/or Sps proteins described herein (including antigenic fragments, analogs or modified version thereof) may be linked, for example, at its carboxy-terminus, to a further component. The further component may serve to facilitate uptake of the Sps protein, or enhance its immunogenicity/processing.

The immune-stimulating compositions of the invention may be optionally mixed with excipients or diluents that are pharmaceutically acceptable as carriers and compatible with the active component(s). The term "pharmaceutically acceptable carrier" refers to a carder(s) that is "acceptable" in the sense of being compatible with the other ingredients of a composition and not deleterious to the recipient thereof. Suitable excipients are well known to the person skilled in the art. Examples include; water, saline (e.g. 0.85% sodium chloride; see Ph.Eur. monograph 2001:0062), buffered saline, fish oil with an emulsifier (e.g. a lecithin, Bolec MT), inactivant (e.g. formaldehyde; see Ph.Eur. monograph 1997:0193), mineral oils, such as light mineral oils, alhydrogel, aluminium hydroxide. Where used herein, the term "oil adjuvant" to embraces both mineral oils and synthetic oils. A preferred adjuvant is Montanide ISA 711 (SeppicQuai D'Orsay, 75321 Paris, France) which is a manide oleate in an oil suspension. In addition, if desired, the immune-stimulating composition (including vaccine) may contain minor amounts of auxiliary substances such as wetting or emulsifying agents, pH buffering agents, and/or adjuvants which enhance the effectiveness of the immune-stimulating composition.

A vaccine composition may be administered as a course of a number of discrete doses over a period of time. For example it may be administered over a period of around 2-21 days.

Vaccination may be repeated at daily, twice-weekly, weekly or monthly intervals. For example a boost vaccination may be administered after the initial dose. For example a boost may be administered at around 4-14 weeks after the vaccination. The initial vaccination and any boost may be carried out using the same or different modes of administration. For example, the initial may be by injection and the boost may be by oral administration. An example regime includes a first vaccination by injection, followed by a course of orally administered boost vaccine, or a booster prior to an expected outbreak. However, it will be appreciated that any suitable route of administration(s) and/or regime(s) may be employed.

Additionally, knowledge of the Sps protein nucleotide and amino acid sequences set forth herein opens up new possibilities for detecting, diagnosing and characterising *Staphylococcus pseudintermedius* in canine populations. For example, an oligonucleotide probe or primer based on a conserved region of one or more of the Sps proteins described herein, may be used to detect the presence of the Sps protein in or on a canine host.

Vaccines may contain one or more of the Sps proteins/nucleic acids/genes described herein (i.e. those shown as SEQ ID NOS: 1-38). In one embodiment, the vaccine may comprise a cocktail of Sps proteins/peptides and or nucleic acids. Typically, a cocktail may comprise 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38 Sps nucleic acid and/or protein/peptide components (for example (2 or more) components having sequences homologous or identical to any of SEQ ID NOS: 1-38).

Furthermore, the vaccines may contain bacterial antigens used to control other diseases, for example diseases caused by other Staphylococcal species and/or antigens to treat, prevent or control diseases and/or conditions with other aetiologies or caused or contributed to by other pathogens. As such, the vaccine compositions described herein may find application in multivalent vaccines including antigens against other canine diseases.

In addition to vaccines and/or immunogenic compositions comprising one or more of the Sps proteins described herein, the present invention further provides compounds for treating infections caused or contributed to by *Staphylococcus pseudintermedius* or compounds for the preparation of medicaments for treating the same.

In one embodiment, the compound may be a small organic molecule, antibody, peptide or carbohydrate which antagonises the interaction between the Sps protein and its ligand (an extracellular matrix (ECM) protein). For example, the compound may be a synthetic peptide comprising or based on, the sequence of an ECM protein known to interact with a particular Sps protein, or the sequence of a protein given above which may interfere with binding between the wild type *S. psedintermedius* protein and its ligand. Additionally or alternatively, binding agents, such as for example, antibodies with specificity or affinity for one or more Sps protein ligands, may also be used to antagonise the Sps/ligand interaction. Therapeutic approaches of this type may prevent *Staphylococcus pseudintermedius* colonising or binding/adhering to cells.

In view of the above, the invention may relate to methods of treating infections caused or contributed to by *Staphylococcus pseudintermedius*, said method comprising administering to an animal a therapeutically effective amount of a compound which antagonises Sps/ligand interactions.

In a further aspect, the present invention provides pharmaceutical compositions comprising a compound which antagonises Sps/ligand interactions together with a pharmaceutical excipient, carrier or diluent.

One of skill will appreciate that the vaccines, methods, uses or medicaments comprising any of the Sps genes/nucleic acids and/or proteins and/or antagonistic compounds (for example Sps protein/nucleic acid fragments and/or antibodies) described herein may be combined with one or more other compounds for treating one or more other conditions—in particular one or more other skin conditions. Said other skin condition may be, for example, atopic dermatitis.

In a further aspect, the present invention provides methods of diagnosing infections, diseases and/or conditions caused or contributed to by *S. pseudintermedius*, said methods comprising the steps of identifying in a sample provided by a subject suspected of suffering from an infection, disease and/or conditions *S. pseudintermedius* caused or contributed to by *S. pseudintermedius*, a level of a protein, peptide or nucleic acid (for example a gene) encoded by a sequence provided by SEQ ID NOS: 1-38 or a fragment, portion, mutant, derivative and/or homologoue/orthologue thereof.

It should be understood that all methods of diagnosis or detection described herein, may include an optional step in which the results are compared with the results of a control sample, which does not comprise sequences derived from *S. pseudintermedius*, in particular sequences corresponding to those provided as SEQ ID NOS: 1-38 disclosed herein.

The term "sample" may be taken to mean any sample comprising protein and/or nucleic acid. For example, a "sample" may comprise a bodily fluids such as whole blood, plasma, serum, saliva, sweat and/or semen. In other instances "samples" such as tissue biopsies and/or scrapings may be used. In particular, cutaneous (i.e. skin) tissue biopsies and/or scrapings may be used. Advantageously such biopsies may comprise cells obtained from lesions suspected of resulting from or being associated with a *S. pseudintermedius*. Specifically, a biopsy, tissue sample or scraping may comprise cells derived from lesions exhibiting pathology characteristic of the *S. pseudintermedius* disease, pyoderma (particularly caninine pyoderma).

In addition, a sample may comprise a tissue or gland secretion and washing protocols may be used to obtain samples of fluid secreted into or onto various tissues, including, for example, the skin. One of skill in this field will appreciate that the samples described above may yield or comprise quantities of nucleic acid (i.e. DNA or RNA) encoding all or part of the various proteins described herein as well as quantities of proteins or peptides (or fragments thereof) encoded thereby. In one embodiment, the sample may comprise quantities of nucleic acid/peptide having or comprising the sequences given as SEQ ID NOS: 1-38.

One of skill in the art will be familiar with the techniques that may be used to identify levels of certain nucleic acid sequences and/or proteins, such as, for example, levels of the sequences given as SEQ ID NOS: 1-38 described herein (or a fragment, portion, mutant, derivative and/or homologoue/orthologue thereof).

For example, PCR based techniques may be used to detect levels of gene expression or gene quantity in a sample. Useful techniques may include, for example, polymerase chain reaction (PCR) or reverse transcriptase (RT)-PCR based techniques in combination with real-time PCR (otherwise known as quantitative PCR).

Additionally, or alternatively, a level of gene/protein expression may be identified by way of microarray analysis. Such a method would involve the use of a DNA microarray which comprises nucleic acid derived from one or more of the nucleic acid sequences described herein (for example SEQ ID NOS: 1, 3, 5, 7, 9, 11, 13, 15, 17, 19, 21, 23, 25, 27, 29, 31, 33, 35, 38). To identify a level of gene expression, one of skill in the art may extract nucleic acid, preferably mRNA, from a sample and subject it to an amplification protocol such as, for example RT-PCR to generate cDNA. Preferably, primers specific for a certain mRNA sequence—in this case a *S. pseudintermedius* sequence comprised with any of, for example, SEQ ID NOS: 1, 3, 5, 7, 9, 11, 13, 15, 17, 19, 21, 23, 25, 27, 29, 31, 33, 35, 38.

The amplified cDNA may be subjected to a further amplification step, optionally in the presence of labelled nucleotides (as described above). Thereafter, the optionally labelled amplified cDNA may be contacted with the microarray under conditions which permit binding with the DNA of the microarray. In this way, it may be possible to identify a level of *S. pseudintermedius* gene expression.

Further information regarding the PCR based techniques described herein may be found in, for example, PCR Primer: A Laboratory Manual, Second Edition Edited by Carl W. Dieffenbach & Gabriela S. Dveksler: Cold Spring Harbour Laboratory Press and Molecular Cloning: A Laboratory Manual by Joseph Sambrook & David Russell: Cold Spring Harbour Laboratory Press.

In addition, other techniques such as deep sequencing and/or pyrosequencing may be used to detect cSCC sequences in any of the samples described above. Further information on these techniques may be found in "Applications of next-generation sequencing technologies in functional genomics", Olena Morozovaa and Marco A. Marra, Genomics Volume 92, Issue 5, November 2008, Pages 255-264 and "Pyrosequencing sheds light on DNA sequencing", Ronaghi, Genome Research, Vol. 11, 2001, pages 3-11.

In addition to the molecular detection methods described above, one of skill will also appreciate that immunological detection techniques such as, for example, enzyme-linked immunosorbent assays (ELISAs) may be used to identify levels of *S. pseudintermedius* proteins in samples. In other embodiments, ELISPOT, dot blot and/or Western blot techniques may also be used. In this way, samples provided by subjects suffering from *S. pseudintermedius* related diseases and/or infections (for example canine subjects suffereing from canine pyoderma), may be probed for levels of one or more *S. pseudintermedius* proteins, particularly those encoded by SEQ ID NOS: 2, 4, 6, 8, 10, 12, 14, 16, 18, 20, 22, 24, 26, 28, 30, 32, 34, 36, or 37 so as to detect the presence of such proteins in a sample which may indicate a *S. pseudintermedius* infection.

Immunological detection techniques, may require the use of a substrate to which an antibody and/or antigen may be bound, conjugated or otherwise immobilised.

Suitable substrates may comprise, for example, glass, nitrocellulose, paper, agarose and/or plastic. A substrate which comprises, for example, a plastic material, may take the form of a microtitre plate.

Further information regarding ELISA procedures and protocols relating to the other immunological techniques described herein may be found in Using Antibodies: A Laboratory Manual by Harlow & Lane (CSHLP: 1999) and Antibodies: A Laboratory Manual by Harlow & Lane (CSHLP: 1988).

The present invention also extends to kits comprising reagents and compositions suitable for diagnosing, detecting or evaluating possible *S. pseudintermedius* infections, diseases and/or conditions. Kits according to this invention may be used to identify and/or detect levels of *S. pseudintermedius* gene(s)/*S. pseudintermedius* protein(s) in samples. Depending on whether or not the kits are intended to be used to identify levels of *S. pseudintermedius* genes and/or *S. pseudintermedius* proteins in samples, the kits may comprise substrates having *S. pseudintermedius* proteins or agents capable of binding *S. pseudintermedius* proteins, bound thereto. In addition, the kits may comprise agents capable of binding *S. pseudintermedius* proteins—particularly where the kit is to be used to identify levels of one or more *S. pseudintermedius* proteins in samples. In other embodiments, the kit may comprise polyclonal antibodies or monoclonal antibodies which exhibit specificity and/or selectivity for one or more *S. pseudintermedius* proteins. Antibodies for inclusion in the kits provided by this invention may be conjugated to detectable moieties. Kits for use in detecting the expression of genes encoding *S. pseudintermedius* proteins may comprise one or more oligonucleotides/primers for detecting/amplifying/probing samples for *S. pseudintermedius* protein encoding sequences. The kits may also comprise other reagents to facilitate, for example, sequencing, PCR and/or RFLP analysis. In one embodiment, the kits may comprise one or more oligonucleotides/primers for detecting/amplifying/probing nucleic acid samples (for example nucleic acid derived from canine skin) for levels of sequences corresponding to all or part of those described as SEQ ID NOS: 1-38 herein.

DETAILED DESCRIPTION

The invention will now be described in more detail with reference to the following Figures which show:

FIG. 1. Genomic location of the 17 genes encoding putative CWA proteins in *S. pseudintermedius* strain ED99. Eight genes are situated in the oriC environ, indicated in orange, and nine are located in the core genome. sps =*S. pseudintermedius* surface protein.

Figure 2:
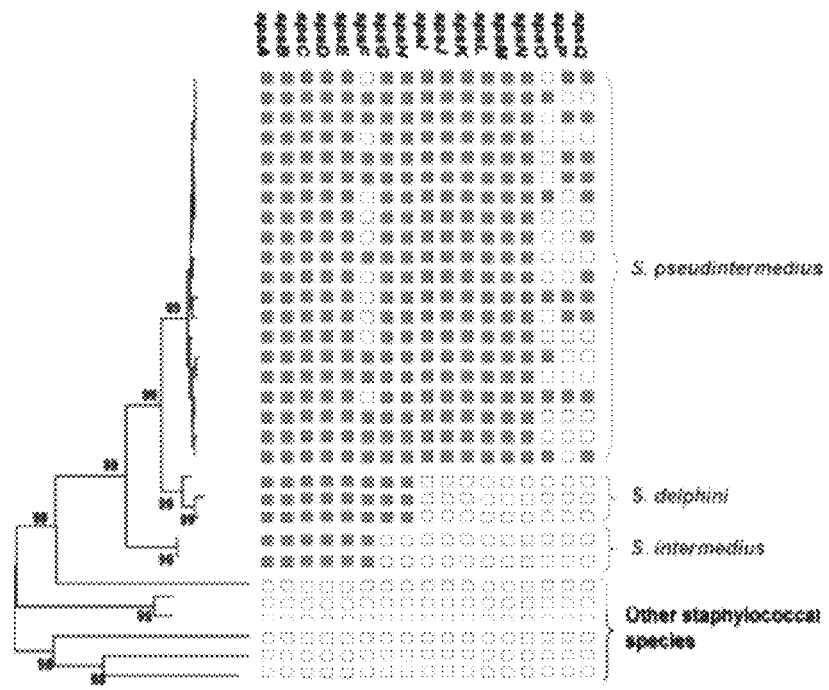

FIG. 2. Distribution of the genes encoding putative CWA proteins among 20 *S. pseudintermedius* strains, representatives of the closely related *S. delphini* and *S. intermedius*, and other staphylococcal species associated with animal skin disease. The diversity of strains is represented a phylogenetic tree; grey squares indicate that the gene is present, blank squares that the gene is absent based on Southern blot analysis (for spsA to spsO), or PCR amplification (for spsP and spsQ).

Figure 3:
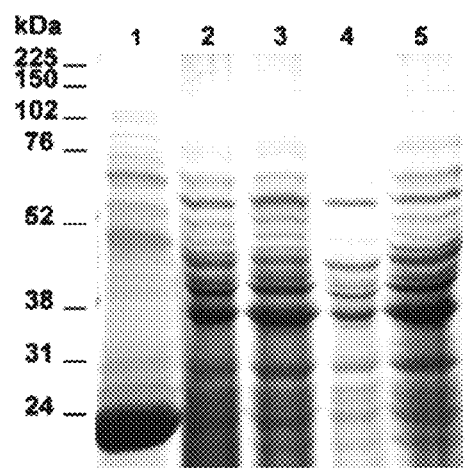
Figure 3B:
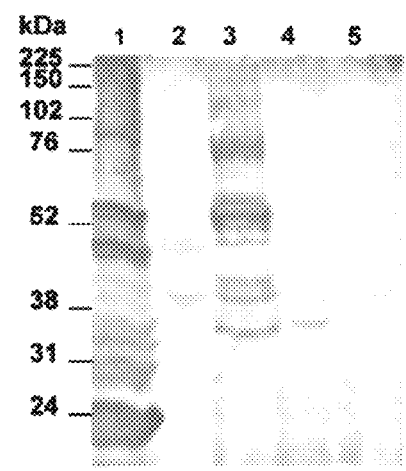

FIG. 3. Western blot analysis of cell wall-associated proteins of *S. pseudintermedius* ED99 and *L. lactis* expressing SpsD, SpsL, and SpsO with sera from dogs diagnosed with pyoderma. (A) SDS PAGE analysis and (B) Western blot analysis of protein fractions from *S. pseudintermedius* ED99 in exponential phase of growth (lane 1); *L. lactis* expressing SpsL (lane 2); *L. lactis* expressing SpsD (lane 3); *L. lactis* expressing SpsO (lane 4); and *L. lactis* with pOri23 alone (lane 5).

Figure 4:
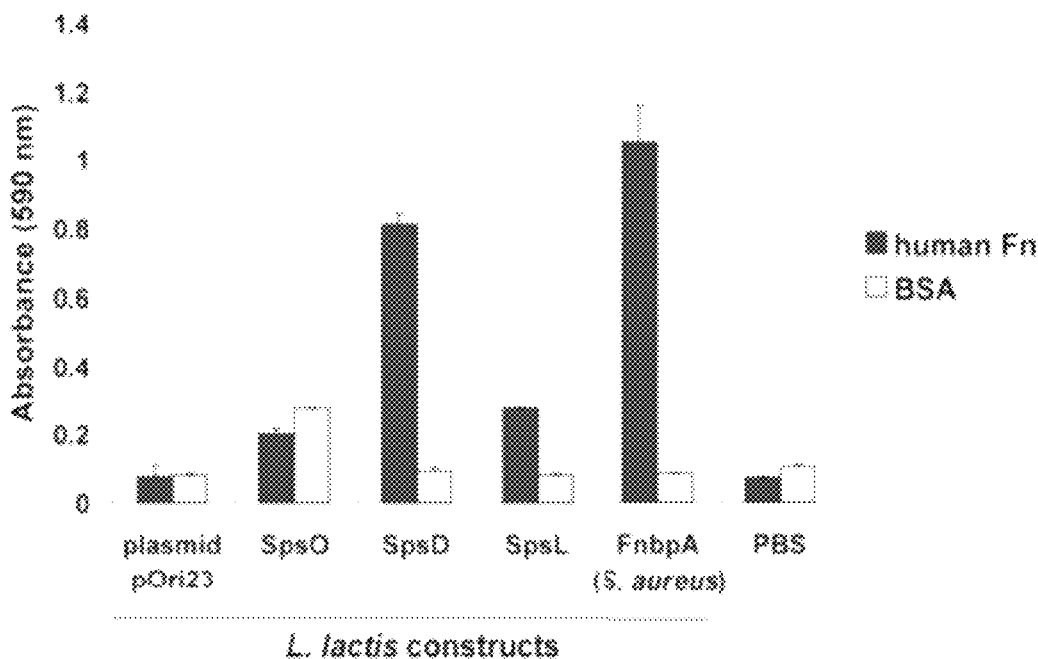

FIG. 4. Adherence of *L. lactis* expressing specified MSCRAMMs to human Fn. Plates were coated with 1 μg of human Fn or 1 μg of BSA per well. Absorbance was measured at 590 nm and results are expressed as mean values of triplicate samples. Error bars indicate standard deviation. *L. lactis* expressing FnbpA from *S. aureus* and PBS were included as controls.

Figure 5:
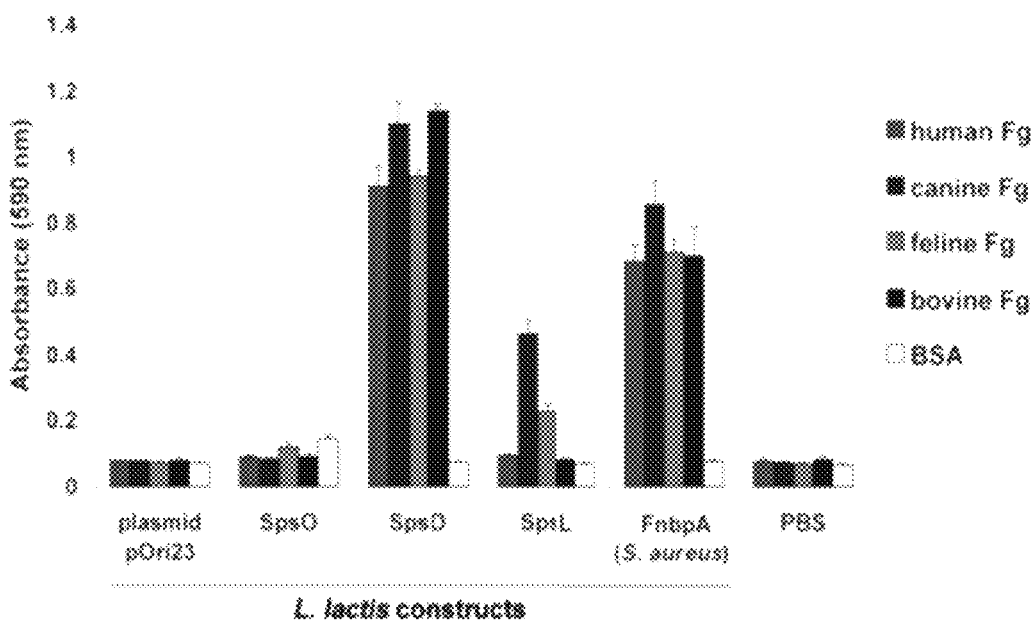

FIG. 5. Adherence of *L. lactis* expressing specified MSCRAMMs to Fg from different animal sources. Plates were coated with 1 μg of Fg or 1 μg of BSA per well. Absorbance was measured at 590 nm and results are expressed as mean values of triplicate samples. Error bars indicate standard deviation. *L. lactis* expressing FnbpA from *S. aureus* and PBS were included as controls.

Figure 6:
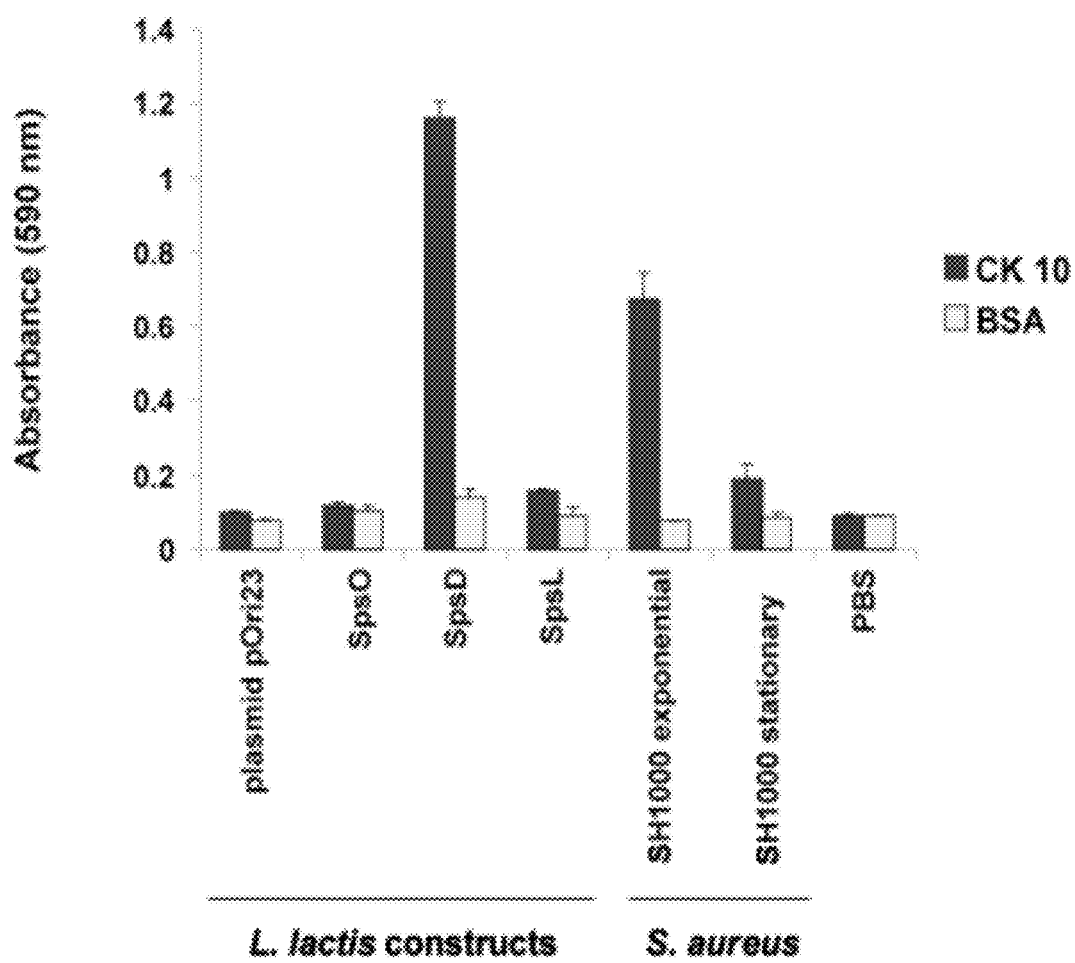

FIG. 6. Adherence of *L. lactis* expressing specified MSCRAMMs to CK10. Plates were coated with 1 μg of recombinant CK10 or 1 μg of BSA per well. Absorbance was measured at 590 nm and results are expressed as mean values of triplicate samples. Error bars indicate standard deviation. *S. aureus* strain SH1000 in exponential and stationary phases of growth and PBS were included as controls.

Figure 7:
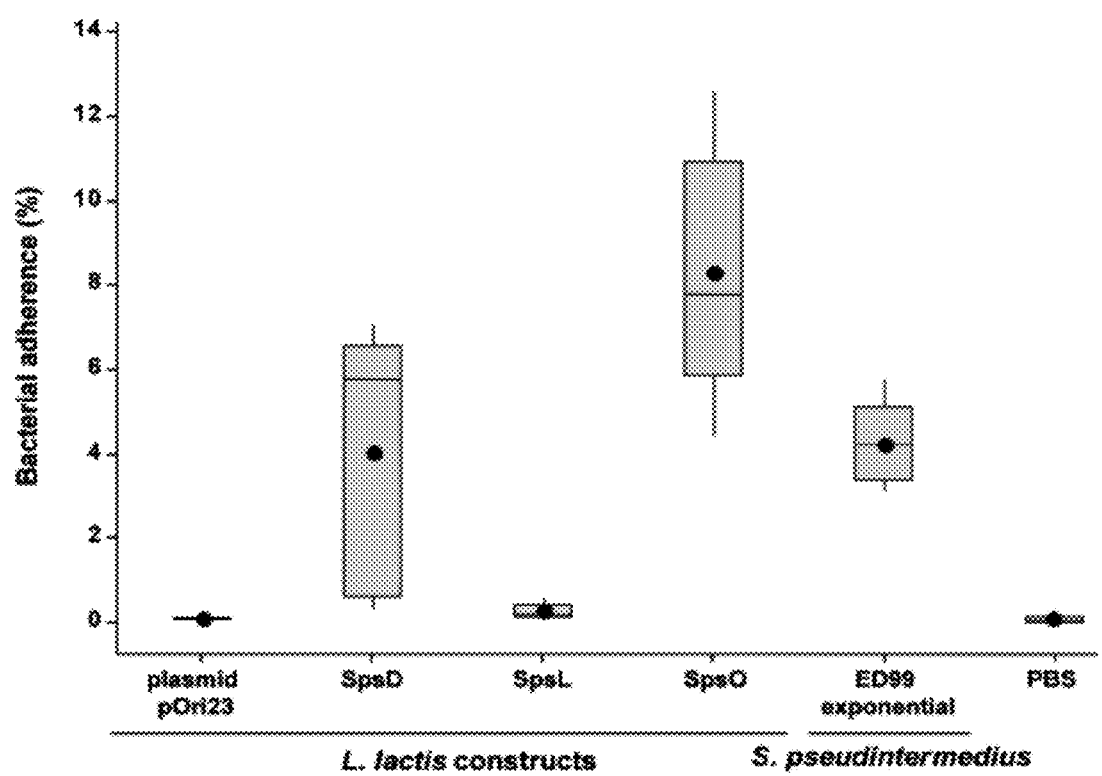

FIG. 7. Adherence of *L. lactis* expressing different MSCRAMMs to canine corneocytes of five dogs. Bacterial adherence is calculated as percentage area covered with bacterial cells per field of corneocytes (ROI=500 μm$^2$). Results are based on the arithmetic mean of duplicate experiments. The bottom of each box represents the first quartile (Q1), the top of the box the third quartile (Q3), the bold lines the median, and the black circles the mean values. The whiskers define the range of the data.

Figure 8:
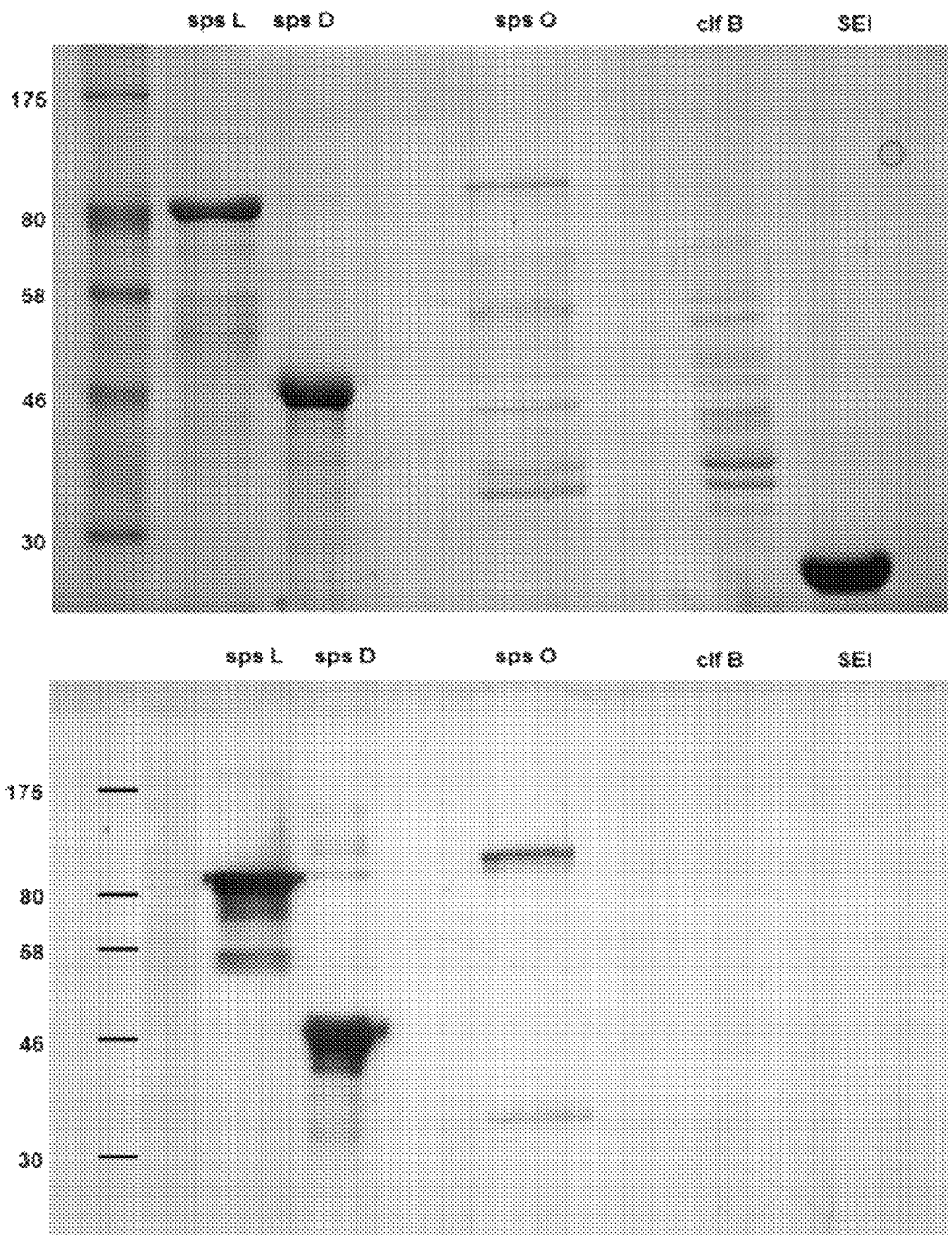

FIG. 8: Reactivity of canine convalescent serum from pyoderma cases to Sps D, Sps L and Sps O recombinant A domain. 1 ug aliquots of rSps D and rSps L, and 10 μl volumes of purified rSps O were subjected to SDS-PAGE under standard conditions and Coomassie stained (A) or Western blot transferred onto a nitrocellulose membrane. Membranes were probed with a 1:1000 dilution of canine serum, followed by a 1:3000 dilution of HRP— conjugated sheep anti-canine IgG. Reactive bands were visualized on Chemi-luminescent Film (B). 5 μl aliquots of recombinant ClfB and the superantigen SEI from *S. aureus* were included in the terminal lanes of each gel as negative controls.

Figure 9:
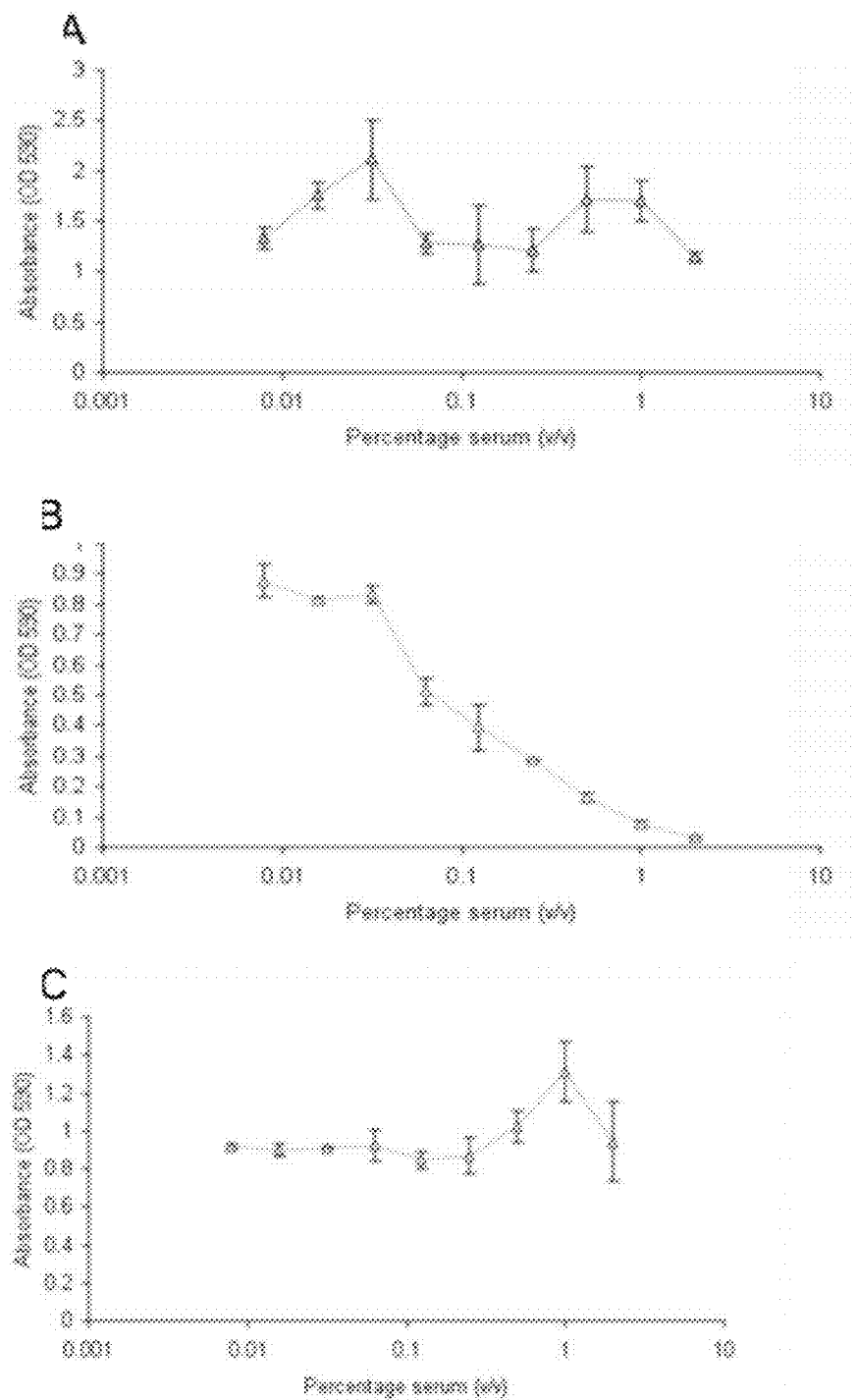

FIG. 9: Inhibition of adherence of *L. lactis* expressing SpsD (A) and SpsL (B) to fibrinogen (2 μg per well) by canine convalescent serum from pyoderma cases. Bacterial cultures, normalised to an OD600 of 1 in PBS were pre-incubated for 2 h with doubling dilutions of serum ranging from 2% to ~0.01% (v/v), prior to inoculation into fibrinogen coated wells. Results (n=3, ±SD) are expressed as absorbance readings at 590 nm minus background levels of fluorescence. Background fluorescence was measured by inoculating control cultures, incubated for 2 h in the absence of serum, into wells coated with BSA (2 µg per well). Incubations of *S. aureus* Newman (C) were included as a negative control.

EXAMPLES

Example 1

Materials and Methods
Genome-Wide Screen for Genes Encoding for Cell-Wall Anchored Proteins The *S. pseudintermedius* strain ED99 draft genome was interrogated for homologous sequences using position specific iterative basic local alignment search tool (PSI-BLAST), available from the National Center for Biotechnology Information (NCBI), USA, and for the presence of a LPX[TSA][GANS] motif pattern by pattern hit initiated basic local alignment search tool (PHI-BLAST), available from NCBI. Signal sequences were predicted by employing the SignalP server (cbs.dtu.dk/services/SignalP/), provided by the Center for Biological Sequence Analysis (CBS), Technical University of Denmark.

In Silico Structural Analysis of Cell-Wall Anchored Proteins

The predicted CWA proteins were searched for functional domains using EMBL-EBI InterPro Scan. Structural analysis was carried out with the PHYRE (Protein Homology/analogY Recognition Engine) fold recognition server, available from the Structural Bioinformatics Group, Imperial College London, UK. Repeat sequences were predicted by generating nucleic acid dot plots, using software available from Colorado State University, USA, applying tandem repeats finder software from Boston University, USA, and variable sequence tandem repeats extraction and architecture modelling (XSTREAM), available from the University of California, USA. Sequence alignments and pair-wise sequence comparisons were generated with ClustalW2. Amino acid composition and molecular weight predictions were generated using ProtParam on the ExPASy Proteomics Server.

Cloning of Selected Genes Encoding Putative MSCRAMMs of *S. Pseudintermedius* ED99 into *L. lactis* MG1363

Oligonucleotides were designed for PCR amplification of the full-length spsD, spsL and spsO genes and either PstI, SalI or BamHI specific restriction sites were inserted on both sides of the DNA fragments. 50 µl PCR reactions contained 2 µl (approximately 100 ng) genomic DNA template, 0.25 µM forward primer, 0.25 µM reverse primer, 1× PFUULTRA™ II reaction buffer (Stratagene, USA), 0.25 mM dNTP's (Promega, USA) and 1 µl PFUULTRA™ II FUSION HS DNA polymerase (Stratagene, USA). The thermocycler programme included an initial denaturation step at 95° C. for 2 min, followed by 30 cycles of denaturation at 95° C. for 20 s, annealing at 50° C. for 20 s and extension at 72° C. for 2 min, followed by a final extension step at 72° C. for 3 min. PCR products were visualised on 0.8% (w/v) agarose gels, gel extracted under avoidance of UV light exposure and purified using QIAQUICK Gel Extraction Kit (Qiagen, UK) according to the manufacturer's instructions. Purified DNA fragments were cloned into the STRATACLONE™ Blunt PCR cloning vector pSC-B (Stratagene, USA) using the STRATACLONE ULTRA™ Blunt PCR Cloning Kit (Stratagene, USA) according to the manufacturer's instructions. Each cloning reaction consisted of 3 µl Strataclone Buffer Blunt (Stratagene, USA), 2 µl purified PCR product and 1 µl STRATACLONE™ Blunt Vector Mix (Stratagene, USA). STRATACLONE™ SOLOPACK® competent cells (Stratagene, USA) were transformed according to the manufacturer's instructions and colonies selected using blue-white screening on LB-ampicillin (100 µg/ml)-X-gal plates. White colonies were transferred into 5 ml LB-ampicillin (100 µg/ml) broth and grown overnight at 37° C. with shaking at 200 rpm. Plasmid was isolated using QIAprep Spin Miniprep Kit (Qiagen, UK) according to the manufacturer's instructions. Purified plasmids were digested using appropriate restriction endonucleases (New England Biolabs, UK), and diagnostic digests were analysed on 0.8% (w/v) agarose gels. For generating DNA constructs, the *E. coli*-*L. lactis* shuttle vector pOri23 (kindly provided by P. Moreillon, University of Lausanne, Switzerland) was used. The pOri23 vector carries the ermAM gene for erythromycin resistance, the high-copy-number oriColE1 replicon for autonomous replication in *E. coli* and the constitutive lactococcal promoter P23 (Que et al., 2000). The multiple cloning site of pOri23 consists of restriction sites for endonucleases PstI, SalI and BamHI (Que et al., 2000).

STRATACLONE™ plasmids containing the DNA inserts of interest and the *E. coli*-*L. lactis* shuttle vector pOri23 were each digested in a 100 µl total reaction volume containing 10 µl plasmid (approximately 2.5 µg), 20 units appropriate restriction endonucleases (New England Biolabs, UK), and suitable buffers (New England Biolabs, UK) according to the manufacturer's instructions. Restriction digestions were performed at 37° C. for 16 h. The restriction fragments to be cloned were extracted from 0.8% (w/v) agarose gels without UV exposure as described in the general Material and Methods and purified using QIAQUICK Gel Extraction Kit (Qiagen, UK) according to the manufacturer's instructions. DNA inserts and restriction-digested pOri23 plasmid were quantified using spectrophotometry (NanoDrop ND-1000, Thermo Scientific, USA) and ligation reactions were carried out with a plasmid to insert ratio of 1:3 in a 10 µl total ligation reaction volume, consisting of 1 µl vector (approximately 10 ng), 400 units T4 DNA ligase (New England Biolabs, UK), 1×T4 DNA ligase reaction buffer (New England Biolabs, UK), x µl DNA insert (depending on DNA concentration), and x µl sterile water (depending on the volume of DNA insert). Ligations were incubated at 16° C. for 16 h.

One 50 µl aliquot of electrocompetent *L. lactis* cells was thawed on ice and 2 µl (~20 ng) pOri23 plasmid carrying the DNA insert of interest was added. Electroporation cuvettes (Sigma-Aldrich, UK) were pre-chilled and *L. lactis* cells plus plasmid were transferred into the cuvettes. Electroporation was performed at standard settings (25 µF, 23 kV, 200 Ohm) and 1 ml GM17 was added immediately. Cells were incubated at 30° C. in a static incubator for 2 h prior to spreading 250 µl of cell suspension per plate onto GM17 plates containing 5 µg/ml erythromycin. Plates were incubated overnight at 30° C.

For screening of *L. lactis* transformants, plasmid was isolated using the Qiagen MiniPrep Kit (Qiagen, UK) with addition of 100 U/ml mutanolysin (Sigma-Aldrich, UK) and 100 µg/ml lysozyme (Sigma-Aldrich, UK) to buffer P1. Diagnostic digests of purified plasmids were carried out with appropriate restriction enzymes and analysed on 0.8% (w/v) agarose gels.

Additionally, colony PCR was performed for pOri23 carrying spsD and spsO using gene-specific oligonucleotides (Table 5.3). *L. lactis* colonies were resuspended in 10 µl 10% (v/v) IGEPAL (Sigma-Aldrich, UK) and incubated for 10 min at 95° C. in a thermocycler machine. 40 µl master mix containing 0.3 µM forward primer, 0.3 µM reverse primer, 0.2 mM dNTP's (Promega, USA), 1× reaction buffer (Promega, USA), 1.5 mM $MgCl_2$ (Promega, USA) and 0.025 u/μl taq polymerase (Promega, USA) was added. The thermocycler programme included an initial denaturation step at 95° C. for 2 min, followed by 30 cycles of denaturation at 95° C. for 1 min, annealing at 50° C. for 1 min and extension at 72° C. for 1 min, followed by a final extension step at 72° C. for 7 min. PCR products were visualised on 0.8% (w/v) agarose gels.

Western Blot Analysis of *L. Lactis* Constructs

Samples were dissolved in 1× Laemmli sample buffer (Sigma-Aldrich, UK), boiled for 10 min and resolved by SDS-PAGE in 10% polyacrylamide gels by standard procedures, and Western blot analysis was carried out as described in the general Materials and Methods. Three canine sera samples from pyoderma cases (obtained from patients at the Hospital for Small Animals, The Royal (Dick) School of Veterinary Studies, The University of Edinburgh) were pooled and used as primary antibody in a 1:1000 dilution. HRP-conjugated sheep anti-dog antibody was used as a secondary antibody in a 1:5000 dilution (Bethyl Laboratories Inc., USA).

Canine Corneocyte Adherence Assay

For preliminary experiments to confirm adherence of *S. pseudintermedius* ED99 and non-adherence of *L. lactis*, corneocytes were obtained from a seven-year-old male neutered Border collie cross-breed with no history or physical signs of systemic or cutaneous disease. Corneocytes for the *L. lactis* adherence study were obtained from five dogs of different breeds (one Labrador retriever, two Border collies and two cross-breeds). Three dogs were ovariohysterectomised females and two were entire males. The median age was seven years (range one to twelve years). The dogs showed no abnormalities on general physical examination and had no history or physical signs of skin disease at the time of corneocyte collection. All dogs were privately owned by staff or students of the Royal (Dick) School of Veterinary Studies, The University of Edinburgh. None of the dogs had received topical or systemic drug treatments for at least three weeks prior to the day of corneocyte collection.

Samples were taken from the ventral abdomen and inner thigh. If necessary, sample sites were clipped with Oster clippers (Oster Cryotech, USA) using a number 40 blade. For collection of corneocytes, the method described by Forsythe et al. (2002) was used. Briefly, the area was cleaned of surface debris and commensal bacteria by applying four strips of single sided adhesive tape (Cellux, Henkel Consumer Adhesives, UK), using each strip once. To collect corneocytes, double-sided, clear, adhesive wig tape (Tropical Tape Super Grip, USA) was mounted onto a microscope slide in 1 cm² pieces and applied to the same area of skin surface 10 times with gentle force. Slides were investigated by microscopic examination and only slides with at least 75% corneocyte coverage were used in the study.

The corneocyte slides were positioned in moisture chambers (NUNC™ Thermo Fisher Scientific, Denmark) as described by Forsythe et al. (2002). The moisture chambers consisted of 30 cm×30 cm plastic trays with lids and were prepared by lining the trays with moistened paper towels. *S. pseudintermedius* ED99 stationary or exponential ($OD_{600}$ of 0.5) phase cultures and *L. lactis* exponential phase cultures ($OD_{600}$ 0.6 to 0.8) were centrifuged at 4000 rpm for 5 min, washed with PBS and resuspended in PBS to a final $OD_{600}$ of 0.5. The moisture chambers were placed in a static incubator and 250 μl of bacterial suspension was added to each 1 cm² of tape, forming a meniscus on the tape. Slides incubated with 250 μl of sterile PBS were included as a control. The slides were incubated at 37° C. for 90 min and washed in PBS. Each slide was stained with 0.5% (w/v) crystal violet (Sigma-Aldrich, UK) for 90 s before rinsing off with PBS. The slides were air-dried and a drop of immersion oil (Cargille Laboratories Inc., USA) and a cover slip (Scientific Laboratory Supplies, UK) were added before microscopic quantification. All slides were prepared in duplicate on the same day and incubated at the same time. Prior to incubation with bacterial suspensions or PBS, each slide was labelled with a letter code to allow identification after the microscopic analysis. The identification code on each slide was hidden by a third party for subsequent image acquisition so that the investigator was blinded to the origin of the slide. For quantification of adherent bacteria, computerised image analysis was used as described previously by Forsythe et al. (2002) with minor modifications. For each slide, bright field images of 1000× oil-immersion fields were acquired with a Sony DXC-390P 3CCD colour video camera (Scion Corporation, USA) connected to a Leica Laborlux S microscope (Leica Microsystems UK Ltd., UK). The RGB video signal from the camera was digitised using Scion Image (Scion Corporation, USA) installed in a G4 Macintosh computer (Apple Computer, USA) fitted with a CG-7 frame grabber (Scion Corporation, USA). For image acquisition, fields equivalent to 14.4 mm² were selected randomly by starting in the bottom left corner of each slide and moving through the slide in a defined way using the scale on the microscope stage. A field was discarded if the corneocyte layer was not confluent, the bacteria were poorly stained against the background or the field could not be focused properly. The software used for quantification of bacterial adherence was set to calculate the percentage area that was covered by bacteria per confluent layer of corneocytes in a defined region of interest (ROI) of 500 μm² within each image field acquired. Previous studies by Forsythe et al. (2002) using the same technique and software have demonstrated that 15 replicates of each duplicate slide resulted in acceptable coefficients of variation of approximately 10%. In this study, 25 replicates of each slide were acquired and the overall mean percentage area of adherence was determined by calculating the mean of all replicates.

Results

Identification of Genes Encoding 17 Putative Cell-Wall-Anchored Proteins in the *S. pseudintermedius* ED99 Genome The initial search for putative CWA proteins identified 34 sequences that fulfilled at least one of the search criteria (homology to characterised MSCRAMMs in the database, predicted (SEQ ID NO: 39) LPXTG motif or variant near the C terminus, predicted signal peptide at the N terminus). After gap closure and combination of incomplete sequences, a total of 17 ORFs encoding putative CWA proteins with a predicted minimum length of approximately 250 amino acids was determined. The 17 predicted CWA proteins were designated 'Sps' for '*Staphylococcus pseudintermedius* surface proteins', followed by a capital letter (SpsA to SpsQ). Their position in the *S. pseudintermedius* ED99 genome is indicated in FIG. 1. Of note, eight genes encoding putative CWA proteins are located near the oriC environ (FIG. 1). Homology searches in the database resulted in sequence identities with known staphylococcal proteins ranging from ~30% to ~80% (Table 1). Signal sequences, necessary for Sec-dependent protein secretion (Foster and Hook, 1998), were predicted for 14 putative Sps proteins, consisting of 29 aa for SpsC and SpsK, 33 aa for SpsN, SpsP, and SpsQ, 36 aa for SpsD, 37 for SpsG, 38 aa for SpsA, SpsB, and SpsL, 39 aa for SpsH, 44 aa for SpsO, and 48 aa for SpsF and SpsM. No signal sequence was predicted for SpsE, Sps1, and SpsJ (FIG. 4.3).

The Putative CWA Proteins SpsD, SpsL, and SpsO have Several MSCRAMM Features.

The Putative CWA Proteins SpsD, SpsL, and SpsO have Several MSCRAMM Features.

Out of the 17 putative CWA proteins of S. pseudintermedius ED99, SpsD, SpsL, and SpsO contained each of the MSCRAMM features screened for, including a signal sequence at the N-terminus, followed by a non-repeated A domain with two IgG-like folds, dividing the A domain into N1, N2, and N3 subdomains, a tandemly repeated domain at the C-terminus (and at the N-terminus for SpsO), and a C-terminal (SEQ ID NO: 39) LPXTG-anchor motif. The main characteristics of SpsD, SpsL, and SpsO are summarised in Table 2. Of interest, a (SEQ ID NO: 40) TYTFTDYVD motif or variant, important for the 'dock, lock and latch' ligand-binding mechanism (Ponnuraj et al., 2003), was found in SpsD, SpsL, and SpsO, and putative latching sequences were identified (Table 2). Further, putative Fn-binding motifs with weak homology to FnbpA-10 of FnbpA in S. aureus were detected in the repeat region of SpsL (24% identity in pair-wise alignments for SpsL1-SpsL6, and 21% for SpsL-7). No homology to Fn-binding motifs of FnbpA was detected in the repeat regions of SpsD and SpsO. Of note, the genes encoding for SpsD, SpsL, and SpsO in the S. pseudintermedius ED99 genome are situated in different genomic contexts. While spsD is located in a well-conserved region of the core genome, spsL is part of the oriC environ (Takeuchi et al., 2005) (FIG. 1). The spsO gene appears to be species-specific as it is not present in the genomes of other staphylococcal species. The region contains two putative transposases, suggesting that the whole region might be subjected to horizontal gene transfer.

Distribution of the 17 Genes Encoding Putative Cell-Wall-Anchored Proteins Among the S. Intermedius Group In order to investigate the distribution of the 17 genes encoding putative CWA proteins identified in the S. pseudintermedius ED99 genome among other members of the SIG and closely related staphylococcal species, Southern blot analysis and PCR amplification were performed. A total of 20 S. pseudintermedius strains representing the breadth of diversity within the species, representatives of the closely related S. delphini and S. intermedius species, and other staphylococcal species associated with animal hosts (FIG. 2) were screened for the presence of the putative CWA encoding genes by Southern blot analysis (spsA to spsO). For the S. aureus spa orthologues spsP and spsQ, PCR amplification was employed, as the genes share 70% nucleotide identity which precluded design of gene-specific probes for Southern blot analysis. For similar reasons, the primers designed for PCR amplification were located upstream of spsP (spsP-F), in the non-repeated region of spsP (spsP-R), in the unique region between spsP and spsQ (spsQ-F), and in a region unique for spsQ (spsQ-R).

Of the 17 genes examined, 13 were found in all S. pseudintermedius strains investigated. The remaining 4 (spsF, spsO, and the S. aureus spa orthologues spsP and spsQ) were present in 11, 6, 7, and 11 of the 20 S. pseudintermedius strains, respectively. Furthermore, 8 of the 17 genes were detected in S. delphini and 6 in S. intermedius, and 9 genes were exclusive to S. pseudintermedius. None of the genes encoding putative CWA proteins was detected in the non-SIG staphylococcal species examined. Results are summarised in FIG. 2. Of note, it cannot be excluded at this point that DNA sequence variation in PCR primer annealing sites for spsP and spsQ, and weak homology (less than approximate 70%) for spsA to spsO among different strains have influenced the results.

Expression of CWA Proteins on the S. Pseudintermedius Bacterial Cell Surface.

The in silico identification of 17 putative CWA proteins in S. pseudintermedius ED99 raises questions about the expression of these proteins and their role in colonisation and disease. Surface proteome analysis of early-, mid-, and late exponential phase S. pseudintermedius ED99 was performed in collaboration with the Moredun Research Institute, Penicuik, Scotland, UK, using liquid chromatography-electrospray ionisation-tandem mass spectrometry (LC-ESI-MS-MS). Six out of the 17 putative CWA proteins predicted in the S. pseudintermedius ED99 genome were detected on the bacterial surface, including SpsD, SpsK, SpsL, SpsN, SpsO, and SpsQ. The putative CWA proteins SpsL, SpsN, and SpsQ were identified in all three phases of growth; SpsK was lacking in early-, SpsO in mid-, and SpsD in late exponential phase. The 11 undetected CWA proteins might not have been expressed under the conditions tested, or the expression level might have been below the detection threshold of the LC-ESI-MS-MS method used.

Cloning and Expression of SpsD, SpsL, and SpsO in L. lactis.

In order to examine the role of putative selected MSCRAMMs independently on the bacterial cell surface, the full-length spsD (3096 bp), spsL (2793 bp) and spsO (5538 bp) genes were cloned into L. lactis using the shuttle vector pOri23 (Que et al., 2000). Positive clones were identified by restriction digestion of purified pOri23 plasmids from single colonies of transformed L. lactis cells (data not shown). The pOri23 construct inserts were verified by DNA sequencing for spsL and spsD. For spsO, DNA sequence was generated for approximately 3000 bp of the total length of 5538 bp. A segment of the repeat region corresponding to ~2500 bp could not be determined due to the existence of identical tandem repeats which did not allow directed sequencing. As a negative control for subsequent MSCRAMM characterisation studies, L. lactis was transformed with the empty vector pOri23, confirmed by restriction digestion analysis. The predicted molecular weights were 115 kDa for SpsD, 103 kDa for SpsL, and 198 kDa for SpsO.

L. lactis expressing SpsD and SpsL Demonstrated Seroreactivity with Canine Sera from Pyoderma Cases.

The potential antibody response to SpsD, SpsL, and SpsO in vivo was investigated by Western blot analysis employing canine sera from staphylococcal pyoderma cases. The pyoderma was clinically manifested at the time of blood sampling and the dogs were also diagnosed with AD (Neuber et al., 2008). Cell wall-associated protein fractions of the L. lactis constructs and of S. pseudintermedius ED99 were subjected to SDS-PAGE, transferred to nitrocellulose membrane and incubated with pooled canine sera from three pyoderma cases as described in Materials and Methods. An array of immunoreactive bands was detected for S. pseudintermedius ED99, ranging from 24 kDa to 102 kDa in molecular weight (FIG. 3). For L. lactis expressing SpsD and L. lactis expressing SpsL, multiple seroreactive bands in the range of 38 kDa to 225 kDa for SpsD, and 38 kDa and 52 kDa for SpsL were detected, which were absent in the protein fractions of L. lactis carrying pOri23 alone (FIG. 3). In contrast, L. lactis expressing SpsO did not demonstrate seroreactivity with sera from dogs diagnosed with pyoderma (FIG. 3).

Adherence of L. Lactis Constructs to Extracellular Matrix Proteins.

L. lactis expressing SpsO, SpsD, SpsL, and L. lactis carrying the vector pOri23 alone were tested for their ability to adhere to human Fn, human, canine, feline, and bovine Fg, and to recombinant mouse CK10 in solid phase assays. The putative MSCRAMMs SpsD and SpsL mediate binding of L. lactis to fibronectin.

L. lactis expressing SpsD and SpsL demonstrated adherence to human Fn, whereas L. lactis expressing SpsO demonstrated increased binding to Fn, but also to BSA, indicative of a non-specific interaction (FIG. 4).

The Putative MSCRAMMs SpsD and SpsL Mediate Binding of L. lactis to Fibrinogen, and SpsL Demonstrates Canine Host-Specificity.

L. lactis expressing SpsD strongly adhered to Fg from several animal sources (FIG. 5). In contrast, L. lactis expressing SpsL adhered to canine and feline Fg only, and did not bind to human and bovine Fg (FIG. 5), indicating a host-specific interaction. L. lactis expressing SpsO did not bind to Fg from any source compared to L. lactis with the pOri23 vector alone (FIG. 5).

The Putative MSCRAMM SpsD Mediates Binding of L. lactis to Cytokeratin 10.

L. lactis expressing SpsD demonstrated strong adherence to CK10, whereas L. lactis expressing SpsO and SpsL did not show increased binding compared to L. lactis with the vector pOri23 alone (FIG. 6).

The Putative MSCRAMMs SpsD and SpsO, but not SpsL, Mediate Adherence of L. lactis to Ex Vivo Canine Corneocytes.

L. lactis expressing SpsD, SpsL, and SpsO were tested for their ability to adhere to ex vivo canine corneocytes in comparison to L. lactis with the empty vector pOri23 and S. pseudintermedius ED99. L. lactis carrying the empty vector pOri23 adhered poorly to canine corneocytes (FIG. 7). For S. pseudintermedius ED99, the mean percentage adherence to canine corneocytes was 4.24% which was significantly different to L. lactis carrying pOri23 alone (P=0.001) (FIG. 7). L. lactis expressing SpsD and L. lactis expressing SpsO adhered to ex vivo canine corneocytes (FIG. 7). The increase in adherence was approaching significance for SpsD (P=0.050), and was significant for SpsO when expressed in L. lactis compared to L. lactis carrying pOri23 alone (P=0.004). Binding of L. lactis expressing SpsL was not significantly different to L. lactis carrying pOri23 alone (P=0.108), indicating that SpsL does not promote adherence to canine corneocytes (FIG. 7).

Purified Recombinant Sps D, Sys L, and Sps O Demonstrate Reactivity with Canine Convalescent Serum.

Reactivity of recombinant A domain from Sps D, Sps L and Sps O with canine convalescent serum from pyoderma cases was examined by Western affinity blot analysis (FIG. 8). rSpsD, rSpsL and rSpsO all crossreacted with IgG present in the canine serum (FIG. 8).

Pre-Incubation with Canine Convalescent Serum Inhibits SpsL-Mediated Binding to fibrinogen.

The ability of the reactive antibody present in convalescent serum to inhibit SpsD and SpsL ligand binding was investigated using a modified solid phase adherence assay. Prior to inoculation into fibrinogen coated wells, PBS normalised cultures of L. lactis expressing SpsD and SpsL were incubated for 2 h with doubling dilutions of convalescent serum at 28° C. (FIG. 9). Convalescent serum inhibited binding of L. lactis expressing SpsL, but not SpsD to canine fibrinogen, with complete inhibition at a final concentration of 2% v/v (FIG. 9).

Discussion

In summary, genome-wide analysis of S. pseudintermedius ED99 revealed the presence of 17 genes encoding putative CWA proteins based on typical MSCRAMM features. All MSCRAMM characteristics searched for were identified for SpsD, SpsL, and SpsO, including a signal sequence, a non-repeated A domain with two IgG-like folds, tandemly repeated regions, and a C-terminal LPXTG-anchor motif. Interestingly, SpsD, SpsL, and SpsO belong to different groups based on Southern blot analysis, with SpsD being present in all SIG members, SpsL in S. pseudintermedius only, and SpsO in only six of the S. pseudintermedius strains investigated, and not in the other SIG species tested. Based on in silico analysis and in vitro expression data, SpsD, SpsL, and SpsO were selected for functional characterisation.

All CWA proteins and in particular, SpsD, SpsL, and SpsO could be employed in passive and active immunisation studies to test their antigenic properties, either singular or in combination, in a similar fashion as proposed for S. aureus ClfA (Josefsson et al., 2001; Hall et al., 2003; Patti, 2004; Nanra et al., 2009). Further, a combinatory vaccine of S. aureus surface proteins IsdA, iron-regulated surface determinant protein B (IsdB), SdrD, and SdrE has proven to be highly protective in a mouse infection model (Stranger-Jones et al., 2006), demonstrating the promising potential of vaccine preparations containing multiple staphylococcal CWA proteins.

In addition, MSCRAMMs with known ligands could be targets of anti-staphylococcal drug development, e.g. by generating synthetic peptides based on the interacting ECM proteins, which antagonise the MSCRAMM-host protein interaction, but do not interfere profoundly with physiological processes in the host. An excellent example is provided by Ganesh et al. (2008) who demonstrated that synthetic peptides, based on the Fg-binding site for ClfA, hinder the ClfA interaction, but do not block binding of the platelet integrin $\alpha_{11b}\beta_3$ to Fg. Recently, Stranger-Jones et al screened the genome of the human pathogen S. aureus for all genes predicted to encode CWA proteins, and immunized mice with each protein to determine their capacity to protect against lethal or invasive infection (Stranger-Jones et al, 2006). Four of the proteins were combined into a multiple protein vaccine which induced high levels of protection against S. aureus invasive disease of mice. These data have stimulated renewed optimism in a vaccine for the prevention of human S. aureus infections. A similar approach could be used to design an effective vaccine for the prevention of S. pseudintermedius canine pyoderma.

Example 2

*Staphylococcus Pseudintermedius* Surface Protein Vaccination Experiment

S. pseudintermedius surface antigens were divided into 2 pools of 3 and 4 antigens, respectively. Vaccine pool 1 contained antigens SpsC, IsaA, and SpsN and vaccine pool 2 contained SpsD A domain, N2,N3 subdomains, SpsL A domain (SEQ ID NO: 37), and SpsA.

Groups of 8 or 9 BalbC mice were vaccinated subcutaneously with pool 1 or pool 2 or PBS, each with complete Freund's adjuvant, followed by additional vaccinations at day 8 and day 23 with incomplete Freund's adjuvant. On day 32, mice were challenged through a subcutaneous route with $10^7$ cfu S. pseudintermedius ED99. Mice were then examined for abscess formation, and weight loss.

Mice vaccinated with pool 2 (comprising the protein having amino acid sequence provided in SEQ ID NO: 37) had significantly reduced lesion size (~50% reduction), and significantly reduced weight loss (~50%) compared to PBS control mock vaccinated animals.

REFERENCES

Bannoehr J, Ben Zakour N L, Waller A S, Guardabassi L, Thoday K L, van den Broek A H, Fitzgerald J R. (2007). Population genetic structure of the *Staphylococcus intermedius* group: insights into agr diversification and the emergence of methicillin-resistant strains. J. Bacteriol. 189:8685-92

Ben Zakour, N. L., Guinane, C. M. & Fitzgerald, J. R. (2008) Pathogenomics of the staphylococci: insights into niche adaptation and the emergence of new virulent strains. *FEMS Microbial Lett*, 289, 1-12.

Clarke, S. R. & Foster, S. J. (2006) Surface adhesins of *Staphylococcus aureus*. *Adv Microb Physiol*, 51, 187-224.

Corrigan, R. M., Miajlovic, H. & Foster, T. J. (2009) Surface proteins that promote adherence of *Staphylococcus aureus* to human desquamated nasal epithelial cells. *BMC Microbial*, 9, 22.

Clarke, S. R., Andre, G., Walsh, E. J., Dufrene, Y. F., Foster, T. J. & Foster, S. J. (2009) Iron-regulated surface determinant protein A mediates adhesion of *Staphylococcus aureus* to human corneocyte envelope proteins. *Infect Immun*, 77, 2408-16.

Curtis, C. F., et al (2006) Masked, controlled study to investigate the efficacy of a *Staphylococcus intermedius* autogenous bacterin for the control of canine idiopathic recurrent superficial pyoderma. *Vet Dermatol* 17, 163-8 (2006).

Forsythe, P. J., Hill, P. B., Thoday, K. L. & Brown, J. (2002) Use of computerized image analysis to quantify staphylococcal adhesion to canine corneocytes: does breed and body site have any relevance to the pathogenesis of pyoderma? *Vet Dermatol*, 13, 29-36.

Foster, T. J. & Hook, M. (1998) Surface protein adhesins of *Staphylococcus aureus*. *Trends Microbiol*, 6, 484-8.

Ganesh, V. K., Rivera, J. J., Smeds, E., Ko, Y. P., Bowden, M. G., Wann, E. R., Gurusiddappa, S., Fitzgerald, J. R. & Hook, M. (2008) A structural model of the *Staphylococcus aureus* ClfA-fibrinogen interaction opens new avenues for the design of anti-staphylococcal therapeutics. *PLoS Pathog*, 4, e1000226

Guardabassi, L., Schwarz, S. & Lloyd, D. H. (2004b) Pet animals as reservoirs of antimicrobial-resistant bacteria. *J Antimicrob Chemother*, 54, 321-32.

Hall, A. E., Domanski, P. J., Patel, P. R., Vernachio, J. H., Syribeys, P. J., Gorovits, E. L., Johnson, M. A., Ross, J. M., Hutchins, J. T. & Patti, J. M. (2003) Characterization of a protective monoclonal antibody recognizing *Staphylococcus aureus* MSCRAMM protein clumping factor A. *Infect Immun*, 71, 6864-70.

Hill, P. B. et al. (2006) Survey of the prevalence, diagnosis and treatment of dermatological conditions in small animals in general practice *Vet Rec* 158, 533-9 (2006).

Josefsson, E., Hartford, O., O'brien, L., Patti, J. M. & Foster, T. (2001) Protection against experimental *Staphylococcus aureus* arthritis by vaccination with clumping factor A, a novel virulence determinant. *J Infect Dis*, 184, 1572-80.

Lindsay, J. A., Moore, C. E., Day, N. P., Peacock, S. J., Witney, A. A., Stabler, R. A., Husain, S. E., Butcher, P. D. & Hinds, J. (2006) Microarrays reveal that each of the ten dominant lineages of *Staphylococcus aureus* has a unique combination of surface-associated and regulatory genes. *J Bacteriol*, 188, 669-76.

Mazmanian, S. K., et al. (1999) *Staphylococcus aureus* sortase, an enzyme that anchors surface proteins to the cell wall. *Science* 285, 760-3 (1999).

Nanra, J. S., Timofeyeva, Y., Buitrago, S. M., Sellman, B. R., Dilts, D. A., Fink, P., Nunez, L., Hagen, M., Matsuka, Y. V., Mininni, T., Zhu, D., Pavliak, V., Green, B. A., Jansen, K. U. & Anderson, A. S. (2009) Heterogeneous in vivo expression of clumping factor A and capsular polysaccharide by *Staphylococcus aureus*: implications for vaccine design. *Vaccine*, 27, 3276-80.

Otto, M. (2008) Targeted immunotherapy for staphylococcal infections: focus on anti-MSCRAMM antibodies. *BioDrugs* 22, 27-36 (2008)

Patti, J. M. (2004) A humanized monoclonal antibody targeting *Staphylococcus aureus*. *Vaccine*, 22 Suppl 1, S39-43.

Pizza, M. et al. (2008) Identification of vaccine candidates against serogroup B meningococcus by whole-genome sequencing. *Science* 287, 1816-1820

TABLE 1

Sequence homology of the 17 predicted cell-wall-anchored proteins against known proteins in the public domain.

| Putative CWA protein | Best Hit (BLAST) | Identity (%) | Similarity (%) |
| --- | --- | --- | --- |
| SpsA | LPXTG cell-wall surface anchor family protein of *S. aureus* COL | 31.2 | 56.9 |
| SpsB | RodA, a rod shape determining protein of *S. epidermidis* ATCC 12228 | 69.7 | 87.8 |
| SpsC | bifunctional autolysin precursor of *S. epidermidis* ATCC 12228 | 50.7 | 65.9 |
| SpsD | Fnbp protein homolog of *S. aureus* Mu50 | 40.7 | 59.1 |
| SpsE | Fibrinogen binding protein of *S. epidermidis* ATCC 12228 | 78.6 | 90.1 |
| SpsF | hypothetical protein, similar to the putative cell-surface adhesin SdrF of *S. haemolyticus* JCSC1435 | 52.8 | 69.3 |
| SpsG | hypothetical protein, cell-wall surface anchor family of *Streptococcus pneumoniae* D39 | 47.7 | 63.6 |
| SpsH | Sdr-repeat family protein SdrH, *S. aureus* USA300 | 36.0 | 53.1 |
| SpsI | serine-aspartate rich, fibrinogen-binding, bone sialoprotein-binding protein *S. epidermidis* ATCC 12228 | 37.3 | 55.5 |
| SpsJ | precursor of a serine-rich adhesin for platelets of *S. haemolyticus* JCSC143S | 52.2 | 61.2 |
| SpsK | IgG-binding protein of *S. aureus* COL | 50.4 | 71.1 |
| SpsL | Fnbp protein homolog of *S. aureus* Mu50 | 33.4 | 51.7 |
| SpsM | hypothetical protein, similar to the putative cell-surface adhesin SdrF, *S. haemolyticus* JCSC1435 | 44.4 | 61.7 |
| SpsN | probable exported protein of *S. aureus* RF122 | 38.0 | 60.0 |
| SpsO | serine-aspartate repeat-containing protein C precursor of *Staphylococcus warneri* L37603 | 50.0 | 68 |
| SpsP | LPXTG-motif cell wall anchor domain of *S. aureus* JH9 | 60.6 | 74.3 |
| SpsQ | IgG-binding protein A precursor of *S. aureus* MRSA252 | 57.0 | 71.7 |

TABLE 2

Main characteristics of the predicted CWA proteins SpsD, SpsL, and SpsO of *S. pseudintermedius* ED99.

| | Amino acids | MW (kDa)[a] | Signal peptide | LPXTG motif | Ig-like fold[b] (position) | TYTFTDYVD-like motif (position)[b] | Putative latching sequence (position)[b] | Repeat region (position) | Copy number repeats |
|---|---|---|---|---|---|---|---|---|---|
| SpsD | 1031 | 115 | 36 aa | LPDTG | 167-320 aa<br>322-519 aa | RYRFMDYVN<br>(267-275 aa) | NNASGEG<br>(491-497 aa) | 867-959 aa | 5 |
| SpsL | 930 | 103 | 38 aa | LPKTG | 220-363 aa<br>364-531 aa | VYTFKDYVN<br>(298-306 aa) | NSASGSG<br>(502-508 aa) | 543-818 aa | 7 |
| SpsO | 1846 | 198 | 44 aa | LPNTG | 339-492 aa<br>487-659 aa | TYTFTDYVD<br>(424-432 aa) | DKSTALG<br>(635-641 aa) | 661-1800 aa<br>97-216 aa[c] | 96<br>4[c] | aa = amino acids;
[a] MW = predicted approximate molecular weight in kDa (kilo dalton);
[b] within the A domain;
[c] N-terminal repeats

---

The invention claimed is:

1. A vaccine for *S. pseudintermedius* infections comprising a protein and one or more adjuvant(s); and wherein the protein comprises SEQ ID NO: 37.

2. The vaccine according to claim 1, wherein the vaccine further comprises one or more Sps protein(s) selected from the group consisting of:
   (i) a protein comprising SEQ ID NO: 2;
   (ii) a protein comprising SEQ ID NO: 4;
   (iii) a protein comprising SEQ ID NO: 6;
   (iv) a protein comprising SEQ ID NO: 8;
   (v) a protein comprising SEQ ID NO: 10;
   (vi) a protein comprising SEQ ID NO: 12;
   (vii) a protein comprising SEQ ID NO: 14;
   (viii) a protein comprising SEQ ID NO: 16;
   (ix) a protein comprising SEQ ID NO: 18;
   (x) a protein comprising SEQ ID NO: 20;
   (xi) a protein comprising SEQ ID NO: 22;
   (xii) a protein comprising SEQ ID NO: 24;
   (xiii) a protein comprising SEQ ID NO: 26;
   (xiv) a protein comprising SEQ ID NO: 28;
   (xv) a protein comprising SEQ ID NO: 30;
   (xvi) a protein comprising SEQ ID NO: 32;
   (xvii) a protein comprising SEQ ID NO: 34; and
   (xviii) a protein comprising SEQ ID NO: 36.

3. The vaccine according to claim 1, wherein the protein is encapsulated in a biodegradable polymer.

* * * * *

SEQUENCE LISTING

<160> NUMBER OF SEQ ID NOS: 40

<210> SEQ ID NO 1
<211> LENGTH: 1044
<212> TYPE: DNA
<213> ORGANISM: Staphylococcus pseudintermedius

<400> SEQUENCE: 1

```
atggaaaaca aaactttttt tagtattcgt aaactatcta ttggtgtagg ttcttgctta    60
atcgcgagtt ctttacttgt aaacacgcca agttttgctg aagaaacaga taatgcgaac   120
attaatgacg cacaacaaaa cgccttttat gaaattttac atttgccaaa cttaactgaa   180
gagcaacaaa atggattcat ccaaagtctt aaagatgatc caagtgtgag caacgacatt   240
ttagtagaag ctaagaaatt aaatgacact caagctaaac ctgattacag tgaagcacaa   300
caaaatgcat tttatgaaat tttacatttg tcaaacttaa ctgaagagca acaaaatgga   360
ttcatccaaa gtcttaaaga tgatccaagt gtgagcaacg acattttagt agaagctaag   420
aagttaaatg acactcaagc taaacctgat tacagtgaag cacaacaaaa tgcattttat   480
gaaattttac atttgtcaaa cttaactgaa gagcaacaaa atgggttcat ccaaagcctt   540
aaagatgatc caagtgtaag taagaaaatt ttagcagaag ctaagaagtt aaatgatagt   600
caagcaccta agttgataa agctaaaaaa actgacaaag ctgaagcgaa agcagatgat   660
aaagctaaag gtgaagaagc caaaaaatct gaagacaaaa aagatagcaa agcagataag   720
gcaaaatcga aaacgctac acatgttgtt aaacctggtg aaactttaga taatattgct   780
aaagatcatc atacaactgt tgataaaatt gctaaagata caaaataaa agataaaaat   840
gtgattaaac taggtcaaaa acttgttgtt gataaacaaa aagcaactca aggaaaacaa   900
gaagctgtag cgaaaaatga agtgaaggct ttacctaata ctggtgaaaa tgatgatatc   960
gcattattca gcacaacagt tgcgggtggc gtaagtatcg ctttaggttc attattatta  1020
ggaagaaaca gaaaaactag ctaa                                         1044
```

<210> SEQ ID NO 2
<211> LENGTH: 347
<212> TYPE: PRT
<213> ORGANISM: Staphylococcus pseudintermedius

```
<400> SEQUENCE: 2

Met Glu Asn Lys Asn Phe Phe Ser Ile Arg Lys Leu Ser Ile Gly Val
1               5                   10                  15

Gly Ser Cys Leu Ile Ala Ser Ser Leu Leu Val Asn Thr Pro Ser Phe
            20                  25                  30

Ala Glu Glu Thr Asp Asn Ala Asn Ile Asn Asp Ala Gln Gln Asn Ala
        35                  40                  45

Phe Tyr Glu Ile Leu His Leu Pro Asn Leu Thr Glu Glu Gln Gln Asn
    50                  55                  60

Gly Phe Ile Gln Ser Leu Lys Asp Asp Pro Ser Val Ser Asn Asp Ile
65                  70                  75                  80

Leu Val Glu Ala Lys Lys Leu Asn Asp Thr Gln Ala Lys Pro Asp Tyr
                85                  90                  95

Ser Glu Ala Gln Gln Asn Ala Phe Tyr Glu Ile Leu His Leu Ser Asn
            100                 105                 110

Leu Thr Glu Glu Gln Gln Asn Gly Phe Ile Gln Ser Leu Lys Asp Asp
        115                 120                 125

Pro Ser Val Ser Asn Asp Ile Leu Val Glu Ala Lys Lys Leu Asn Asp
    130                 135                 140

Thr Gln Ala Lys Pro Asp Tyr Ser Glu Ala Gln Gln Asn Ala Phe Tyr
145                 150                 155                 160

Glu Ile Leu His Leu Ser Asn Leu Thr Glu Glu Gln Gln Asn Gly Phe
                165                 170                 175

Ile Gln Ser Leu Lys Asp Asp Pro Ser Val Ser Lys Glu Ile Leu Ala
            180                 185                 190

Glu Ala Lys Lys Leu Asn Asp Ser Gln Ala Pro Lys Val Asp Lys Ala
        195                 200                 205

Lys Lys Thr Asp Lys Ala Glu Ala Lys Ala Asp Asp Lys Ala Lys Gly
    210                 215                 220

Glu Glu Ala Lys Lys Ser Glu Asp Lys Lys Asp Ser Lys Ala Asp Lys
225                 230                 235                 240

Ala Lys Ser Lys Asn Ala Thr His Val Val Lys Pro Gly Glu Thr Leu
                245                 250                 255

Asp Asn Ile Ala Lys Asp His His Thr Thr Val Asp Lys Ile Ala Lys
            260                 265                 270

Asp Asn Lys Ile Lys Asp Lys Asn Val Ile Lys Leu Gly Gln Lys Leu
        275                 280                 285

Val Val Asp Lys Gln Lys Ala Thr Gln Gly Lys Gln Glu Ala Val Ala
    290                 295                 300

Lys Asn Glu Val Lys Ala Leu Pro Asn Thr Gly Glu Asn Asp Asp Ile
305                 310                 315                 320

Ala Leu Phe Ser Thr Thr Val Ala Gly Gly Val Ser Ile Ala Leu Gly
                325                 330                 335

Ser Leu Leu Leu Gly Arg Asn Arg Lys Thr Ser
            340                 345

<210> SEQ ID NO 3
<211> LENGTH: 1389
<212> TYPE: DNA
<213> ORGANISM: Staphylococcus pseudintermedius

<400> SEQUENCE: 3
atggaaaaca aaaactttt  cagcattcgt aaattatcaa ttggggtggg ttcatgttta      60
atcgcgagct ctttacttgt gaatacacca agtttcgcag aagaaggaga taataacgca     120
```

-continued

```
gaagcgcaac aaaacgcttt ctctgaggta gtaaaattac ctaaccttag cgaagaacaa    180
cgtaatggtt tcattcaaag ccttaaagat gatccaagta caagtcaaga tgtgcttaat    240
gaagctaaaa aattaaatga tagtcaagag ggatctcaac ctgctcctga ttacagtgat    300
gaacaacaaa atgcatttta tgaaatttta caccttccaa acttaactga gaacaacgc     360 aatggctata ttcaaagtct taagatgac ccaagtgtaa gcgctaatat tcttgttgaa     420
gctaaaaata tgaatgttaa ccaaacacct acacaacctg cgccaagttt cgatgaagcg    480
caacaaaatg cattctatga gattgtaaac ttaccaaatc ttactgaaga gcaacgtaac    540
ggtttcatcc aaagccttaa agacgatcca agtgtaagta agatatcct tgttgaagct    600 aaaaagttaa atgacagcca agcaaaacct gattacagtg aagcgcaaca aaatgcattt    660
tatgaaattt tacaccttcc aaacttaact gaagaacaac gtaacggttt catccaaagc    720
cttaaagacg atccgagtgt aagtagtgat attcttgctg aagctaagaa attaaatgac    780
agccaagcgc taaagaaga caacaacgta aagacaata attcaggtga aacaaagct      840 gaagacaaag caacaaaga aacaaagct gaagataaag cagcaaaga agacaaagct      900 gaagataaag cagcaaaga agacaaagct gaagataaag cagcaaaga agacaaagct     960 gaagataaag cagcaaaga agacaaagct gaagataaag cagcataga agataaagct    1020 aaagacaaag acaacaaaga aggcaaagct gcagacaaag gtatggacaa agcgaaagat   1080
gcaatgcatg tcgttcaacc tggtgaaaca gtagaaaaaa ttgctaaagc taataacaca   1140
actgtagaac aaatcgctaa agataatcat ttagaagata aaaacatgat tttaccaggt   1200
caaaaacttg ttgttgacaa ccaaaaagca atgaaagaca gccaagaagc taaagcaaac   1260
cacgaaatga agctttacc tgaaacaggt gaagaaaacg atatggcatt attcggtaca    1320
tcacttacag gtggtcttag cttagcatta ggtttataca tcttaggacg tggcagaaaa   1380
acaaactaa                                                           1389
```

<210> SEQ ID NO 4
<211> LENGTH: 462
<212> TYPE: PRT
<213> ORGANISM: Staphylococcus pseudintermedius

<400> SEQUENCE: 4

```
Met Glu Asn Lys Asn Phe Phe Ser Ile Arg Lys Leu Ser Ile Gly Val
1               5                   10                  15

Gly Ser Cys Leu Ile Ala Ser Ser Leu Leu Val Asn Thr Pro Ser Phe
            20                  25                  30

Ala Glu Glu Gly Asp Asn Asn Ala Glu Ala Gln Gln Asn Ala Phe Ser
        35                  40                  45

Glu Val Val Lys Leu Pro Asn Leu Ser Glu Glu Arg Asn Gly Phe
    50                  55                  60

Ile Gln Ser Leu Lys Asp Asp Pro Ser Thr Ser Gln Asp Val Leu Asn
65                  70                  75                  80

Glu Ala Lys Lys Leu Asn Asp Ser Gln Glu Gly Ser Gln Pro Ala Pro
                85                  90                  95

Asp Tyr Ser Asp Glu Gln Gln Asn Ala Phe Tyr Glu Ile Leu His Leu
            100                 105                 110

Pro Asn Leu Thr Glu Glu Gln Arg Asn Gly Tyr Ile Gln Ser Leu Lys
        115                 120                 125

Asp Asp Pro Ser Val Ser Ala Asn Ile Leu Val Glu Ala Lys Asn Met
    130                 135                 140
```

```
Asn Val Asn Gln Thr Pro Thr Gln Pro Ala Pro Ser Phe Asp Glu Ala
145                 150                 155                 160

Gln Gln Asn Ala Phe Tyr Glu Ile Val Asn Leu Pro Asn Leu Thr Glu
                165                 170                 175

Glu Gln Arg Asn Gly Phe Ile Gln Ser Leu Lys Asp Asp Pro Ser Val
            180                 185                 190

Ser Lys Asp Ile Leu Val Glu Ala Lys Lys Leu Asn Asp Ser Gln Ala
        195                 200                 205

Lys Pro Asp Tyr Ser Glu Ala Gln Asn Ala Phe Tyr Glu Ile Leu
    210                 215                 220

His Leu Pro Asn Leu Thr Glu Glu Gln Arg Asn Gly Phe Ile Gln Ser
225                 230                 235                 240

Leu Lys Asp Asp Pro Ser Val Ser Ser Asp Ile Leu Ala Glu Ala Lys
                245                 250                 255

Lys Leu Asn Asp Ser Gln Ala Pro Lys Glu Asp Asn Val Lys Asp
            260                 265                 270

Asn Asn Ser Gly Glu Asn Lys Ala Glu Asp Lys Gly Asn Lys Glu Asn
        275                 280                 285

Lys Ala Glu Asp Lys Gly Ser Lys Glu Asp Lys Ala Glu Asp Lys Gly
290                 295                 300

Ser Lys Glu Asp Lys Ala Glu Asp Lys Gly Ser Lys Glu Asp Lys Ala
305                 310                 315                 320

Glu Asp Lys Gly Ser Lys Glu Asp Lys Ala Glu Asp Lys Gly Ser Ile
            325                 330                 335

Glu Asp Lys Ala Lys Asp Lys Asp Lys Glu Gly Lys Ala Ala Asp
        340                 345                 350

Lys Gly Met Asp Lys Ala Lys Asp Ala Met His Val Val Gln Pro Gly
            355                 360                 365

Glu Thr Val Glu Lys Ile Ala Lys Ala Asn Asn Thr Thr Val Glu Gln
370                 375                 380

Ile Ala Lys Asp Asn His Leu Glu Asp Lys Asn Met Ile Leu Pro Gly
385                 390                 395                 400

Gln Lys Leu Val Val Asp Asn Gln Lys Ala Met Lys Asp Ser Gln Glu
                405                 410                 415

Ala Lys Ala Asn His Glu Met Lys Ala Leu Pro Glu Thr Gly Glu Glu
            420                 425                 430

Asn Asp Met Ala Leu Phe Gly Thr Ser Leu Thr Gly Gly Leu Ser Leu
        435                 440                 445

Ala Leu Gly Leu Tyr Ile Leu Gly Arg Gly Arg Lys Thr Asn
    450                 455                 460

<210> SEQ ID NO 5
<211> LENGTH: 2793
<212> TYPE: DNA
<213> ORGANISM: Staphylococcus pseudintermedius

<400> SEQUENCE: 5
gtgtacaaaa atgaagaaga aaagcattca ataagaaagt tatctatagg agccgcatct      60
gtcattgttg ggggactcat gtatggtgtt ttgggaaatg atgaagctca agcgaatgaa     120
gatgtcactg aaacaactgg gagaaattca gtgacaacgc aagcttctga gcaacatttg     180
caagtggaag cagtacctca agaaggcaat aatgtaaatg tatcctctgt aaaagtacct     240
acgaatacgg caacgcaagc acaagaagat gttgcaagtg tatccgatgt taaagcacat     300
```

```
gctgatgatg cattacaagt acaagaaagt agtcatactg atggtgtttc ttcagaattc      360
aagcaggaga cagcttatgc gaatcctcaa acagctgaga cagttaaacc taatagtgaa      420
gcagtgcatc agtctgaata cgaggataag caaaaacccg tatcatctag ccgcaaagaa      480
gatgagacta tgcttcagca gcaacaagtt gaagccaaaa atgttgtgag tgcggaggaa      540
gtgtctaaag aagaaaatac tcaagtgatg caatcccctc aagacgttga acaacatgta      600
ggtggtaaag atatctctaa tgaggttgta gtggatagga gtgatatcaa aggatttaac      660
agcgaaacta ctattcgacc tcatcaggga caaggtggta ggttgaatta tcaattaaag      720
tttcctagca atgtaaagcc aggcgatcag tttactataa aattatctga caatatcaat      780
acacatggtg tttctgttga aagaaccgca ccgagaatca tggctaaaaa tactgaaggt      840
gcgacggatg taattgctga aggtctagtg ttggaagatg gtaaaaccat cgtatataca      900
tttaaagact atgtaaatgg caagcaaaat ttgactgctg agttatcagt gagctatttc      960
gtaagtccgg aaaaagtctt gactactggg acacaaacat tcacgacgat gatcggtaat     1020
cattcaacgc aatccaatat tgacgtttat tatgataata gtcattatgt agatggacgt     1080
atttcgcaag tgaacaaaaa agaagctaaa tttcaacaaa tagcatacat taaccctaat     1140
ggctatttaa atggcagggg gacaattgca gttaatggtg aagtggtcag tggtacgact     1200
aaagacttaa tgcaacctac agtgcgtgta tatcaatata aggacaagg tgttcctcct      1260 gaaagtatta ctatagaccc taatatgtgg gaagaaatca gcataaacga tactatggta     1320
agaaaatatg atggtggcta tagcttgaat ctggatacca gcaagaatca aaaatatgcc     1380
atctattatg aaggggcata tgatgcgcaa gctgacacac tgttgtatag aacatatata     1440
cagtcattaa acagttacta tccgttcagt taccaaaaaa tgaacggtgt gaagttttac     1500
gaaaacagtc gagtggaag cggtgagttg aaaccgaaac cacctgaaca accaaaacca     1560
gaacctgaaa ttcaagctga tgtagtagat attattgaag atagccatgt gattgatata     1620
ggatggaata cagcagttgg agaagaaagt ggagcaaacc aaggccctca agaagaaatc     1680
acggaaaatc acgacatcga agtcattgag gaaaacaact tggtggaaat gacagaagat     1740
acagcagttg gagaagaaag tggagcaaac caaggccctc aagaagaaat cacggaaaat     1800
cacgacatcg aagtcattga gaaaacaac ttagtggaaa tgacagaaga tacagcgttg     1860
gaagaagaaa gtggagcaaa tcaaggtcct caagaagaga tcacagaaaa ccacgatatc     1920
gaagtcattg aagaaaacaa cttggtggaa atgacagaag atacagcgtt ggaagaagaa     1980
agtggagcaa atcaaggtcc tcaagaagag atcacagaaa accacgacat cgaagtcatt     2040
gaagaaaata acttagtaga atgacagaa gatacagcag ttggagaaga agtggagca      2100 aatcaaggtc ctcaagaaga gatcacagaa accacgata tcgaagtcat tgaggaaaac      2160
aacttagtgg aaatgacaga agatacagca gttggagaag aaagtggagc aaaccaaggt     2220
cctcaagaag aaatcacgga aaatcacgac atcgaagtca ttgaagaaaa caacttggtg     2280
gaaatgacag aagatacagc gttggaagaa gaaagtggag caaatcaagg tcctcaagaa     2340
gagatcacag aaaaccacaa catcgaagtc attgaagaaa acaacttggt ggaaatgaca     2400
gaagatacag cagttggaga agaaagtgga gcaaacccag gacctcaaga agaagtaaca     2460
gagaatcaac ctcagcaaga gaaatcatg gaaaccaag aagtcgaaaa gaaaggcgat      2520
agtaacttgg tagaaagtac aaaaaactcca aaggccgaag aatcagttag cgttcagcca     2580 acttttagaag caaaaacac aaagaaccac gttaacacag tagtagtgaa tacgaaggta     2640
tctgaagtta agaaaaagga tccccaccat acaaaagcac taccagatac ggggacaacc     2700
```

```
tctcgaagtc attccatgat gattcctctc cttcttgttg ctgggtcagt agtgttgtta    2760
cgtcgaaaga aaaagcatag taaggtgaat taa                                 2793
```

<210> SEQ ID NO 6
<211> LENGTH: 930
<212> TYPE: PRT
<213> ORGANISM: Staphylococcus pseudintermedius

<400> SEQUENCE: 6

```
Val Tyr Lys Asn Glu Glu Lys His Ser Ile Arg Lys Leu Ser Ile
1               5                   10                  15

Gly Ala Ala Ser Val Ile Val Gly Gly Leu Met Tyr Gly Val Leu Gly
                20                  25                  30

Asn Asp Glu Ala Gln Ala Asn Glu Asp Val Thr Glu Thr Thr Gly Arg
            35                  40                  45

Asn Ser Val Thr Thr Gln Ala Ser Glu Gln His Leu Gln Val Glu Ala
        50                  55                  60

Val Pro Gln Glu Gly Asn Val Asn Val Ser Ser Val Lys Val Pro
65                  70                  75                  80

Thr Asn Thr Ala Thr Gln Ala Gln Glu Asp Val Ala Ser Val Ser Asp
                85                  90                  95

Val Lys Ala His Ala Asp Asp Ala Leu Gln Val Gln Glu Ser Ser His
            100                 105                 110

Thr Asp Gly Val Ser Ser Glu Phe Lys Gln Glu Thr Ala Tyr Ala Asn
        115                 120                 125

Pro Gln Thr Ala Glu Thr Val Lys Pro Asn Ser Glu Ala Val His Gln
    130                 135                 140

Ser Glu Tyr Glu Asp Lys Gln Lys Pro Val Ser Ser Ser Arg Lys Glu
145                 150                 155                 160

Asp Glu Thr Met Leu Gln Gln Gln Val Glu Ala Lys Asn Val Val
                165                 170                 175

Ser Ala Glu Glu Val Ser Lys Glu Glu Asn Thr Gln Val Met Gln Ser
            180                 185                 190

Pro Gln Asp Val Glu Gln His Val Gly Gly Lys Asp Ile Ser Asn Glu
        195                 200                 205

Val Val Val Asp Arg Ser Asp Ile Lys Gly Phe Asn Ser Glu Thr Thr
    210                 215                 220

Ile Arg Pro His Gln Gly Gln Gly Arg Leu Asn Tyr Gln Leu Lys
225                 230                 235                 240

Phe Pro Ser Asn Val Lys Pro Gly Asp Gln Phe Thr Ile Lys Leu Ser
                245                 250                 255

Asp Asn Ile Asn Thr His Gly Val Ser Val Glu Arg Thr Ala Pro Arg
            260                 265                 270

Ile Met Ala Lys Asn Thr Glu Gly Ala Thr Asp Val Ile Ala Glu Gly
        275                 280                 285

Leu Val Leu Glu Asp Gly Lys Thr Ile Val Tyr Thr Phe Lys Asp Tyr
    290                 295                 300

Val Asn Gly Lys Gln Asn Leu Thr Ala Glu Leu Ser Val Ser Tyr Phe
305                 310                 315                 320

Val Ser Pro Glu Lys Val Leu Thr Thr Gly Thr Gln Thr Phe Thr Thr
                325                 330                 335

Met Ile Gly Asn His Ser Thr Gln Ser Asn Ile Asp Val Tyr Tyr Asp
            340                 345                 350
```

```
Asn Ser His Tyr Val Asp Gly Arg Ile Ser Gln Val Asn Lys Lys Glu
            355                 360                 365
Ala Lys Phe Gln Gln Ile Ala Tyr Ile Asn Pro Asn Gly Tyr Leu Asn
        370                 375                 380
Gly Arg Gly Thr Ile Ala Val Asn Gly Glu Val Val Ser Gly Thr Thr
385                 390                 395                 400
Lys Asp Leu Met Gln Pro Thr Val Arg Val Tyr Gln Tyr Lys Gly Gln
                405                 410                 415
Gly Val Pro Pro Glu Ser Ile Thr Ile Asp Pro Asn Met Trp Glu Glu
            420                 425                 430
Ile Ser Ile Asn Asp Thr Met Val Arg Lys Tyr Asp Gly Gly Tyr Ser
        435                 440                 445
Leu Asn Leu Asp Thr Ser Lys Asn Gln Lys Tyr Ala Ile Tyr Tyr Glu
    450                 455                 460
Gly Ala Tyr Asp Ala Gln Ala Asp Thr Leu Leu Tyr Arg Thr Tyr Ile
465                 470                 475                 480
Gln Ser Leu Asn Ser Tyr Tyr Pro Phe Ser Tyr Gln Lys Met Asn Gly
                485                 490                 495
Val Lys Phe Tyr Glu Asn Ser Ala Ser Gly Ser Gly Glu Leu Lys Pro
            500                 505                 510
Lys Pro Pro Glu Gln Pro Lys Pro Glu Pro Glu Ile Gln Ala Asp Val
        515                 520                 525
Val Asp Ile Ile Glu Asp Ser His Val Ile Asp Ile Gly Trp Asn Thr
    530                 535                 540
Ala Val Gly Glu Glu Ser Gly Ala Asn Gln Gly Pro Gln Glu Glu Ile
545                 550                 555                 560
Thr Glu Asn His Asp Ile Glu Val Ile Glu Glu Asn Asn Leu Val Glu
                565                 570                 575
Met Thr Glu Asp Thr Ala Val Gly Glu Glu Ser Gly Ala Asn Gln Gly
            580                 585                 590
Pro Gln Glu Glu Ile Thr Glu Asn His Asp Ile Glu Val Ile Glu Glu
        595                 600                 605
Asn Asn Leu Val Glu Met Thr Glu Asp Thr Ala Leu Glu Glu Glu Ser
    610                 615                 620
Gly Ala Asn Gln Gly Pro Gln Glu Glu Ile Thr Glu Asn His Asp Ile
625                 630                 635                 640
Glu Val Ile Glu Glu Asn Asn Leu Val Glu Met Thr Glu Asp Thr Ala
                645                 650                 655
Leu Glu Glu Glu Ser Gly Ala Asn Gln Gly Pro Gln Glu Glu Ile Thr
            660                 665                 670
Glu Asn His Asp Ile Glu Val Ile Glu Glu Asn Asn Leu Val Glu Met
        675                 680                 685
Thr Glu Asp Thr Ala Val Gly Glu Glu Ser Gly Ala Asn Gln Gly Pro
    690                 695                 700
Gln Glu Glu Ile Thr Glu Asn His Asp Ile Glu Val Ile Glu Glu Asn
705                 710                 715                 720
Asn Leu Val Glu Met Thr Glu Asp Thr Ala Val Gly Glu Glu Ser Gly
                725                 730                 735
Ala Asn Gln Gly Pro Gln Glu Glu Ile Thr Glu Asn His Asp Ile Glu
            740                 745                 750
Val Ile Glu Glu Asn Asn Leu Val Glu Met Thr Glu Asp Thr Ala Leu
        755                 760                 765
Glu Glu Glu Ser Gly Ala Asn Gln Gly Pro Gln Glu Glu Ile Thr Glu
```

```
                770             775             780
Asn His Asn Ile Glu Val Ile Glu Glu Asn Asn Leu Val Glu Met Thr
785             790             795             800

Glu Asp Thr Ala Val Gly Glu Ser Gly Ala Asn Pro Gly Pro Gln
        805             810             815

Glu Glu Val Thr Glu Asn Gln Pro Gln Gln Glu Ile Met Glu Asn
        820             825             830

Gln Glu Val Glu Lys Lys Gly Asp Ser Asn Leu Val Glu Ser Thr Lys
        835             840             845

Thr Pro Lys Ala Glu Glu Ser Val Ser Val Gln Pro Thr Leu Glu Asp
850             855             860

Lys Asn Thr Lys Asn His Val Asn Thr Val Val Asn Thr Lys Val
865             870             875             880

Ser Glu Val Lys Glu Lys Asp Pro His His Thr Lys Ala Leu Pro Asp
        885             890             895

Thr Gly Thr Thr Ser Arg Ser His Ser Met Met Ile Pro Leu Leu Leu
            900             905             910

Val Ala Gly Ser Val Val Leu Leu Arg Arg Lys Lys Lys His Ser Lys
        915             920             925

Val Asn
    930

<210> SEQ ID NO 7
<211> LENGTH: 4323
<212> TYPE: DNA
<213> ORGANISM: Staphylococcus pseudintermedius

<400> SEQUENCE: 7
atgaataaat caagaactaa acattttaat tttttatcaa acgtcagaa tcggtatgct      60
attcgccact tttcagctgg tactgtgtca gtgcttgtag gagcagcttt cttgctaggt     120
gtccatacga gtgatgcatc tgctgcagaa caagatcaaa catctgaagc aaagcaaaac     180
ctctttgatg cttccgctat ttttggcgct ttaacagaga cgaacgaaaa ggtagcacaa     240
gtgacgccaa cagaaaaaaa tctttcatca gttgaagaaa tgagagataa aggcgcaact     300
ggaaatggac catcaataac atcactacaa actgtagaac aaaataatgc agtacaacct     360
acagcaacac ctattaatga cacagaaaat tcaaccgaag cccctatgaa agaacaatcg     420
aatgatgcac aaacgactga cgaaagtaac aatgccactc agaaaaataa tactgaaccc     480
caagcaaaca tgaaatatc agcgcgtaat gcaaaaacaa cagcatattt aacaagtgaa     540
accttacaa cagcaacgtc tacaactgat atgcctacac agaaacaaga atatccatct     600
ttagaaaatc aacaaatca atcgcaaacg aacagagcac aaccaccaac aatggaagca     660
cccaaactgg cagaaggatt agacaatcta ttaaaaaat caactttcga agtatgtac     720
gtgacaaaaa gaaatcaatt tgacaaagag acggcttcta aaacaaaagc atggccgagt     780
gatgttgttc cagaaaatca gtagagata cttgctgatg caattcaaaa tggctatatc     840
aaatctgtaa atgatgtgac caataaagca catacgttat ctggacgtgc atggatgtta     900
gaccacggaa caccaacgac aatagctaat ggtttaacac tgttccaga gggcactaaa     960
gtttatttgc ggtggataga tcaagatggt gccacttcgc caatgtatac agcaaaaacg    1020
acaagtagat taagcgctgc ggatggtaat caagtgggtc caggtgctta tgctttcgat    1080
ttacgcacag gttggataga tgctaaagga aacaccacg tatatagagc agtaaagggt    1140
caatattata aaatatggat caatgatttt agaactaaag acggtaatat cgctacaatg    1200
```

```
ttacgtgttg caggaggata tgttccggga acgtacgtgg attctgtgac atacaacaat    1260
atgggccaat ttccattaat tggtacaaat atgcaacgta caggtatctt tatgacaacg    1320
ataccttcag aaaaatattt aatatcaaaa cattacgtga agatacaaaa aggtgctgca    1380
gcaaatccag ccgtcacgat aattgaaaat aactttgtga gcggcaaagt ttggatagaa    1440
acaggtgctg agattatgt gaactcagcg acaggtccaa accacaatgc gaaagatgtc    1500
gttgcctctg gatacaaagt ggtcatgtca tcattaacag atcaaggtgc taaagcctac    1560
gatgcgcaag tcaatcgctt gccgaagaaa gatcgagcag aagcagcacg tcaattatta    1620
ataaaacatc cagaatatat cgcagcaact gtagaaggga taacgaatga gtgggggaga    1680
tatacattgc gtttccctaa aggcacattc aacaaagacc atctttacgg ttacgtattg    1740
gattttgatg tgaaattgt aaaaacttat tcaggtttta cttcaccaga gttccggaga    1800
ccgaattata atttgaccgt tacaccgcaa acagctccct attatagacc cgttcgacgt    1860
gcatgggtca atgttaattt tgcggttatt gaagcaccac aatctcaaat cgaaataaaa    1920
gaatttgatg caacctctaa ccctgcgcat cgtgggcaaa cagcaactat tgatatcata    1980
ggtatgccta aaacttcatt acttacacgt gtacaatgga agattcatc gggcagtatt    2040 gttgaggata gtggtcctgt ttttacggaa gaagaggctg aacatatagc ggaatttgta    2100
ataccgtcta gcgcaaaatc aggcgaagtg tatactgtac aactcgtggt aggtaatcat    2160
atcgtagctt cggactctct tattgtacat gtcaatgaag aagcggcgac atatcatccg    2220
atatacccat cgacaacagt agaatcaggt caaagagtaa cgattccagc acctaagaat    2280
atggatggca aacctttact agatggcaca acttttgaaa aaggtcatca cgtaccaact    2340
tgggctttag tgaatggtga tggctcgatt acagtaaaac ctggagaaaa agtagcagag    2400
ggtgagtatg atattccagt gattgtgaca tatccagatg gttctaaaaa cacaatcttt    2460
gcacctgtga ccgttgaaga aaaacaacca atggcatcgc aatatgagcc aataacaact    2520
ggagtatcga aaccatttgg aaacccagta atgccaactg atgtaacaga ttcaattcaa    2580
gtaccgaact atccattgga agggcaacaa ccgacagtaa cagtggatga tgaaagtcaa    2640
ttaccagatg gaacaacaga aggttacaag gatatagatg taacagtgac atacccagac    2700
ggaacaaagg atcgtgtcaa agttccagtc gtaacggaac aacaattaga tagtgataaa    2760
tatgatccgg tcgcaacagg tatcttgaaa ccgtttggta ctccaacaac agaggaagac    2820
gttataaaat tagtggagat accgaaatat ccaacagact aacacaacc aaaagtaaca    2880 gtgacggttc caaatacttt accggatggg caaacgccag gtaaagtaga cgttgatgtg    2940
acagtaacgt atccagatgg ttccacagat cacatttcag ttccagtttg gacaaacaag    3000
catctggata aagacaaata taccccaata acgactgggg tatcgaaacc atttggaatc    3060
ccagtaacgc caactgatgt aacagattca attcaagtac cgaactatcc attggaaggg    3120
caacaactga cagtaacagt ggatgatgaa acacaattac agatggaac aacagaaggt    3180 cacaaggata tagatgtaac agtgacatac ccagacggaa caaaggatca tatcaaagtt    3240
ccagtcgtaa cggaaaaaca atcagataat gaaaaatatg agccaacaac taacggaatc    3300
acgaaaaagt acggtatccc tacgacagag gatgaagtga tagatatagt tcgaattcca    3360
tattttccag tagatggcgt gcaacctatt gtaacggtaa atgatcctag actattgcca    3420
aatggtcaaa aagaaggtca aatcaatgtt ccagtcacag tgacgtatcc ggatggcaca    3480
aaagatctca tgacagttcc ggttattaca ggtaagcaag cagaaaatga aaaatacgat    3540
```

-continued

```
ccaatcacat taggagtaac taaagattat ggtgatccta caactgcaaa cgatgtgaca    3600
aagtcaatcc aaataccaac atatccagca ggtggcgaac aaccaatcgc aacagcggat    3660
gatgaaagtc aattaccgga tggcacagta gaaggtaaag tggatattcc agtcacagtg    3720
acgtatccgg atggtactca ggatcatatc actgtcccag tatttaccaa tcaacaacga    3780
gataatcaaa aagccagtaa agctgtgacg aaaatacatg gtatatcggt aacaggcact    3840
gatatgacag atactaagaa aaatcataac tatccagcag gtggtgaaca acctaaagtt    3900
actgtgaaag atgacgatca attatcagag ggtaaagtcg attcaacagt gggtgcggat    3960
aatgtgacaa ctacagatga tttatcaagc gtaactgcgg tatctcatgg tcatcaaaca    4020
agtgtacaaa caacaaaaga gaaccaatca gtgcatgatg aagaggtgac gatcccaaca    4080
gttgcacatg tgtctacaat aatgacaggt gtggtaaagg gtgagcaaga agcgacggat    4140
atcgtggcta gaccacatgt tgaaacaact caactcccat caatttcagc tcaagcaaca    4200
gttaaaaaac taccagaaac gggtgaaaac aatgaacaat caggtgtttt attaggtgga    4260
tttattgcgt tcatgggtag cttacttta ttcggcagac gtcgcaaacc aaagaaagat    4320
taa                                                                  4323
```

<210> SEQ ID NO 8
<211> LENGTH: 1440
<212> TYPE: PRT
<213> ORGANISM: Staphylococcus pseudintermedius

<400> SEQUENCE: 8

```
Met Asn Lys Ser Arg Thr Lys His Phe Asn Phe Leu Ser Lys Arg Gln
1               5                   10                  15

Asn Arg Tyr Ala Ile Arg His Phe Ser Ala Gly Thr Val Ser Val Leu
            20                  25                  30

Val Gly Ala Ala Phe Leu Leu Gly Val His Thr Ser Asp Ala Ser Ala
        35                  40                  45

Ala Glu Gln Asp Gln Thr Ser Glu Ala Lys Gln Asn Leu Phe Asp Ala
    50                  55                  60

Ser Ala Ile Phe Gly Ala Leu Thr Glu Thr Asn Glu Lys Val Ala Gln
65                  70                  75                  80

Val Thr Pro Thr Glu Lys Asn Leu Ser Ser Val Glu Glu Met Arg Asp
                85                  90                  95

Lys Gly Ala Thr Gly Asn Gly Pro Ser Ile Thr Ser Leu Gln Thr Val
            100                 105                 110

Glu Gln Asn Asn Ala Val Gln Pro Thr Ala Thr Pro Ile Asn Asp Thr
        115                 120                 125

Glu Asn Ser Thr Glu Ala Pro Met Lys Glu Gln Ser Asn Asp Ala Gln
    130                 135                 140

Thr Thr Asp Glu Ser Asn Asn Ala Thr Gln Lys Asn Asn Thr Glu Pro
145                 150                 155                 160

Gln Ala Asn Asn Glu Ile Ser Ala Arg Asn Ala Lys Thr Thr Ala Tyr
                165                 170                 175

Leu Thr Ser Glu Thr Phe Thr Thr Ala Thr Ser Thr Thr Asp Met Pro
            180                 185                 190

Thr Gln Lys Gln Glu Tyr Pro Ser Leu Glu Asn Pro Thr Asn Gln Ser
        195                 200                 205

Gln Thr Asn Arg Ala Gln Pro Pro Thr Met Glu Ala Pro Lys Leu Ala
    210                 215                 220

Glu Gly Leu Asp Asn Leu Leu Lys Lys Ser Thr Phe Glu Ser Met Tyr
```

-continued

```
            225                 230                 235                 240
Val Thr Lys Arg Asn Gln Phe Asp Lys Glu Thr Ala Ser Lys Thr Lys
                245                 250                 255
Ala Trp Pro Ser Asp Val Val Pro Glu Asn Gln Val Glu Ile Leu Ala
                260                 265                 270
Asp Ala Ile Gln Asn Gly Tyr Ile Lys Ser Val Asn Asp Val Thr Asn
                275                 280                 285
Lys Ala His Thr Leu Ser Gly Arg Ala Trp Met Leu Asp His Gly Thr
            290                 295                 300
Pro Thr Thr Ile Ala Asn Gly Leu Thr Pro Val Pro Glu Gly Thr Lys
305                 310                 315                 320
Val Tyr Leu Arg Trp Ile Asp Gln Asp Gly Ala Thr Ser Pro Met Tyr
                325                 330                 335
Thr Ala Lys Thr Thr Ser Arg Leu Ser Ala Ala Asp Gly Asn Gln Val
                340                 345                 350
Gly Pro Gly Ala Tyr Ala Phe Asp Leu Arg Thr Gly Trp Ile Asp Ala
                355                 360                 365
Lys Gly Lys His His Val Tyr Arg Ala Val Lys Gly Gln Tyr Tyr Lys
            370                 375                 380
Ile Trp Ile Asn Asp Phe Arg Thr Lys Asp Gly Asn Ile Ala Thr Met
385                 390                 395                 400
Leu Arg Val Ala Gly Gly Tyr Val Pro Gly Thr Tyr Val Asp Ser Val
                405                 410                 415
Thr Tyr Asn Asn Met Gly Gln Phe Pro Leu Ile Gly Thr Asn Met Gln
                420                 425                 430
Arg Thr Gly Ile Phe Met Thr Thr Ile Pro Ser Glu Lys Tyr Leu Ile
                435                 440                 445
Ser Lys His Tyr Val Lys Asp Thr Lys Gly Ala Ala Ala Asn Pro Ala
            450                 455                 460
Val Thr Ile Ile Glu Asn Asn Phe Val Ser Gly Lys Val Trp Ile Glu
465                 470                 475                 480
Thr Gly Ala Gly Asp Tyr Val Asn Ser Ala Thr Gly Pro Asn His Asn
                485                 490                 495
Ala Lys Asp Val Val Ala Ser Gly Tyr Lys Val Val Met Ser Ser Leu
                500                 505                 510
Thr Asp Gln Gly Ala Lys Ala Tyr Asp Ala Gln Val Asn Arg Leu Pro
            515                 520                 525
Lys Lys Asp Arg Ala Glu Ala Ala Arg Gln Leu Leu Ile Lys His Pro
            530                 535                 540
Glu Tyr Ile Ala Ala Thr Val Glu Gly Ile Thr Asn Glu Trp Gly Arg
545                 550                 555                 560
Tyr Thr Leu Arg Phe Pro Lys Gly Thr Phe Asn Lys Asp His Leu Tyr
                565                 570                 575
Gly Tyr Val Leu Asp Phe Asp Gly Glu Ile Val Lys Thr Tyr Ser Gly
                580                 585                 590
Phe Thr Ser Pro Glu Phe Arg Arg Pro Asn Tyr Asn Leu Thr Val Thr
                595                 600                 605
Pro Gln Thr Ala Pro Tyr Tyr Arg Pro Val Arg Arg Ala Trp Val Asn
            610                 615                 620
Val Asn Phe Ala Val Ile Glu Ala Pro Gln Ser Gln Ile Glu Ile Lys
625                 630                 635                 640
Glu Phe Asp Ala Thr Ser Asn Pro Ala His Arg Gly Gln Thr Ala Thr
                645                 650                 655
```

-continued

```
Ile Asp Ile Ile Gly Met Pro Lys Thr Ser Leu Leu Thr Arg Val Gln
            660                 665                 670

Trp Lys Asp Ser Ser Gly Ser Ile Val Glu Asp Ser Gly Pro Val Phe
        675                 680                 685

Thr Glu Glu Ala Glu His Ile Ala Glu Phe Val Ile Pro Ser Ser
690                 695                 700

Ala Lys Ser Gly Glu Val Tyr Thr Val Gln Leu Val Val Gly Asn His
705                 710                 715                 720

Ile Val Ala Ser Asp Ser Leu Ile Val His Val Asn Glu Glu Ala Ala
                725                 730                 735

Thr Tyr His Pro Ile Tyr Pro Ser Thr Thr Val Glu Ser Gly Gln Arg
            740                 745                 750

Val Thr Ile Pro Ala Pro Lys Asn Met Asp Gly Lys Pro Leu Leu Asp
            755                 760                 765

Gly Thr Thr Phe Glu Lys Gly His His Val Pro Thr Trp Ala Leu Val
770                 775                 780

Asn Gly Asp Gly Ser Ile Thr Val Lys Pro Gly Glu Lys Val Ala Glu
785                 790                 795                 800

Gly Glu Tyr Asp Ile Pro Val Ile Val Thr Tyr Pro Asp Gly Ser Lys
                805                 810                 815

Asn Thr Ile Phe Ala Pro Val Thr Val Glu Glu Lys Gln Pro Met Ala
                820                 825                 830

Ser Gln Tyr Glu Pro Ile Thr Thr Gly Val Ser Lys Pro Phe Gly Asn
            835                 840                 845

Pro Val Met Pro Thr Asp Val Thr Asp Ser Ile Gln Val Pro Asn Tyr
            850                 855                 860

Pro Leu Glu Gly Gln Gln Pro Thr Val Thr Val Asp Asp Glu Ser Gln
865                 870                 875                 880

Leu Pro Asp Gly Thr Thr Glu Gly Tyr Lys Asp Ile Asp Val Thr Val
                885                 890                 895

Thr Tyr Pro Asp Gly Thr Lys Asp Arg Val Lys Val Pro Val Val Thr
                900                 905                 910

Glu Gln Gln Leu Asp Ser Asp Lys Tyr Asp Pro Val Ala Thr Gly Ile
            915                 920                 925

Leu Lys Pro Phe Gly Thr Pro Thr Thr Glu Glu Asp Val Ile Lys Leu
            930                 935                 940

Val Glu Ile Pro Lys Tyr Pro Thr Asp Leu Thr Gln Pro Lys Val Thr
945                 950                 955                 960

Val Thr Val Pro Asn Thr Leu Pro Asp Gly Gln Thr Pro Gly Lys Val
                965                 970                 975

Asp Val Asp Val Thr Val Thr Tyr Pro Asp Gly Ser Asp His Ile
            980                 985                 990

Ser Val Pro Val Trp Thr Asn Lys His Leu Asp Lys Asp Lys Tyr Asn
        995                 1000                1005

Pro Ile Thr Thr Gly Val Ser Lys Pro Phe Gly Ile Pro Val Thr
    1010                1015                1020

Pro Thr Asp Val Thr Asp Ser Ile Gln Val Pro Asn Tyr Pro Leu
    1025                1030                1035

Glu Gly Gln Gln Leu Thr Val Thr Val Asp Asp Glu Thr Gln Leu
    1040                1045                1050

Pro Asp Gly Thr Thr Glu Gly His Lys Asp Ile Asp Val Thr Val
    1055                1060                1065
```

| Thr | Tyr | Pro | Asp | Gly | Thr | Lys | Asp | His | Ile | Lys | Val | Pro | Val | Val |
| | 1070 | | | | 1075 | | | | 1080 | | | | | |

Thr Glu Lys Gln Ser Asp Asn Glu Lys Tyr Glu Pro Thr Thr Asn
    1085            1090            1095

Gly Ile Thr Lys Lys Tyr Gly Ile Pro Thr Thr Glu Asp Glu Val
    1100            1105            1110

Ile Asp Ile Val Arg Ile Pro Tyr Phe Pro Val Asp Gly Val Gln
    1115            1120            1125

Pro Ile Val Thr Val Asn Asp Pro Arg Leu Leu Pro Asn Gly Gln
    1130            1135            1140

Lys Glu Gly Gln Ile Asn Val Pro Val Thr Val Thr Tyr Pro Asp
    1145            1150            1155

Gly Thr Lys Asp Leu Met Thr Val Pro Val Ile Thr Gly Lys Gln
    1160            1165            1170

Ala Glu Asn Glu Lys Tyr Asp Pro Ile Thr Leu Gly Val Thr Lys
    1175            1180            1185

Asp Tyr Gly Asp Pro Thr Thr Ala Asn Asp Val Thr Lys Ser Ile
    1190            1195            1200

Gln Ile Pro Thr Tyr Pro Ala Gly Gly Glu Gln Pro Ile Ala Thr
    1205            1210            1215

Ala Asp Asp Glu Ser Gln Leu Pro Asp Gly Thr Val Glu Gly Lys
    1220            1225            1230

Val Asp Ile Pro Val Thr Val Thr Tyr Pro Asp Gly Thr Gln Asp
    1235            1240            1245

His Ile Thr Val Pro Val Phe Thr Asn Gln Gln Arg Asp Asn Gln
    1250            1255            1260

Lys Ala Ser Lys Ala Val Thr Lys Ile His Gly Ile Ser Val Thr
    1265            1270            1275

Gly Thr Asp Met Thr Asp Thr Lys Lys Asn His Asn Tyr Pro Ala
    1280            1285            1290

Gly Gly Glu Gln Pro Lys Val Thr Val Lys Asp Asp Gln Leu
    1295            1300            1305

Ser Glu Gly Lys Val Asp Ser Thr Val Gly Ala Asp Asn Val Thr
    1310            1315            1320

Thr Thr Asp Asp Leu Ser Ser Val Thr Ala Val Ser His Gly His
    1325            1330            1335

Gln Thr Ser Val Gln Thr Thr Lys Glu Asn Gln Ser Val His Asp
    1340            1345            1350

Glu Glu Val Thr Ile Pro Thr Val Ala His Val Ser Thr Ile Met
    1355            1360            1365

Thr Gly Val Val Lys Gly Glu Gln Glu Ala Thr Asp Ile Val Ala
    1370            1375            1380

Arg Pro His Val Glu Thr Thr Gln Leu Pro Ser Ile Ser Ala Gln
    1385            1390            1395

Ala Thr Val Lys Lys Leu Pro Glu Thr Gly Glu Asn Asn Glu Gln
    1400            1405            1410

Ser Gly Val Leu Leu Gly Gly Phe Ile Ala Phe Met Gly Ser Leu
    1415            1420            1425

Leu Leu Phe Gly Arg Arg Arg Lys Pro Lys Lys Asp
    1430            1435            1440

<210> SEQ ID NO 9
<211> LENGTH: 4701
<212> TYPE: DNA

<213> ORGANISM: Staphylococcus pseudintermedius

<400> SEQUENCE: 9

```
atgtttaatc aacaaaaaca acactatggt atccggaaat atgcaatcgg gacttcatca        60
gtattattag gcatgacatt atttatcaca catgacgcaa ctgcatctgc agctgaaaac       120
aatacaactg caaagacaga gacaaatcaa gcagcaacaa tttcttctcg cacttcgcca       180
accgacgtcg ctcaacctaa tgcagacacg aatgctacaa cggcgactaa agagacaaca       240
ccacaatcag attcaacagc attaccgcaa gcagcagcgc aacctcaaac gggccaaaca       300
gcatcgaaag acacagtaga tacaaataaa acgcaaacag cagattccac aaccgctcct       360
cctgtgacag acgcgccaaa agctaatgac gacacaacac agccagaagc tgcgactgta       420
gccaaaaaag aagatgctca gacaccatcg actgcagacc ctacaccaca agcgcaacaa       480
ccgcctcagt caaaagcacc tcaagaaacg caacaacaat caacagttga agatacaacg       540
ccacaacaaa acgcatcaac tgaagcacac cctaaaaatg tagataccgc ttcaacaaaa       600
caacaacaaa caacgccatc aaccgcaccg acaccttaca cacaacaagc agacgaagca       660
atgacagatg tcacaacaac cagtgtcgac agcaacgtac agccgttagc ccctgcagaa       720
gatcaaccta aaaatacgaa cacagctgac aaagcaaccg ttgcgacacc accacgtgac       780
aatgctaaga ctgctgatcc gaacaaaaag atgacacgtg cagcaacgac acaacaagat       840
gatgccgtcg atacattgaa gtcaaaagaa atgacagcaa cgatcgataa aagttttcca       900
gccgttaaat attacacgtt gaaaaatggt aaaaaagtcg atgcacaact gacggatgca       960
cgtcaaatca tcgtcaatgg tgaagtcatt acaccaacag tcaaatacaa caaaattgat      1020
gatcatacgg ctgaatatga cttaacagca caaaatgatt cacgttcgat tgatgccaat      1080
tttaaatttc gtttatcagt tgaaggtaag accgttgatt tacaaatgac agattacacg      1140
aacaacaaca cagatccaca aaacgtcatt cgcaacttta gctttgtaag tcaatcgctc      1200
gtatctgtaa acaatcaaca gaaaaatgcc aaactgcaaa catcgaaact gtctacaaat      1260
acaatgaaaa gcggcgataa atcatatcat atcgatgaaa atttcaaaaa cgacttcaac      1320
gactttatga tgtacggttt cgtgtcaaat gatgattaca gtgcaggatt gtggagtaac      1380
gcacaaattg gcgtcggcat tggtgaacaa gacttcttac gtgtctacgc acagtctata      1440
caaacagata tcggggtcgc tgtcggttta ggctcaatgc catggtttat ccaaaaagac      1500
gctgcacatc cagatgcgaa aaatcaagga ctactcccac atgtcaaagt tgcaattgcg      1560
gaagatgaaa atcaagatgg tgaaattaac tggcaagacg gtgcaattgc ttatcgtagc      1620
attatgaaca atccatatgg tgccgaagaa gtacctgacc ttgttgggta ccgtatcgcg      1680
atgaactttg gttctcaagc gcaaaaccca tttttaaaga cgttagatgg tgtgaaaaaa      1740
ttctatctca atacagatgg tttagggcaa tccattttat taaaaggtta taacagtgaa      1800
ggccacgact ctggtcattt agattacgcg aatattggtc aacgtatagg tggcgtgaaa      1860
gactttaaaa cgttacttca aaaggggca gattatggcg cacgtttcgg tcttcatgtg      1920
aatgcatctg aaacatatcc agagtctcaa gcattcaatc ctgccctctt acgtaaagat      1980
gcgaatggaa actatatgta tggctggaac tggctcgatc aaggctttaa catcgatgca      2040
gattacgatt taatacacgg gcgtaaagaa cgcttcgaag cactcaaaca aattgtcggt      2100
gatgaccctcg actttattta tgtcgatgta tgggggaatg gacaatccgg cgacaataca      2160
gcttggccat cacatcaatt agccaaagaa atcaacgact aggatggcg cgtcggtgtc      2220
gaatggggtc acggtatgga atatgactcc acgttccaac attgggcagc cgacttaacg      2280
```

```
tatgatcgt accaaaataa agggattaac tcagaggtag cacgcttctt acgcaaccat    2340 caaaagatt catgggtcgg taactatcca aaatactcag gtgcagctga cttcccattg    2400
ctcggcggtt atgacatgaa agattttgaa ggttggcaag gtcgtaacga ttactctgct    2460
tacattaaaa atattttcaa tgttgatgta ccaacaaagt ttttacaaca ttataaagtg    2520
atgcgtattg tcgatggtga gcctgttaaa atgactgcca atggtcaaac gattgactgg    2580
acaccagaaa tgcaagtcga tttacaaaat gaagccggtg atcaagtcac tgttaaacgt    2640
aaatctaacg actatgaaaa cgacactgac aactaccgct cacgtacaat cgaattgaat    2700
ggtcgcacag tactcgatgg cgattcatac cttttaccat ggaattggga tgcgaacggc    2760
caaccattaa ctggcgataa cgaaaaatta tatcactgga ataaaaaagg cggttcaacg    2820
acttggacac tgcctgaatc atgggataca gaccaagtcg tgctatacga attatctgaa    2880
acgggtcgta agtcaccacg tacagtggca gtgaaagacc atcaagtgac actcgataat    2940
attaaagcag acacaccgta tgtcgtttat aaagtcgcac aaccagacaa cacagatgtg    3000
aactggagcg aagacatgca cgtgaaagat gccggcttca actcacaaca actgacacct    3060
tggacaatcg aaggcaatcg agataaagtg agcatcgaaa agtcgacaac atcaaatgaa    3120
atgctaaaaa tcgatagtcc aacaaaaaca acgcaattaa cgcaacaatt gacaggttta    3180
gtgccaggac aacgttacgc tgtctatgtt ggcatcgata accgcagtga tgcagcggcg    3240
catattgcag tgacacataa cggtaaaacg ctcgcaagta acgaaacagg tcaatcgatc    3300
gcgaaaaact atgtgaaagc agatgcacat agtaacaatg ctgcgacgtt taaaaatggc    3360
ggtagttact tccaaaacat gtacgtgtac ttcgttgcgc cagaagatgg taaagcagac    3420
ttgacgattc aacgcgaccc aggtgaaggg gccacttatt tcgatgatat tcgtgtgtta    3480
gaaaataacg cgaatctcct tcaaaacggc acattcaacc aagacttcga aaatgtacca    3540
caagggttat tcccgttcgt cgtgtcagaa gttgaaggcg ttgaagataa tcgcgttcac    3600
ttatctgaaa agcacgcacc gtatacacaa cgcggatgga ataataaacg tgtcgatgat    3660
gtcattgatg gcaaatggtc acttaaagta aacggtcaaa caggtaaaga taaaatggtc    3720
atccaaacga ttccgcaaaa cttctacttc gaaccaggaa aaacgtatga agtgtcattt    3780
gattatgaag caggttctga tgatacgtat gcatttgcga caggtagtgg ggacatttct    3840
aaaaatcgta actttgaaaa gacaccattg aaaaatacag tcgatggtgg caaagcgaaa    3900
cgggtgacat ttaaagtgac gggtgatgaa atggtcaaa cttggatcgg tatttactca    3960
acgaaaacac ccaatgatcc acgaggcgtg aaaaatggca atcaaatcaa cttcgaaggg    4020
acgaaagatt tcattctaga caacctttct atccgtgaaa ttgacgcacc gaagcctgat    4080
gccacacaag aaagcggtga tagcgcacca atgaatgaaa cagatgagcg taacgtcaat    4140
tcaaacggta cattagccga tcatagtgag acaactgatg tcaatgtcag tgcaacggca    4200
gatgatacag cagtcaaagg cgaaatgacg acaaacagaa cagatgcacc aactgttaca    4260
ctgcctgaag caacgatagt agatgaaggc acgtcaaatc ctgtcactac aacaccaacg    4320
aatacaacac aagctatgac aaataaggct gatgagatgc cacaaacgat gaacaatgtt    4380
cctttaacta gcatcgctac cgatatgatg cagtctcatg cggtggattc catggcagca    4440
acactagcag ctacaaatca agtggcggca cctgtgcgtc aaacagcagg acctatgcaa    4500
catggtatgg acagtgcttc aacgcaacac gcacccatac aagttgacaa tgtcacagca    4560
ccaccattac cagatgaaca gtttgccgaa ttacctaaaa ctgggatac gactccaaat    4620
```

```
acacgtggac ctttaatggc gatgatagtt ggcgcagtct taacagcatt cggattcaga    4680
cgccaacgta aagaaaaata g                                              4701
```

<210> SEQ ID NO 10
<211> LENGTH: 1566
<212> TYPE: PRT
<213> ORGANISM: Staphylococcus pseudintermedius

<400> SEQUENCE: 10

```
Met Phe Asn Gln Gln Lys Gln His Tyr Gly Ile Arg Lys Tyr Ala Ile
1               5                   10                  15

Gly Thr Ser Ser Val Leu Leu Gly Met Thr Leu Phe Ile Thr His Asp
            20                  25                  30

Ala Thr Ala Ser Ala Ala Glu Asn Asn Thr Ala Lys Thr Glu Thr
        35                  40                  45

Asn Gln Ala Ala Thr Ile Ser Ser Arg Thr Ser Pro Thr Asp Val Ala
    50                  55                  60

Gln Pro Asn Ala Asp Thr Asn Ala Thr Thr Ala Thr Lys Glu Thr Thr
65                  70                  75                  80

Pro Gln Ser Asp Ser Thr Ala Leu Pro Gln Ala Ala Gln Pro Gln
                85                  90                  95

Thr Gly Gln Thr Ala Ser Lys Asp Thr Val Asp Thr Asn Lys Thr Gln
            100                 105                 110

Thr Ala Asp Ser Thr Thr Ala Pro Pro Val Thr Asp Ala Pro Lys Ala
        115                 120                 125

Asn Asp Asp Thr Thr Gln Pro Glu Ala Ala Thr Val Ala Lys Lys Glu
    130                 135                 140

Asp Ala Gln Thr Pro Ser Thr Ala Asp Pro Thr Pro Gln Ala Gln Gln
145                 150                 155                 160

Pro Pro Gln Ser Lys Ala Pro Gln Glu Thr Gln Gln Ser Thr Val
                165                 170                 175

Glu Asp Thr Thr Pro Gln Gln Asn Ala Ser Thr Glu Ala His Pro Lys
            180                 185                 190

Asn Val Asp Thr Ala Ser Thr Lys Gln Gln Gln Thr Thr Pro Ser Thr
        195                 200                 205

Ala Pro Thr Pro Tyr Thr Gln Gln Ala Asp Glu Ala Met Thr Asp Val
    210                 215                 220

Thr Thr Thr Ser Val Asp Ser Asn Val Gln Pro Leu Ala Pro Ala Glu
225                 230                 235                 240

Asp Gln Pro Lys Asn Thr Asn Thr Ala Asp Lys Ala Thr Val Ala Thr
                245                 250                 255

Pro Pro Arg Asp Asn Ala Lys Thr Ala Asp Pro Asn Lys Lys Met Thr
            260                 265                 270

Arg Ala Ala Thr Thr Gln Gln Asp Asp Ala Val Asp Thr Leu Lys Ser
        275                 280                 285

Lys Glu Met Thr Ala Thr Ile Asp Lys Ser Phe Pro Ala Val Lys Tyr
    290                 295                 300

Tyr Thr Leu Lys Asn Gly Lys Lys Val Asp Ala Gln Leu Thr Asp Ala
305                 310                 315                 320

Arg Gln Ile Ile Val Asn Gly Glu Val Ile Thr Pro Thr Val Lys Tyr
                325                 330                 335

Asn Lys Ile Asp Asp His Thr Ala Glu Tyr Asp Leu Thr Ala Gln Asn
            340                 345                 350

Asp Ser Arg Ser Ile Asp Ala Asn Phe Lys Phe Arg Leu Ser Val Glu
```

```
                355                 360                 365
Gly Lys Thr Val Asp Leu Gln Met Thr Asp Tyr Thr Asn Asn Thr
        370                 375                 380
Asp Pro Gln Asn Val Ile Arg Asn Phe Ser Phe Val Ser Gln Ser Leu
385                 390                 395                 400
Val Ser Val Asn Asn Gln Lys Asn Ala Lys Leu Gln Thr Ser Lys
                405                 410                 415
Leu Ser Thr Asn Thr Met Lys Ser Gly Asp Lys Ser Tyr His Ile Asp
                420                 425                 430
Glu Asn Phe Lys Asn Asp Phe Asn Asp Phe Met Met Tyr Gly Phe Val
        435                 440                 445
Ser Asn Asp Asp Tyr Ser Ala Gly Leu Trp Ser Asn Ala Gln Ile Gly
450                 455                 460
Val Gly Ile Gly Glu Gln Asp Phe Leu Arg Val Tyr Ala Gln Ser Ile
465                 470                 475                 480
Gln Thr Asp Ile Gly Val Ala Val Gly Leu Gly Ser Met Pro Trp Phe
                485                 490                 495
Ile Gln Lys Asp Ala Ala His Pro Asp Ala Lys Asn Gln Gly Leu Leu
                500                 505                 510
Pro His Val Lys Val Ala Ile Ala Glu Asp Glu Asn Gln Asp Gly Glu
        515                 520                 525
Ile Asn Trp Gln Asp Gly Ala Ile Ala Tyr Arg Ser Ile Met Asn Asn
530                 535                 540
Pro Tyr Gly Ala Glu Glu Val Pro Asp Leu Val Gly Tyr Arg Ile Ala
545                 550                 555                 560
Met Asn Phe Gly Ser Gln Ala Gln Asn Pro Phe Leu Lys Thr Leu Asp
                565                 570                 575
Gly Val Lys Lys Phe Tyr Leu Asn Thr Asp Gly Leu Gly Gln Ser Ile
                580                 585                 590
Leu Leu Lys Gly Tyr Asn Ser Glu Gly His Asp Ser Gly His Leu Asp
        595                 600                 605
Tyr Ala Asn Ile Gly Gln Arg Ile Gly Gly Val Lys Asp Phe Lys Thr
610                 615                 620
Leu Leu Gln Lys Gly Ala Asp Tyr Gly Ala Arg Phe Gly Leu His Val
625                 630                 635                 640
Asn Ala Ser Glu Thr Tyr Pro Glu Ser Gln Ala Phe Asn Pro Ala Leu
                645                 650                 655
Leu Arg Lys Asp Ala Asn Gly Asn Tyr Met Tyr Gly Trp Asn Trp Leu
                660                 665                 670
Asp Gln Gly Phe Asn Ile Asp Ala Asp Tyr Asp Leu Ile His Gly Arg
        675                 680                 685
Lys Glu Arg Phe Glu Ala Leu Lys Gln Ile Val Gly Asp Asp Leu Asp
        690                 695                 700
Phe Ile Tyr Val Asp Val Trp Gly Asn Gly Gln Ser Gly Asp Asn Thr
705                 710                 715                 720
Ala Trp Pro Ser His Gln Leu Ala Lys Glu Ile Asn Asp Leu Gly Trp
                725                 730                 735
Arg Val Gly Val Glu Trp Gly His Gly Met Glu Tyr Asp Ser Thr Phe
                740                 745                 750
Gln His Trp Ala Ala Asp Leu Thr Tyr Gly Ser Tyr Gln Asn Lys Gly
        755                 760                 765
Ile Asn Ser Glu Val Ala Arg Phe Leu Arg Asn His Gln Lys Asp Ser
        770                 775                 780
```

-continued

```
Trp Val Gly Asn Tyr Pro Lys Tyr Ser Gly Ala Ala Asp Phe Pro Leu
785                 790                 795                 800

Leu Gly Gly Tyr Asp Met Lys Asp Phe Glu Gly Trp Gln Gly Arg Asn
            805                 810                 815

Asp Tyr Ser Ala Tyr Ile Lys Asn Ile Phe Asn Val Asp Val Pro Thr
        820                 825                 830

Lys Phe Leu Gln His Tyr Lys Val Met Arg Ile Val Asp Gly Glu Pro
            835                 840                 845

Val Lys Met Thr Ala Asn Gly Gln Thr Ile Asp Trp Thr Pro Glu Met
850                 855                 860

Gln Val Asp Leu Gln Asn Glu Ala Gly Asp Gln Val Thr Val Lys Arg
865                 870                 875                 880

Lys Ser Asn Asp Tyr Glu Asn Asp Thr Asp Asn Tyr Arg Ser Arg Thr
                885                 890                 895

Ile Glu Leu Asn Gly Arg Thr Val Leu Asp Gly Asp Ser Tyr Leu Leu
            900                 905                 910

Pro Trp Asn Trp Asp Ala Asn Gly Gln Pro Leu Thr Gly Asp Asn Glu
        915                 920                 925

Lys Leu Tyr His Trp Asn Lys Lys Gly Gly Ser Thr Thr Trp Thr Leu
        930                 935                 940

Pro Glu Ser Trp Asp Thr Asp Gln Val Val Leu Tyr Glu Leu Ser Glu
945                 950                 955                 960

Thr Gly Arg Lys Ser Pro Arg Thr Val Ala Val Lys Asp His Gln Val
                965                 970                 975

Thr Leu Asp Asn Ile Lys Ala Asp Thr Pro Tyr Val Val Tyr Lys Val
            980                 985                 990

Ala Gln Pro Asp Asn Thr Asp Val  Asn Trp Ser Glu Asp  Met His Val
                995                  1000                 1005

Lys Asp  Ala Gly Phe Asn Ser  Gln Gln Leu Thr Pro  Trp Thr Ile
    1010             1015                 1020

Glu Gly  Asn Arg Asp Lys Val  Ser Ile Glu Lys Ser  Thr Thr Ser
    1025             1030                 1035

Asn Glu  Met Leu Lys Ile Asp  Ser Pro Thr Lys Thr  Thr Gln Leu
    1040             1045                 1050

Thr Gln  Gln Leu Thr Gly Leu  Val Pro Gly Gln Arg  Tyr Ala Val
    1055             1060                 1065

Tyr Val  Gly Ile Asp Asn Arg  Ser Asp Ala Ala Ala  His Ile Ala
    1070             1075                 1080

Val Thr  His Asn Gly Lys Thr  Leu Ala Ser Asn Glu  Thr Gly Gln
    1085             1090                 1095

Ser Ile  Ala Lys Asn Tyr Val  Lys Ala Asp Ala His  Ser Asn Asn
    1100             1105                 1110

Ala Ala  Thr Phe Lys Asn Gly  Gly Ser Tyr Phe Gln  Asn Met Tyr
    1115             1120                 1125

Val Tyr  Phe Val Ala Pro Glu  Asp Gly Lys Ala Asp  Leu Thr Ile
    1130             1135                 1140

Gln Arg  Asp Pro Gly Glu Gly  Ala Thr Tyr Phe Asp  Asp Ile Arg
    1145             1150                 1155

Val Leu  Glu Asn Asn Ala Asn  Leu Leu Gln Asn Gly  Thr Phe Asn
    1160             1165                 1170

Gln Asp  Phe Glu Asn Val Pro  Gln Gly Leu Phe Pro  Phe Val Val
    1175             1180                 1185
```

```
Ser Glu Val Glu Gly Val Glu Asp Asn Arg Val His Leu Ser Glu
1190                1195                1200

Lys His Ala Pro Tyr Thr Gln Arg Gly Trp Asn Asn Lys Arg Val
1205                1210                1215

Asp Asp Val Ile Asp Gly Lys Trp Ser Leu Lys Val Asn Gly Gln
1220                1225                1230

Thr Gly Lys Asp Lys Met Val Ile Gln Thr Ile Pro Gln Asn Phe
1235                1240                1245

Tyr Phe Glu Pro Gly Lys Thr Tyr Glu Val Ser Phe Asp Tyr Glu
1250                1255                1260

Ala Gly Ser Asp Asp Thr Tyr Ala Phe Ala Thr Gly Ser Gly Asp
1265                1270                1275

Ile Ser Lys Asn Arg Asn Phe Glu Lys Thr Pro Leu Lys Asn Thr
1280                1285                1290

Val Asp Gly Gly Lys Ala Lys Arg Val Thr Phe Lys Val Thr Gly
1295                1300                1305

Asp Glu Asn Gly Gln Thr Trp Ile Gly Ile Tyr Ser Thr Lys Thr
1310                1315                1320

Pro Asn Asp Pro Arg Gly Val Lys Asn Gly Asn Gln Ile Asn Phe
1325                1330                1335

Glu Gly Thr Lys Asp Phe Ile Leu Asp Asn Leu Ser Ile Arg Glu
1340                1345                1350

Ile Asp Ala Pro Lys Pro Asp Ala Thr Gln Glu Ser Gly Asp Ser
1355                1360                1365

Ala Pro Met Asn Glu Thr Asp Glu Arg Asn Val Asn Ser Asn Gly
1370                1375                1380

Thr Leu Ala Asp His Ser Glu Thr Thr Asp Val Asn Val Ser Ala
1385                1390                1395

Thr Ala Asp Asp Thr Ala Val Lys Gly Glu Met Thr Thr Asn Arg
1400                1405                1410

Thr Asp Ala Pro Thr Val Thr Leu Pro Glu Ala Thr Ile Val Asp
1415                1420                1425

Glu Gly Thr Ser Asn Pro Val Thr Thr Pro Thr Asn Thr Thr
1430                1435                1440

Gln Ala Met Thr Asn Lys Ala Asp Glu Met Pro Gln Thr Met Asn
1445                1450                1455

Asn Val Pro Leu Thr Ser Ile Ala Thr Asp Met Met Gln Ser His
1460                1465                1470

Ala Val Asp Ser Met Ala Ala Thr Leu Ala Ala Thr Asn Gln Val
1475                1480                1485

Ala Ala Pro Val Arg Gln Thr Ala Gly Pro Met Gln His Gly Met
1490                1495                1500

Asp Ser Ala Ser Thr Gln His Ala Pro Ile Gln Val Asp Asn Val
1505                1510                1515

Thr Ala Pro Pro Leu Pro Asp Glu Gln Phe Ala Glu Leu Pro Lys
1520                1525                1530

Thr Gly Asp Thr Thr Pro Asn Thr Arg Gly Pro Leu Met Ala Met
1535                1540                1545

Ile Val Gly Ala Val Leu Thr Ala Phe Gly Phe Arg Arg Gln Arg
1550                1555                1560

Lys Glu Lys
1565
```

<210> SEQ ID NO 11
<211> LENGTH: 10509
<212> TYPE: DNA
<213> ORGANISM: Staphylococcus pseudintermedius

<400> SEQUENCE: 11

| | | | | | |
|---|---|---|---|---|---|
| atgacaagaa | aatttaggga | atttaagaaa | agtttaagtg | aagaaaaagc | aagagtgaaa | 60 |
| ctttacaagt | caggtaaaaa | ctgggttaaa | gctggaatta | agaatttca | gttattaaaa | 120 |
| gcattaggct | tatctttttt | aagccatgac | attgtaaagg | atgaaaatgg | agaagtaacg | 180 |
| acacaatttg | gggaacagtt | gaagaaaaat | gcattaagaa | caactgcttt | tgcgggtgga | 240 |
| atgttcacag | ttaatatgtt | gcatgaccaa | caagcatttg | cggcgtcgga | tgcacctata | 300 |
| acttctgaac | tggcaaccaa | aagtcaaact | attggcgatc | aaacatcaat | tgttattgaa | 360 |
| aagtctacat | cgtcagatca | atcaacgaac | ccaataacag | aaagtgaaag | taaacacgat | 420 |
| tctgaaagta | tctcattatc | tgagcatcaa | acatcagagt | caacaagtct | ttcaacgtca | 480 |
| acttccaaat | caatatcaac | ttcagtagag | gaatcagaat | caacatcaaa | agattctcat | 540 |
| actaaaactc | aagatagtca | atcagatagt | catcagtcaa | caagtcaaga | ggtaaatggc | 600 |
| tcttccaacc | acgagcaatc | aacaccacac | actgcacaaa | gtcttacgag | cctatctatt | 660 |
| gagagccaaa | cgtcgacttc | aaatacatca | ttgaaggaaa | ctaaagaagg | ggaattgtca | 720 |
| aaaacctt | cgaagttatc | tcaaaatcaa | aacatcaaac | ttcatgaaga | acatacgatg | 780 |
| cgttcagcag | atttgagctc | aggttataca | ggatttagag | cggcttacta | tgtaccaaga | 840 |
| tcaagaacaa | caccaacgac | aaaagtctac | acagggcaag | gaagcttcag | aggtagaggt | 900 |
| agaattaaat | ataatatttt | ctacaaagtt | gtcgttacaa | gtaatggcaa | agaaatgaag | 960 |
| atccgctata | cattgagtca | agatgatcca | aacacgtcta | atgttgaaaa | acctaggtgg | 1020 |
| gcaggacaga | aacgatttgg | tattcataat | acttgggatg | aaggtcctgg | tcgcgggcaa | 1080 |
| ttaaagttag | ggtcggcatt | cggcaaacca | acagttatac | aaggagaaac | tagaccgaat | 1140 |
| tatggtagct | gggttggcac | acctataacg | aaatatgttt | caggcgatcg | tacaaatggt | 1200 |
| ttttactggc | aagctgctgt | acttgcaccg | agacatggag | agaagggaga | aggaatcaca | 1260 |
| gcagaaatta | cagttcctat | tgttaaccct | tctggaagat | taattggga | attccatcct | 1320 |
| gtcggtcaac | aggacggagt | tggtggcaaa | actgactact | tgaaaatgt | atggattcga | 1380 |
| gactatgacc | catattacaa | atatattcaa | actaaggaag | gcagagcctc | agtttcgcac | 1440 |
| tctatttctc | aggtgaaagc | aagtgaatcg | agatcgacat | cgctcataca | atcggagtct | 1500 |
| attagaagat | cacagtccat | atctgagagt | gaatctattg | tagccgcaag | tcattcggca | 1560 |
| agtgtagcaa | aatcgcaatc | catctcgaga | agtcaatctg | tggcgaaatc | acaatcgatc | 1620 |
| tcaagaagtc | agtcgatcgc | acacagccga | tcagcaagtg | tggcaaaatc | gcaatccatc | 1680 |
| tcaagaagtc | agtcgatcgc | acacagccga | tcagcaagtg | tggcaaaatc | acaatcgatt | 1740 |
| tcaagaagtc | agtcgatcgc | acacagccga | tcagcaagtg | tggcgaaatc | tcaatcgatt | 1800 |
| tcaagaagtc | agtcaattgc | gcagagccaa | tcagcaagtg | tggcaaaatc | acagtcgatt | 1860 |
| tcaagaagtc | agtcaattgc | gcagagccaa | tcagcaagtg | tggcgaaatc | gcaatcgatt | 1920 |
| tcaagaagtc | agtcgattgc | acatagccga | tcagcaagta | gcggaatc | acagtcgatt | 1980 |
| tcaagaagtc | agtcgattgc | gaatagccaa | tctgtagcag | cgagtgaatc | agagagtcta | 2040 |
| tcaatatcat | tgtctaaaaa | gcagtcaata | tcgatgagta | attctgaaag | tgcagcaaaa | 2100 |
| tcacactcgc | tttcggtgaa | aaggtctaac | tggattaaaa | agtcaaaagc | ggcttcagta | 2160 |

```
agaaagtcac attcactttc ggtaagaaaa tctaattcgg cgaaaaggtc acatgctatt    2220
tcggtaagaa agtcaaagtc attatcagtt aaaaagtcaa tttcgcagag ccaatcagca    2280
agtgtggcga aatcgcaatc gatttcaaga agtcaatcag tagcagcgag tgagtcggca    2340
tcgctaagta agtcgaagag cacatcgctc agtaactcag tgagtgcaga gaaatcgacg    2400
tcattaagtc gttcagcaag tgtagcaaaa tcgcaatcga tttcaagaag ccaatcagta    2460
gtagcgagcg aatcggcatc gttaagtaag tcgaagagca catcgctcag taactcagtg    2520
agtgcagaga aatcgacgtc attaagtcga tcagcaagtg tagcaaaatc gcaatcgatt    2580
tcaagaagcc aatcggtggc agcgagcgaa tcggcatcgt taagtaagtc gaagagcaca    2640
tcgctcagta actcagtgag tgcagagaaa tcgacgtcat taagtcgatc agcaagtgta    2700
gcaaaatcgc aatcgatttc aagaagccaa tcggtggcag cgagcgaatc ggcatcgtta    2760
agtaagtcga agagcacatc gctcagtaac tcagtgagtg cagagaaatc gacgtcatta    2820
agtcgatcag caagtgtggc aaaatcgcaa tcgatttcaa gaagccaatc agtagtagcg    2880
agcgaatcgg catcgttaag taagtcgaag agcacatcgc tcagtaactc agtgagtgca    2940
gagaaatcga cgtcattaag tcgatcagca agtgtagcaa aatcgcaatc gatttcaaga    3000
agccaatcgg tggcagcgag cgaatcggca tcgttaagta agtcgaagag cacatcgctc    3060
agtaactcag tgagtgcaga gaaatcgacg tcattaagtc gatcagcaag tgtggcaaaa    3120
tcgcaatcga tttcaagaag ccagtcagta gcagcaagtg agtcggcatc attaagtaag    3180
tcgaagagca catctttaag caactcagtg agtgtagaga atcgacgtc  attaagtcga    3240 tcagcaagtg tggcgaaatc gcaatcgatt tcaagaagtc aatcagtagc agcgagtgag    3300
tcggcatcgc taagtaagtc gaagagcaca tcgctcagta actcagtgag tgcagagaaa    3360
tcgacgtcat taagtcgttc agcaagtgta gcaaaatcgc aatcgatttc aagaagccag    3420
tcagtagcag caagtgagtc ggcatcattg agtaaatcaa caagtacgtc aacaagtgac    3480
tcagatagcg cgtcaacatc aacatctgta tcagatagcg attcagcttc attgagtaag    3540
tcgactagta catcaacaag cgattcagac agcgcgtcag catcattgag caagtcaaca    3600
agtacatcaa cgagcgactc agatagcgca tcgacatcaa catcagtatc agatagcgac    3660
tccgcatcgt tgagtaaatc gacaagcacg tcaacaagtg attcagacag cacgtctact    3720
tcattgagta agtcgacaag tacatcgaca agtgattcag atagtgcgtc aaaatcaacg    3780
tcagtatcag acagtacgtc cgcatcattg agtaaatcga caagcacgtc aacaagtgat    3840
tcagatagtg catcaaaatc aacgtcggta tcagatagca cgtcagcatc attaagaaag    3900
tcggcaagta cgtcaacgag tgactcagac agcacgtcta cttcattgag taagtcgaca    3960 agtcacatcga caagtgattc agatagtgca tcaaaatcaa catcagtatc agatagcgat    4020
tcagcttcat tgagtaagtc gactagtaca tcaacaagcg attcagatag tgcgtcaaaa    4080
tcaacgtcgg tatcagatag cgactccgca tcgttgagta agtcgacaag tacgtcaaca    4140
agcgattcag acagtgcatc aaaatcaacg tcggtatcag acagtacgtc aacatcatta    4200
agtaagtcga caagtacatc aacaagcgat tcagatagtg cgtcaacatc gacatcagta    4260
tcggacagta cgtctgcatc attgagtaag tcgacaagca catcgacaag tgattcagat    4320
agcgcatcaa catcagtgtc agatagcgat tcagcatcac taagcaagtc aacaagtaca    4380
tcgacaagcg attcagacag cgtatcaaca tcaacatcag tatcagatag tgattccgcg    4440
tcattaagta agtcgacaag tacgtcaaca agcgattcag atagtgcgtc aaaatcaaca    4500
tcagtatcag atagcacgtc aacatcattg agtaaatcaa caagtacatc gacaagtgac    4560
```

```
tcagatagtg cgtcaacatc ggtatcagac agtacgtccg catcattgag taaatcgaca    4620
agcacgtcaa caagtgattc agatagtgca tcaaaatcaa catcagtatc agatagcgat    4680
tcagcatcat taagcaagtc gacaagtaca tcgacaagtg attcagatag tgcgtcaaca    4740
tcaacgtcag tgtcagatag cgattcagct tcattaagca aatcaacaag tacgtcaaca    4800
agtgactcag atagcgcatc aacatcatta agcaagtcaa caagtacatc gacaagcgat    4860
tcagacagta cgtctacatc attaagtaag tcaacaagta catcaacaag tgattcggat    4920
agtgcgtcaa aatcaacatc agtatcagat agcgactcag cttcattaag caagtcgaca    4980
agtacgtcaa caagtgactc agacagtgcg tcaaaatcaa catctgtgtc agatagcgac    5040
tccgcatcgt tgagtaagtc gacaagtacg tcaacgagcg attcggatag tgcgtcaaaa    5100
tcaacatcag tatcagatag tgaatccgcg tcattaagca agtcgacaag cacatcgaca    5160
agtgactcag atagtgcgtc aacatcgaca tcggtatcag acagcacatc agtttcatta    5220
agcaagtcga caagcacgtc aacaagcgat tcagacagta cgtctacttc attaagcaag    5280
tcgacaagca cgtcaacaag tgactcagat agtgactcag cttcgttgag taaatcgaca    5340
agcacgtcaa cgagcgattc agatagcgtg tcaacatcaa catctgtgtc agatagcgat    5400
tcagcttcat taagcaaatc gacaagtaca tcaacaagcg attcagatag tgcgtcaaca    5460
tcaacgtcgg tatcagatag cggctccgca tcgttgagta agtcgacaag tacgtcaacg    5520
agcgattcag acagtgcatc aaaatcaacg tcggtatcag atagtgattc agcatcacta    5580
agcaaatcga caagcacgtc aacaagtgac tcagacagtg cgtcaacatc gacatcggta    5640
tcagatagca catccgcgtc gttaagcaag tcgacaagta cgtcaacaag tgattcagac    5700
agcgcatcga catcaacatc agtatcagat agcgactccg catcgttgag taaatcgaca    5760
agcacgtcaa caagtgattc ggacagtgcg tcaaaatcaa catcagtgtc agatagcgat    5820
tcagcttcat tgagtaagtc gacaagcacg tcaacaagcg aatcgacacg cgcgtcaaaa    5880
tcaacgtcag tgtcagatag cgattccgca tcattaagta aatcgacaag cacgtcaaca    5940
agtgactcag atagtgcatc gacatcaacg tcagtatcag atagtgattc cgcgtcatta    6000
agcaagtcga caagtacgtc aacaagtgac tcagacagtg cgtcaaaatc aacatcagta    6060
tcagatagcg attccgcatc attgagtaag tcgacaagca cgtcaacaag cgaatcagac    6120
agtgcgtcaa catcgacatt agtatcggat agtacgtcgg tttcattgag ccaatcaaca    6180
agtgtggata aagatagtac agcgaaggga tcgacagaat tagtaaatgt tgcatcactt    6240
tcaatcagtg cgagtcaatc aagtagttta tctgcttcaa catccacatc gattgaaaag    6300
tctgagtcta catcaacaag tggctcaaat tcaactaatg cgtcgttaag tagctcatct    6360
tcacttagta catcagcaag tacttctgta agcgaagtga catctgtcac acattctgaa    6420
aatgatttaa gtgcatctaa cgatagagat acatccggat cagtaagtca atttgcttct    6480
gaaaatacat cattaagtga ttctgcatca attagtggcg aagtttctag tagtacgtcc    6540
gcgtcaactt cgaaatcatc atcactttca gcaagcgcgt acatgataaa gcatgtatca    6600
gaaagcactt ctgcatcatt aagtagtgga gattcaagtc gtgcttcggc atcagtgtca    6660
acgtcattat cagaatcaga tagtgcgtta atagactctg aatcaattag cgtttccgag    6720
cacacatcaa cattacaatc aggtagtcat tcactatcac aacaacaatc agcagaatta    6780
tcacaatcag agcaaacatc acaatcacaa cgcatttcaa caagtgcgtc agtatcggct    6840
atgaaatcag aaagtgctgc taaggtatct gaatcgctat ctacgtctca atcaaaagta    6900
```

```
gatagtcaat cacaatcggt atctgaatca gcgagcaact cacgagtgtc aagagattca   6960
aaatcaacaa gcgcttcaat gcatcgatca ttgtcagagt cagtatctca aagtatgtca   7020
cttattgatc agtcagaaag tgattcaaca tctatatcga tttcgacgtc aatcagtgat   7080
gaagactcta tgctgtattc tatgagtgat tccgcatcga tcagtactaa ggcatcaagt   7140
agtatgtcta cttcgacaag cgaagagcat gccaacagtc attctcagtc tgaatcgaca   7200
gcatcggttg aagtatctca agaaatgagt gcatcggctt caacaagcaa atctgagtct   7260
caatcagagt cagtatcagt aagtaacgaa gaatcaaata tctcatctat gcaagagtct   7320
tttgtagaga gtgcaaaagc atcgcgtagt gcatctatga gcgttgcaaa atctgaagcc   7380
tctgaatcac agctattaag tgagtctaat gcttcggtaa gccaatcagc aagcacaagt   7440
agtaaagcat cagcaagtac gtcagaatct atttcaacgt cactcagcgt atctgaagca   7500
actcatggaa aaccgagaaa tcattcagaa agtgcatcag caagtcaatt attagaagaa   7560
aatgagtcat taagcgattc agcatcaaca agtgttgaag attcagaaag tgcatcagca   7620
tctctgtcgg tgtatcaatc acaatcagca agtgcattga atcaacaca tgcatcagaa    7680 aaagcttcag tgaatacaag tgcaaacgca tcgaagcgtg catcagcatc gacatctatc   7740
tctaactcga aatctaaagt cattgcgagt gaatcgaagt caacaagcat atcaacatat   7800
gaatcgttgt caatatcgac tagtaaagaa caatcaacgc gtgtatcagt gagtgagtcg   7860
acatcaacgt ctaaagtgaa gtcagaaagc gactcggcat caacgtcgac atctgaatca   7920
atctcaatta gcgcaaatcg ttcaggttac acatcgtcta aacgttcggt acaaatgagt   7980
gaagcacaat caacgagcga ttcattatca gtaatgcaat ctgaaggttc agtaagtgta   8040
tcgcaatctt taagtatatc agataagaca tcacagtcct tatcggaatc aatatcgcat   8100
tcagaaagtg actctgatag taactcagtg tctattagtc aagagacatc tgaacaacat   8160
tcggtgtcag acagtgactc gatgtcaatt tcggaaagcg aatctattgc atatagtcaa   8220
tcagcgagtg aatcagaatc aacaagtatc gcaaaatctg atagtatttc gaactcatta   8280
tctgtttcat taagtgaatc agaaagtgaa gcaagcacat cagcttcagt gagtacatct   8340
gaaagtacgc ctgtaaaggg ttctctatca acaagtatct gaacagtca atcagcatct    8400 actcatcaat caacagaagc ttctcaaagt acatcaactt caaaagttga ggaagcatca   8460
ttgagtgact ctgcttctgt atcagattca caatcacttt caatgagtca tgagaaatca   8520
caaagtgcat cgacttcaaa atctacgagt ctgtcaaaaa ctatttctga gtcagagtct   8580
gtgagtgcat caacatcaac aagtgaagct gtaagtacag aagcaagcga atttgtatca   8640
gcagtagact cattgagtca agtaacttct aacggaagca caacgaaaga agatgcgagt   8700
acatttgtat ccacagtaga ttcattgaaa gacaaagcat caaataatgg tacaccatca   8760
gagtttgcgt cagcagtgaa atcaacacac gcatcagtga gtgtgtcagc atcagaaagt   8820
acgtcagcat caacatcaac aagtgaagct gtaagtacag aagcaagcga atttgtatca   8880
gcagtgaatt cgttgagtga agcgacttct aacggaagca caacgaaaga agatgcgagt   8940
acatttgtat ccacagtaga ttcattgaaa gacaaagcat caaataatgg tacaccatca   9000
gagtttgcgt cagcagtgaa atcaacacac gcatcagtga gtgtgtcagc atcagaaagt   9060
acatcagcat caacatcaac aagtgaagct gtaagtacag aagcaagcga atttgtatca   9120
gcagtagact cattgagtca agtaacttct aacggaagca caacgaaaga agatgcaagc   9180
acatttgtat ccacagtaga ttcattgaaa gataaagcat caaacaatgg tacaccatca   9240
gaatttgaat cagttgtgaa atcagtacac ggatcaatga gtgcatcagc aagtgcgtca   9300
```

-continued

```
acatcagcat ctacatcagc atctacatct acaagtgaag ctgcaagtgc agaagcaagc    9360
gaattagaat cagtaaggaa atcattatcc aatggagcat caaacggtag cacagcaaga    9420
gaaggtgcaa gcacatttgt atcaacggta gattcattga agataaagc atcaaacaat    9480
ggtacagcat cagaatttga atcagttgtg aagtcagtac acggatcaac aagtgcatca    9540
gcaagtgcgt caacgtcagc atcaacatca gcaagtgaat cagcaagtac agaagcaagt    9600
gaatttgtat cagcagtggc atcattaagc agttcagcat ggaacggaag cactacagga    9660
gaaggtgcaa gcacatttgt atcaacagtt gattcatcga agattcagc gtcagacaaa    9720
gcttcaccat cagaatcaga atcagttgtg aagtcagtac acggatcaac gagtacatca    9780
gcaagtgtgt cagcgtcggc aagtacatca gcatcgacat caacaagtga agctgtaagc    9840
acagaagcaa gtgagtttgt atcagcagtg aactcattaa gcagtgaagc atcgaacggc    9900
agcacaacaa gagaaggtgc aagcacattt gtatcaacag tagattcatt gaaagacaaa    9960
gcatcaaaca atggtacagc atcagaattt gaatcagttg tgaagtcagt acacggatca   10020
atgagtacat cagcaagtgt gtcagcatca gaaagtacgt cggcatcgac atcgacaagt   10080
gaagctgtaa gtacagaagc aagcgagtca gcatcgataa gtgtatcaat gtcagtgagc   10140
gcatcaacaa gtgcttcaat gagcgtatca gtgtcaaaca gtgtgtcagt gagtgactct   10200
atttcagtaa gtgcatcaac aagtgaacct aactcggtaa gcacttctat gagtagttct   10260
cttttcaacat cggcatcaac gccatcagaa attacttcaa gttcgtcatc aagcgattca   10320
gcgacagttc aaaaagtagt ttctaaagat gaacagcacg ctacaaataa agttgaaaaa   10380
ttacctgaca caggtcaatc aacgacacaa actggtttat gggtggagt aggtgcttta   10440
cttacaggcc ttggtttact caaaaaatca agaaaacaaa aagatgaaga aacatcatca   10500
catgaataa                                                           10509
```

<210> SEQ ID NO 12
<211> LENGTH: 3502
<212> TYPE: PRT
<213> ORGANISM: Staphylococcus pseudintermedius

<400> SEQUENCE: 12

```
Met Thr Arg Lys Phe Arg Glu Phe Lys Lys Ser Leu Ser Glu Glu Lys
1               5                   10                  15

Ala Arg Val Lys Leu Tyr Lys Ser Gly Lys Asn Trp Val Lys Ala Gly
            20                  25                  30

Ile Lys Glu Phe Gln Leu Leu Lys Ala Leu Gly Leu Ser Phe Leu Ser
        35                  40                  45

His Asp Ile Val Lys Asp Glu Asn Gly Glu Val Thr Thr Gln Phe Gly
    50                  55                  60

Glu Gln Leu Lys Lys Asn Ala Leu Arg Thr Thr Ala Phe Ala Gly Gly
65                  70                  75                  80

Met Phe Thr Val Asn Met Leu His Asp Gln Ala Phe Ala Ala Ser
                85                  90                  95

Asp Ala Pro Ile Thr Ser Glu Leu Ala Thr Lys Ser Gln Thr Ile Gly
            100                 105                 110

Asp Gln Thr Ser Ile Val Ile Glu Lys Ser Thr Ser Asp Gln Ser
        115                 120                 125

Thr Asn Pro Ile Thr Glu Ser Glu Ser Lys His Asp Ser Glu Ser Ile
    130                 135                 140

Ser Leu Ser Glu His Gln Thr Ser Glu Ser Thr Ser Leu Ser Thr Ser
```

```
              145                 150                 155                 160
         Thr Ser Lys Ser Ile Ser Thr Ser Val Glu Glu Ser Glu Ser Thr Ser
                         165                 170                 175

Lys Asp Ser His Thr Lys Thr Gln Asp Ser Gln Ser Asp Ser His Gln
                         180                 185                 190

Ser Thr Ser Gln Glu Val Asn Gly Ser Ser Asn His Glu Gln Ser Thr
                         195                 200                 205

Pro His Thr Ala Gln Ser Leu Thr Ser Leu Ser Ile Glu Ser Gln Thr
                         210                 215                 220

Ser Thr Ser Asn Thr Ser Leu Lys Glu Thr Lys Glu Gly Glu Leu Ser
         225                 230                 235                 240

Lys Asn Leu Ser Lys Leu Ser Gln Asn Gln Asn Ile Lys Leu His Glu
                         245                 250                 255

Glu His Thr Met Arg Ser Ala Asp Leu Ser Ser Gly Tyr Thr Gly Phe
                         260                 265                 270

Arg Ala Ala Tyr Tyr Val Pro Arg Ser Arg Thr Thr Pro Thr Thr Lys
                         275                 280                 285

Val Tyr Thr Gly Gln Gly Ser Phe Arg Gly Arg Gly Arg Ile Lys Tyr
                         290                 295                 300

Asn Ile Phe Tyr Lys Val Val Thr Ser Asn Gly Lys Glu Met Lys
         305                 310                 315                 320

Ile Arg Tyr Thr Leu Ser Gln Asp Asp Pro Asn Thr Ser Asn Val Glu
                         325                 330                 335

Lys Pro Arg Trp Ala Gly Gln Lys Arg Phe Gly Ile His Asn Thr Trp
                         340                 345                 350

Asp Glu Gly Pro Gly Arg Gly Gln Leu Lys Leu Gly Ser Ala Phe Gly
                         355                 360                 365

Lys Pro Thr Val Ile Gln Gly Glu Thr Arg Pro Asn Tyr Gly Ser Trp
                         370                 375                 380

Val Gly Thr Pro Ile Thr Lys Tyr Val Ser Gly Asp Arg Thr Asn Gly
         385                 390                 395                 400

Phe Tyr Trp Gln Ala Ala Val Leu Ala Pro Arg His Gly Glu Lys Gly
                         405                 410                 415

Glu Gly Ile Thr Ala Glu Ile Thr Val Pro Ile Val Asn Pro Ser Gly
                         420                 425                 430

Arg Phe Asn Trp Glu Phe His Pro Val Gly Gln Gln Asp Gly Val Gly
                         435                 440                 445

Gly Lys Thr Asp Tyr Phe Glu Asn Val Trp Ile Arg Asp Tyr Asp Pro
                         450                 455                 460

Tyr Tyr Lys Tyr Ile Gln Thr Lys Glu Gly Arg Ala Ser Val Ser His
         465                 470                 475                 480

Ser Ile Ser Gln Val Lys Ala Ser Glu Arg Ser Thr Ser Leu Ile
                         485                 490                 495

Gln Ser Glu Ser Ile Arg Arg Ser Gln Ser Ile Ser Glu Ser Glu Ser
                         500                 505                 510

Ile Val Ala Ala Ser His Ser Ala Ser Val Ala Lys Ser Gln Ser Ile
                         515                 520                 525

Ser Arg Ser Gln Ser Val Ala Lys Ser Gln Ser Ile Ser Arg Ser Gln
                         530                 535                 540

Ser Ile Ala His Ser Arg Ser Ala Ser Val Ala Lys Ser Gln Ser Ile
         545                 550                 555                 560

Ser Arg Ser Gln Ser Ile Ala His Ser Arg Ser Ala Ser Val Ala Lys
                         565                 570                 575
```

-continued

```
Ser Gln Ser Ile Ser Arg Ser Gln Ser Ile Ala His Ser Arg Ser Ala
            580                 585                 590

Ser Val Ala Lys Ser Gln Ser Ile Arg Ser Gln Ser Ile Ala Gln
            595                 600                 605

Ser Gln Ser Ala Ser Val Ala Lys Ser Gln Ser Ile Ser Arg Ser Gln
            610                 615                 620

Ser Ile Ala Gln Ser Gln Ser Ala Ser Val Ala Lys Ser Gln Ser Ile
625                 630                 635                 640

Ser Arg Ser Gln Ser Ile Ala His Ser Arg Ser Ala Ser Val Ala Glu
                    645                 650                 655

Ser Gln Ser Ile Ser Arg Ser Gln Ser Ile Ala Asn Ser Gln Ser Val
            660                 665                 670

Ala Ala Ser Glu Ser Glu Ser Leu Ser Ile Ser Leu Ser Lys Lys Gln
            675                 680                 685

Ser Ile Ser Met Ser Asn Ser Glu Ser Ala Ala Lys Ser His Ser Leu
            690                 695                 700

Ser Val Lys Arg Ser Asn Trp Ile Lys Lys Ser Lys Ala Ala Ser Val
705                 710                 715                 720

Arg Lys Ser His Ser Leu Ser Val Arg Lys Ser Asn Ser Ala Lys Arg
                    725                 730                 735

Ser His Ala Ile Ser Val Arg Lys Ser Lys Ser Leu Ser Val Lys Lys
            740                 745                 750

Ser Ile Ser Gln Ser Gln Ser Ala Ser Val Ala Lys Ser Gln Ser Ile
            755                 760                 765

Ser Arg Ser Gln Ser Val Ala Ala Ser Glu Ser Ala Ser Leu Ser Lys
            770                 775                 780

Ser Lys Ser Thr Ser Leu Ser Asn Ser Val Ser Ala Glu Lys Ser Thr
785                 790                 795                 800

Ser Leu Ser Arg Ser Ala Ser Val Ala Lys Ser Gln Ser Ile Ser Arg
                    805                 810                 815

Ser Gln Ser Val Val Ala Ser Glu Ser Ala Ser Leu Ser Lys Ser Lys
            820                 825                 830

Ser Thr Ser Leu Ser Asn Ser Val Ser Ala Glu Lys Ser Thr Ser Leu
            835                 840                 845

Ser Arg Ser Ala Ser Val Ala Lys Ser Gln Ser Ile Ser Arg Ser Gln
            850                 855                 860

Ser Val Ala Ala Ser Glu Ser Ala Ser Leu Ser Lys Ser Lys Ser Thr
865                 870                 875                 880

Ser Leu Ser Asn Ser Val Ser Ala Glu Lys Ser Thr Ser Leu Ser Arg
                    885                 890                 895

Ser Ala Ser Val Ala Lys Ser Gln Ser Ile Ser Arg Ser Gln Ser Val
            900                 905                 910

Ala Ala Ser Glu Ser Ala Ser Leu Ser Lys Ser Lys Ser Thr Ser Leu
            915                 920                 925

Ser Asn Ser Val Ser Ala Glu Lys Ser Thr Ser Leu Ser Arg Ser Ala
            930                 935                 940

Ser Val Ala Lys Ser Gln Ser Ile Ser Arg Ser Gln Ser Val Val Ala
945                 950                 955                 960

Ser Glu Ser Ala Ser Leu Ser Lys Ser Lys Ser Thr Ser Leu Ser Asn
                    965                 970                 975

Ser Val Ser Ala Glu Lys Ser Thr Ser Leu Ser Arg Ser Ala Ser Val
            980                 985                 990
```

```
Ala Lys Ser Gln Ser Ile Ser Arg  Ser Gln Ser Val Ala  Ala Ser Glu
    995                 1000                    1005

Ser Ala Ser Leu Ser Lys Ser  Lys Ser Thr Ser Leu  Ser Asn Ser
    1010                1015                1020

Val Ser Ala Glu Lys Ser Thr  Ser Leu Ser Arg Ser  Ala Ser Val
    1025                1030                1035

Ala Lys Ser Gln Ser Ile Ser  Arg Ser Gln Ser Val  Ala Ala Ser
    1040                1045                1050

Glu Ser Ala Ser Leu Ser Lys  Ser Lys Ser Thr Ser  Leu Ser Asn
    1055                1060                1065

Ser Val Ser Val Glu Lys Ser  Thr Ser Leu Ser Arg  Ser Ala Ser
    1070                1075                1080

Val Ala Lys Ser Gln Ser Ile  Ser Arg Ser Gln Ser  Val Ala Ala
    1085                1090                1095

Ser Glu Ser Ala Ser Leu Ser  Lys Ser Lys Ser Thr  Ser Leu Ser
    1100                1105                1110

Asn Ser Val Ser Ala Glu Lys  Ser Thr Ser Leu Ser  Arg Ser Ala
    1115                1120                1125

Ser Val Ala Lys Ser Gln Ser  Ile Ser Arg Ser Gln  Ser Val Ala
    1130                1135                1140

Ala Ser Glu Ser Ala Ser Leu  Ser Lys Ser Thr Ser  Thr Ser Thr
    1145                1150                1155

Ser Asp Ser Asp Ser Ala Ser  Thr Ser Thr Ser Val  Ser Asp Ser
    1160                1165                1170

Asp Ser Ala Ser Leu Ser Lys  Ser Thr Ser Thr Ser  Thr Ser Asp
    1175                1180                1185

Ser Asp Ser Ala Ser Ala Ser  Leu Ser Lys Ser Thr  Ser Thr Ser
    1190                1195                1200

Thr Ser Asp Ser Asp Ser Ala  Ser Thr Ser Thr Ser  Val Ser Asp
    1205                1210                1215

Ser Asp Ser Ala Ser Leu Ser  Lys Ser Thr Ser Thr  Ser Thr Ser
    1220                1225                1230

Asp Ser Asp Ser Thr Ser Thr  Ser Leu Ser Lys Ser  Thr Ser Thr
    1235                1240                1245

Ser Thr Ser Asp Ser Asp Ser  Ala Ser Lys Ser Thr  Ser Val Ser
    1250                1255                1260

Asp Ser Thr Ser Ala Ser Leu  Ser Lys Ser Thr Ser  Thr Ser Thr
    1265                1270                1275

Ser Asp Ser Asp Ser Ala Ser  Lys Ser Thr Ser Val  Ser Asp Ser
    1280                1285                1290

Thr Ser Ala Ser Leu Arg Lys  Ser Ala Ser Thr Ser  Thr Ser Asp
    1295                1300                1305

Ser Asp Ser Thr Ser Thr Ser  Leu Ser Lys Ser Thr  Ser Thr Ser
    1310                1315                1320

Thr Ser Asp Ser Asp Ser Ala  Ser Lys Ser Thr Ser  Val Ser Asp
    1325                1330                1335

Ser Asp Ser Ala Ser Leu Ser  Lys Ser Thr Ser Thr  Ser Thr Ser
    1340                1345                1350

Asp Ser Asp Ser Ala Ser Lys  Ser Thr Ser Val Ser  Asp Ser Asp
    1355                1360                1365

Ser Ala Ser Leu Ser Lys Ser  Thr Ser Thr Ser Thr  Ser Asp Ser
    1370                1375                1380

Asp Ser Ala Ser Lys Ser Thr  Ser Val Ser Asp Ser  Thr Ser Thr
```

-continued

```
             1385                1390                1395

Ser  Leu  Ser  Lys  Ser  Thr  Ser  Thr  Ser  Thr  Ser  Asp  Ser  Asp  Ser
     1400                1405                1410

Ala  Ser  Thr  Ser  Thr  Ser  Val  Ser  Asp  Ser  Thr  Ser  Ala  Ser  Leu
     1415                1420                1425

Ser  Lys  Ser  Thr  Ser  Thr  Ser  Thr  Ser  Asp  Ser  Asp  Ser  Ala  Ser
     1430                1435                1440

Thr  Ser  Val  Ser  Asp  Ser  Asp  Ser  Ala  Ser  Leu  Ser  Lys  Ser  Thr
     1445                1450                1455

Ser  Thr  Ser  Thr  Ser  Asp  Ser  Asp  Ser  Val  Ser  Thr  Ser  Thr  Ser
     1460                1465                1470

Val  Ser  Asp  Ser  Asp  Ser  Ala  Ser  Leu  Ser  Lys  Ser  Thr  Ser  Thr
     1475                1480                1485

Ser  Thr  Ser  Asp  Ser  Asp  Ser  Ala  Ser  Lys  Ser  Thr  Ser  Val  Ser
     1490                1495                1500

Asp  Ser  Thr  Ser  Thr  Ser  Leu  Ser  Lys  Ser  Thr  Ser  Thr  Ser  Thr
     1505                1510                1515

Ser  Asp  Ser  Asp  Ser  Ala  Ser  Thr  Ser  Val  Ser  Asp  Ser  Thr  Ser
     1520                1525                1530

Ala  Ser  Leu  Ser  Lys  Ser  Thr  Ser  Thr  Ser  Thr  Ser  Asp  Ser  Asp
     1535                1540                1545

Ser  Ala  Ser  Lys  Ser  Thr  Ser  Val  Ser  Asp  Ser  Asp  Ser  Ala  Ser
     1550                1555                1560

Leu  Ser  Lys  Ser  Thr  Ser  Thr  Ser  Thr  Ser  Asp  Ser  Asp  Ser  Ala
     1565                1570                1575

Ser  Thr  Ser  Thr  Ser  Val  Ser  Asp  Ser  Asp  Ser  Ala  Ser  Leu  Ser
     1580                1585                1590

Lys  Ser  Thr  Ser  Thr  Ser  Thr  Ser  Asp  Ser  Asp  Ser  Ala  Ser  Thr
     1595                1600                1605

Ser  Leu  Ser  Lys  Ser  Thr  Ser  Thr  Ser  Thr  Ser  Asp  Ser  Asp  Ser
     1610                1615                1620

Thr  Ser  Thr  Ser  Leu  Ser  Lys  Ser  Thr  Ser  Thr  Ser  Thr  Ser  Asp
     1625                1630                1635

Ser  Asp  Ser  Ala  Ser  Lys  Ser  Thr  Ser  Val  Ser  Asp  Ser  Asp  Ser
     1640                1645                1650

Ala  Ser  Leu  Ser  Lys  Ser  Thr  Ser  Thr  Ser  Thr  Ser  Asp  Ser  Asp
     1655                1660                1665

Ser  Ala  Ser  Lys  Ser  Thr  Ser  Val  Ser  Asp  Ser  Asp  Ser  Ala  Ser
     1670                1675                1680

Leu  Ser  Lys  Ser  Thr  Ser  Thr  Ser  Thr  Ser  Asp  Ser  Asp  Ser  Ala
     1685                1690                1695

Ser  Lys  Ser  Thr  Ser  Val  Ser  Asp  Ser  Glu  Ser  Ala  Ser  Leu  Ser
     1700                1705                1710

Lys  Ser  Thr  Ser  Thr  Ser  Thr  Ser  Asp  Ser  Asp  Ser  Ala  Ser  Thr
     1715                1720                1725

Ser  Thr  Ser  Val  Ser  Asp  Ser  Thr  Ser  Val  Ser  Leu  Ser  Lys  Ser
     1730                1735                1740

Thr  Ser  Thr  Ser  Thr  Ser  Asp  Ser  Asp  Ser  Thr  Ser  Thr  Ser  Leu
     1745                1750                1755

Ser  Lys  Ser  Thr  Ser  Thr  Ser  Thr  Ser  Asp  Ser  Asp  Ser  Asp  Ser
     1760                1765                1770

Ala  Ser  Leu  Ser  Lys  Ser  Thr  Ser  Thr  Ser  Thr  Ser  Asp  Ser  Asp
     1775                1780                1785
```

-continued

```
Ser Val Ser Thr Ser Thr Ser Val Ser Asp Ser Asp Ser Ala Ser
    1790            1795            1800

Leu Ser Lys Ser Thr Ser Thr Ser Thr Ser Asp Ser Asp Ser Ala
    1805            1810            1815

Ser Thr Ser Thr Ser Val Ser Asp Ser Gly Ser Ala Ser Leu Ser
    1820            1825            1830

Lys Ser Thr Ser Thr Ser Thr Ser Asp Ser Asp Ser Ala Ser Lys
    1835            1840            1845

Ser Thr Ser Val Ser Asp Ser Asp Ser Ala Ser Leu Ser Lys Ser
    1850            1855            1860

Thr Ser Thr Ser Thr Ser Asp Ser Asp Ser Ala Ser Thr Ser Thr
    1865            1870            1875

Ser Val Ser Asp Ser Thr Ser Ala Ser Leu Ser Lys Ser Thr Ser
    1880            1885            1890

Thr Ser Thr Ser Asp Ser Asp Ser Ala Ser Thr Ser Thr Ser Val
    1895            1900            1905

Ser Asp Ser Asp Ser Ala Ser Leu Ser Lys Ser Thr Ser Thr Ser
    1910            1915            1920

Thr Ser Asp Ser Asp Ser Ala Ser Lys Ser Thr Ser Val Ser Asp
    1925            1930            1935

Ser Asp Ser Ala Ser Leu Ser Lys Ser Thr Ser Thr Ser Thr Ser
    1940            1945            1950

Glu Ser Asp Ser Ala Ser Lys Ser Thr Ser Val Ser Asp Ser Asp
    1955            1960            1965

Ser Ala Ser Leu Ser Lys Ser Thr Ser Thr Ser Thr Ser Asp Ser
    1970            1975            1980

Asp Ser Ala Ser Thr Ser Thr Ser Val Ser Asp Ser Asp Ser Ala
    1985            1990            1995

Ser Leu Ser Lys Ser Thr Ser Thr Ser Thr Ser Asp Ser Asp Ser
    2000            2005            2010

Ala Ser Lys Ser Thr Ser Val Ser Asp Ser Asp Ser Ala Ser Leu
    2015            2020            2025

Ser Lys Ser Thr Ser Thr Ser Thr Ser Glu Ser Asp Ser Ala Ser
    2030            2035            2040

Thr Ser Thr Leu Val Ser Asp Ser Thr Ser Val Ser Leu Ser Gln
    2045            2050            2055

Ser Thr Ser Val Asp Lys Asp Ser Thr Ala Lys Gly Ser Thr Glu
    2060            2065            2070

Leu Val Asn Val Ala Ser Leu Ser Ile Ser Ala Ser Gln Ser Ser
    2075            2080            2085

Ser Leu Ser Ala Ser Thr Ser Thr Ser Ile Glu Lys Ser Glu Ser
    2090            2095            2100

Thr Ser Thr Ser Gly Ser Asn Ser Thr Asn Ala Ser Leu Ser Ser
    2105            2110            2115

Ser Ser Ser Leu Ser Thr Ser Ala Ser Thr Ser Val Ser Glu Val
    2120            2125            2130

Thr Ser Val Thr His Ser Glu Asn Asp Leu Ser Ala Ser Asn Asp
    2135            2140            2145

Arg Asp Thr Ser Gly Ser Val Ser Gln Phe Ala Ser Glu Asn Thr
    2150            2155            2160

Ser Leu Ser Asp Ser Ala Ser Ile Ser Gly Glu Val Ser Ser Ser
    2165            2170            2175
```

```
Thr Ser Ala Ser Thr Ser Lys Ser Ser Ser Leu Ser Ala Ser Ala
    2180                2185                2190

Leu His Asp Lys His Val Ser Glu Ser Thr Ser Ala Ser Leu Ser
    2195                2200                2205

Ser Gly Asp Ser Ser Arg Ala Ser Ala Ser Val Ser Thr Ser Leu
    2210                2215                2220

Ser Glu Ser Asp Ser Ala Leu Ile Asp Ser Glu Ser Ile Ser Val
    2225                2230                2235

Ser Glu His Thr Ser Thr Leu Gln Ser Gly Ser His Ser Leu Ser
    2240                2245                2250

Gln Gln Gln Ser Ala Glu Leu Ser Gln Ser Glu Gln Thr Ser Gln
    2255                2260                2265

Ser Gln Arg Ile Ser Thr Ser Ala Ser Val Ser Ala Met Lys Ser
    2270                2275                2280

Glu Ser Ala Ala Lys Val Ser Glu Ser Leu Ser Thr Ser Gln Ser
    2285                2290                2295

Lys Val Asp Ser Gln Ser Gln Ser Val Ser Glu Ser Ala Ser Asn
    2300                2305                2310

Ser Arg Val Ser Arg Asp Ser Lys Ser Thr Ser Ala Ser Met His
    2315                2320                2325

Arg Ser Leu Ser Glu Ser Val Ser Gln Ser Met Ser Leu Ile Asp
    2330                2335                2340

Gln Ser Glu Ser Asp Ser Thr Ser Ile Ser Ile Ser Thr Ser Ile
    2345                2350                2355

Ser Asp Glu Asp Ser Met Leu Tyr Ser Met Ser Asp Ser Ala Ser
    2360                2365                2370

Ile Ser Thr Lys Ala Ser Ser Met Ser Thr Ser Thr Ser Glu
    2375                2380                2385

Glu His Ala Asn Ser His Ser Gln Ser Glu Ser Thr Ala Ser Val
    2390                2395                2400

Glu Val Ser Gln Glu Met Ser Ala Ser Ala Ser Thr Ser Lys Ser
    2405                2410                2415

Glu Ser Gln Ser Glu Ser Val Ser Val Ser Asn Glu Glu Ser Asn
    2420                2425                2430

Ile Ser Ser Met Gln Glu Ser Phe Val Glu Ser Ala Lys Ala Ser
    2435                2440                2445

Arg Ser Ala Ser Met Ser Val Ala Lys Ser Glu Ala Ser Glu Ser
    2450                2455                2460

Gln Leu Leu Ser Glu Ser Asn Ala Ser Val Ser Gln Ser Ala Ser
    2465                2470                2475

Thr Ser Ser Lys Ala Ser Ala Ser Thr Ser Glu Ser Ile Ser Thr
    2480                2485                2490

Ser Leu Ser Val Ser Glu Ala Thr His Gly Lys Pro Arg Asn His
    2495                2500                2505

Ser Glu Ser Ala Ser Ala Ser Gln Leu Leu Glu Glu Asn Glu Ser
    2510                2515                2520

Leu Ser Asp Ser Ala Ser Thr Ser Val Glu Asp Ser Glu Ser Ala
    2525                2530                2535

Ser Ala Ser Leu Ser Val Tyr Gln Ser Gln Ser Ala Ser Ala Leu
    2540                2545                2550

Lys Ser Thr His Ala Ser Glu Lys Ala Ser Val Asn Thr Ser Ala
    2555                2560                2565

Asn Ala Ser Lys Arg Ala Ser Ala Ser Thr Ser Ile Ser Asn Ser
```

-continued

Lys Ser Lys Val Ile Ala Ser Glu Ser Lys Ser Thr Ser Ile Ser
2585                2590                2595

Thr Tyr Glu Ser Leu Ser Ile Ser Thr Ser Lys Glu Gln Ser Thr
2600                2605                2610

Arg Val Ser Val Ser Glu Ser Thr Ser Thr Ser Lys Val Lys Ser
2615                2620                2625

Glu Ser Asp Ser Ala Ser Thr Ser Thr Ser Glu Ser Ile Ser Ile
2630                2635                2640

Ser Ala Asn Arg Ser Gly Tyr Thr Ser Ser Lys Arg Ser Val Gln
2645                2650                2655

Met Ser Glu Ala Gln Ser Thr Ser Asp Ser Leu Ser Val Met Gln
2660                2665                2670

Ser Glu Gly Ser Val Ser Val Ser Gln Ser Leu Ser Ile Ser Asp
2675                2680                2685

Lys Thr Ser Gln Ser Leu Ser Glu Ser Ile Ser His Ser Glu Ser
2690                2695                2700

Asp Ser Asp Ser Asn Ser Val Ser Ile Ser Gln Glu Thr Ser Glu
2705                2710                2715

Gln His Ser Val Ser Asp Ser Asp Ser Met Ser Ile Ser Glu Ser
2720                2725                2730

Glu Ser Ile Ala Tyr Ser Gln Ser Ala Ser Glu Ser Glu Ser Thr
2735                2740                2745

Ser Ile Ala Lys Ser Asp Ser Ile Ser Asn Ser Leu Ser Val Ser
2750                2755                2760

Leu Ser Glu Ser Glu Ser Glu Ala Ser Thr Ser Ala Ser Val Ser
2765                2770                2775

Thr Ser Glu Ser Thr Ser Val Lys Gly Ser Leu Ser Thr Ser Ile
2780                2785                2790

Leu Asn Ser Gln Ser Ala Ser Thr His Gln Ser Thr Glu Ala Ser
2795                2800                2805

Gln Ser Thr Ser Thr Ser Lys Val Glu Glu Ala Ser Leu Ser Asp
2810                2815                2820

Ser Ala Ser Val Ser Asp Ser Gln Ser Leu Ser Met Ser His Glu
2825                2830                2835

Lys Ser Gln Ser Ala Ser Thr Ser Lys Ser Thr Ser Leu Ser Lys
2840                2845                2850

Thr Ile Ser Glu Ser Glu Ser Val Ser Ala Ser Thr Ser Thr Ser
2855                2860                2865

Glu Ala Val Ser Thr Glu Ala Ser Glu Phe Val Ser Ala Val Asp
2870                2875                2880

Ser Leu Ser Gln Val Thr Ser Asn Gly Ser Thr Thr Lys Glu Asp
2885                2890                2895

Ala Ser Thr Phe Val Ser Thr Val Asp Ser Leu Lys Asp Lys Ala
2900                2905                2910

Ser Asn Asn Gly Thr Pro Ser Glu Phe Ala Ser Ala Val Lys Ser
2915                2920                2925

Thr His Ala Ser Val Ser Val Ser Ala Ser Glu Ser Thr Ser Ala
2930                2935                2940

Ser Thr Ser Thr Ser Glu Ala Val Ser Thr Glu Ala Ser Glu Phe
2945                2950                2955

Val Ser Ala Val Asn Ser Leu Ser Glu Ala Thr Ser Asn Gly Ser
2960                2965                2970

-continued

Thr Thr Lys Glu Asp Ala Ser Thr Phe Val Ser Thr Val Asp Ser
2975                2980                2985

Leu Lys Asp Lys Ala Ser Asn Asn Gly Thr Pro Ser Glu Phe Ala
2990                2995                3000

Ser Ala Val Lys Ser Thr His Ala Ser Val Ser Val Ser Ala Ser
3005                3010                3015

Glu Ser Thr Ser Ala Ser Ser Thr Ser Glu Ala Val Ser Thr
3020                3025                3030

Glu Ala Ser Glu Phe Val Ser Ala Val Asp Ser Leu Ser Gln Val
3035                3040                3045

Thr Ser Asn Gly Ser Thr Thr Lys Glu Asp Ala Ser Thr Phe Val
3050                3055                3060

Ser Thr Val Asp Ser Leu Lys Asp Lys Ala Ser Asn Asn Gly Thr
3065                3070                3075

Pro Ser Glu Phe Glu Ser Val Val Lys Ser Val His Gly Ser Met
3080                3085                3090

Ser Ala Ser Ala Ser Ala Ser Thr Ser Ala Ser Thr Ser Ala Ser
3095                3100                3105

Thr Ser Thr Ser Glu Ala Ala Ser Ala Glu Ala Ser Glu Leu Glu
3110                3115                3120

Ser Val Arg Lys Ser Leu Ser Asn Gly Ala Ser Asn Gly Ser Thr
3125                3130                3135

Ala Arg Glu Gly Ala Ser Thr Phe Val Ser Thr Val Asp Ser Leu
3140                3145                3150

Lys Asp Lys Ala Ser Asn Asn Gly Thr Ala Ser Glu Phe Glu Ser
3155                3160                3165

Val Val Lys Ser Val His Gly Ser Thr Ser Ala Ser Ala Ser Ala
3170                3175                3180

Ser Thr Ser Ala Ser Thr Ser Ala Ser Glu Ser Ala Ser Thr Glu
3185                3190                3195

Ala Ser Glu Phe Val Ser Ala Val Ala Ser Leu Ser Ser Ser Ala
3200                3205                3210

Trp Asn Gly Ser Thr Thr Gly Glu Gly Ala Ser Thr Phe Val Ser
3215                3220                3225

Thr Val Asp Ser Ser Lys Asp Ser Ala Ser Asp Lys Ala Ser Pro
3230                3235                3240

Ser Glu Ser Glu Ser Val Val Lys Ser Val His Gly Ser Thr Ser
3245                3250                3255

Thr Ser Ala Ser Val Ser Ala Ser Ala Ser Thr Ser Ala Ser Thr
3260                3265                3270

Ser Thr Ser Glu Ala Val Ser Thr Glu Ala Ser Glu Phe Val Ser
3275                3280                3285

Ala Val Asn Ser Leu Ser Ser Glu Ala Ser Asn Gly Ser Thr Thr
3290                3295                3300

Arg Glu Gly Ala Ser Thr Phe Val Ser Thr Val Asp Ser Leu Lys
3305                3310                3315

Asp Lys Ala Ser Asn Asn Gly Thr Ala Ser Glu Phe Glu Ser Val
3320                3325                3330

Val Lys Ser Val His Gly Ser Met Ser Thr Ser Ala Ser Val Ser
3335                3340                3345

Ala Ser Glu Ser Thr Ser Ala Ser Thr Ser Thr Ser Glu Ala Val
3350                3355                3360

```
Ser Thr Glu Ala Ser Glu Ser Ala Ser Ile Ser Val Ser Met Ser
    3365            3370                3375

Val Ser Ala Ser Thr Ser Ala Ser Met Ser Val Ser Val Ser Asn
    3380            3385                3390

Ser Val Ser Val Ser Asp Ser Ile Ser Val Ser Ala Ser Thr Ser
    3395            3400                3405

Glu Pro Asn Ser Val Ser Thr Ser Met Ser Ser Ser Leu Ser Thr
    3410            3415                3420

Ser Ala Ser Thr Pro Ser Glu Ile Thr Ser Ser Ser Ser Ser Ser
    3425            3430                3435

Asp Ser Ala Thr Val Gln Lys Val Val Ser Lys Asp Glu Gln His
    3440            3445                3450

Ala Thr Asn Lys Val Glu Lys Leu Pro Asp Thr Gly Gln Ser Thr
    3455            3460                3465

Thr Gln Thr Gly Leu Leu Gly Gly Val Gly Ala Leu Leu Thr Gly
    3470            3475                3480

Leu Gly Leu Leu Lys Lys Ser Arg Lys Gly Lys Asp Glu Glu Thr
    3485            3490                3495

Ser Ser His Glu
    3500

<210> SEQ ID NO 13
<211> LENGTH: 5688
<212> TYPE: DNA
<213> ORGANISM: Staphylococcus pseudintermedius

<400> SEQUENCE: 13
atgaaaaagt ctagaaaaaa gcgtatcgat ttttaccta accgtcaaaa tcgatatgcg    60
atacgtcgtt tttcagtagg cactgcgtca attctcgttg gagcaacatt aatttttgga   120
attcattcaa atgatgcatc ggcagcagta gaagacgcaa catctcaaga agcaggaaca   180
actaacgaaa attcaaatag tacagaagaa gcaacaacaa acgaaagtac aactgttgaa   240
gcaccaacaa gtgaagaagc aacaacggaa gagcaatcag tagaggcgcc aacaagtgaa   300
gaagtaacaa cggaagagca atcagtagag gcaccaacaa gtgaagaagt aacaacggaa   360
gagcaatcag tagaagcgcc aacaagtgaa gaagtaacaa cggaagagca atcagtagaa   420
gcgccaacaa gtgaagaagt aacaacggaa gagcaatcag tagaggcacc aacaagtgaa   480
gaagtaacaa cggaagagca atcagtagag gcaccaacta gtgaagaagt aactacggaa   540
gagcaatcag tagaagcacc aacaagtgaa gaagcaacaa cggaagagca atcagtagaa   600
gcaccaacaa gtgaagaagc aactacaaaa actcctgtaa aagaagaaac atcctcaaca   660
caagaaaatt cacccacgac tacactagaa gaacaatttt caaatgaatt caatcagtta   720
acatctacag aagataaaac aaactacaca cgtgaatatt taactcaaaa cacaaatctt   780
tcggcagaac aagtggaagc aacagttgaa cgcttgaatt taagtcaaga aaatgtaaca   840
gcccaagata tctatttcgc attacttaaa gatttagctg atcaacaaga tgccttatta   900
ccacgtgtaa cacttttggc cgctagagat tctgagctca caaacgaagc gtctatcgct   960
ttaactgaaa atagtccaat gttccgcgca gcattagcga atagtccttc tggcaatgat  1020
gtggtgtcag aagaagataa tattattgtg gctgatgcac tcgcaaatgg atacatcaat  1080
tcacaaacag atgcaacaaa tgcggcaaat acattgtctg gtcgtgcatg ggttgtggat  1140
acagggacac cagcgacaat gtcaacggc ttaacagctg ttccagaagg cacaaaagtc  1200
tacatgcaat ggattgatac agatggcgcg gtttcaccag tgtatcaagc aagcacaaca  1260
```

```
aataaattga gttcaagtgg tggtagccaa gtaggtccag gtgcatatgc atttgattta    1320
cgtgaagcat ggatagactc aaatggcaaa gcgcacagat atgaagcgtc aagtggccaa    1380
tattatcgtt tatggattga tgactacaaa acagtagatg ggaatacggc aaccatgtta    1440
cgccaagcag gtggtttctt ccctggttca tatgttaatt cggtgacagg taacaatatt    1500
ggtcaattcc cacttatcgg aacgaacatg caacgtacag gtatctttat gggtgtgata    1560
ccaacgaacg attacatgac tacagataca agcaattgga ttcaagataa tgaaggacct    1620
atttcaaacc cagcagtaac gagcacaagt gaatttgtca gtggtaaagt atggtctgag    1680
acaggttcag gtgactatgc gaactctgcg acaggtccaa actttaactc aggtgatatt    1740
gcacgtgaag gttatcaagt tgtcatgtct tcattaacaa gtgctggtgc ccaagcgtat    1800
aaagcacaag tcgaatcgtt gccaacagac caacaagcgg cagcagcaca ccaattattc    1860
aaagaccacc cagaatttat ttctgcgaca gtgacgggta aaactgatgc aaacggtgcg    1920
tatacattac gtttcccttc aggctcattg agtaaagatt atctttatgg ttatgtgatg    1980
gataataagg gcaacttggt taagggctat tcatcattca cgtcaccttt attccgttcg    2040
cctaacagta acttatcttt cgcgccacaa acagcgccat atcatagacc agccaaaaat    2100
gcttgggtga atgtgaactt tgcgcttgta gaaacaattg aaacaagtat agacatcacg    2160
aactttgatg tgacagccaa cccagcgcaa cgtggtgata cggctatcat tgatgtgact    2220
tctacagcat tgtcaccatt acctacgcat gttgagtgga gagattcaaa agggaatgtc    2280
gttcaaaaaa gtggagatgt cactacggta gaagaagctg aaacggcagg cacatttact    2340
attcctgatg atgcgaaaac aggtgaaatc tatacagttt atattgtttc aggaggcaat    2400
gaagttgcag cagactcact gattgtccaa gtgcaagaaa atgcggcaac ctatgaacct    2460
gtatatccaa caacaacagt tgaacaagac caaactgtaa caattcctac acctacaaat    2520
gaagatggtt tagcattacc agacggaaca aagttcgaag gtggcaacaa tgtacctgaa    2580
tgggcaactg tgaatgaaga tggttctatt tcaatttcac caaatcaaga tgtggaaaaa    2640
ggtaactata atgtgcctgt tgtcgtcaca tatccagatg gttcaaaaga aacagtattt    2700
gcaccagttt tagttcaaga agctgttcca actgcagaac aatacgatcc aacaattgaa    2760
acaattaata aggaatatgg tactactgca acagaagatg aaattaaagg cgcaatcaca    2820
attccggatt acccaacaga tggagatcaa ccaacaatca cgattgacga cccaactcaa    2880
attccaaatg aacagaaga aggcacagtg aatgtaggtg tcactgtcac ttatccagat    2940
ggttcaacag acaaattaac agtaccagtc gttacaggta agcaagcgga taacgataag    3000
tacacaccag aaacaacacc aattacgaaa gacttcggta caggtgtaac agaagacgaa    3060
gtgaaaggtg cagtcactgt tccggattac ccaacagatg gagaccaacc aacaattacg    3120
attgacgacc caagtcagtt gcctgatggt tcaaaagaag gaacaacgga tgtcgacgta    3180
acagtggaat atccagacgg cacaacagat cacatcacag ttccagtgac tgttggaaag    3240
caagcggata atgataagta cacaccagaa acaacaccaa ttacgaaaga cttcggtaca    3300
ggtgtaacag aagacgaagt gaaaggtgca gtcactgttc cggattaccc aacagacggt    3360
gaccaaccaa caattacaat tgatgatcca aatcaattac cggacggttc acaagaaggt    3420
acgactgatg taaatgtaac agtggaatat ccagatggca acagatca catcacagtt    3480
ccagtgactg ttgaaaagca agcggataat gataagtaca caccagaaac aacaccaatt    3540
acgaaagact tcggtacagg tgtaacagaa gacgaagtga aggtgcagt cactgttccg    3600
```

```
gattacccaa cagatggaga tcaaccaacg gttacaattg atgatccaaa tcaattaccg    3660
gacggttcac aagaaggtac gactgatgta aatgtaacag tggaatatcc agacggcaca    3720
acagatcaca tcacagttcc agtgactgtt ggaaagcaag cggataatga taagtacaca    3780
ccagaaacaa caccaattac gaaagacttc ggtacaggtg taacagaaga cgaagtgaaa    3840
ggtgcagtca ctgttccgga ttacccaaca gacggtgacc aaccaacggt tacaattgat    3900
gatccaaatc aattaccgga cggttcacaa gaaggtacga ctgatgtaaa tgtaacagtg    3960
gaatatccag atggcacaac agatcacatc acagttccag tgactgttgg aaagcaagcg    4020
gataacgata gtacacacc agaaacaaca ccaattacga aagacttcgg tacaggtgta    4080
acagaagacg aagtgaaagg tgcagtcact gttccggatt acccaacaga tggagatcaa    4140
ccaacggtta caattgacga tccgagtcag ttaccagatg gctcacaaga aggcacaaca    4200
gatgtgaatg taacagtgga atatccagat ggcacaacag accacatcac agttccagtg    4260
actgttggta agcaagcaga taacgataag tacacgccag aaacaacacc aattacgaaa    4320
gacttcggta caggtgtaac agaagacgaa gtgaaaggtg cagtcactgt tccggattac    4380
ccaacagatg gagaccaacc aacaattaca attgacgatc cgagtcagtt accagacggt    4440
tcacaagaag gtacgactga tgtaaatgta acagtggaat atccagatgg cacaacagat    4500
cacatcacag ttccagtgac tgttggtaag caagcagata cgataagta cacaccagaa    4560 acaacaccaa ttacgaaaga cttcggtaca ggtgtaacag aagacgaagt gaaaggtgca    4620
gtcactgttc cggattaccc aacagatgga gaccaaccaa caattacaat tgacgatccg    4680
agtcagttac agacggttc acaagaaggt acgactgatg taaatgtaac agtggaatat    4740
ccagatggca acagatca catcacagtt ccagtgactg ttggaaagca agcagataac    4800
gataagtaca caccagaaac aacaccaatt acgaaagact cggtacagg tgtaacagaa    4860 ggcgaagtga agattcaat cacaattccc ggttacccaa cagatggaga ccaaccaaca    4920
attacaattg acgacccaag tcagttacca gatggttcac aagaaggtac gactgatgtc    4980
gatgtaacag tggaatatcc agacggcaca acagatcaca ttacagttcc agtgactgtt    5040
ggaaagcaag cagataacga taagtacaca ccagaaacag aaggtgtcaa caaagatcat    5100
ggtacgtcag taacagaaga tgaagtgaaa ggtgcagtca ctgttccggg atacccaaca    5160
gatggagatc aaccaacggt tacaattgat gatccaagtc aattgccgga cggttcacaa    5220
gaaggtacga ctgatgtaaa tgtaacagtg aatatccag acggcacaac agaccacatt    5280
acagtcccag taactgttgg taacaacct actaaagata cggggctac agataatgat    5340 ggcgacatga atcaaggcac agatgaagga aatagtgcta ctgatcatgg cgacaatgta    5400
aaacaagatt caaacggaaa ctatacgccg gttaacaac gtgacaatca tgcgacttca    5460
cctgcaacag atatggatcc aatgccaagc aatagccaaa caacttttga tggcataaat    5520
gcaaaaggtt caacttcaga gaaagcaaac cataaacaac agtctgagca attaccagac    5580
acaggtgaaa gcaatacaca aaatggtgca ctttttaggcg gattattgc agcacttgga    5640 ggcttattct taatcggcag acgtcgtaaa gaaaaagaag gcaaataa              5688
```

<210> SEQ ID NO 14
<211> LENGTH: 1895
<212> TYPE: PRT
<213> ORGANISM: Staphylococcus pseudintermedius

<400> SEQUENCE: 14

Met Lys Lys Ser Arg Lys Lys Arg Ile Asp Phe Leu Pro Asn Arg Gln

```
1               5                    10                   15
Asn Arg Tyr Ala Ile Arg Arg Phe Ser Val Gly Thr Ala Ser Ile Leu
                20                   25                   30
Val Gly Ala Thr Leu Ile Phe Gly Ile His Ser Asn Asp Ala Ser Ala
                35                   40                   45
Ala Val Glu Asp Ala Thr Ser Gln Glu Ala Gly Thr Thr Asn Glu Asn
                50                   55                   60
Ser Asn Ser Thr Glu Glu Ala Thr Thr Asn Glu Ser Thr Thr Val Glu
65                   70                   75                   80
Ala Pro Thr Ser Glu Glu Ala Thr Thr Glu Glu Gln Ser Val Glu Ala
                85                   90                   95
Pro Thr Ser Glu Glu Val Thr Thr Glu Glu Gln Ser Val Glu Ala Pro
                100                  105                  110
Thr Ser Glu Glu Val Thr Thr Glu Glu Gln Ser Val Glu Ala Pro Thr
                115                  120                  125
Ser Glu Glu Val Thr Thr Glu Glu Gln Ser Val Glu Ala Pro Thr Ser
                130                  135                  140
Glu Glu Val Thr Thr Glu Glu Gln Ser Val Glu Ala Pro Thr Ser Glu
145                  150                  155                  160
Glu Val Thr Thr Glu Glu Gln Ser Val Glu Ala Pro Thr Ser Glu Glu
                165                  170                  175
Val Thr Thr Glu Glu Gln Ser Val Glu Ala Pro Thr Ser Glu Glu Ala
                180                  185                  190
Thr Thr Glu Glu Gln Ser Val Glu Ala Pro Thr Ser Glu Glu Ala Thr
                195                  200                  205
Thr Lys Thr Pro Val Lys Glu Glu Thr Ser Ser Thr Gln Glu Asn Ser
                210                  215                  220
Pro Thr Thr Thr Leu Glu Glu Gln Phe Ser Asn Glu Phe Asn Gln Leu
225                  230                  235                  240
Thr Ser Thr Glu Asp Lys Thr Asn Tyr Thr Arg Glu Tyr Leu Thr Gln
                245                  250                  255
Asn Thr Asn Leu Ser Ala Glu Gln Val Glu Ala Thr Val Glu Arg Leu
                260                  265                  270
Asn Leu Ser Gln Glu Asn Val Thr Ala Gln Asp Ile Tyr Phe Ala Leu
                275                  280                  285
Leu Lys Asp Leu Ala Asp Gln Gln Asp Ala Leu Leu Pro Arg Val Thr
                290                  295                  300
Leu Leu Ala Ala Arg Asp Ser Glu Leu Thr Asn Glu Ala Ser Ile Ala
305                  310                  315                  320
Leu Thr Glu Asn Ser Pro Met Phe Arg Ala Ala Leu Ala Asn Ser Pro
                325                  330                  335
Ser Gly Asn Asp Val Val Ser Glu Glu Asp Asn Ile Ile Val Ala Asp
                340                  345                  350
Ala Leu Ala Asn Gly Tyr Ile Asn Ser Gln Thr Asp Ala Thr Asn Ala
                355                  360                  365
Ala Asn Thr Leu Ser Gly Arg Ala Trp Val Val Asp Thr Gly Thr Pro
                370                  375                  380
Ala Thr Met Ser Asn Gly Leu Thr Ala Val Pro Glu Gly Thr Lys Val
385                  390                  395                  400
Tyr Met Gln Trp Ile Asp Thr Asp Gly Ala Val Ser Pro Val Tyr Gln
                405                  410                  415
Ala Ser Thr Thr Asn Lys Leu Ser Ser Ser Gly Gly Ser Gln Val Gly
                420                  425                  430
```

```
Pro Gly Ala Tyr Ala Phe Asp Leu Arg Glu Ala Trp Ile Asp Ser Asn
        435                 440                 445

Gly Lys Ala His Arg Tyr Glu Ala Ser Ser Gly Gln Tyr Tyr Arg Leu
        450                 455                 460

Trp Ile Asp Asp Tyr Lys Thr Val Asp Gly Asn Thr Ala Thr Met Leu
465                 470                 475                 480

Arg Gln Ala Gly Gly Phe Phe Pro Gly Ser Tyr Val Asn Ser Val Thr
                485                 490                 495

Gly Asn Asn Ile Gly Gln Phe Pro Leu Ile Gly Thr Asn Met Gln Arg
                500                 505                 510

Thr Gly Ile Phe Met Gly Val Ile Pro Thr Asn Asp Tyr Met Thr Thr
        515                 520                 525

Asp Thr Ser Asn Trp Ile Gln Asp Asn Glu Gly Pro Ile Ser Asn Pro
530                 535                 540

Ala Val Thr Ser Thr Ser Glu Phe Val Ser Gly Lys Val Trp Ser Glu
545                 550                 555                 560

Thr Gly Ser Gly Asp Tyr Ala Asn Ser Ala Thr Gly Pro Asn Phe Asn
                565                 570                 575

Ser Gly Asp Ile Ala Arg Glu Gly Tyr Gln Val Val Met Ser Ser Leu
                580                 585                 590

Thr Ser Ala Gly Ala Gln Ala Tyr Lys Ala Gln Val Glu Ser Leu Pro
        595                 600                 605

Thr Asp Gln Gln Ala Ala Ala His Gln Leu Phe Lys Asp His Pro
        610                 615                 620

Glu Phe Ile Ser Ala Thr Val Thr Gly Lys Thr Asp Ala Asn Gly Ala
625                 630                 635                 640

Tyr Thr Leu Arg Phe Pro Ser Gly Ser Leu Ser Lys Asp Tyr Leu Tyr
                645                 650                 655

Gly Tyr Val Met Asp Asn Lys Gly Asn Leu Val Lys Gly Tyr Ser Ser
                660                 665                 670

Phe Thr Ser Pro Leu Phe Arg Ser Pro Asn Ser Asn Leu Ser Phe Ala
        675                 680                 685

Pro Gln Thr Ala Pro Tyr His Arg Pro Ala Lys Asn Ala Trp Val Asn
        690                 695                 700

Val Asn Phe Ala Leu Val Glu Thr Ile Glu Thr Ser Ile Asp Ile Thr
705                 710                 715                 720

Asn Phe Asp Val Thr Ala Asn Pro Ala Gln Arg Gly Asp Thr Ala Ile
                725                 730                 735

Ile Asp Val Thr Ser Thr Ala Leu Ser Pro Leu Pro Thr His Val Glu
                740                 745                 750

Trp Arg Asp Ser Lys Gly Asn Val Val Gln Lys Ser Gly Asp Val Thr
        755                 760                 765

Thr Val Glu Glu Ala Glu Thr Ala Gly Thr Phe Thr Ile Pro Asp Asp
        770                 775                 780

Ala Lys Thr Gly Glu Ile Tyr Thr Val Tyr Ile Val Ser Gly Gly Asn
785                 790                 795                 800

Glu Val Ala Ala Asp Ser Leu Ile Val Gln Val Gln Glu Asn Ala Ala
                805                 810                 815

Thr Tyr Glu Pro Val Tyr Pro Thr Thr Val Glu Gln Asp Gln Thr
                820                 825                 830

Val Thr Ile Pro Thr Pro Thr Asn Glu Asp Gly Leu Ala Leu Pro Asp
        835                 840                 845
```

-continued

Gly Thr Lys Phe Glu Gly Gly Asn Asn Val Pro Glu Trp Ala Thr Val
850                 855                 860

Asn Glu Asp Gly Ser Ile Ser Ile Ser Pro Asn Gln Asp Val Glu Lys
865                 870                 875                 880

Gly Asn Tyr Asn Val Pro Val Val Thr Tyr Pro Asp Gly Ser Lys
            885                 890                 895

Glu Thr Val Phe Ala Pro Val Leu Val Gln Glu Ala Val Pro Thr Ala
                900                 905                 910

Glu Gln Tyr Asp Pro Thr Ile Glu Thr Ile Asn Lys Glu Tyr Gly Thr
            915                 920                 925

Thr Ala Thr Glu Asp Glu Ile Lys Gly Ala Ile Thr Ile Pro Asp Tyr
930                 935                 940

Pro Thr Asp Gly Asp Gln Pro Thr Ile Thr Ile Asp Asp Pro Thr Gln
945                 950                 955                 960

Ile Pro Asn Gly Thr Glu Gly Thr Val Asn Val Gly Val Thr Val
                965                 970                 975

Thr Tyr Pro Asp Gly Ser Thr Asp Lys Leu Thr Val Pro Val Val Thr
            980                 985                 990

Gly Lys Gln Ala Asp Asn Asp Lys Tyr Thr Pro Glu Thr Thr Pro Ile
995                 1000                1005

Thr Lys Asp Phe Gly Thr Gly Val Thr Glu Asp Glu Val Lys Gly
1010                1015                1020

Ala Val Thr Val Pro Asp Tyr Pro Thr Asp Gly Asp Gln Pro Thr
1025                1030                1035

Ile Thr Ile Asp Asp Pro Ser Gln Leu Pro Asp Gly Ser Lys Glu
1040                1045                1050

Gly Thr Thr Asp Val Asp Val Thr Val Glu Tyr Pro Asp Gly Thr
1055                1060                1065

Thr Asp His Ile Thr Val Pro Val Thr Val Gly Lys Gln Ala Asp
1070                1075                1080

Asn Asp Lys Tyr Thr Pro Glu Thr Thr Pro Ile Thr Lys Asp Phe
1085                1090                1095

Gly Thr Gly Val Thr Glu Asp Glu Val Lys Gly Ala Val Thr Val
1100                1105                1110

Pro Asp Tyr Pro Thr Asp Gly Asp Gln Pro Thr Ile Thr Ile Asp
1115                1120                1125

Asp Pro Asn Gln Leu Pro Asp Gly Ser Gln Glu Gly Thr Thr Asp
1130                1135                1140

Val Asn Val Thr Val Glu Tyr Pro Asp Gly Thr Thr Asp His Ile
1145                1150                1155

Thr Val Pro Val Thr Val Gly Lys Gln Ala Asp Asn Asp Lys Tyr
1160                1165                1170

Thr Pro Glu Thr Thr Pro Ile Thr Lys Asp Phe Gly Thr Gly Val
1175                1180                1185

Thr Glu Asp Glu Val Lys Gly Ala Val Thr Val Pro Asp Tyr Pro
1190                1195                1200

Thr Asp Gly Asp Gln Pro Val Thr Ile Asp Asp Pro Asn Gln
1205                1210                1215

Leu Pro Asp Gly Ser Gln Glu Gly Thr Thr Asp Val Asn Val Thr
1220                1225                1230

Val Glu Tyr Pro Asp Gly Thr Asp His Ile Thr Val Pro Val
1235                1240                1245

Thr Val Gly Lys Gln Ala Asp Asn Asp Lys Tyr Thr Pro Glu Thr

```
                    1250                  1255                  1260

Thr  Pro  Ile  Thr  Lys  Asp  Phe  Gly  Thr  Gly  Val  Thr  Glu  Asp  Glu
          1265                  1270                  1275

Val  Lys  Gly  Ala  Val  Thr  Val  Pro  Asp  Tyr  Pro  Thr  Asp  Gly  Asp
     1280                  1285                  1290

Gln  Pro  Thr  Val  Thr  Ile  Asp  Asp  Pro  Asn  Gln  Leu  Pro  Asp  Gly
          1295                  1300                  1305

Ser  Gln  Glu  Gly  Thr  Thr  Asp  Val  Asn  Val  Thr  Val  Glu  Tyr  Pro
     1310                  1315                  1320

Asp  Gly  Thr  Thr  Asp  His  Ile  Thr  Val  Pro  Val  Thr  Val  Gly  Lys
     1325                  1330                  1335

Gln  Ala  Asp  Asn  Asp  Lys  Tyr  Thr  Pro  Glu  Thr  Thr  Pro  Ile  Thr
     1340                  1345                  1350

Lys  Asp  Phe  Gly  Thr  Gly  Val  Thr  Glu  Asp  Glu  Val  Lys  Gly  Ala
     1355                  1360                  1365

Val  Thr  Val  Pro  Asp  Tyr  Pro  Thr  Asp  Gly  Asp  Gln  Pro  Thr  Val
     1370                  1375                  1380

Thr  Ile  Asp  Asp  Pro  Ser  Gln  Leu  Pro  Asp  Gly  Ser  Gln  Glu  Gly
     1385                  1390                  1395

Thr  Thr  Asp  Val  Asn  Val  Thr  Val  Glu  Tyr  Pro  Asp  Gly  Thr  Thr
     1400                  1405                  1410

Asp  His  Ile  Thr  Val  Pro  Val  Thr  Val  Gly  Lys  Gln  Ala  Asp  Asn
     1415                  1420                  1425

Asp  Lys  Tyr  Thr  Pro  Glu  Thr  Thr  Pro  Ile  Thr  Lys  Asp  Phe  Gly
     1430                  1435                  1440

Thr  Gly  Val  Thr  Glu  Asp  Glu  Val  Lys  Gly  Ala  Val  Thr  Val  Pro
     1445                  1450                  1455

Asp  Tyr  Pro  Thr  Asp  Gly  Asp  Gln  Pro  Thr  Ile  Thr  Ile  Asp  Asp
     1460                  1465                  1470

Pro  Ser  Gln  Leu  Pro  Asp  Gly  Ser  Gln  Glu  Gly  Thr  Thr  Asp  Val
     1475                  1480                  1485

Asn  Val  Thr  Val  Glu  Tyr  Pro  Asp  Gly  Thr  Thr  Asp  His  Ile  Thr
     1490                  1495                  1500

Val  Pro  Val  Thr  Val  Gly  Lys  Gln  Ala  Asp  Asn  Asp  Lys  Tyr  Thr
     1505                  1510                  1515

Pro  Glu  Thr  Thr  Pro  Ile  Thr  Lys  Asp  Phe  Gly  Thr  Gly  Val  Thr
     1520                  1525                  1530

Glu  Asp  Glu  Val  Lys  Gly  Ala  Val  Thr  Val  Pro  Asp  Tyr  Pro  Thr
     1535                  1540                  1545

Asp  Gly  Asp  Gln  Pro  Thr  Ile  Thr  Ile  Asp  Asp  Pro  Ser  Gln  Leu
     1550                  1555                  1560

Pro  Asp  Gly  Ser  Gln  Glu  Gly  Thr  Thr  Asp  Val  Asn  Val  Thr  Val
     1565                  1570                  1575

Glu  Tyr  Pro  Asp  Gly  Thr  Thr  Asp  His  Ile  Thr  Val  Pro  Val  Thr
     1580                  1585                  1590

Val  Gly  Lys  Gln  Ala  Asp  Asn  Asp  Lys  Tyr  Thr  Pro  Glu  Thr  Thr
     1595                  1600                  1605

Pro  Ile  Thr  Lys  Asp  Phe  Gly  Thr  Gly  Val  Thr  Glu  Gly  Glu  Val
     1610                  1615                  1620

Lys  Asp  Ser  Ile  Thr  Ile  Pro  Gly  Tyr  Pro  Thr  Asp  Gly  Asp  Gln
     1625                  1630                  1635

Pro  Thr  Ile  Thr  Ile  Asp  Asp  Pro  Ser  Gln  Leu  Pro  Asp  Gly  Ser
     1640                  1645                  1650
```

Gln Glu Gly Thr Thr Asp Val Asp Val Thr Val Glu Tyr Pro Asp
   1655                1660                1665

Gly Thr Thr Asp His Ile Thr Val Pro Val Thr Val Gly Lys Gln
   1670                1675                1680

Ala Asp Asn Asp Lys Tyr Thr Pro Glu Thr Glu Gly Val Asn Lys
   1685                1690                1695

Asp His Gly Thr Ser Val Thr Glu Asp Glu Val Lys Gly Ala Val
   1700                1705                1710

Thr Val Pro Gly Tyr Pro Thr Asp Gly Asp Gln Pro Thr Val Thr
   1715                1720                1725

Ile Asp Asp Pro Ser Gln Leu Pro Asp Gly Ser Gln Glu Gly Thr
   1730                1735                1740

Thr Asp Val Asn Val Thr Val Glu Tyr Pro Asp Gly Thr Thr Asp
   1745                1750                1755

His Ile Thr Val Pro Val Thr Val Gly Lys Gln Pro Thr Lys Asp
   1760                1765                1770

Asn Gly Ala Thr Asp Asn Asp Gly Asp Met Asn Gln Gly Thr Asp
   1775                1780                1785

Glu Gly Asn Ser Ala Thr Asp His Gly Asp Asn Val Lys Gln Asp
   1790                1795                1800

Ser Asn Gly Asn Tyr Thr Pro Val Glu Gln Arg Asp Asn His Ala
   1805                1810                1815

Thr Ser Pro Ala Thr Asp Met Asp Pro Met Pro Ser Asn Ser Gln
   1820                1825                1830

Thr Thr Phe Asp Gly Ile Asn Ala Lys Gly Ser Thr Ser Glu Lys
   1835                1840                1845

Ala Asn His Lys Gln Gln Ser Glu Gln Leu Pro Asp Thr Gly Glu
   1850                1855                1860

Ser Asn Thr Gln Asn Gly Ala Leu Leu Gly Gly Leu Phe Ala Ala
   1865                1870                1875

Leu Gly Gly Leu Phe Leu Ile Gly Arg Arg Arg Lys Glu Lys Glu
   1880                1885                1890

Gly Lys
   1895

<210> SEQ ID NO 15
<211> LENGTH: 1860
<212> TYPE: DNA
<213> ORGANISM: Staphylococcus pseudintermedius

<400> SEQUENCE: 15
atgacagaac gaaatccccc ttcatctcaa aacatgcgtc atcgtttagt caaagctggt      60
actgtccttt tattggttgg tagtggactg caaatgcctt caacattgtc acacgaaatg     120
acagcgatag ctcagacaga tgcgactgat gatttgaaaa cattacgtga aaatgcagat     180 aaaaagtga agcgttaca atatttaaat acgattata aaaatgaatt tcttgcgtta        240
attcgtgaat atgatacgtc gtcaaaaaat attgaagtgg ttgttgacga agcagaagca     300
gccaatcgtc tagctcatga cgctcaatcg gacgatgaaa tacaacctga attagatgcc     360
attgatgaaa aaattagcgc gttaaaggca aaggttgatg aaggtcaacg agaatcaact     420
gaagcgcgtc aagatgtaac gtcaacagag acaaagagtg ctgaatcaga aggaagagag     480
ccatccactg aaggcgagag caaagtaaag gagtcatctt cagcacaaac gattgtagca     540
cctcatcatg gtcaacaaga tgtgagcgca ctgaaagacc atattaagaa cgatgtcgat     600

```
acacttaaac aagactatgc aacgcaagac aagcaagtga caccactcca gggcattgac    660
agtgcaatca cacgcattga ccatttcgtt tcagaaagcg tggatcacaa gtctgacaat    720
tattttgaag aaaaacgtca acatttacaa aactttgaac aagacattaa aaaacgtacg    780
gacatttctg ggactgagaa ggcgactttg cttgatgatg cgaaaacggt agccaaccaa    840
ctgaacgcgc aaaatgatac gattttaact gaacttcaac agcatgacga taaacgtgca    900
gcagttgaat cgatattagg tgagattttt aatgcacaag aagcggctga acgtgcgaaa    960
cagatagatg ttaaaggtaa aacagatcaa caattggcaa acgaaattca tcaacaagcg   1020
gacggactta tcaaaacgtc gagtgatgat ttattgttag gaatgttgga aaataattca   1080
aatacacaag gtctagtgga aagcatttta cgaacacgct ttgacaaaca agaagcgcac   1140
aaaattgccg gcgaaatcat gcaaggcaag ccttcaaata cagcgatact cgaccgcttg   1200
aaagaccatt ttaaagcgaa tggtaaggcg agtggagatg atattttaaa tgcgttaatt   1260
aataatacgg atgcagatgc tgaagtgatt gaatcaattc tagggggccg tcttaatgca   1320
gaaaatgcaa aattgattgc cgatcgtgta cagcaagata aaaagaagac acatcaaaac   1380
ttaaaggcga ttgaagacga acttagtgcg caagcgaatc gattgttaac gttacggaag   1440
caattgcaac aaatccgtca taatacgcaa acagatatga atgacttgtt tgcaccactg   1500
cgtcgtattg caaatattct cggtggtggt ttaaatcgtg acgacattca ctcttcaggt   1560
cgtacgaatg acaaattgca gcaactgtta aatcgtgatc attcgttgtt aggtcgtggt   1620
ggtgatttat tcaaacatga ttttgcgcca aagccgaata tcgatccata tcaagcgatt   1680
aatagtcaaa cggcatcaga aggttttta gatggtttat ttgatcaaaa tggcgatttc   1740
aatttaccga atacaggtga aatagtgaag cggacttggc taccgttggg tattttagtc   1800
gttgcaatcg gtgtactgat cttaacggtg agatttcata aaaaaacacg caaacaataa   1860
```

<210> SEQ ID NO 16
<211> LENGTH: 619
<212> TYPE: PRT
<213> ORGANISM: Staphylococcus pseudintermedius

<400> SEQUENCE: 16

```
Met Thr Glu Arg Lys Ser Pro Ser Ser Gln Asn Met Arg His Arg Leu
1               5                   10                  15

Val Lys Ala Gly Thr Val Leu Leu Val Gly Ser Gly Leu Gln Met
            20                  25                  30

Pro Ser Thr Leu Ser His Glu Met Thr Ala Ile Ala Gln Thr Asp Ala
        35                  40                  45

Thr Asp Asp Leu Lys Thr Leu Arg Glu Asn Ala Asp Lys Lys Val Lys
    50                  55                  60

Ala Leu Gln Tyr Leu Asn Thr Asp Tyr Lys Asn Glu Phe Leu Ala Leu
65                  70                  75                  80

Ile Arg Glu Tyr Asp Thr Ser Ser Lys Asn Ile Glu Val Val Asp
                85                  90                  95

Glu Ala Glu Ala Ala Asn Arg Leu Ala His Asp Ala Gln Ser Asp Asp
            100                 105                 110

Glu Ile Gln Pro Glu Leu Asp Ala Ile Asp Glu Lys Ile Ser Ala Leu
        115                 120                 125

Lys Ala Lys Val Asp Glu Gly Gln Arg Glu Ser Thr Glu Ala Arg Gln
    130                 135                 140

Asp Val Thr Ser Thr Glu Thr Lys Ser Ala Glu Ser Glu Gly Arg Glu
```

```
            145                 150                 155                 160
        Pro Ser Thr Glu Gly Glu Ser Lys Val Lys Glu Ser Ser Ala Gln
                        165                 170                 175

Thr Ile Val Ala Pro His His Gly Gln Gln Asp Val Ser Ala Leu Lys
                        180                 185                 190

Asp His Ile Lys Asn Asp Val Asp Thr Leu Lys Gln Asp Tyr Ala Thr
                        195                 200                 205

Gln Asp Lys Gln Val Thr Pro Leu Gln Gly Ile Asp Ser Ala Ile Thr
                210                 215                 220

Arg Ile Asp His Phe Val Ser Glu Ser Val Asp His Lys Ser Asp Asn
        225                 230                 235                 240

Tyr Phe Glu Glu Lys Arg Gln His Leu Gln Asn Phe Glu Gln Asp Ile
                        245                 250                 255

Lys Lys Arg Thr Asp Ile Ser Gly Thr Glu Lys Ala Thr Leu Leu Asp
                        260                 265                 270

Asp Ala Lys Thr Val Ala Asn Gln Leu Asn Ala Gln Asn Asp Thr Ile
                        275                 280                 285

Leu Thr Glu Leu Gln Gln His Asp Asp Lys Arg Ala Ala Val Glu Ser
                290                 295                 300

Ile Leu Gly Glu Ile Phe Asn Ala Gln Glu Ala Ala Glu Arg Ala Lys
        305                 310                 315                 320

Gln Ile Asp Val Lys Gly Lys Thr Asp Gln Gln Leu Ala Asn Glu Ile
                        325                 330                 335

His Gln Gln Ala Asp Gly Leu Ile Lys Thr Ser Ser Asp Asp Leu Leu
                        340                 345                 350

Leu Gly Met Leu Glu Asn Asn Ser Asn Thr Gln Gly Leu Val Glu Ser
                        355                 360                 365

Ile Leu Arg Thr Arg Phe Asp Lys Gln Glu Ala His Lys Ile Ala Gly
                370                 375                 380

Glu Ile Met Gln Gly Lys Pro Ser Asn Thr Ala Ile Leu Asp Arg Leu
        385                 390                 395                 400

Lys Asp His Phe Lys Ala Asn Gly Lys Ala Ser Gly Asp Asp Ile Leu
                        405                 410                 415

Asn Ala Leu Ile Asn Asn Thr Asp Ala Asp Ala Glu Val Ile Glu Ser
                        420                 425                 430

Ile Leu Gly Gly Arg Leu Asn Ala Glu Asn Ala Lys Leu Ile Ala Asp
                        435                 440                 445

Arg Val Gln Gln Asp Lys Lys Lys Thr His Gln Asn Leu Lys Ala Ile
        450                 455                 460

Glu Asp Glu Leu Ser Ala Gln Ala Asn Arg Leu Leu Thr Leu Arg Lys
        465                 470                 475                 480

Gln Leu Gln Gln Ile Arg His Asn Thr Gln Thr Asp Met Asn Asp Leu
                        485                 490                 495

Phe Ala Pro Leu Arg Arg Ile Ala Asn Ile Leu Gly Gly Leu Asn
                        500                 505                 510

Arg Asp Asp Ile His Ser Ser Gly Arg Thr Asn Asp Lys Leu Gln Gln
                        515                 520                 525

Leu Leu Asn Arg Asp His Ser Leu Leu Gly Arg Gly Gly Asp Leu Phe
                        530                 535                 540

Lys His Asp Phe Ala Pro Lys Pro Asn Ile Asp Pro Tyr Gln Ala Ile
        545                 550                 555                 560

Asn Ser Gln Thr Ala Ser Glu Gly Phe Leu Asp Gly Leu Phe Asp Gln
                        565                 570                 575
```

```
Asn Gly Asp Phe Asn Leu Pro Asn Thr Gly Glu Ile Val Lys Arg Thr
            580                 585                 590

Trp Leu Pro Leu Gly Ile Leu Val Ala Ile Gly Val Leu Ile Leu
        595                 600                 605

Thr Val Arg Phe His Lys Lys Thr Arg Lys Gln
    610                 615

<210> SEQ ID NO 17
<211> LENGTH: 729
<212> TYPE: DNA
<213> ORGANISM: Staphylococcus pseudintermedius

<400> SEQUENCE: 17
atgttaaaaa aattaattgt tacaggtttg attgctacag cggcgacaca agtttatgcg      60
catgacacgc aagcggcgga aaagggtgct acagatgctc cgaatgtgat ggttaaggat    120
gaggcgaaaa aagaagtgac accgataatc cataaaccga cttgcattta cccgcatcta    180
gaaggcgaag atgatgctgc gtatttaaaa cgtatggcaa cgaatccacc agaaggcgca    240
gtgccgtacg gtgtattgaa taaagatgga tcgattacag aaccgaatac aaatccacat    300
tttgatgttt taaaaattga agatccaaat gcgatgaaaa atttggttga tacaccggca    360
gatgatcaag atacggtacc gagtgattta caaattgaac caccagcatt aataggacca    420
gctactaaac atacgatgg tacgggagac gcaaaatcta atgatgacca aaagtaaca     480 aaatcttcgg gagcgtcagc ccaagatatg aagaaaaaag acgtgacaac acaaactgca    540
caaccaaaag cagataaaaa gatggcgact gcaaaagtag caccagcgaa acaacaagat    600
aaagcagcca aatgttacc agcagcaggg gaaccacaag tgaatgcaat cagtcaaaca    660
gcacttgcac tttcaatgat cgcattaggt gtcatcgcgt tctttacacg acgacgcaaa    720
acaaattaa                                                           729

<210> SEQ ID NO 18
<211> LENGTH: 242
<212> TYPE: PRT
<213> ORGANISM: Staphylococcus pseudintermedius

<400> SEQUENCE: 18

Met Leu Lys Lys Leu Ile Val Thr Gly Leu Ile Ala Thr Ala Ala Thr
1               5                   10                  15

Gln Val Tyr Ala His Asp Thr Gln Ala Ala Glu Lys Gly Ala Thr Asp
            20                  25                  30

Ala Pro Asn Val Met Val Lys Asp Glu Ala Lys Lys Glu Val Thr Pro
        35                  40                  45

Ile Ile His Lys Pro Thr Cys Ile Tyr Pro His Leu Glu Gly Glu Asp
    50                  55                  60

Asp Ala Ala Tyr Leu Lys Arg Met Ala Thr Asn Pro Pro Glu Gly Ala
65                  70                  75                  80

Val Pro Tyr Gly Val Leu Asn Lys Asp Gly Ser Ile Thr Glu Pro Asn
                85                  90                  95

Thr Asn Pro His Phe Asp Val Leu Lys Ile Glu Asp Pro Asn Ala Met
            100                 105                 110

Lys Asp Leu Val Asp Thr Pro Ala Asp Asp Gln Asp Thr Val Pro Ser
        115                 120                 125

Asp Leu Gln Ile Glu Pro Pro Ala Leu Ile Gly Pro Ala Thr Lys His
    130                 135                 140
```

```
Thr Asp Gly Thr Gly Asp Ala Lys Ser Asn Asp His Lys Val Thr
145                 150                 155                 160

Lys Ser Ser Gly Ala Ser Ala Gln Asp Met Lys Lys Asp Val Thr
            165                 170                 175

Thr Gln Thr Ala Gln Pro Lys Ala Asp Lys Lys Met Ala Thr Ala Lys
            180                 185                 190

Val Ala Pro Ala Lys Gln Gln Asp Lys Ala Ala Lys Met Leu Pro Ala
            195                 200                 205

Ala Gly Glu Pro Gln Val Asn Ala Ile Ser Gln Thr Ala Leu Ala Leu
        210                 215                 220

Ser Met Ile Ala Leu Gly Val Ile Ala Phe Phe Thr Arg Arg Arg Lys
225                 230                 235                 240

Thr Asn

<210> SEQ ID NO 19
<211> LENGTH: 1362
<212> TYPE: DNA
<213> ORGANISM: Staphylococcus pseudintermedius

<400> SEQUENCE: 19
atggtagaat ataaaaaaga acatagcgta aagcgactat taaaattagg aatcggttca        60
acgagtattt tatgtgttgt atcacctctt ttattaacac atgacgttgt tcaagcagca       120
gatatcaata acaggatgcc agctttgaat acattgaaga ccacttcttc atatgatcaa       180
agggcacaca tggatgaatt acgaaacgcc attacttcag atagtgacac tactcaaaca       240
ccatcattca atgagataac tgtgtcttca actaatgaaa cggatgcagc gtcaacggaa       300
aatgtgaacc cgagtgatga ggtcccggca aaggatgaaa gtgaatcaac gacaccgagt       360
acagaacaag acacatctat agaagaaacg ggtactgaag aagtgccatc tcatgaagac       420
aatcatcaca cacccccaag tcaagaagag caaccgtctc cgcctgatca accaggaaca       480
aacaaagatg aagagagtgg agaaaaaccg aataaagaaa tcatcggaa gccgaatcaa       540 ccgaacaaag accaaccttc aaaagatgag aataaaaaac ctgacaaagg aaacaaacca       600
gcaccaccgt ctaaaatgcc aaatcgcccg gatcaaaagg aagatggttc aaacaacacc       660
ccaccacctg ccactgataa cggtggaaac agtaatgacg gtacaacaac gggtcccaat       720
ggtggaggtg gcagtgaagc aagtccacca ccgaatgagc aaccgtcaaa tggcaatgca       780
agcgataccc atcaaaacgg ttcagtttca agcaccaatc attcgaatca gtatggtaca       840
tcggcttatg atgaatacgc aggtttattg aataataatt ataaatataa tccattgttt       900
aaagaagagg ttgcgcgttt aagtcaattt ggaagtcaag atcaacatga tattgcaagt       960
ttgagtcgta agaacaatt ttctcaaaat gcattttttag atgacttgca acaaagtaca      1020
gattatttta gatatcaata ttttaacccg ctttccacag agcaatacta tcatcgttta      1080
gataaacaag tattagcact cgttacgggg gaatttggtt cgatgccaga tttcaagaaa      1140
agtggtgata agtcattggt taataagcat cagcaagata agtgaagaa aattgaacag      1200 caaggagaaa atattaatac gcatcatatg aaaaatacga agaagatac aggaaaatca      1260 ttaagttaca agccgatgat atatattggc attgtcatgg tcggttttgt cggcctgatc      1320
agtatgattt tatggaaacg actgcatcat ttttggaaat aa                        1362

<210> SEQ ID NO 20
<211> LENGTH: 453
<212> TYPE: PRT
<213> ORGANISM: Staphylococcus pseudintermedius
```

<400> SEQUENCE: 20

Met Val Glu Tyr Lys Lys Glu His Ser Val Lys Arg Leu Leu Lys Leu
1               5                   10                  15

Gly Ile Gly Ser Thr Ser Ile Leu Cys Val Val Ser Pro Leu Leu Leu
            20                  25                  30

Thr His Asp Val Val Gln Ala Ala Asp Ile Asn Asn Arg Met Pro Ala
        35                  40                  45

Leu Asn Thr Leu Lys Thr Thr Ser Ser Tyr Asp Gln Arg Ala His Met
50                  55                  60

Asp Glu Leu Arg Asn Ala Ile Thr Ser Asp Ser Asp Thr Thr Gln Thr
65                  70                  75                  80

Pro Ser Phe Asn Glu Ile Thr Val Ser Ser Thr Asn Glu Thr Asp Ala
                85                  90                  95

Ala Ser Thr Glu Asn Val Asn Pro Ser Asp Glu Val Pro Ala Lys Asp
            100                 105                 110

Glu Ser Glu Ser Thr Thr Pro Ser Thr Glu Gln Asp Thr Ser Ile Glu
        115                 120                 125

Glu Thr Gly Thr Glu Glu Val Pro Ser His Glu Asp Asn His His Asn
130                 135                 140

Thr Pro Ser Gln Glu Glu Gln Pro Ser Pro Pro Asp Gln Pro Gly Thr
145                 150                 155                 160

Asn Lys Asp Glu Glu Ser Gly Glu Lys Pro Asn Lys Glu Asn His Arg
                165                 170                 175

Lys Pro Asn Gln Pro Asn Lys Asp Gln Pro Ser Lys Asp Glu Asn Lys
            180                 185                 190

Lys Pro Asp Lys Gly Asn Lys Pro Ala Pro Pro Ser Lys Met Pro Asn
        195                 200                 205

Arg Pro Asp Gln Lys Glu Asp Gly Ser Asn Asn Thr Pro Pro Pro Ala
        210                 215                 220

Thr Asp Asn Gly Gly Asn Ser Asn Asp Gly Thr Thr Thr Gly Pro Asn
225                 230                 235                 240

Gly Gly Gly Gly Ser Glu Ala Ser Pro Pro Asn Glu Gln Pro Pro Ser
                245                 250                 255

Asn Gly Asn Ala Ser Asp Thr His Gln Asn Gly Ser Val Ser Ser Thr
            260                 265                 270

Asn His Ser Asn Gln Tyr Gly Thr Ser Ala Tyr Asp Glu Tyr Ala Gly
        275                 280                 285

Leu Leu Asn Asn Asn Tyr Lys Tyr Asn Pro Leu Phe Lys Glu Glu Val
290                 295                 300

Ala Arg Leu Ser Gln Phe Gly Ser Gln Asp Gln His Asp Ile Ala Ser
305                 310                 315                 320

Leu Ser Arg Lys Glu Gln Phe Ser Gln Asn Ala Phe Leu Asp Asp Leu
                325                 330                 335

Gln Gln Ser Thr Asp Tyr Phe Arg Tyr Gln Tyr Phe Asn Pro Leu Ser
            340                 345                 350

Thr Glu Gln Tyr Tyr His Arg Leu Asp Lys Gln Val Leu Ala Leu Val
        355                 360                 365

Thr Gly Glu Phe Gly Ser Met Pro Asp Phe Lys Lys Ser Gly Asp Lys
370                 375                 380

Ser Leu Val Asn Lys His Gln Gln Asp Lys Val Lys Lys Ile Glu Gln
385                 390                 395                 400

Gln Gly Glu Asn Ile Asn Thr His His Met Lys Asn Thr Lys Glu Asp 405 410 415
Thr Gly Lys Ser Leu Ser Tyr Lys Pro Met Ile Tyr Ile Gly Ile Val
        420                 425                 430
Met Val Gly Phe Val Gly Leu Ile Ser Met Ile Leu Trp Lys Arg Leu
        435                 440                 445
His His Phe Trp Lys
    450

<210> SEQ ID NO 21
<211> LENGTH: 3096
<212> TYPE: DNA
<213> ORGANISM: Staphylococcus pseudintermedius

<400> SEQUENCE: 21

```
gtgattacaa ataaaaatat atatagtatt cgaaagcata acttggcgt ggcatcattc      60
ttattgggga cattatttgt tgtagggcat gcaaataatg ctgaagcttc agaagtgagc    120
gcaacaacac aagaacataa tgtcgagact gagcaaacaa aactgaggg cgaactaaca    180
actgaggtag cacaacaagc agtcagcgaa tcagcaccta gctgaaaa catgcagaaa    240
acaacatcag tggcaagtga aaatgcgaaa gaggttacag cttctgatag cacacaagaa    300
gtcacaaaaa ctgaagcaaa agatacagca acaatgaaag attcagaaat tgcacaacct    360
gtatcagaag tgaataaacc tgttactcaa acagctgcac ccgtagcaga accatcaaca    420
gcaaacaaac aaacttcacc acgacaagta caagaactta ctgcaccaat ggacacaaaa    480
gtaattaatg tagaaaacgg aacagatgtg acagtaaag tgaaagttga aaatcgtca    540
attacagggc atcagaataa agataaaaca tatcatcaat cgaacactgt aaatccacat    600
aaagctgaac gtgtgacatt aaattatgat tggtcatttg aaaatggaat taaagctggt    660
gattattttg acttccaatt aagcgataat gtcgatacaa atggaatatc aacaataaaa    720
aaagtcccac acattatgga tagtcaaaat agcgaacaaa ttattgctta cggggaaatt    780
aatgaaaaca accgtgtccg ttaccgattt atggactatg taaatcaaaa agaaaattta    840
aaaggtaaat tgtcattaaa cttatttatt aaaccagata aagttcaaga tgaaggaaaa    900
atcactgtca cttcacaatt gggcaaggaa atgacaagtc aggaatttga cattaaatat    960
attgatggtg taaaaagccc ttcaggtatc acattaaacg gtcgtcttga tgaattatca   1020
aaagcagatc aatcatttac gcattattct atatttaaac ctaagcataa aacttaact   1080
aatgtaactt taagaggcac agtttcaaat aacgcacagc aaaatgaaaa aaatggtcaa   1140
gttaatgttt acgaatatat tggtcaagga gaattgccac aaagtgctta tgccaatgta   1200
aatgatacga agcagttcaa tgacattact aagagtatga atcaatcaa aaataacagt   1260
aatggctatg aaattacttt tgacatgaac aaagacaatc atccttatat catagtatat   1320
caaggtcact ttaacaataa tgcaaaagac tttgatttct caacaaatgc gacaggttat   1380
caaaatttaa atcaatcgga atatagttat tattggcctt acaattattc attcaattta   1440
acatgggata atggtgttgc tttctactct aataatgcaa gtggggaagg gaacgacaaa   1500
cctgtaccgc cgacttatgg atatagtccg acagtaaata caattcaaga tactcatgcg   1560
gattatcctg taatgacttt ccaacaacct ggaactctag aggagacaga agacagtatg   1620
ccaatcacta cacttaccga atctggtgag atcgtggtg aaaatacttc tccaattatc   1680
gagacaacag aagattcaca gcctgttgag tttgaagaag agacaaatca tggcattcaa   1740
gacgtgacac ttcatgcaga tgctgttgat tttgaggaag aaacaaacca tggtgaacaa   1800
```

```
gacacggtac accactctga tgtcgttgaa tacgacgaag atacgacaac tggcatgtta    1860
acaggtgcca tttctgacca tacaacagaa gaaggcacga tggagtacac aactgatggc    1920
ttattgattg agtttgatga tgaaatgaat cctaatgtga gcggtcagta cgatgacatc    1980
acaacggata cgatagagga atcatctcat attgacacat tcactgaact tgaatctgaa    2040
tttggtcaac atgacggtat agtgacattt gaagaagata ctatcgttga aagccgaaa     2100 acagaaaagg gtaaccgagt accacttgta attgatttat caacaccaaa acataaccat    2160
cagttcaata ttcaacctac cgatccaaat attgatacct ctgctacgta tcgaattggc    2220
aattttgtat ggcgcgatga agatcacaat ggcgtacaaa atgatggtga acatggtctt    2280
gaaggtgttc ttgtcacact taaaacagct gatggtgtcg ttttaaatac aacgacaagt    2340
gatgccaatg gacactacca gttcactaat gttcaaaaag gaaatatat  tgttgaattc    2400 actacacctg aaggttatga agcaacaagc aaacatacta cagcgaatac tgaaaaagac    2460
tctgatgggt taatcgcaaa tatcgatgtt actcaagatg atatgtcaat cgatgctggt    2520
ttcttcccgt tagaaaactg gaatcctcag ccagagccga aaaccctga tgatagagag    2580 aaaccggcac ctgagcaacc tgatgtacct cagccagaac cgaaaaaccc tgatgataga    2640
gagaaaccgg cacctgagca acctgatgta cctcagccag aaccgaaaaa tcctgatgat    2700
agagagaaac cggcacctga gcaacctgat gtacctcaac cagagccgaa aaatcctgat    2760
gataaagaga accggcacc tgagcaacct gatgtacctc aaccagagcc gaaaaatcct     2820
gatgataaag agaaaccggc acctgagcaa cctgatgcac ctcaaccaaa gccgatgctc    2880
ccaggtgaaa aggtgaaacc caaaccaact catcccggtg aagctatgca acaacacct     2940 caggacaaat caacatctca aacagatgaa gcacttccta aaacaggtga atcatcatca    3000
caatcatctg ctttaatctt cggtggttta ctcagtctat taggacttgg tttattacgt    3060
cgatcatcta aacaaaaccg ttcttcaatg aaataa                              3096
```

<210> SEQ ID NO 22
<211> LENGTH: 1031
<212> TYPE: PRT
<213> ORGANISM: Staphylococcus pseudintermedius

<400> SEQUENCE: 22

```
Val Ile Thr Asn Lys Asn Ile Tyr Ser Ile Arg Lys His Lys Leu Gly
  1               5                  10                  15

Val Ala Ser Phe Leu Leu Gly Thr Leu Phe Val Val Gly His Ala Asn
             20                  25                  30

Asn Ala Glu Ala Ser Glu Val Ser Ala Thr Thr Gln Glu His Asn Val
         35                  40                  45

Glu Thr Glu Gln Thr Lys Thr Glu Gly Glu Leu Thr Thr Glu Val Ala
     50                  55                  60

Gln Gln Ala Val Ser Glu Ser Ala Pro Ile Ala Glu Asn Met Gln Lys
 65                  70                  75                  80

Thr Thr Ser Val Ala Ser Glu Asn Ala Lys Glu Val Thr Ala Ser Asp
                 85                  90                  95

Ser Thr Gln Glu Val Thr Lys Thr Glu Ala Lys Asp Thr Ala Thr Met
            100                 105                 110

Lys Asp Ser Glu Ile Ala Gln Pro Val Ser Glu Val Asn Lys Pro Val
        115                 120                 125

Thr Gln Thr Ala Ala Pro Val Ala Glu Pro Ser Thr Ala Asn Lys Gln
    130                 135                 140
```

```
Thr Ser Pro Arg Gln Val Gln Glu Leu Thr Ala Pro Met Asp Thr Lys
145                 150                 155                 160

Val Ile Asn Val Glu Asn Gly Thr Asp Val Thr Ser Lys Val Lys Val
            165                 170                 175

Glu Lys Ser Ser Ile Thr Gly His Gln Asn Lys Asp Lys Thr Tyr His
        180                 185                 190

Gln Ser Asn Thr Val Asn Pro His Lys Ala Glu Arg Val Thr Leu Asn
    195                 200                 205

Tyr Asp Trp Ser Phe Glu Asn Gly Ile Lys Ala Gly Asp Tyr Phe Asp
210                 215                 220

Phe Gln Leu Ser Asp Asn Val Asp Thr Asn Gly Ile Ser Thr Ile Lys
225                 230                 235                 240

Lys Val Pro His Ile Met Asp Ser Gln Asn Ser Glu Gln Ile Ile Ala
            245                 250                 255

Tyr Gly Glu Ile Asn Glu Asn Asn Arg Val Arg Tyr Arg Phe Met Asp
            260                 265                 270

Tyr Val Asn Gln Lys Glu Asn Leu Lys Gly Lys Leu Ser Leu Asn Leu
        275                 280                 285

Phe Ile Lys Pro Asp Lys Val Gln Asp Glu Gly Lys Ile Thr Val Thr
290                 295                 300

Ser Gln Leu Gly Lys Glu Met Thr Ser Gln Glu Phe Asp Ile Lys Tyr
305                 310                 315                 320

Ile Asp Gly Val Lys Ser Pro Ser Gly Ile Thr Leu Asn Gly Arg Leu
            325                 330                 335

Asp Glu Leu Ser Lys Ala Asp Gln Ser Phe Thr His Tyr Ser Ile Phe
        340                 345                 350

Lys Pro Lys His Asn Asn Leu Thr Asn Val Thr Leu Arg Gly Thr Val
        355                 360                 365

Ser Asn Asn Ala Gln Gln Asn Glu Lys Asn Gly Gln Val Asn Val Tyr
    370                 375                 380

Glu Tyr Ile Gly Gln Gly Glu Leu Pro Gln Ser Ala Tyr Ala Asn Val
385                 390                 395                 400

Asn Asp Thr Lys Gln Phe Asn Asp Ile Thr Lys Ser Met Lys Ser Ile
            405                 410                 415

Lys Asn Asn Ser Asn Gly Tyr Glu Ile Thr Phe Asp Met Asn Lys Asp
            420                 425                 430

Asn His Pro Tyr Ile Ile Val Tyr Gln Gly His Phe Asn Asn Asn Ala
        435                 440                 445

Lys Asp Phe Asp Phe Ser Thr Asn Ala Thr Gly Tyr Gln Asn Leu Asn
450                 455                 460

Gln Ser Glu Tyr Ser Tyr Tyr Trp Pro Tyr Asn Tyr Ser Phe Asn Leu
465                 470                 475                 480

Thr Trp Asp Asn Gly Val Ala Phe Tyr Ser Asn Asn Ala Ser Gly Glu
            485                 490                 495

Gly Asn Asp Lys Pro Val Pro Thr Tyr Gly Tyr Ser Pro Thr Val
            500                 505                 510

Asn Thr Ile Gln Asp Thr His Ala Asp Tyr Pro Val Met Thr Phe Gln
            515                 520                 525

Gln Pro Gly Thr Leu Glu Glu Thr Glu Asp Ser Met Pro Ile Thr Thr
            530                 535                 540

Leu Thr Glu Ser Gly Glu Asp Arg Gly Glu Asn Thr Ser Pro Ile Ile
545                 550                 555                 560

Glu Thr Thr Glu Asp Ser Gln Pro Val Glu Phe Glu Glu Glu Thr Asn
```

-continued

```
                565                 570                 575
His Gly Ile Gln Asp Val Thr Leu His Ala Asp Ala Val Asp Phe Glu
            580                 585                 590

Glu Glu Thr Asn His Gly Glu Gln Asp Thr Val His His Ser Asp Val
        595                 600                 605

Val Glu Tyr Asp Glu Asp Thr Thr Gly Met Leu Thr Gly Ala Ile
    610                 615                 620

Ser Asp His Thr Thr Glu Glu Gly Thr Met Glu Tyr Thr Thr Asp Gly
625                 630                 635                 640

Leu Leu Ile Glu Phe Asp Asp Glu Met Asn Pro Asn Val Ser Gly Gln
                645                 650                 655

Tyr Asp Asp Ile Thr Thr Asp Thr Ile Glu Glu Ser Ser His Ile Asp
            660                 665                 670

Thr Phe Thr Glu Leu Glu Ser Glu Phe Gly Gln His Asp Gly Ile Val
        675                 680                 685

Thr Phe Glu Glu Asp Thr Ile Val Glu Lys Pro Lys Thr Glu Lys Gly
    690                 695                 700

Asn Arg Val Pro Leu Val Ile Asp Leu Ser Thr Pro Lys His Asn His
705                 710                 715                 720

Gln Phe Asn Ile Gln Pro Thr Asp Pro Asn Ile Asp Thr Ser Ala Thr
                725                 730                 735

Tyr Arg Ile Gly Asn Phe Val Trp Arg Asp Glu Asp His Asn Gly Val
            740                 745                 750

Gln Asn Asp Gly Glu His Gly Leu Glu Gly Val Leu Val Thr Leu Lys
        755                 760                 765

Thr Ala Asp Gly Val Val Leu Asn Thr Thr Thr Ser Asp Ala Asn Gly
    770                 775                 780

His Tyr Gln Phe Thr Asn Val Gln Lys Gly Lys Tyr Ile Val Glu Phe
785                 790                 795                 800

Thr Thr Pro Glu Gly Tyr Glu Ala Thr Ser Lys His Thr Thr Ala Asn
                805                 810                 815

Thr Glu Lys Asp Ser Asp Gly Leu Ile Ala Asn Ile Asp Val Thr Gln
            820                 825                 830

Asp Asp Met Ser Ile Asp Ala Gly Phe Phe Pro Leu Glu Asn Trp Asn
        835                 840                 845

Pro Gln Pro Glu Pro Lys Asn Pro Asp Asp Arg Glu Lys Pro Ala Pro
    850                 855                 860

Glu Gln Pro Asp Val Pro Gln Pro Glu Pro Lys Asn Pro Asp Asp Arg
865                 870                 875                 880

Glu Lys Pro Ala Pro Glu Gln Pro Asp Val Pro Gln Pro Glu Pro Lys
                885                 890                 895

Asn Pro Asp Asp Arg Glu Lys Pro Ala Pro Glu Gln Pro Asp Val Pro
            900                 905                 910

Gln Pro Glu Pro Lys Asn Pro Asp Asp Lys Glu Lys Pro Ala Pro Glu
        915                 920                 925

Gln Pro Asp Val Pro Gln Pro Glu Pro Lys Asn Pro Asp Asp Lys Glu
    930                 935                 940

Lys Pro Ala Pro Glu Gln Pro Asp Ala Pro Gln Pro Lys Pro Met Leu
945                 950                 955                 960

Pro Gly Glu Lys Val Lys Pro Lys Pro Thr His Pro Gly Glu Ala Met
                965                 970                 975

Gln Thr Thr Pro Gln Asp Lys Ser Thr Ser Gln Thr Asp Glu Ala Leu
            980                 985                 990
```

```
Pro Lys Thr Gly Glu Ser Ser  Ser  Gln Ser Ser Ala Leu  Ile Phe Gly
        995                 1000                1005

Gly Leu  Leu Ser Leu Leu Gly  Leu Gly Leu Leu Arg  Arg Ser Ser
   1010             1015                1020

Lys Gln  Asn Arg Ser Ser Met  Lys
   1025             1030

<210> SEQ ID NO 23
<211> LENGTH: 1704
<212> TYPE: DNA
<213> ORGANISM: Staphylococcus pseudintermedius

<400> SEQUENCE: 23
atggcatttg atggtatgtt tacaagaaaa atggtagaag atttacaatt tctcgtttct       60
gggcgtattc ataaaatcaa tcaaccggaa acgatacaa tcatcatggt tataagacag      120
caacgccaaa atcatcaatt gttgttgtcg attcacccga attttgcacg gattcacctc      180
actacaaaaa aatatgataa tccatttgaa ccgccgatgt tgcgcgcgt ctttcgtaaa       240 catttagaag gtggacgtat ccttgccatt cgccaaatcg gaaatgaccg tcgcatcgaa      300
atggacgtgg aaagtaaaga tgaaattggt gacacgattc atcgtacagt gattttagaa      360
attatgggca acatagtaa tctcattctc gttaatgaag aacgtaaaat tttagaaggt       420
tttaaacacc ttcaccaaa tacgaatcaa tttagaaccg tgatgccagg ttttcaatat      480
gaagtgccgc aacacaaca taaacagaac ccttatgcat atactggtgc gcaagtgctc      540
caacatattg atttcaatgc gggcaaaatt gatcgccaac tgcttcaaac gtttgaaggt      600
ttttcaccgt taatcacaaa agaaatcaca tcaagacgcc atttatgac cacacaaact      660 ttacctgaag cttttgacga agtgatggcc gaaacgaaag cgacacccca accggtattt      720
cataaaaata cgaaacagg taagaagac ttttattta tgaagttaca tcagttttac        780
gatgattgcg tcacatatga ttcactccat gaactgctcg accgttttta tgatgcacgc      840
ggtgaacgtg aacgcgtcaa acaacgtgca acgatttag tcaaactcgt ccaacaatta       900
cttcaaaaat atcaaaataa attaagtaag ctcgtcgatg aacaagcggg gactgaagaa      960
aaagaaaatc aacaattgta cggcgagtta atcacagcga atatttatca actcaaacct     1020
ggagatcgcc agttagaaac agtaaattat tatacaggag aaaacgtgac tattccgtta     1080
aatccacaaa agtcacctgc tgaaaatgcg caatactatt acaagcaata caaccgaatg     1140
aaaacacgtg agcgcgaatt gacccatcaa attactttaa cggaagaaaa tatcgcttat     1200
tttgaaaata tcgagcaaca gttgtcacac attcaagttc atgaaattga cgatattcgt     1260
gaagaactag cagaacaagg ctttatcaaa caaagaaac agcagaaaaa gaaaagcaa      1320 caaaaaatcc agttacaatc ctacgttttcg actgatggcg atacgatttt agtcggtaaa    1380
aataataagc aaaatgatta tttaacgaat aaacgtgcgc aaaaatcgca tttatggttc     1440
catacaaaag atatcccagg aagccatgtc gtgattttaa atgatgcgcc aagtgacaaa     1500
acgattgaag aagcggcgat gattgcagcg tactttcaa aggcggggca atcgggacaa      1560
attccagtgg attatacaac aattcgcaat gtgcataagc cgagtggcag taaacctgga    1620
tttgtaacgt acgataacca gaagacgctt tacgcaacgc cggattatga catgattcgt    1680
cgattgaaag ctgaagaagc gtaa                                            1704

<210> SEQ ID NO 24
<211> LENGTH: 567
```

<212> TYPE: PRT
<213> ORGANISM: Staphylococcus pseudintermedius

<400> SEQUENCE: 24

```
Met Ala Phe Asp Gly Met Phe Thr Arg Lys Met Val Glu Asp Leu Gln
1               5                   10                  15

Phe Leu Val Ser Gly Arg Ile His Lys Ile Asn Gln Pro Glu Asn Asp
            20                  25                  30

Thr Ile Ile Met Val Ile Arg Gln Gln Arg Gln Asn His Gln Leu Leu
        35                  40                  45

Leu Ser Ile His Pro Asn Phe Ala Arg Ile His Leu Thr Thr Lys Lys
    50                  55                  60

Tyr Asp Asn Pro Phe Glu Pro Pro Met Phe Ala Arg Val Phe Arg Lys
65                  70                  75                  80

His Leu Glu Gly Gly Arg Ile Leu Ala Ile Arg Gln Ile Gly Asn Asp
                85                  90                  95

Arg Arg Ile Glu Met Asp Val Glu Ser Lys Asp Glu Ile Gly Asp Thr
            100                 105                 110

Ile His Arg Thr Val Ile Leu Glu Ile Met Gly Lys His Ser Asn Leu
        115                 120                 125

Ile Leu Val Asn Glu Glu Arg Lys Ile Leu Glu Gly Phe Lys His Leu
    130                 135                 140

Thr Pro Asn Thr Asn Gln Phe Arg Thr Val Met Pro Gly Phe Gln Tyr
145                 150                 155                 160

Glu Val Pro Pro Thr Gln His Lys Gln Asn Pro Tyr Ala Tyr Thr Gly
                165                 170                 175

Ala Gln Val Leu Gln His Ile Asp Phe Asn Ala Gly Lys Ile Asp Arg
            180                 185                 190

Gln Leu Leu Gln Thr Phe Glu Gly Phe Ser Pro Leu Ile Thr Lys Glu
        195                 200                 205

Ile Thr Ser Arg Arg His Phe Met Thr Thr Gln Thr Leu Pro Glu Ala
    210                 215                 220

Phe Asp Glu Val Met Ala Glu Thr Lys Ala Thr Pro Gln Pro Val Phe
225                 230                 235                 240

His Lys Asn Asn Glu Thr Gly Lys Glu Asp Phe Tyr Phe Met Lys Leu
                245                 250                 255

His Gln Phe Tyr Asp Asp Cys Val Thr Tyr Asp Ser Leu His Glu Leu
            260                 265                 270

Leu Asp Arg Phe Tyr Asp Ala Arg Gly Glu Arg Glu Arg Val Lys Gln
        275                 280                 285

Arg Ala Asn Asp Leu Val Lys Leu Val Gln Gln Leu Leu Gln Lys Tyr
    290                 295                 300

Gln Asn Lys Leu Ser Lys Leu Val Asp Glu Gln Ala Gly Thr Glu Glu
305                 310                 315                 320

Lys Glu Asn Gln Gln Leu Tyr Gly Glu Leu Ile Thr Ala Asn Ile Tyr
                325                 330                 335

Gln Leu Lys Pro Gly Asp Arg Gln Leu Glu Thr Val Asn Tyr Tyr Thr
            340                 345                 350

Gly Glu Asn Val Thr Ile Pro Leu Asn Pro Gln Lys Ser Pro Ala Glu
        355                 360                 365

Asn Ala Gln Tyr Tyr Lys Gln Tyr Asn Arg Met Lys Thr Arg Glu
    370                 375                 380

Arg Glu Leu Thr His Gln Ile Thr Leu Thr Glu Glu Asn Ile Ala Tyr
385                 390                 395                 400
```

```
Phe Glu Asn Ile Glu Gln Gln Leu Ser His Ile Gln Val His Glu Ile
                405                 410                 415
Asp Asp Ile Arg Glu Glu Leu Ala Glu Gln Gly Phe Ile Lys Gln Lys
            420                 425                 430
Lys Gln Gln Lys Lys Lys Gln Gln Lys Ile Gln Leu Gln Ser Tyr
        435                 440                 445
Val Ser Thr Asp Gly Asp Thr Ile Leu Val Gly Lys Asn Asn Lys Gln
    450                 455                 460
Asn Asp Tyr Leu Thr Asn Lys Arg Ala Gln Lys Ser His Leu Trp Phe
465                 470                 475                 480
His Thr Lys Asp Ile Pro Gly Ser His Val Val Ile Leu Asn Asp Ala
                485                 490                 495
Pro Ser Asp Lys Thr Ile Glu Glu Ala Ala Met Ile Ala Ala Tyr Phe
            500                 505                 510
Ser Lys Ala Gly Gln Ser Gly Gln Ile Pro Val Asp Tyr Thr Thr Ile
        515                 520                 525
Arg Asn Val His Lys Pro Ser Gly Ser Lys Pro Gly Phe Val Thr Tyr
    530                 535                 540
Asp Asn Gln Lys Thr Leu Tyr Ala Thr Pro Asp Tyr Asp Met Ile Arg
545                 550                 555                 560
Arg Leu Lys Ala Glu Glu Ala
                565

<210> SEQ ID NO 25
<211> LENGTH: 4167
<212> TYPE: DNA
<213> ORGANISM: Staphylococcus pseudintermedius

<400> SEQUENCE: 25
atggtcaaaa aatttggtta taaaacacct acaatcgttg cacttacttt ggctggaact    60
gcattttctg cacaccaagc caatgccgct gaacaagttg cacctgaaaa aacacctacg   120
aatgtacttg atgatcaata cgcattaaaa caagctgatg atgcgaaaca aacgacacaa   180 ggaacaaac  ttgcaggttc aaaagaatac aaggatcctt cacaaattga tacgactcaa   240
gtcgatacag cagcacaaac tgaaacgccc gtagaaggag gcaacaagaa cgcacaacaa   300
cctactacaa ctgatgaagc gacatcaaca gatcatactg tatcaaaagg tacaaacgaa   360
agtgcatcac ctgcaacagc ttctatagat gaaggaacat taaacgcaca agtcaattca   420
gatgaaacgg ctactaaccg tacacaagac gtcactgaaa atgtgacaaa atatccttat   480
cattcaagtg aaatcgatac acatgaagac gcaactgtgt caccagatac atatcatgca   540
ctggacacgc atgcgcaaca accttcagca atggatgtaa gcgattcaac atcagcacaa   600
actgaagcga cgcaagtaaa tacgtcaaca aatgtaaatg acaaagaggc cgtttcgaca   660
acagaagatg cacctactac acaacttcaa gcagctgtac aatctgaagc caacaaagaa   720
gcgaaggcaa ctactgaaac agctcaaaat aaaacacctc aagttgaaaa gaaagcaaca   780
gcaactcaaa atacagcaca gttagcaacg gggcatcagg atattactga caaagtctca   840
aaacgcgtag cagtgacaaa tgaaacgaaa gcggatgcca acagcgaa acacaagca     900 cctacttcag tgacacatca agctgataca caagcaaaaa cgataacaga caagaaggca   960
acaacttaca gtgcacaaac cgcaactgac caagacataa atgcgaatcc ggacggtcca  1020
acacctccac gcgttggcgg taagggggt ccccctgctt cactttcact ccaatcgact  1080
ggtcaaacag cattccgttc agctgtcgct agtaaaccga gtgcatatca acctaaagtg  1140
```

```
aaatcgtcta ttaatgacta tattcgtaag caaaactaca aagtgcctgt atatgaagaa      1200
gattattcaa gttacttccc taaatacggt tatcgtaatg gtgtcggtaa acctgagggc      1260
atcatcgtgc atgatacagc aaatgacaac tctacaattg atggcgaaat cagttacatg      1320
aaaagaaatt atcaaaatgc tttcgtacat ggctttatta atggtcaacg tattgttgaa      1380
acgcaaccta cagattattt agcatggggt gcaggtgcga ttgcgaatga acgctttatt      1440
catatcgaac tcgttcatgt tcacagtaaa gaagatttcg cacgtcaaat gaacaatatg      1500
gcagattatg cggcgacgaa cttacaatat tatggccttt ctccagatag tgcggaatat      1560
gatggtcgtg ggacagtttg gacacatgat gctgtttcta gattttttagg tggtacagac      1620 cataccgatc cgcacggcta tttaaaacaa catggttatt cctttgatgc gttgtatgat      1680
ttaatcaatg aaaatatca agtgaaaatg ggtatgcct cacctgctaa ctcgtcttca      1740
aaaccatcaa caaatactgg cttaacagtt aaaaacacaa caggtttcgg ccgtattaac      1800
acaacaaata gcggtttata tacgaccgtt tatgatcaaa aagtaaagc gacgaatcaa      1860 acgaatcaaa cgttaaaagt tacaaaagaa gcgacgttaa atggcaacaa attctattta      1920
atgagtgatg caaaatctaa tcaaacactc ggttgggtca aatcaaacga cgcaacatat      1980
caagctgccc aagctgagaa aaagtaacg aaaacgtata ctgtcaaacc aggaacaaca      2040
gtatatcaag tgccttgggg tgcctcatct caaacagtag gcaaagctcc aggtacgtca      2100
aaccaatcat tcaaatcaac gaaagaacaa actgttgcga aaacgaaatg gctttatggg      2160
acagttggca aagtgacagg ctggattaat gcaagtagtg ttgtagcaaa tgatcaaaaa      2220
ccatcgacga ataccgcact aaaagtaaca actgacactg gtctcggtcg cattaaagac      2280
aaaaatagtg gttatacgc aacggtatat gataaactg gtaaaagcac ttcagccact      2340
aaccaaacat taaaagtaac gaaaaaagca agtgtcaatg gccaatcatt ctatttagta      2400
tcagattatg ctaaaggtac aaatgttggt tgggtgaaac agtcagatgt cgaatatcaa      2460
acaagtaaag ccccttctaa agtgaatcaa aattatacga ttaaatcggg tgcgaaattg      2520
tatcaagtgc cttggggtac aagtaaacaa gttgccggta cagtgacagg tgctgcgaca      2580
caaacattta aggcaacaca atctcaaact gtaggtaaag caacatactt gtatgggaca      2640
gttggcaaat tatctggttg gattaattca acagcattag cagctcaaaa aacaacaacg      2700
aatgttacta aaacaatttc tcaaatcggt caactgaaca cgaaaaatag cggtgtcaaa      2760
gcttctattt atgacaaaac agcaaaagat gcatccaaat gggcaggtca aacttataaa      2820
attactaaaa cagcttctgc caataacgaa gactatgtat tactgcaaaa tagtacagga      2880
ggcacgccac tcggttggtt caatgttaaa gacgtcacaa cacgcaactt aggtgctgaa      2940
acagctgtta aagggcggta cactgttaat agtaaaaacat ctggactcta cgctatgcct      3000
tggggtacaa cgaagcaacg tgtcgataca ttaaaaaatg ccacaagtcg tttatttaca      3060
gcttcaaaat cagttaaagt cggtaatgat acattcttat tcggtacagt gaatcaaaaa      3120
ttgggctgga ttaatcaaaa agacttaaca gctgtagcag caaaagttgc aaacatgaaa      3180
actgcatcga atagcgcagt caaaggtgcc gcaatcacaa cttttgaaaaa agtagaagat      3240 tatgtgatta cgaataaaaa tggttattat tacactaaag ttggagattc aaaaacagct      3300
ggtgctttaa aaggtttta tcaacaaatt tttaaagtcg aaaaaacatc tttactgaac      3360
ggcattactt ggtactatgg cgcattccaa aacgggacga aaggatggat taaagcagct      3420
gacatacgtt catcattcat tcaacatact gcggtcagta gcacattgaa agcagcactc      3480
```

-continued

```
gataaacaaa tggcgctgac ttacccgcct caagttcaac gtgtagccgg taaatgggtc    3540
aatgcgaatc gtgcagaaac tgaaaaagca atgaataccg cagcaattga aaaagatccg    3600
actctcattt accaattttt aaaacttgat aaataccaag gtcttggcgt agaagaactt    3660
aataaattgt taagaggcaa aggcatttta gaaggtcaag gtgccgcatt taaagaagcc    3720
gcacaaaaac acaatattaa tgaggtttac ttaatgtctc acgcattttt agaaacaggt    3780
aacgggactt ctcaattagc caatggcggt cacgtagata aaataataa agtcgtaaca     3840 aacggtaaac cgaagtatta caacatgttc ggtatcgggg caattgatac agacgcttta    3900
cgcaatggct ttaaaactgc tgaaaaatat ggttggaata cggtcagcaa agcgattatc    3960
ggtggcgcaa aattcatccg tgatcagtac atcggttcag gacaaaacac attgtatcgt    4020
atgcgttgga atccagaaca ccctgccaca catcagtatg cgactgatat taattgggca    4080
aatgtaaacg cacaacgcat gaaatatttc tatgatcaaa ttggtgaaac aggtaaatat    4140
ttcgacgtcg atgtatataa gaagtag                                       4167
```

<210> SEQ ID NO 26
<211> LENGTH: 1388
<212> TYPE: PRT
<213> ORGANISM: Staphylococcus pseudintermedius

<400> SEQUENCE: 26

```
Met Val Lys Lys Phe Gly Tyr Lys Thr Pro Thr Ile Val Ala Leu Thr
1               5                   10                  15

Leu Ala Gly Thr Ala Phe Ser Ala His Gln Ala Asn Ala Ala Glu Gln
            20                  25                  30

Val Ala Pro Glu Lys Thr Pro Thr Asn Val Leu Asp Asp Gln Tyr Ala
        35                  40                  45

Leu Lys Gln Ala Asp Asp Ala Lys Gln Thr Thr Gln Gly Thr Thr Leu
    50                  55                  60

Ala Gly Ser Lys Glu Tyr Lys Asp Pro Ser Gln Ile Asp Thr Thr Gln
65                  70                  75                  80

Val Asp Thr Ala Ala Gln Thr Glu Thr Pro Val Glu Gly Gly Gln Gln
                85                  90                  95

Asp Ala Gln Gln Pro Thr Thr Thr Asp Glu Ala Thr Ser Thr Asp His
            100                 105                 110

Thr Val Ser Lys Gly Thr Asn Glu Ser Ala Ser Pro Ala Thr Ala Ser
        115                 120                 125

Ile Asp Glu Gly Thr Leu Asn Ala Gln Val Asn Ser Asp Glu Thr Ala
    130                 135                 140

Thr Asn Arg Thr Gln Asp Val Thr Glu Asn Val Thr Lys Tyr Pro Tyr
145                 150                 155                 160

His Ser Ser Glu Ile Asp Thr His Glu Asp Ala Thr Val Ser Pro Asp
                165                 170                 175

Thr Tyr His Ala Leu Asp Thr His Ala Gln Gln Pro Ser Ala Met Asp
            180                 185                 190

Val Ser Asp Ser Thr Ser Ala Gln Thr Glu Ala Thr Gln Val Asn Thr
        195                 200                 205

Ser Thr Asn Val Asn Asp Lys Glu Ala Val Ser Thr Glu Asp Ala
    210                 215                 220

Pro Thr Gln Leu Gln Ala Ala Val Gln Ser Glu Ala Asn Lys Glu
225                 230                 235                 240

Ala Lys Ala Thr Thr Glu Thr Ala Gln Asn Lys Thr Pro Gln Val Glu
                245                 250                 255
```

```
Lys Lys Ala Thr Ala Thr Gln Asn Thr Ala Gln Leu Ala Thr Gly His
            260                 265                 270

Gln Asp Ile Thr Asp Lys Val Ser Lys Arg Val Ala Val Thr Asn Glu
            275                 280                 285

Thr Lys Ala Asp Ala Thr Thr Ala Lys Thr Gln Ala Pro Thr Ser Val
            290                 295                 300

Thr His Gln Ala Asp Thr Gln Ala Lys Thr Ile Thr Asp Lys Lys Ala
305                 310                 315                 320

Thr Thr Tyr Ser Ala Gln Thr Ala Thr Asp Gln Asp Ile Asn Ala Asn
                325                 330                 335

Pro Asp Gly Pro Thr Pro Pro Arg Val Gly Gly Lys Gly Gly Pro Pro
            340                 345                 350

Ala Ser Leu Ser Leu Gln Ser Thr Gly Gln Thr Ala Phe Arg Ser Ala
            355                 360                 365

Val Ala Ser Lys Pro Ser Ala Tyr Gln Pro Lys Val Lys Ser Ser Ile
            370                 375                 380

Asn Asp Tyr Ile Arg Lys Gln Asn Tyr Lys Val Pro Val Tyr Glu Glu
385                 390                 395                 400

Asp Tyr Ser Ser Tyr Phe Pro Lys Tyr Gly Tyr Arg Asn Gly Val Gly
            405                 410                 415

Lys Pro Glu Gly Ile Ile Val His Asp Thr Ala Asn Asp Asn Ser Thr
            420                 425                 430

Ile Asp Gly Glu Ile Ser Tyr Met Lys Arg Asn Tyr Gln Asn Ala Phe
            435                 440                 445

Val His Gly Phe Ile Asn Gly Gln Arg Ile Val Glu Thr Gln Pro Thr
            450                 455                 460

Asp Tyr Leu Ala Trp Gly Ala Gly Ala Ile Ala Asn Glu Arg Phe Ile
465                 470                 475                 480

His Ile Glu Leu Val His Val His Ser Lys Glu Asp Phe Ala Arg Gln
            485                 490                 495

Met Asn Asn Met Ala Asp Tyr Ala Ala Thr Asn Leu Gln Tyr Tyr Gly
            500                 505                 510

Leu Ser Pro Asp Ser Ala Glu Tyr Asp Gly Arg Gly Thr Val Trp Thr
            515                 520                 525

His Asp Ala Val Ser Arg Phe Leu Gly Gly Thr Asp His Thr Asp Pro
            530                 535                 540

His Gly Tyr Leu Lys Gln His Gly Tyr Ser Phe Asp Ala Leu Tyr Asp
545                 550                 555                 560

Leu Ile Asn Glu Lys Tyr Gln Val Lys Met Gly Tyr Ala Ser Pro Ala
            565                 570                 575

Asn Ser Ser Lys Pro Ser Thr Asn Thr Gly Leu Thr Val Lys Asn
            580                 585                 590

Thr Thr Gly Phe Gly Arg Ile Asn Thr Thr Asn Ser Gly Leu Tyr Thr
            595                 600                 605

Thr Val Tyr Asp Gln Lys Gly Lys Ala Thr Asn Gln Thr Asn Gln Thr
            610                 615                 620

Leu Lys Val Thr Lys Glu Ala Thr Leu Asn Gly Asn Lys Phe Tyr Leu
625                 630                 635                 640

Met Ser Asp Ala Lys Ser Asn Gln Thr Leu Gly Trp Val Lys Ser Asn
            645                 650                 655

Asp Ala Thr Tyr Gln Ala Ala Gln Ala Glu Lys Lys Val Thr Lys Thr
            660                 665                 670
```

Tyr Thr Val Lys Pro Gly Thr Val Tyr Gln Val Pro Trp Gly Ala
            675                 680                 685

Ser Ser Gln Thr Val Gly Lys Ala Pro Gly Thr Ser Asn Gln Ser Phe
690                 695                 700

Lys Ser Thr Lys Glu Gln Thr Val Ala Lys Thr Lys Trp Leu Tyr Gly
705                 710                 715                 720

Thr Val Gly Lys Val Thr Gly Trp Ile Asn Ala Ser Ser Val Val Ala
            725                 730                 735

Asn Asp Gln Lys Pro Ser Thr Asn Thr Ala Leu Lys Val Thr Thr Asp
            740                 745                 750

Thr Gly Leu Gly Arg Ile Lys Asp Lys Asn Ser Gly Leu Tyr Ala Thr
            755                 760                 765

Val Tyr Asp Lys Thr Gly Lys Ser Thr Ser Ala Thr Asn Gln Thr Leu
            770                 775                 780

Lys Val Thr Lys Lys Ala Ser Val Asn Gly Gln Ser Phe Tyr Leu Val
785                 790                 795                 800

Ser Asp Tyr Ala Lys Gly Thr Asn Val Gly Trp Val Lys Gln Ser Asp
            805                 810                 815

Val Glu Tyr Gln Thr Ser Lys Ala Pro Ser Lys Val Asn Gln Asn Tyr
            820                 825                 830

Thr Ile Lys Ser Gly Ala Lys Leu Tyr Gln Val Pro Trp Gly Thr Ser
            835                 840                 845

Lys Gln Val Ala Gly Thr Val Thr Gly Ala Ala Thr Gln Thr Phe Lys
            850                 855                 860

Ala Thr Gln Ser Gln Thr Val Gly Lys Ala Thr Tyr Leu Tyr Gly Thr
865                 870                 875                 880

Val Gly Lys Leu Ser Gly Trp Ile Asn Ser Thr Ala Leu Ala Ala Gln
            885                 890                 895

Lys Thr Thr Thr Asn Val Thr Lys Thr Ile Ser Gln Ile Gly Gln Leu
            900                 905                 910

Asn Thr Lys Asn Ser Gly Val Lys Ala Ser Ile Tyr Asp Lys Thr Ala
            915                 920                 925

Lys Asp Ala Ser Lys Trp Ala Gly Gln Thr Tyr Lys Ile Thr Lys Thr
            930                 935                 940

Ala Ser Ala Asn Asn Glu Asp Tyr Val Leu Leu Gln Asn Ser Thr Gly
945                 950                 955                 960

Gly Thr Pro Leu Gly Trp Phe Asn Val Lys Asp Val Thr Thr Arg Asn
            965                 970                 975

Leu Gly Ala Glu Thr Ala Val Lys Gly Arg Tyr Thr Val Asn Ser Lys
            980                 985                 990

Thr Ser Gly Leu Tyr Ala Met Pro Trp Gly Thr Thr Lys Gln Arg Val
            995                 1000                1005

Asp Thr Leu Lys Asn Ala Thr Ser Arg Leu Phe Thr Ala Ser Lys
            1010                1015                1020

Ser Val Lys Val Gly Asn Asp Thr Phe Leu Phe Gly Thr Val Asn
            1025                1030                1035

Gln Lys Leu Gly Trp Ile Asn Gln Lys Asp Leu Thr Ala Val Ala
            1040                1045                1050

Ala Lys Val Ala Asn Met Lys Thr Ala Ser Asn Ser Ala Val Lys
            1055                1060                1065

Gly Ala Ala Ile Thr Thr Leu Lys Lys Val Glu Asp Tyr Val Ile
            1070                1075                1080

Thr Asn Lys Asn Gly Tyr Tyr Tyr Thr Lys Val Gly Asp Ser Lys

```
                1085                1090                1095
Thr Ala Gly Ala Leu Lys Gly Phe Tyr Gln Gln Ile Phe Lys Val
        1100                1105                1110
Glu Lys Thr Ser Leu Leu Asn Gly Ile Thr Trp Tyr Tyr Gly Ala
        1115                1120                1125
Phe Gln Asn Gly Thr Lys Gly Trp Ile Lys Ala Ala Asp Ile Arg
        1130                1135                1140
Ser Ser Phe Ile Gln His Thr Ala Val Ser Ser Thr Leu Lys Ala
        1145                1150                1155
Ala Leu Asp Lys Gln Met Ala Leu Thr Tyr Pro Pro Gln Val Gln
        1160                1165                1170
Arg Val Ala Gly Lys Trp Val Asn Ala Asn Arg Ala Glu Thr Glu
        1175                1180                1185
Lys Ala Met Asn Thr Ala Ala Ile Glu Lys Asp Pro Thr Leu Ile
        1190                1195                1200
Tyr Gln Phe Leu Lys Leu Asp Lys Tyr Gln Gly Leu Gly Val Glu
        1205                1210                1215
Glu Leu Asn Lys Leu Leu Arg Gly Lys Gly Ile Leu Glu Gly Gln
        1220                1225                1230
Gly Ala Ala Phe Lys Glu Ala Ala Gln Lys His Asn Ile Asn Glu
        1235                1240                1245
Val Tyr Leu Met Ser His Ala Phe Leu Glu Thr Gly Asn Gly Thr
        1250                1255                1260
Ser Gln Leu Ala Asn Gly Gly His Val Asp Lys Asn Asn Lys Val
        1265                1270                1275
Val Thr Asn Gly Lys Pro Lys Tyr Tyr Asn Met Phe Gly Ile Gly
        1280                1285                1290
Ala Ile Asp Thr Asp Ala Leu Arg Asn Gly Phe Lys Thr Ala Glu
        1295                1300                1305
Lys Tyr Gly Trp Asn Thr Val Ser Lys Ala Ile Ile Gly Gly Ala
        1310                1315                1320
Lys Phe Ile Arg Asp Gln Tyr Ile Gly Ser Gly Gln Asn Thr Leu
        1325                1330                1335
Tyr Arg Met Arg Trp Asn Pro Glu His Pro Ala Thr His Gln Tyr
        1340                1345                1350
Ala Thr Asp Ile Asn Trp Ala Asn Val Asn Ala Gln Arg Met Lys
        1355                1360                1365
Tyr Phe Tyr Asp Gln Ile Gly Glu Thr Gly Lys Tyr Phe Asp Val
        1370                1375                1380
Asp Val Tyr Lys Lys
        1385

<210> SEQ ID NO 27
<211> LENGTH: 3435
<212> TYPE: DNA
<213> ORGANISM: Staphylococcus pseudintermedius

<400> SEQUENCE: 27
gtgtcgacag aaaacaaga tgatacacaa gcaaaagcga atgcactttc tacagatgat      60
tcaacaccta caacagaaca atcaaaaagt gataccgaac caacgcaaaa tcaagaagtg     120
aatgaaaaag aagcaacaca agttgagcaa actccagata atgcatcatc agaatttaaa     180
gacagtgcag cacaagatga acaacatcg aagacgctg acattgctca acaaaagaa       240 gcaaaaaatg aagcattgca aagtgactca tcagcaaacc tatcaaatca agaagcagaa     300
```

```
aaagaaaaca caactaacag tgaatctcaa gtaaatgaac aacctaaagc agatacaact    360
tctgattcac aagtttcaaa tacacctcaa caagatccta catcgacagt accttcacca    420
gaaacatcag aagacaatcg accttcaaca gaattaaaaa atagtgaaac aactgcttct    480
caaacaactt taaacgaaca acctactgaa tcaacatcca atcaaactga aacgacaaaa    540
gcaccaacaa atacaacagt cgcaaacaaa aaagcacctg cacaattaaa agacattaaa    600
ggtacaactc aacttcgcgc agtcagtgca agtcaaccta ctgctgttgc agctggtggg    660
acaaacgtaa atgacaaagt aacagcatca aatatgaaaa taactgaatc ttatatcgag    720
ccaaacaact caggaaactt ttatttaaaa agtaacttta acgtaaacgg gactgttaaa    780
gaaggtgact actttactgt aaaaatgcct gacactgtca atacttttgg tgacacgcgc    840
cattcacctg actttagaga aaaaattaca aatcaaaaag gtgaagttgt ggctttaggt    900
gaatatgatg ttgccaacca tactatgaca tacacgttca ctaatgtcgt taataattta    960
gaaaatgtgt ccggttcgtt taacttgact caatttatgg atcgtaaagt ggcaacagat   1020
tctcaaacat atccattaaa atacgacatt gcaggcgaat ctttagatac acaaattaaa   1080
gtgaattacg gtcaatatta cagtgaaggt gattctaact taaatcaat gatcacttca   1140
gaagatccta aaactgggga atatgatcaa tacatttatg tcaacccatt acaaaaaacg   1200
gcaaacggta cagttgtaag agttcaaggg ttccaagttg atccaactaa gagtaatggg   1260
caagtgaaac cagatacaac gcagatcaag attttaaaag ttgctgatgg tcaaccactt   1320
aatagtagtt tcggtgtgaa tgacagtgaa tatgaagatg tcacaaaaca atttaatatt   1380
gtttatcgtg ataataattt ggcagatatt tactttggaa acttaaatgg gcaacgctat   1440
atcgttaaag tgacgagcaa agaaaatttg gattctaaag aggatttaaa cttgcgtgct   1500
attatggcca ctcaaaaccg atatggtcaa tataactata ttacttggga taacgatatt   1560
gtgaaaagct cttctggtgg tacagccgac ggaaatgaag catcatatca attaggcgac   1620
aaagtttgga atgatgtgaa taaaaatggt atccaagatc aaggtgaaac tggtattgct   1680
gatgtaaagg ttacttaaa agatcttgat ggcaacattt tggatacaac ttatacaaac   1740
acgaatggta aatatatctt tgataattta aaaaatggta attatcaagt gggttttgaa   1800
acaccggaag gctatgctgc aagtccatcc aaccaaggta atgacgccct tgactctgat   1860
ggtcctacaa atgtacaagc tgtcattagt gatgggaaca acttaactat cgaccaaggt   1920
tttaccaaa ctgaaacacc aacacacaac gtcggcgaca agtttggga agacttaaat   1980
aaagatggca tccaagacca aaatgaacca ggtatcgcta acgttaaggt cacttaaaaa   2040
gacgcggatg gtaacgttgt ggatacacgt acgactgatg ataaagggaa ttacttattc   2100
gaaaagtta agaaggcga atatacaatt gaatttgaaa cgcctgaagg ttatacaccg   2160
acacaaacag gccaaggcag agtcagcact gactctaatg ggacatcttc ccttatttta   2220
gtcgaaggta acgatgactt aacaatcgat agcggtttct acaaagaacc tgttacacac   2280
aaagttggcg acaaagtttg ggatgactta aataaagacg gtatccaaga tgacaatgaa   2340
ccaggcatct ctgacgttaa agtcacttta aaagatgcgg atggtaacgt cgtagataca   2400
cgtacaactg atgctaacgg taactattta tttgaaaacg tgaaagaagg cgactatacg   2460
attgaatttg aaacgcctga aggttacaca ccgactgtta caggtcaagg tacagctgat   2520
aatgactcta acggtacatc tacaaaagtt acagttaaag atggcgatga cttaacaatt   2580
gacagtggtt tcactcaagt tacacctgag ccaccgacac ataatgttgg cgacaaagtt   2640
```

-continued

```
tgggatgact taaataaaga cggtatccaa gatgacaatg aaccaggcat ctctgacgtt      2700
aaagtcactt taaagatgc ggatggtaac gtcgtagata cacgtacaac tgatgctaac       2760
ggtaactatt tatttgaaaa cgtgaaagaa ggcgactata cgattgaatt tgaaacgcct      2820
gaaggttaca caccgactgt tacaggtcaa ggtacagctg ataatgactc taacggtaca      2880
tctacaaaag ttacagttaa agatggcgat gacttaacaa ttgacagtgg tttcactcaa      2940
gttacacctg agccaccgac tgaacctgaa aaccctagtc cagagcaacc ttctgaaccg      3000
ggtcaacctg aaaatcctag tccagagcaa ccttctgaac caggtcaacc tgaaaatcct      3060
agtccagagc aaccttctga accaggtcaa cctgaaaatc ctagtccaga caaccttct       3120 gaaccgggtc aacctgaaaa tcctagtcca gaacagccct ctgagccagg acaacctaaa      3180
aatcctagtc cagaacagcc aaataatcca agtgtgccag gtgttcaaaa tcctgaaaaa      3240
ccaagcttaa ctccagtcac acaaccggtt cattcaaacg gcaataaagc aaaaccatct      3300
caacaacaaa aagctttacc tgaaacaggt gaaactgaat cacatcaagg tacattattc      3360
ggtggtattt tagctgcttt aggcgcatta ctctttgcac gtaaaaaacg ccacgataaa      3420
aaacaatcac actaa                                                       3435
```

<210> SEQ ID NO 28
<211> LENGTH: 1144
<212> TYPE: PRT
<213> ORGANISM: Staphylococcus pseudintermedius

<400> SEQUENCE: 28

```
Val Ser Thr Glu Lys Gln Asp Asp Thr Gln Ala Lys Ala Asn Ala Leu
1               5                   10                  15

Ser Thr Asp Asp Ser Thr Pro Thr Thr Glu Gln Ser Lys Ser Asp Thr
            20                  25                  30

Glu Pro Thr Gln Asn Gln Glu Val Asn Glu Lys Glu Ala Thr Gln Val
        35                  40                  45

Glu Gln Thr Pro Asp Asn Ala Ser Ser Glu Phe Lys Asp Ser Ala Ala
    50                  55                  60

Gln Asp Glu Thr Thr Ser Lys Asp Ala Asp Ile Ala Gln Thr Lys Glu
65                  70                  75                  80

Ala Lys Asn Glu Ala Leu Gln Ser Asp Ser Ser Ala Asn Leu Ser Asn
                85                  90                  95

Gln Glu Ala Glu Lys Glu Asn Thr Thr Asn Ser Glu Ser Gln Val Asn
            100                 105                 110

Glu Gln Pro Lys Ala Asp Thr Thr Ser Asp Ser Gln Val Ser Asn Thr
        115                 120                 125

Pro Gln Gln Asp Pro Thr Ser Thr Val Pro Ser Pro Glu Thr Ser Glu
    130                 135                 140

Asp Asn Arg Pro Ser Thr Glu Leu Lys Asn Ser Glu Thr Thr Ala Ser
145                 150                 155                 160

Gln Thr Thr Leu Asn Glu Gln Pro Thr Glu Ser Thr Ser Asn Gln Thr
                165                 170                 175

Glu Thr Thr Lys Ala Pro Thr Asn Thr Val Ala Asn Lys Lys Ala
            180                 185                 190

Pro Ala Gln Leu Lys Asp Ile Lys Gly Thr Thr Gln Leu Arg Ala Val
        195                 200                 205

Ser Ala Ser Gln Pro Thr Ala Val Ala Ala Gly Gly Thr Asn Val Asn
    210                 215                 220

Asp Lys Val Thr Ala Ser Asn Met Lys Ile Thr Glu Ser Tyr Ile Glu
```

```
            225                 230                 235                 240
        Pro Asn Ser Gly Asn Phe Tyr Leu Lys Ser Asn Phe Asn Val Asn
                        245                 250                 255

Gly Thr Val Lys Glu Gly Asp Tyr Phe Thr Val Lys Met Pro Asp Thr
                        260                 265                 270

Val Asn Thr Phe Gly Asp Thr Arg His Ser Pro Asp Phe Arg Glu Lys
                        275                 280                 285

Ile Thr Asn Gln Lys Gly Glu Val Val Ala Leu Gly Glu Tyr Asp Val
            290                 295                 300

Ala Asn His Thr Met Thr Tyr Thr Phe Thr Asn Val Val Asn Asn Leu
        305                 310                 315                 320

Glu Asn Val Ser Gly Ser Phe Asn Leu Thr Gln Phe Met Asp Arg Lys
                        325                 330                 335

Val Ala Thr Asp Ser Gln Thr Tyr Pro Leu Lys Tyr Asp Ile Ala Gly
                        340                 345                 350

Glu Ser Leu Asp Thr Gln Ile Lys Val Asn Tyr Gly Gln Tyr Tyr Ser
                        355                 360                 365

Glu Gly Asp Ser Asn Leu Lys Ser Met Ile Thr Ser Glu Asp Pro Lys
                    370                 375                 380

Thr Gly Glu Tyr Asp Gln Tyr Ile Tyr Val Asn Pro Leu Gln Lys Thr
        385                 390                 395                 400

Ala Asn Gly Thr Val Val Arg Val Gln Gly Phe Gln Val Asp Pro Thr
                        405                 410                 415

Lys Ser Asn Gly Gln Val Lys Pro Asp Thr Thr Gln Ile Lys Ile Leu
                        420                 425                 430

Lys Val Ala Asp Gly Gln Pro Leu Asn Ser Ser Phe Gly Val Asn Asp
                    435                 440                 445

Ser Glu Tyr Glu Asp Val Thr Lys Gln Phe Asn Ile Val Tyr Arg Asp
                    450                 455                 460

Asn Asn Leu Ala Asp Ile Tyr Phe Gly Asn Leu Asn Gly Gln Arg Tyr
        465                 470                 475                 480

Ile Val Lys Val Thr Ser Lys Glu Asn Leu Asp Ser Lys Glu Asp Leu
                        485                 490                 495

Asn Leu Arg Ala Ile Met Ala Thr Gln Asn Arg Tyr Gly Gln Tyr Asn
                    500                 505                 510

Tyr Ile Thr Trp Asp Asn Asp Ile Val Lys Ser Ser Ser Gly Gly Thr
                    515                 520                 525

Ala Asp Gly Asn Glu Ala Ser Tyr Gln Leu Gly Asp Lys Val Trp Asn
        530                 535                 540

Asp Val Asn Lys Asn Gly Ile Gln Asp Gln Gly Glu Thr Gly Ile Ala
        545                 550                 555                 560

Asp Val Lys Val Thr Leu Lys Asp Leu Asp Gly Asn Ile Leu Asp Thr
                        565                 570                 575

Thr Tyr Thr Asn Thr Asn Gly Lys Tyr Ile Phe Asp Asn Leu Lys Asn
                    580                 585                 590

Gly Asn Tyr Gln Val Gly Phe Glu Thr Pro Glu Gly Tyr Ala Ala Ser
                    595                 600                 605

Pro Ser Asn Gln Gly Asn Asp Ala Leu Asp Ser Asp Gly Pro Thr Asn
                    610                 615                 620

Val Gln Ala Val Ile Ser Asp Gly Asn Asn Leu Thr Ile Asp Gln Gly
        625                 630                 635                 640

Phe Tyr Gln Thr Glu Thr Pro Thr His Asn Val Gly Asp Lys Val Trp
                        645                 650                 655
```

```
Glu Asp Leu Asn Lys Asp Gly Ile Gln Asp Gln Asn Glu Pro Gly Ile
            660                 665                 670
Ala Asn Val Lys Val Thr Leu Lys Asp Ala Asp Gly Asn Val Val Asp
            675                 680                 685
Thr Arg Thr Thr Asp Asp Lys Gly Asn Tyr Leu Phe Glu Lys Val Lys
690                 695                 700
Glu Gly Glu Tyr Thr Ile Glu Phe Glu Thr Pro Glu Gly Tyr Thr Pro
705                 710                 715                 720
Thr Gln Thr Gly Gln Gly Arg Val Ser Thr Asp Ser Asn Gly Thr Ser
            725                 730                 735
Ser Leu Ile Leu Val Glu Gly Asn Asp Asp Leu Thr Ile Asp Ser Gly
            740                 745                 750
Phe Tyr Lys Glu Pro Val Thr His Lys Val Gly Asp Lys Val Trp Asp
            755                 760                 765
Asp Leu Asn Lys Asp Gly Ile Gln Asp Asp Asn Glu Pro Gly Ile Ser
            770                 775                 780
Asp Val Lys Val Thr Leu Lys Asp Ala Asp Gly Asn Val Val Asp Thr
785                 790                 795                 800
Arg Thr Thr Asp Ala Asn Gly Asn Tyr Leu Phe Glu Asn Val Lys Glu
            805                 810                 815
Gly Asp Tyr Thr Ile Glu Phe Glu Thr Pro Glu Gly Tyr Thr Pro Thr
            820                 825                 830
Val Thr Gly Gln Gly Thr Ala Asp Asn Asp Ser Asn Gly Thr Ser Thr
            835                 840                 845
Lys Val Thr Val Lys Asp Gly Asp Leu Thr Ile Asp Ser Gly Phe
            850                 855                 860
Thr Gln Val Thr Pro Glu Pro Pro Thr His Asn Val Gly Asp Lys Val
865                 870                 875                 880
Trp Asp Asp Leu Asn Lys Asp Gly Ile Gln Asp Asp Asn Glu Pro Gly
            885                 890                 895
Ile Ser Asp Val Lys Val Thr Leu Lys Asp Ala Asp Gly Asn Val Val
            900                 905                 910
Asp Thr Arg Thr Thr Asp Ala Asn Gly Asn Tyr Leu Phe Glu Asn Val
            915                 920                 925
Lys Glu Gly Asp Tyr Thr Ile Glu Phe Glu Thr Pro Glu Gly Tyr Thr
            930                 935                 940
Pro Thr Val Thr Gly Gln Gly Thr Ala Asp Asn Asp Ser Asn Gly Thr
945                 950                 955                 960
Ser Thr Lys Val Thr Val Lys Asp Gly Asp Leu Thr Ile Asp Ser
            965                 970                 975
Gly Phe Thr Gln Val Thr Pro Glu Pro Pro Thr Glu Pro Glu Asn Pro
            980                 985                 990
Ser Pro Glu Gln Pro Ser Glu Pro Gly Gln Pro Glu Asn Pro Ser Pro
            995                 1000                1005
Glu Gln Pro Ser Glu Pro Gly Gln Pro Glu Asn Pro Ser Pro Glu
            1010                1015                1020
Gln Pro Ser Glu Pro Gly Gln Pro Glu Asn Pro Ser Pro Glu Gln
            1025                1030                1035
Pro Ser Glu Pro Gly Gln Pro Glu Asn Pro Ser Pro Glu Gln Pro
            1040                1045                1050
Ser Glu Pro Gly Gln Pro Lys Asn Pro Ser Pro Glu Gln Pro Asn
            1055                1060                1065
```

-continued

Asn Pro Ser Val Pro Gly Val Gln Asn Pro Glu Lys Pro Ser Leu
   1070                1075                1080

Thr Pro Val Thr Gln Pro Val His Ser Asn Gly Asn Lys Ala Lys
   1085                1090                1095

Pro Ser Gln Gln Gln Lys Ala Leu Pro Glu Thr Gly Glu Thr Glu
   1100                1105                1110

Ser His Gln Gly Thr Leu Phe Gly Gly Ile Leu Ala Ala Leu Gly
   1115                1120                1125

Ala Leu Leu Phe Ala Arg Lys Lys Arg His Asp Lys Lys Gln Ser
   1130                1135                1140

His

<210> SEQ ID NO 29
<211> LENGTH: 660
<212> TYPE: DNA
<213> ORGANISM: Staphylococcus pseudintermedius

<400> SEQUENCE: 29
atgaagaaaa caatttcagt acttggtcta gggctattag caacatttt tgtaagtaac      60
gaatcatatg ccgcagaaac gattcaaaac aatacgtcat caagtgaaac gaatcaaaat     120
tcagatcaga cgccgttaga tcattatatt cgaaaagcag atggcacact ggttgaaccg     180
aacgtgtacc cacataaaga ttatgtagag aatgaaggac ctttaccaga gtttaaattt     240
caagttgact ctaagaaaga ttcatctgat ccaaatcaag caccgttaga tcattatatt     300
cgaaaagcgg atggcacgtt ggttgaaccg aatgtatatc cacacaaaga ttatgtcgaa     360
aatgaagggc ctttaccaga gtttaaattt atgtatgctg acaaacaaaa tcatcatgac     420
caacagagta aaacaacaa ggataagcag cgtgcaaatt acagtgacaa aaagcataat      480
gatcagccgg tcatccaaa gcagtcacg ccagctgtac aacatgataa agcagtcact       540
tcaaacgcta ctgtaaaagc attgccaaac acaggtgaat ctgataaaac aacacaatta     600
ccaatcgtat tatcattgtt atctgtgggg attttagttt tattaaaatt gagaaaataa     660

<210> SEQ ID NO 30
<211> LENGTH: 219
<212> TYPE: PRT
<213> ORGANISM: Staphylococcus pseudintermedius

<400> SEQUENCE: 30

Met Lys Lys Thr Ile Ser Val Leu Gly Leu Gly Leu Leu Ala Thr Phe
1               5                   10                  15

Phe Val Ser Asn Glu Ser Tyr Ala Ala Glu Thr Ile Gln Asn Asn Thr
            20                  25                  30

Ser Ser Ser Glu Thr Asn Gln Asn Ser Asp Gln Thr Pro Leu Asp His
        35                  40                  45

Tyr Ile Arg Lys Ala Asp Gly Thr Leu Val Glu Pro Asn Val Tyr Pro
    50                  55                  60

His Lys Asp Tyr Val Glu Asn Glu Gly Pro Leu Pro Glu Phe Lys Phe
65                  70                  75                  80

Gln Val Asp Ser Lys Lys Asp Ser Ser Asp Pro Asn Gln Ala Pro Leu
                85                  90                  95

Asp His Tyr Ile Arg Lys Ala Asp Gly Thr Leu Val Glu Pro Asn Val
            100                 105                 110

Tyr Pro His Lys Asp Tyr Val Glu Asn Glu Gly Pro Leu Pro Glu Phe
        115                 120                 125

```
Lys Phe Met Tyr Ala Asp Lys Gln Asn His His Asp Gln Gln Ser Lys
        130                 135                 140

Asn Asn Lys Asp Lys Gln Arg Ala Asn Tyr Ser Asp Lys Lys His Asn
145                 150                 155                 160

Asp Gln Pro Gly His Pro Lys Ala Val Thr Pro Ala Val Gln His Asp
                165                 170                 175

Lys Ala Val Thr Ser Asn Ala Thr Val Lys Ala Leu Pro Asn Thr Gly
            180                 185                 190

Glu Ser Asp Lys Thr Thr Gln Leu Pro Ile Val Leu Ser Leu Leu Ser
        195                 200                 205

Val Gly Ile Leu Val Leu Leu Lys Leu Arg Lys
        210                 215

<210> SEQ ID NO 31
<211> LENGTH: 5541
<212> TYPE: DNA
<213> ORGANISM: Staphylococcus pseudintermedius

<400> SEQUENCE: 31
```

| | | | | | |
|---|---|---|---|---|---|
| atgaaaagta | aatatgattt | tttacctaat | agacttaata | aattttctat | acgaaaattt | 60 |
| actgttggta | gtgtatcagt | gctaatagga | gccactttat | tattcgggtt | tgtagaagga | 120 |
| gaagcatcag | catcagtaaa | agaaggtcaa | caaagtataa | attctagtga | aaagaaagc | 180 |
| gccgatccta | cagtagttga | tttaattagt | aagaaagaaa | caaatttaga | tggactagat | 240 |
| gtatcaagag | aagaaacgac | caaagtacca | ataaatgaaa | acaaaagagg | tgaggaacaa | 300 |
| agtatttctg | ataaagctat | aacagaaaaa | gctgatacac | cagtaagcaa | tttatcaagt | 360 |
| aaggaagttg | aggagcaagg | tgtttctgat | aaagctataa | cagaaaaagc | tgatacacca | 420 |
| gtaaccaatt | tatcaagtaa | ggaagctaag | gagcaaggtg | cttctgatag | agttataaca | 480 |
| gaaaaagctg | atacaccagt | aagcaattta | tcaagtaagg | aagctaagga | gcaaggtgct | 540 |
| tctgatagtt | tataacagaa | aaagctgata | caccagtaag | caatttatc | aagtaaggaa | 600 |
| gttgaggagc | aaggtgtttc | tgataaagct | atagagaaaa | tagctgatgc | atcagctact | 660 |
| gatttgtcaa | gtaaggaaga | agtagaacaa | gatatatcta | cacaaggtaa | agtaaaatca | 720 |
| aaggaagcag | tacaagtaga | aagtagtcag | ttacaaaatt | taaatagtga | aataaatgct | 780 |
| gaacctaatg | aaattaaggc | aatagataga | agttcaatat | tacctttaaa | tttaaatgat | 840 |
| gaagaaaata | caaaaaagt | taataaaggg | actcgggttc | cagaagctac | attaagaaat | 900 |
| gcctctaata | accaactcaa | tacacgaatg | agatcagtga | gtttatttag | agttgctaga | 960 |
| ctaacagaaa | tcaatagaaa | tgttaatgat | aaagtaaagg | tttcggatat | cgacatcgca | 1020 |
| atagccccac | cgcatactaa | ccctaaaact | ggaaaagaag | aattttgggc | gacatcttct | 1080 |
| tcagttttaa | agttaaaggc | aagctatgaa | ttggataata | gcatttctaa | aggggatcaa | 1140 |
| tttactattc | aatttggtca | aaatattcgt | ccaggtggat | taaatttacc | aagaccttat | 1200 |
| aattttttat | atgataagga | taaaaaatta | gttgcaactg | gccgttacaa | taagaatca | 1260 |
| aatacaatca | catatacatt | tacggattat | gtagataaac | atcaaaacat | taaggtagt | 1320 |
| tttgagatga | atgcattttc | tagaaaggaa | aatgctacta | ctgacaaaac | agcatatcca | 1380 |
| atggatgtta | ctattgcgaa | tcaaaaatat | agtgaaaata | ttattgtaga | ctatggtaat | 1440 |
| aaaaagaatg | ctgctattat | ttcaagtaca | gaatatattg | atttagatgg | tagtagaaaa | 1500 |
| atgacaaacat | atattaatca | aaatggtagt | aaaaattcca | tctatcgtgc | tgatatgcaa | 1560 |
| attgatttga | acggttataa | atttgatcca | tccaaaaaca | atttaaaat | ttatgaagtg | 1620 |

-continued

```
gaaaatagca gtgactttgt ggatagcttt tcaccagatg tgagcaagtt aagggatgtt    1680
acgagtcaat ttaatattca atatacaaat aataatacaa tggcaaaagt ggatttttggt   1740 actaaccttt ggaggggtaa aaaatatatt attcagcaag tggcgaatat agacgacagt    1800
aaattagtga aaaatgcttc aatcaattat acattgaata aaatggattt taataataaa    1860
agaacggtag aaacacataa caatacttat tctacagtga aagataaatc aacagcacta    1920
ggtgacgtac aggaaagtca atctattagt gagagccaat cagttagtga aagcgagtca    1980
ctaagtgaga gccaatcaat cagtgaaagc gaatcattaa gtgagagcca atcaatcagt    2040
gaaagcgaat cattaagtga aagtcaatca atctcagaga gcgaatcact aagtgaaagt    2100
cagtcaattt cagaaagcga atcattaagt gaaagccaat caatctcaga gagtgaatca    2160
ttaagtgaaa gtcagtcaat ttcagagagt gaatcactaa gtgaaagtca gtcaatttca    2220
gaaagcgaat cattaagcga gagtcagtca atttcagaaa gcgaatcatt aagcgagagt    2280
cagtcaattt cagaaagcga atcattaagt gaaagccaat caatcagtga aagcgaatca    2340
ctaagcgaga gccaatcaat ctcagagagt gaatcattaa gcgagagtca atcaatctca    2400
gagagcgaat cattaagtga gagtcaatca atcagtgaaa gcgagtcact aagtgagagt    2460
caatcaattt cagagagcga atcattaagt gaaagccaat caatctcaga gagtgaatca    2520
ctaagtgaga gccaatcaat ctcagagagt gaatcattaa gtgagagcca atcaatctca    2580
gagagcgagt cactaagcga gagccaatca atttcagaga gtgaatcact aagtgaaagt    2640
caatcaattt cagagagcga atcactaagt gagagccaat caatctcaga gagcgaatca    2700
ctaagtgaaa gtcaatcaat ttcagagagt gaatcactaa gcgagagcca atcaatctca    2760
gagagtgaat cattaagtga aagtcagtca atttcagaga gtgaatcact aagtgaaagt    2820
cagtcaattt cagaaagcga atcattaagt gaaagccaat caatcagtga aagcgaatca    2880
ctaagcgaga gtcaatcaat ctcagagagc gaatcattaa gtgaaagtca atcaatttca    2940
gaaagcgagt cattaagcga gagtcagtca atctcagaga gcgaatcact aagcgagagt    3000
caatcaatct cagagagtga atcattaagt gagagccaat cagttagtga agcgaatca     3060 ctaagtgaaa gtcagtcaat ttcagaaagc gaatcattaa gtgagagtca atcaatttca    3120
gaaagcgaat cattaagtga aagccaatca atcagtgaaa gcgaatcact aagcgagagc    3180
caatcaatca gtgaaagcga atcattaagt gagagtcaat caatctcaga aagcgaatca    3240
ttaagtgaga gtcaatcaat cagtgaaagc gaatcactaa gcgagagcca atcaatctca    3300
gagagcgaat cactaagcga gagccaatca atctcagaga gcgagtcact aagcgagagc    3360
caatcaatca gtgaaagcga atcattaagt gagagtcaat caatcagtga agcgagtca     3420 ctaagtgaga gccaatcaat ctcagagagt gaatcattga gtgagagcca atcaatctca    3480
gagagcgagt cactaagtga gagtcaatca atttcagaga gcgaatcatt aagtgaaagc    3540
caatcaatct cagagagtga atcattgagt gagagccaat cagttagtga agcgagtca     3600 ctaagtgaga gtcaatcaat cagtgaaagc gagtcactaa gtgagagtca atcaatttca    3660
gagagcgaat cattaagcga gagtcagtca atctcagaga gtgaatcact aagtgagagc    3720
caatcaatct cagagagtga atcattaagt gagagccaat caatctcaga gagtgaatca    3780
ctaagtgaga gtcaatcaat cagtgaaagc gaatcactaa gcgagagcca atcaatttca    3840
gagagtgaat cattaagtga gagccaatca gttagtgaaa gcgaatcact aagcgagagc    3900
caatcaatct cagagagcga atcattgagt gagagccaat caatctcaga gagtgaatca    3960
```

-continued

```
ttgagtgaga gtcaatcaat cagtgaaagc gaatcactaa gcgaaagtca atcaatttca   4020
gagagtgaat cattgagtga gagccaatca atttcagaga gtgaatcact aagtgaaagt   4080
cagtcaattt cagaaagcga atcactaagc gagagccaat caatctcaga gagcgaatca   4140
ctaagtgaaa gtcagtcaat ttcagaaagc gaatcattaa gtgaaagcca atcaatctca   4200
gagagtgaat cattaagtga aagtcagtca atttcagaga gtgaatcact aagtgaaagt   4260
cagtcaattt cagaaagcga atcattaagc gagagtcagt caatttcaga aagcgaatca   4320
ttaagtgaaa gccaatcaat cagtgaaagc gaatcactaa gcgagagcca atcaatctca   4380
gagagcgaat cactaagcga gagccaatca atctcagaga gcgaatcact aagtgaaagt   4440
caatcaattt cagagagtga atcattgagt gagagtcaat caatttcaga gagtgaatca   4500
ctaagtgaaa gtcaatcaat ttcagagagt gaatcactaa gcgagagcca atcaatctca   4560
gagagtgaat cattaagtga aagtcagtca atttcagaga gggaatcact aagtgaaagt   4620
cagtcaattt cagaaagcga atcattaagt gaaagccaat caatcagtga agcgaatca    4680
ctaagtgaaa gtcaatcaat ctcagagagt gaatcactaa gtgagagcca atcaatctca   4740
gagagtgaat cattgagtga gagccaatca atctcagaga gcgaatcact aagtgaaagt   4800
caatcaattt cagaaagcga gtcattaagc gagagtcagt caatctcaga gagtgaatca   4860
ctaagtgaga gccaatcaat ctcagagagt gaatcactaa gtgagagtca atcaatcagt   4920
gaaagcgaat cactaagcga gagccaatca atttcagaga gtgaatcatt aagtgagagc   4980
caatcagtta gtgaaagcga atcactaagc gagagccaat caatctcaga gagcgagtca   5040
ctaagcgaga gtcaatcaat ctcagagagt gaatcactaa gtgaaagtca gtcaatttca   5100
gaaagcgagt cactaagcga gagtcaatca atctcagaga gtgaatcatt gagtgagagc   5160
caatcaatct cagagagcga atcattgagt gagagccaat caatctcaga gagtgaatca   5220
ttgagtgaga gccaatcaat ttcagagagc gaatcactaa gcgagagcca atcaatcagt   5280
gaaagcgaat cattaagtga gagtcagtca attagcgaaa gcgaatcact aagtgagagt   5340
caatcaatct cagagagtga atcactaagt gaaagtcagt caatcagcga aagcgaatct   5400
aaatctttac ctaataccgg tactggagaa aagatttcta attatccagg tattttagga   5460
ggattattaa gcatattagg tataagtttg cttaaaagaa aagacagaga gaaaaaatta   5520
ggacaaaaat ctaataagta g                                             5541
```

<210> SEQ ID NO 32
<211> LENGTH: 1846
<212> TYPE: PRT
<213> ORGANISM: Staphylococcus pseudintermedius

<400> SEQUENCE: 32

```
Met Lys Ser Lys Tyr Asp Phe Leu Pro Asn Arg Leu Asn Lys Phe Ser
1               5                   10                  15

Ile Arg Lys Phe Thr Val Gly Ser Val Ser Val Leu Ile Gly Ala Thr
            20                  25                  30

Leu Leu Phe Gly Phe Val Glu Gly Glu Ala Ser Ala Ser Val Lys Glu
        35                  40                  45

Gly Gln Gln Ser Ile Asn Ser Glu Lys Ser Ala Asp Pro Thr
    50                  55                  60

Val Val Asp Leu Ile Ser Lys Lys Glu Thr Asn Leu Asp Gly Leu Asp
65                  70                  75                  80

Val Ser Arg Glu Glu Thr Thr Lys Val Pro Ile Asn Glu Asn Lys Arg
                85                  90                  95
```

```
Gly Glu Glu Gln Ser Ile Ser Asp Lys Ala Ile Thr Glu Lys Ala Asp
            100                 105                 110

Thr Pro Val Ser Asn Leu Ser Ser Lys Glu Val Glu Gln Gly Val
            115                 120                 125

Ser Asp Lys Ala Ile Thr Glu Lys Ala Asp Thr Pro Val Thr Asn Leu
130                 135                 140

Ser Ser Lys Glu Ala Lys Glu Gln Gly Ala Ser Asp Arg Val Ile Thr
145                 150                 155                 160

Glu Lys Ala Asp Thr Pro Val Ser Asn Leu Ser Ser Lys Glu Ala Lys
                165                 170                 175

Glu Gln Gly Ala Ser Asp Arg Val Ile Thr Glu Lys Ala Asp Thr Pro
            180                 185                 190

Val Ser Asn Leu Ser Ser Lys Glu Val Glu Gln Gly Val Ser Asp
            195                 200                 205

Lys Ala Ile Glu Lys Ile Ala Asp Ala Ser Ala Thr Asp Leu Ser Ser
            210                 215                 220

Lys Glu Glu Val Glu Gln Asp Ile Ser Thr Gln Gly Lys Val Lys Ser
225                 230                 235                 240

Lys Glu Ala Val Gln Val Glu Ser Ser Gln Leu Gln Asn Leu Asn Ser
                245                 250                 255

Glu Ile Asn Ala Glu Pro Asn Glu Ile Lys Ala Ile Asp Arg Ser Ser
            260                 265                 270

Ile Leu Pro Leu Asn Leu Asn Asp Glu Glu Asn Asn Lys Lys Val Asn
            275                 280                 285

Lys Gly Thr Arg Val Pro Glu Ala Thr Leu Arg Asn Ala Ser Asn Asn
            290                 295                 300

Gln Leu Asn Thr Arg Met Arg Ser Val Ser Leu Phe Arg Val Ala Arg
305                 310                 315                 320

Leu Thr Glu Ile Asn Arg Asn Val Asn Asp Lys Val Lys Val Ser Asp
                325                 330                 335

Ile Asp Ile Ala Ile Ala Pro Pro His Thr Asn Pro Lys Thr Gly Lys
            340                 345                 350

Glu Glu Phe Trp Ala Thr Ser Ser Val Leu Lys Leu Lys Ala Ser
            355                 360                 365

Tyr Glu Leu Asp Asn Ser Ile Ser Lys Gly Asp Gln Phe Thr Ile Gln
370                 375                 380

Phe Gly Gln Asn Ile Arg Pro Gly Gly Leu Asn Leu Pro Arg Pro Tyr
385                 390                 395                 400

Asn Phe Leu Tyr Asp Lys Asp Lys Lys Leu Val Ala Thr Gly Arg Tyr
                405                 410                 415

Asn Lys Glu Ser Asn Thr Ile Thr Tyr Thr Phe Thr Asp Tyr Val Asp
            420                 425                 430

Lys His Gln Asn Ile Lys Gly Ser Phe Glu Met Asn Ala Phe Ser Arg
            435                 440                 445

Lys Glu Asn Ala Thr Thr Asp Lys Thr Ala Tyr Pro Met Asp Val Thr
            450                 455                 460

Ile Ala Asn Gln Lys Tyr Ser Glu Asn Ile Ile Val Asp Tyr Gly Asn
465                 470                 475                 480

Lys Lys Asn Ala Ala Ile Ile Ser Ser Thr Glu Tyr Ile Asp Leu Asp
                485                 490                 495

Gly Ser Arg Lys Met Thr Thr Tyr Ile Asn Gln Asn Gly Ser Lys Asn
            500                 505                 510
```

```
Ser Ile Tyr Arg Ala Asp Met Gln Ile Asp Leu Asn Gly Tyr Lys Phe
            515                 520                 525

Asp Pro Ser Lys Asn Asn Phe Lys Ile Tyr Glu Val Glu Asn Ser Ser
530                 535                 540

Asp Phe Val Asp Ser Phe Ser Pro Asp Val Ser Lys Leu Arg Asp Val
545                 550                 555                 560

Thr Ser Gln Phe Asn Ile Gln Tyr Thr Asn Asn Thr Met Ala Lys
            565                 570                 575

Val Asp Phe Gly Thr Asn Leu Trp Arg Gly Lys Lys Tyr Ile Ile Gln
            580                 585                 590

Gln Val Ala Asn Ile Asp Asp Ser Lys Leu Val Lys Asn Ala Ser Ile
            595                 600                 605

Asn Tyr Thr Leu Asn Lys Met Asp Phe Asn Asn Lys Arg Thr Val Glu
            610                 615                 620

Thr His Asn Asn Thr Tyr Ser Thr Val Lys Asp Lys Ser Thr Ala Leu
625                 630                 635                 640

Gly Asp Val Gln Glu Ser Gln Ser Ile Ser Glu Ser Gln Ser Val Ser
            645                 650                 655

Glu Ser Glu Ser Leu Ser Glu Ser Gln Ser Ile Ser Glu Ser Glu Ser
            660                 665                 670

Leu Ser Glu Ser Gln Ser Ile Ser Glu Ser Glu Ser Leu Ser Glu Ser
            675                 680                 685

Gln Ser Ile Ser Glu Ser Glu Ser Leu Ser Glu Ser Gln Ser Ile Ser
            690                 695                 700

Glu Ser Glu Ser Leu Ser Glu Ser Gln Ser Ile Ser Glu Ser Glu Ser
705                 710                 715                 720

Leu Ser Glu Ser Gln Ser Ile Ser Glu Ser Glu Ser Leu Ser Glu Ser
            725                 730                 735

Gln Ser Ile Ser Glu Ser Glu Ser Leu Ser Glu Ser Gln Ser Ile Ser
            740                 745                 750

Glu Ser Glu Ser Leu Ser Glu Ser Gln Ser Ile Ser Glu Ser Glu Ser
            755                 760                 765

Leu Ser Glu Ser Gln Ser Ile Ser Glu Ser Glu Ser Leu Ser Glu Ser
            770                 775                 780

Gln Ser Ile Ser Glu Ser Glu Ser Leu Ser Glu Ser Gln Ser Ile Ser
785                 790                 795                 800

Glu Ser Glu Ser Leu Ser Glu Ser Gln Ser Ile Ser Glu Ser Glu Ser
                    805                 810                 815

Leu Ser Glu Ser Gln Ser Ile Ser Glu Ser Glu Ser Leu Ser Glu Ser
            820                 825                 830

Gln Ser Ile Ser Glu Ser Glu Ser Leu Ser Glu Ser Gln Ser Ile Ser
            835                 840                 845

Glu Ser Glu Ser Leu Ser Glu Ser Gln Ser Ile Ser Glu Ser Glu Ser
850                 855                 860

Leu Ser Glu Ser Gln Ser Ile Ser Glu Ser Glu Ser Leu Ser Glu Ser
865                 870                 875                 880

Gln Ser Ile Ser Glu Ser Glu Ser Leu Ser Glu Ser Gln Ser Ile Ser
                    885                 890                 895

Glu Ser Glu Ser Leu Ser Glu Ser Gln Ser Ile Ser Glu Ser Glu Ser
                    900                 905                 910

Leu Ser Glu Ser Gln Ser Ile Ser Glu Ser Glu Ser Leu Ser Glu Ser
            915                 920                 925

Gln Ser Ile Ser Glu Ser Glu Ser Leu Ser Glu Ser Gln Ser Ile Ser
```

```
                930             935             940
Glu Ser Glu Ser Leu Ser Glu Ser Gln Ser Ile Ser Glu Ser Glu Ser
945                 950             955                 960

Leu Ser Glu Ser Gln Ser Ile Ser Glu Ser Glu Ser Leu Ser Glu Ser
                965             970                 975

Gln Ser Ile Ser Glu Ser Glu Ser Leu Ser Glu Ser Gln Ser Ile Ser
            980             985                 990

Glu Ser Glu Ser Leu Ser Glu Ser Gln Ser Ile Ser Glu Ser Glu Ser
        995             1000            1005

Leu Ser Glu Ser Gln Ser Val Ser Glu Ser Glu Ser Leu Ser Glu
    1010            1015            1020

Ser Gln Ser Ile Ser Glu Ser Glu Ser Leu Ser Glu Ser Gln Ser
    1025            1030            1035

Ile Ser Glu Ser Glu Ser Leu Ser Glu Ser Gln Ser Ile Ser Glu
    1040            1045            1050

Ser Glu Ser Leu Ser Glu Ser Gln Ser Ile Ser Glu Ser Glu Ser
    1055            1060            1065

Leu Ser Glu Ser Gln Ser Ile Ser Glu Ser Glu Ser Leu Ser Glu
    1070            1075            1080

Ser Gln Ser Ile Ser Glu Ser Glu Ser Leu Ser Glu Ser Gln Ser
    1085            1090            1095

Ile Ser Glu Ser Glu Ser Leu Ser Glu Ser Gln Ser Ile Ser Glu
    1100            1105            1110

Ser Glu Ser Leu Ser Glu Ser Gln Ser Ile Ser Glu Ser Glu Ser
    1115            1120            1125

Leu Ser Glu Ser Gln Ser Ile Ser Glu Ser Glu Ser Leu Ser Glu
    1130            1135            1140

Ser Gln Ser Ile Ser Glu Ser Glu Ser Leu Ser Glu Ser Gln Ser
    1145            1150            1155

Ile Ser Glu Ser Glu Ser Leu Ser Glu Ser Gln Ser Ile Ser Glu
    1160            1165            1170

Ser Glu Ser Leu Ser Glu Ser Gln Ser Ile Ser Glu Ser Glu Ser
    1175            1180            1185

Leu Ser Glu Ser Gln Ser Val Ser Glu Ser Glu Ser Leu Ser Glu
    1190            1195            1200

Ser Gln Ser Ile Ser Glu Ser Glu Ser Leu Ser Glu Ser Gln Ser
    1205            1210            1215

Ile Ser Glu Ser Glu Ser Leu Ser Glu Ser Gln Ser Ile Ser Glu
    1220            1225            1230

Ser Glu Ser Leu Ser Glu Ser Gln Ser Ile Ser Glu Ser Glu Ser
    1235            1240            1245

Leu Ser Glu Ser Gln Ser Ile Ser Glu Ser Glu Ser Leu Ser Glu
    1250            1255            1260

Ser Gln Ser Ile Ser Glu Ser Glu Ser Leu Ser Glu Ser Gln Ser
    1265            1270            1275

Ile Ser Glu Ser Glu Ser Leu Ser Glu Ser Gln Ser Val Ser Glu
    1280            1285            1290

Ser Glu Ser Leu Ser Glu Ser Gln Ser Ile Ser Glu Ser Glu Ser
    1295            1300            1305

Leu Ser Glu Ser Gln Ser Ile Ser Glu Ser Glu Ser Leu Ser Glu
    1310            1315            1320

Ser Gln Ser Ile Ser Glu Ser Glu Ser Leu Ser Glu Ser Gln Ser
    1325            1330            1335
```

-continued

```
Ile Ser Glu Ser Glu Ser Leu Ser Glu Ser Gln Ser Ile Ser Glu
    1340            1345                1350
Ser Glu Ser Leu Ser Glu Ser Gln Ser Ile Ser Glu Ser Glu Ser
    1355            1360                1365
Leu Ser Glu Ser Gln Ser Ile Ser Glu Ser Glu Ser Leu Ser Glu
    1370            1375                1380
Ser Gln Ser Ile Ser Glu Ser Glu Ser Leu Ser Glu Ser Gln Ser
    1385            1390                1395
Ile Ser Glu Ser Glu Ser Leu Ser Glu Ser Gln Ser Ile Ser Glu
    1400            1405                1410
Ser Glu Ser Leu Ser Glu Ser Gln Ser Ile Ser Glu Ser Glu Ser
    1415            1420                1425
Leu Ser Glu Ser Gln Ser Ile Ser Glu Ser Glu Ser Leu Ser Glu
    1430            1435                1440
Ser Gln Ser Ile Ser Glu Ser Glu Ser Leu Ser Glu Ser Gln Ser
    1445            1450                1455
Ile Ser Glu Ser Glu Ser Leu Ser Glu Ser Gln Ser Ile Ser Glu
    1460            1465                1470
Ser Glu Ser Leu Ser Glu Ser Gln Ser Ile Ser Glu Ser Glu Ser
    1475            1480                1485
Leu Ser Glu Ser Gln Ser Ile Ser Glu Ser Glu Ser Leu Ser Glu
    1490            1495                1500
Ser Gln Ser Ile Ser Glu Ser Glu Ser Leu Ser Glu Ser Gln Ser
    1505            1510                1515
Ile Ser Glu Ser Glu Ser Leu Ser Glu Ser Gln Ser Ile Ser Glu
    1520            1525                1530
Arg Glu Ser Leu Ser Glu Ser Gln Ser Ile Ser Glu Ser Glu Ser
    1535            1540                1545
Leu Ser Glu Ser Gln Ser Ile Ser Glu Ser Glu Ser Leu Ser Glu
    1550            1555                1560
Ser Gln Ser Ile Ser Glu Ser Glu Ser Leu Ser Glu Ser Gln Ser
    1565            1570                1575
Ile Ser Glu Ser Glu Ser Leu Ser Glu Ser Gln Ser Ile Ser Glu
    1580            1585                1590
Ser Glu Ser Leu Ser Glu Ser Gln Ser Ile Ser Glu Ser Glu Ser
    1595            1600                1605
Leu Ser Glu Ser Gln Ser Ile Ser Glu Ser Glu Ser Leu Ser Glu
    1610            1615                1620
Ser Gln Ser Ile Ser Glu Ser Glu Ser Leu Ser Glu Ser Gln Ser
    1625            1630                1635
Ile Ser Glu Ser Glu Ser Leu Ser Glu Ser Gln Ser Ile Ser Glu
    1640            1645                1650
Ser Glu Ser Leu Ser Glu Ser Gln Ser Val Ser Glu Ser Glu Ser
    1655            1660                1665
Leu Ser Glu Ser Gln Ser Ile Ser Glu Ser Glu Ser Leu Ser Glu
    1670            1675                1680
Ser Gln Ser Ile Ser Glu Ser Glu Ser Leu Ser Glu Ser Gln Ser
    1685            1690                1695
Ile Ser Glu Ser Glu Ser Leu Ser Glu Ser Gln Ser Ile Ser Glu
    1700            1705                1710
Ser Glu Ser Leu Ser Glu Ser Gln Ser Ile Ser Glu Ser Glu Ser
    1715            1720                1725
```

```
Leu Ser Glu Ser Gln Ser Ile Ser Glu Ser Glu Ser Leu Ser Glu
    1730                1735                1740

Ser Gln Ser Ile Ser Glu Glu Ser Leu Ser Glu Ser Gln Ser
    1745                1750                1755

Ile Ser Glu Ser Glu Ser Leu Ser Glu Ser Gln Ser Ile Ser Glu
    1760                1765                1770

Ser Glu Ser Leu Ser Glu Ser Gln Ser Ile Ser Glu Ser Glu Ser
    1775                1780                1785

Leu Ser Glu Ser Gln Ser Ile Ser Glu Ser Glu Ser Lys Ser Leu
    1790                1795                1800

Pro Asn Thr Gly Thr Gly Glu Lys Ile Ser Asn Tyr Pro Gly Ile
    1805                1810                1815

Leu Gly Gly Leu Leu Ser Ile Leu Gly Ile Ser Leu Leu Lys Arg
    1820                1825                1830

Lys Asp Arg Glu Lys Lys Leu Gly Gln Lys Ser Asn Lys
    1835                1840                1845

<210> SEQ ID NO 33
<211> LENGTH: 1953
<212> TYPE: DNA
<213> ORGANISM: Staphylococcus pseudintermedius

<400> SEQUENCE: 33
atgttaagaa caaattataa actaagaaag cttaaagtag gtttagtatc gacaggtgtg      60
gcgttgactt ttgtgatggc aagtgggaat gcagaggcgt cggagaacga gcagactgaa     120
gtaaaagggg aggcgcaagt tgcttctgtg aatgaaaaag agagtgaagc agaattacct     180
gtagcgcaac aagaagcatc tattcaacta gacaaagtac aaccaggcga tgcacagctt     240
tcaggctata cacagccaaa caaagcgatt tctgtaaaga tcgacaataa agatattgtg     300
tctgtagatg atggctatga gaggtattta tcggatgata caggtaaatt tgtatatgat     360
ttgaaagggc gtcaaattgt ttacaatcaa aaagttgatg ttgaagcgat gacgccattt     420
aattttgaag attttgatga atcagcactt gagagcgaag aggcattgga ggcgttaggt     480
caattggaag acgaagaaac agcgacagct tctgtgacga cgcctagata tgaaggtgcg     540
tatacagttc ctgaagaacg cttgacaccc attcaaggcc aacagcaagt attcatcgaa     600
cctattttag aaggggcaag taaaatcaaa ggacatacat ctgtacaagg taaagtcgcg     660
ttagcaatca atcaagaaca tgtgcaccta ggtgatacgt tagaagaaca agcagcactc     720
actgatcaag agtggcaagg tcgttatgac gggatttggc gccatattga tgatcaaggg     780
tttttcgagt ttgacttgaa ccgtctttac aataaatctt acccattgaa gtctggcgat     840
ttagtgactt tatcttttaa atctaatgac gaagtaggcc cattattcaa tgtgaacgtt     900
gagcctttcg aacgtgtggc acaagctaaa acaaagtatg agcagaatga cagtccagta     960
gtcaacaaat tggatgatac taaaagtgac ttggaggttc aacctatcta tggagacctt    1020
acacaagcag cagtacatgg cgagtcgaaa gtgttgatac cggggacgtc aaaagttgaa    1080
ggacgtacga attatgcaca tgcatggata gagatggcat ctaatttagg ggaatatcgt    1140
agtttcccta aattcaagc tgatgcgaca ggtgcgttta tatttgattt aaaagcggca    1200
gacatacaat tgttaaacgg agaacgtttg acattcagag ccgttgaccc acatacaaaa    1260
caacagttag ctgaaactac atcagaagta cgcccagtag atatgcaaga tgaagagtca    1320
gaggttgtgc agacttcaag cactgagaaa tcagcacttg cggatgaaat tcttcgttct    1380
atgacaattg acaaatcatt taatcctgaa gttaccgaga taccgggtca tgtatatcct    1440
```

```
aagaaaacag aggataaagg tgctgaaaat acagaacaag cctcagagaa ttctgagaag    1500
ccatctcaga ctacagaatc tcaaaatgat gccgtacaag atgtagagaa atcctctgtt    1560
aatgaggagg ttacgccacc ttcaacagaa tctgctcaag ttgaaaaggg gcaaaataca    1620 gaagggggctt tgcttccaaa aaatgtagaa caacatgtag agagtatacc ataccaaaaa    1680
cgtaaagcgt tgataggact gacaaaacat caaggatcag ggcacatgcc gccattttct    1740
ttaagcttta ataataaga agatgacgta tccacaaagg ttaacgaagc aaacgagcat    1800
gaacgtaagc agggtacagt ttatccagag caaatagaac aattacctca aacaggttta    1860
actgaaaaat cgccattctg ggcattgtta tttgttgtat caggcacagg tttattatta    1920
ttcaaacgtt ctagacgaca acgccaatct taa                                 1953
```

<210> SEQ ID NO 34
<211> LENGTH: 650
<212> TYPE: PRT
<213> ORGANISM: Staphylococcus pseudintermedius
<400> SEQUENCE: 34

```
Met Leu Arg Thr Asn Tyr Lys Leu Arg Lys Leu Lys Val Gly Leu Val
1               5                   10                  15

Ser Thr Gly Val Ala Leu Thr Phe Val Met Ala Ser Gly Asn Ala Glu
            20                  25                  30

Ala Ser Glu Asn Glu Gln Thr Glu Val Lys Gly Glu Ala Gln Val Ala
        35                  40                  45

Ser Val Asn Glu Lys Glu Ser Glu Ala Glu Leu Pro Val Ala Gln Gln
    50                  55                  60

Glu Ala Ser Ile Gln Leu Asp Lys Val Gln Pro Gly Asp Ala Gln Leu
65                  70                  75                  80

Ser Gly Tyr Thr Gln Pro Asn Lys Ala Ile Ser Val Lys Ile Asp Asn
                85                  90                  95

Lys Asp Ile Val Ser Val Asp Asp Gly Tyr Glu Glu Val Leu Ser Asp
            100                 105                 110

Asp Thr Gly Lys Phe Val Tyr Asp Leu Lys Gly Arg Gln Ile Val Tyr
        115                 120                 125

Asn Gln Lys Val Asp Val Glu Ala Met Thr Pro Phe Asn Phe Glu Asp
    130                 135                 140

Phe Asp Glu Ser Ala Leu Glu Ser Glu Glu Ala Leu Glu Ala Leu Gly
145                 150                 155                 160

Gln Leu Glu Asp Glu Glu Thr Ala Thr Ala Ser Val Thr Thr Pro Arg
                165                 170                 175

Tyr Glu Gly Ala Tyr Thr Val Pro Glu Glu Arg Leu Thr Pro Ile Gln
            180                 185                 190

Gly Gln Gln Gln Val Phe Ile Glu Pro Ile Leu Glu Gly Ala Ser Lys
        195                 200                 205

Ile Lys Gly His Thr Ser Val Gln Gly Lys Val Ala Leu Ala Ile Asn
    210                 215                 220

Gln Glu His Val His Leu Gly Asp Thr Leu Glu Glu Gln Ala Ala Leu
225                 230                 235                 240

Thr Asp Gln Glu Trp Gln Gly Arg Tyr Asp Gly Ile Trp Arg His Ile
                245                 250                 255

Asp Asp Gln Gly Phe Phe Glu Phe Asp Leu Asn Arg Leu Tyr Asn Lys
            260                 265                 270

Ser Tyr Pro Leu Lys Ser Gly Asp Leu Val Thr Leu Ser Phe Lys Ser
```

```
            275                 280                 285
Asn Asp Glu Val Gly Pro Leu Phe Asn Val Asn Val Glu Pro Phe Glu
    290                 295                 300

Arg Val Ala Gln Ala Lys Thr Lys Tyr Glu Gln Asn Asp Ser Pro Val
305                 310                 315                 320

Val Asn Lys Leu Asp Asp Thr Lys Ser Asp Leu Glu Val Gln Pro Ile
                325                 330                 335

Tyr Gly Asp Leu Thr Gln Ala Ala Val His Gly Glu Ser Lys Val Leu
            340                 345                 350

Ile Pro Gly Thr Ser Lys Val Glu Gly Arg Thr Asn Tyr Ala His Ala
        355                 360                 365

Trp Ile Glu Met Ala Ser Asn Leu Gly Glu Tyr Arg Ser Phe Pro Lys
    370                 375                 380

Leu Gln Ala Asp Ala Thr Gly Ala Phe Ile Phe Asp Leu Lys Ala Ala
385                 390                 395                 400

Asp Ile Gln Leu Leu Asn Gly Glu Arg Leu Thr Phe Arg Ala Val Asp
                405                 410                 415

Pro His Thr Lys Gln Gln Leu Ala Glu Thr Thr Ser Glu Val Arg Pro
            420                 425                 430

Val Asp Met Gln Asp Glu Glu Ser Glu Val Val Gln Thr Ser Ser Thr
        435                 440                 445

Glu Lys Ser Ala Leu Ala Asp Glu Ile Leu Arg Ser Met Thr Ile Asp
    450                 455                 460

Lys Ser Phe Asn Pro Glu Val Thr Glu Ile Pro Gly His Val Tyr Pro
465                 470                 475                 480

Lys Lys Thr Glu Asp Lys Gly Ala Glu Asn Thr Glu Gln Ala Ser Glu
                485                 490                 495

Asn Ser Glu Lys Pro Ser Gln Thr Glu Ser Gln Asn Asp Ala Val
            500                 505                 510

Gln Asp Val Glu Lys Ser Ser Val Asn Glu Glu Val Thr Pro Pro Ser
        515                 520                 525

Thr Glu Ser Ala Gln Val Glu Lys Gly Gln Asn Thr Glu Gly Ala Leu
    530                 535                 540

Leu Pro Lys Asn Val Glu Gln His Val Glu Ser Ile Pro Tyr Gln Lys
545                 550                 555                 560

Arg Lys Ala Leu Ile Gly Leu Thr Lys His Gln Gly Ser Gly His Met
                565                 570                 575

Pro Pro Phe Ser Leu Ser Phe Asn Asn Lys Glu Asp Asp Val Ser Thr
            580                 585                 590

Lys Val Asn Glu Ala Asn Glu His Glu Arg Lys Gln Gly Thr Val Tyr
        595                 600                 605

Pro Glu Gln Ile Glu Gln Leu Pro Gln Thr Gly Leu Thr Glu Lys Ser
    610                 615                 620

Pro Phe Trp Ala Leu Leu Phe Val Val Ser Gly Thr Gly Leu Leu Leu
625                 630                 635                 640

Phe Lys Arg Ser Arg Arg Gln Arg Gln Ser
                645                 650

<210> SEQ ID NO 35
<211> LENGTH: 1491
<212> TYPE: DNA
<213> ORGANISM: Staphylococcus pseudintermedius

<400> SEQUENCE: 35
```

-continued

| | |
|---|---|
| atgaaaacta aatacacagc aaaattatta attggggcag caacaatatc tttagcaaca | 60 |
| tttatttcac aagggaacgc acatgcgagc gaacaaacta caggactcgc accggcacaa | 120 |
| cctgtcaact ttgattcaat caatgtaacg ccagaccaaa aacattcta tcaagtctta | 180 |
| catatggaag gcatttcaga agaccaacgt gaacaatatt tgaaacaatt gcacgaagac | 240 |
| ccaagtagcg cacaaaatgt tttttcagaa tcaattaaag atgccatcca cccggaacgt | 300 |
| cgtgttgcgc aacaaaatgc gttttacagc gtattacaca cgatgactt atccgaagag | 360 |
| caacgtgatg catacattgg tagaattaaa gaagatccag atcaaagcca agaagtattt | 420 |
| gttgagtctt taaatgtggc acctaaagca gaatcacatg aagatcgcct cattgaatta | 480 |
| caaaacaaaa atttaatgga agcgaatgaa gcacttaaag cgttacaaca agaagacagc | 540 |
| attcagaata gacgtgcggc tcaacgtgct gtcaacaaat tgacgccgga tagcgcgaac | 600 |
| gcattccaaa agaattaga tcaaatcaat gccccacgcg acgctaaaat taaagctgac | 660 |
| gctgaagcaa aaaacaagc acctgaagta agcgcaccac aaattgaaga tgcacctact | 720 |
| actgaagttg caccatctcc aaaacaagat atgccaaaag tagataaaaa agaagaagat | 780 |
| aaagtagaaa gtgatactga ggtcaaagaa gtacctaaag ctgatacaga gaaaaaccct | 840 |
| caatctaaag acacttctaa aactgaacaa gctaaagaaa cacctaaagt agagcaatca | 900 |
| cctaaaacag aaaaggctga agaagcacct aaagcagaaa cacctcaaaa tggaaataaa | 960 |
| gcacaaactg aagaagctaa accagaagta aaagacaatg tgaaaaacac tccatctgca | 1020 |
| cctgtgttac ctgaaacagg aaaagcaaca acttcaacac ttgaaagcta ctggaattct | 1080 |
| ttcaaagaca gtgtgaataa aggttatact tacattaaac aaagcttaga aagtggttat | 1140 |
| caatatttaa aaggtcaata cgactatatc actaaaaaat acaatgatgc gaaatactat | 1200 |
| acaaaaatgt attcaaatca taagtctaca attgatcagt ctgtattagc tatattaggt | 1260 |
| aaaactggat ctagcgcata tatcaagcca ttaaatatcg aagaaaattc aaacgtattt | 1320 |
| tacaaagctt atgcaaaaac aagaaacttt gctacagaaa gcattaacac aggaaaagta | 1380 |
| ttatacacat tatatcaaaa ccctactgta gttaaatctg ctttcactgc aattgaaaca | 1440 |
| gcaaatacag taaaaaatgc aataagcaat cttttctctc tcttcaaata a | 1491 |

<210> SEQ ID NO 36
<211> LENGTH: 496
<212> TYPE: PRT
<213> ORGANISM: Staphylococcus pseudintermedius

<400> SEQUENCE: 36

Met Lys Thr Lys Tyr Thr Ala Lys Leu Leu Ile Gly Ala Ala Thr Ile
1               5                   10                  15

Ser Leu Ala Thr Phe Ile Ser Gln Gly Asn Ala His Ala Ser Glu Gln
            20                  25                  30

Thr Thr Gly Leu Ala Pro Ala Gln Pro Val Asn Phe Asp Ser Ile Asn
        35                  40                  45

Val Thr Pro Asp Gln Lys Thr Phe Tyr Gln Val Leu His Met Glu Gly
    50                  55                  60

Ile Ser Glu Asp Gln Arg Glu Gln Tyr Leu Lys Gln Leu His Glu Asp
65                  70                  75                  80

Pro Ser Ser Ala Gln Asn Val Phe Ser Glu Ser Ile Lys Asp Ala Ile
                85                  90                  95

His Pro Glu Arg Arg Val Ala Gln Gln Asn Ala Phe Tyr Ser Val Leu
            100                 105                 110

His Asn Asp Leu Ser Glu Glu Gln Arg Asp Ala Tyr Ile Gly Arg
            115                 120                 125

Ile Lys Glu Asp Pro Asp Gln Ser Gln Glu Val Phe Val Glu Ser Leu
130                 135                 140

Asn Val Ala Pro Lys Ala Glu Ser His Glu Asp Arg Leu Ile Glu Leu
145                 150                 155                 160

Gln Asn Lys Asn Leu Met Glu Ala Asn Glu Ala Leu Lys Ala Leu Gln
                165                 170                 175

Gln Glu Asp Ser Ile Gln Asn Arg Ala Ala Gln Arg Ala Val Asn
            180                 185                 190

Lys Leu Thr Pro Asp Ser Ala Asn Ala Phe Gln Lys Glu Leu Asp Gln
            195                 200                 205

Ile Asn Ala Pro Arg Asp Ala Lys Ile Lys Ala Asp Ala Glu Ala Lys
210                 215                 220

Lys Gln Ala Pro Glu Val Ser Ala Pro Gln Ile Glu Asp Ala Pro Thr
225                 230                 235                 240

Thr Glu Val Ala Pro Ser Pro Lys Gln Asp Met Pro Lys Val Asp Lys
                245                 250                 255

Lys Glu Glu Asp Lys Val Glu Ser Asp Thr Glu Val Lys Glu Val Pro
            260                 265                 270

Lys Ala Asp Thr Glu Lys Asn Pro Gln Ser Lys Asp Thr Ser Lys Thr
            275                 280                 285

Glu Gln Ala Lys Glu Thr Pro Lys Val Glu Gln Ser Pro Lys Thr Glu
            290                 295                 300

Lys Ala Glu Glu Ala Pro Lys Ala Glu Thr Pro Gln Asn Gly Asn Lys
305                 310                 315                 320

Ala Gln Thr Glu Glu Ala Lys Pro Glu Val Lys Asp Asn Val Lys Asn
                325                 330                 335

Thr Pro Ser Ala Pro Val Leu Pro Glu Thr Gly Lys Ala Thr Thr Ser
            340                 345                 350

Thr Leu Glu Ser Tyr Trp Asn Ser Phe Lys Asp Ser Val Asn Lys Gly
            355                 360                 365

Tyr Thr Tyr Ile Lys Gln Ser Leu Glu Ser Gly Tyr Gln Tyr Leu Lys
370                 375                 380

Gly Gln Tyr Asp Tyr Ile Thr Lys Lys Tyr Asn Asp Ala Lys Tyr Tyr
385                 390                 395                 400

Thr Lys Met Tyr Ser Asn His Lys Ser Thr Ile Asp Gln Ser Val Leu
                405                 410                 415

Ala Ile Leu Gly Lys Thr Gly Ser Ser Ala Tyr Ile Lys Pro Leu Asn
            420                 425                 430

Ile Glu Glu Asn Ser Asn Val Phe Tyr Lys Ala Tyr Ala Lys Thr Arg
            435                 440                 445

Asn Phe Ala Thr Glu Ser Ile Asn Thr Gly Lys Val Leu Tyr Thr Leu
450                 455                 460

Tyr Gln Asn Pro Thr Val Val Lys Ser Ala Phe Thr Ala Ile Glu Thr
465                 470                 475                 480

Ala Asn Thr Val Lys Asn Ala Ile Ser Asn Leu Phe Ser Leu Phe Lys
                485                 490                 495

<210> SEQ ID NO 37
<211> LENGTH: 504
<212> TYPE: PRT
<213> ORGANISM: Staphylococcus pseudintermedius

<400> SEQUENCE: 37

```
Asn Glu Asp Val Thr Glu Thr Gly Arg Asn Ser Val Thr Thr Gln
  1               5                  10                  15

Ala Ser Glu Gln His Leu Gln Val Glu Ala Val Pro Gln Glu Gly Asn
                 20                  25                  30

Asn Val Asn Val Ser Ser Val Lys Val Pro Thr Asn Thr Ala Thr Gln
             35                  40                  45

Ala Gln Glu Asp Val Ala Ser Val Ser Asp Val Lys Ala His Ala Asp
     50                  55                  60

Asp Ala Leu Gln Val Gln Glu Ser Ser His Thr Asp Gly Val Ser Ser
 65                  70                  75                  80

Glu Phe Lys Gln Glu Thr Ala Tyr Ala Asn Pro Gln Thr Ala Glu Thr
                 85                  90                  95

Val Lys Pro Asn Ser Glu Ala Val His Gln Ser Glu Tyr Glu Asp Lys
            100                 105                 110

Gln Lys Pro Val Ser Ser Arg Lys Glu Asp Glu Thr Met Leu Gln
            115                 120                 125

Gln Gln Gln Val Glu Ala Lys Asn Val Val Ser Ala Glu Glu Val Ser
    130                 135                 140

Lys Glu Glu Asn Thr Gln Val Met Gln Ser Pro Gln Asp Val Glu Gln
145                 150                 155                 160

His Val Gly Gly Lys Asp Ile Ser Asn Glu Val Val Asp Arg Ser
                165                 170                 175

Asp Ile Lys Gly Phe Asn Ser Glu Thr Thr Ile Arg Pro His Gln Gly
            180                 185                 190

Gln Gly Gly Arg Leu Asn Tyr Gln Leu Lys Phe Pro Ser Asn Val Lys
        195                 200                 205

Pro Gly Asp Gln Phe Thr Ile Lys Leu Ser Asp Asn Ile Asn Thr His
    210                 215                 220

Gly Val Ser Val Glu Arg Thr Ala Pro Arg Ile Met Ala Lys Asn Thr
225                 230                 235                 240

Glu Gly Ala Thr Asp Val Ile Ala Glu Gly Leu Val Leu Glu Asp Gly
                245                 250                 255

Lys Thr Ile Val Tyr Thr Phe Lys Asp Tyr Val Asn Gly Lys Gln Asn
                260                 265                 270

Leu Thr Ala Glu Leu Ser Val Ser Tyr Phe Val Ser Pro Glu Lys Val
        275                 280                 285

Leu Thr Thr Gly Thr Gln Thr Phe Thr Thr Met Ile Gly Asn His Ser
    290                 295                 300

Thr Gln Ser Asn Ile Asp Val Tyr Tyr Asp Asn Ser His Tyr Val Asp
305                 310                 315                 320

Gly Arg Ile Ser Gln Val Asn Lys Lys Glu Ala Lys Phe Gln Gln Ile
                325                 330                 335

Ala Tyr Ile Asn Pro Asn Gly Tyr Leu Asn Gly Arg Gly Thr Ile Ala
                340                 345                 350

Val Asn Gly Glu Val Val Ser Gly Thr Thr Lys Asp Leu Met Gln Pro
            355                 360                 365

Thr Val Arg Val Tyr Gln Tyr Lys Gly Gln Gly Val Pro Pro Glu Ser
        370                 375                 380

Ile Thr Ile Asp Pro Asn Met Trp Glu Glu Ile Ser Ile Asn Asp Thr
385                 390                 395                 400

Met Val Arg Lys Tyr Asp Gly Gly Tyr Ser Leu Asn Leu Asp Thr Ser
                405                 410                 415
```

```
Lys Asn Gln Lys Tyr Ala Ile Tyr Tyr Glu Gly Ala Tyr Asp Ala Gln
            420                 425                 430

Ala Asp Thr Leu Leu Tyr Arg Thr Tyr Ile Gln Ser Leu Asn Ser Tyr
        435                 440                 445

Tyr Pro Phe Ser Tyr Gln Lys Met Asn Gly Val Lys Phe Tyr Glu Asn
    450                 455                 460

Ser Ala Ser Gly Ser Gly Glu Leu Lys Pro Lys Pro Pro Glu Gln Pro
465                 470                 475                 480

Lys Pro Glu Pro Glu Ile Gln Ala Asp Val Val Asp Ile Ile Glu Asp
                485                 490                 495

Ser His Val Ile Asp Ile Gly Trp
            500
```

<210> SEQ ID NO 38
<211> LENGTH: 1512
<212> TYPE: DNA
<213> ORGANISM: Staphylococcus pseudintermedius

<400> SEQUENCE: 38

```
aatgaagatg tcactgaaac aactgggaga aattcagtga caacgcaagc ttctgagcaa     60
catttgcaag tggaagcagt acctcaagaa ggcaataatg taaatgtatc ctctgtaaaa    120
gtacctacga atacggcaac gcaagcacaa gaagatgttg caagtgtatc cgatgttaaa    180
gcacatgctg atgatgcatt acaagtacaa gaaagtagtc atactgatgg tgtttcttca    240
gaattcaagc aggagacagc ttatgcgaat cctcaaacag ctgagacagt taaacctaat    300
agtgaagcag tgcatcagtc tgaatacgag gataagcaaa aacccgtatc atctagccgc    360
aaagaagatg agactatgct tcagcagcaa caagttgaag ccaaaaatgt tgtgagtgcg    420
gaggaagtgt ctaaagaaga aaatactcaa gtgatgcaat cccctcaaga cgttgaacaa    480
catgtaggtg gtaaagatat ctctaatgag gttgtagtgg ataggagtga tatcaaagga    540
tttaacagcg aaactactat tcgacctcat cagggacaag gtggtaggtt gaattatcaa    600
ttaaagtttc ctagcaatgt aaagccaggc gatcagttta ctataaaatt atctgacaat    660
atcaatacac atggtgtttc tgttgaaaga accgcaccga gaatcatggc taaaaatact    720
gaaggtgcga cggatgtaat tgctgaaggt ctagtgttgg aagatggtaa aaccatcgta    780
tatacattta aagactatgt aaatggcaag caaaatttga ctgctgagtt atcagtgagc    840
tatttcgtaa gtccggaaaa agtcttgact actgggacac aaacattcac gacgatgatc    900
ggtaatcatt caacgcaatc caatattgac gtttattatg ataatagtca ttatgtagat    960
ggacgtattt cgcaagtgaa caaaaaagaa gctaaatttc aacaaatagc atacattaac   1020
cctaatggct atttaaatgg cagggggaca attgcagtta atggtgaagt ggtcagtggt   1080
acgactaaag acttaatgca acctacagtg cgtgtatatc aatataaagg acaaggtgtt   1140
cctcctgaaa gtattactat agaccctaat atgtgggaag aaatcagcat aaacgatact   1200
atggtaagaa aatatgatgg tggctatagc ttgaatctgg ataccagcaa gaatcaaaaa   1260
tatgccatct attatgaagg ggcatatgat gcgcaagctg acacactgtt gtatagaaca   1320
tatatacagt cattaaacag ttactatccg ttcagttacc aaaaaatgaa cggtgtgaag   1380
ttttacgaaa acagtgcgag tggaagcggt gagttgaaac cgaaaccacc tgaacaacca   1440
aaaccagaac ctgaaattca agctgatgta gtagatatta ttgaagatag ccatgtgatt   1500
gatataggat gg                                                       1512
```

```
<210> SEQ ID NO 39
<211> LENGTH: 5
<212> TYPE: PRT
<213> ORGANISM: Staphylococcus pseudintermedius
<220> FEATURE:
<221> NAME/KEY: misc_feature
<222> LOCATION: (3)..(3)
<223> OTHER INFORMATION: Xaa can be any naturally occurring amino acid

<400> SEQUENCE: 39

Leu Pro Xaa Thr Gly
1               5

<210> SEQ ID NO 40
<211> LENGTH: 9
<212> TYPE: PRT
<213> ORGANISM: Staphylococcus pseudintermedius

<400> SEQUENCE: 40

Thr Tyr Thr Phe Thr Asp Tyr Val Asp
1               5
```